US011274303B2

(12) United States Patent
Pajukanta et al.

(10) Patent No.: US 11,274,303 B2
(45) Date of Patent: Mar. 15, 2022

(54) ***OLMALINC* AS A DIAGNOSTIC AND THERAPEUTIC TARGET FOR NAFLD, NASH, METABOLIC SYNDROME, AND HEPATIC FIBROSIS**

(71) Applicants: THE REGENTS OF THE UNIVERSITY OF CALIFORNIA, Oakland, CA (US); UNITED STATES GOVERNMENT REPRESENTED BY THE DEPARTMENT OF VETERANS AFFAIRS, Washington, DC (US); UNIVERSITY OF EASTERN FINLAND, Kuopio (FI)

(72) Inventors: Paivi E. Pajukanta, Los Angeles, CA (US); Joseph R. Pisegna, Los Angeles, CA (US); Jihane N. Benhammou, Los Angeles, CA (US); Arthur Ko, Los Angeles, CA (US); Jussi Pihlajamäki, Kuopio (FI)

(73) Assignees: THE REGENTS OF THE UNIVERSITY OF CALIFORNIA, Oakland, CA (US); UNITED STATES GOVERNMENT REPRESENTED BY THE DEPARTMENT OF VETERANS AFFAIRS, Washington, DC (US); UNIVERSITY OF EASTERN FINLAND, Kuopio (FI)

( * ) Notice: Subject to any disclaimer, the term of this patent is extended or adjusted under 35 U.S.C. 154(b) by 7 days.

(21) Appl. No.: 16/753,962

(22) PCT Filed: Oct. 5, 2018

(86) PCT No.: PCT/US2018/054735

§ 371 (c)(1),
(2) Date: Apr. 6, 2020

(87) PCT Pub. No.: WO2019/071214

PCT Pub. Date: Apr. 11, 2019

(65) Prior Publication Data

US 2020/0283767 A1 Sep. 10, 2020

Related U.S. Application Data

(60) Provisional application No. 62/569,397, filed on Oct. 6, 2017.

(51) Int. Cl.
*C12N 15/113* (2010.01)
*A61K 45/06* (2006.01)

(52) U.S. Cl.
CPC ............ *C12N 15/113* (2013.01); *A61K 45/06* (2013.01); *C12N 2310/113* (2013.01); *C12N 2310/14* (2013.01); *C12N 2310/20* (2017.05); *C12N 2320/30* (2013.01)

(58) Field of Classification Search
None
See application file for complete search history.

(56) References Cited

U.S. PATENT DOCUMENTS

2012/0276192 A1 11/2012 Reich et al.
2013/0317202 A1 11/2013 Kawamura et al.
2016/0339022 A1 11/2016 Tamang et al.

FOREIGN PATENT DOCUMENTS

WO WO2016071513 A1 5/2016

OTHER PUBLICATIONS

Benhammou, Jihane N., et al. "The role of a novel long intergenic non-coding RNA, Olmalinc, in the regulation of lipid metabolism", Poster presented Oct. 6, 2017 at UCLA Specialty Training and Advanced Research (STAR) Program.

Mills, James D., et al. "High Expression of Long Intervening Non-Coding RNA OLMALINC in the Human Cortical White Matter is Associated With Regulation of Oligodendrocyte Maturation", Mol Brain. Jan. 10, 2015;8:2. doi: 10.1186/s13041-014-0091-9.

International Search Report for PCT/US18/54735 (WO2019071214 Published Apr. 11, 2019), dated Jan. 22, 2019.

*Primary Examiner* — Sean Mcgarry
(74) *Attorney, Agent, or Firm* — Karen S. Canady; canady + lortz LLP

(57) ABSTRACT

An oligonucleotide that inhibits expression of an OLMALINC nucleic acid molecule, such as a small inhibitory RNA (siRNA) molecule, can be used for inhibiting the expression of OLMALINC in a subject. Methods of assaying for OLMALINC in a tissue sample can be used for detecting a disorder associated with obesity and/or type 2 diabetes in a tissue sample obtained from a subject. A method of ameliorating symptoms associated with obesity and/or type 2 diabetes comprises administering to a subject in need thereof an effective amount of an oligonucleotide of the invention or an antibody or equivalent thereof that specifically binds to and inactivates an OLMALINC nucleic acid molecule. Representative examples of a disorder associated with obesity and/or type 2 diabetes include, but are not limited to, a disorder of appetite, glycemia, body weight, liver steatosis, NASH, NAFLD, or a lipid disorder.

10 Claims, 30 Drawing Sheets

Specification includes a Sequence Listing.

Cellular RNA-seq 5436 DE genes

| *Gene* | *FC* | *FDR* | *Rank* |
|---|---|---|---|
| *OLMALINC* | 0.63 | 0.002 | 3517 |
| *HMGCS1* | 2.04 | 2.0E-27 | 148 |
| *HMGCR1* | 1.75 | 6.9E-14 | 543 |
| *MVK* | 1.97 | 1.5E-07 | 1351 |
| *SQLE* | 1.53 | 3.6E-09 | 1007 |
| *FDPS* | 1.36 | 4.0E-05 | 2242 |
| *FDFT1* | 1.36 | 1.8E-05 | 2066 |
| *LDLR* | 2.4 | 2.5E-48 | 37 |
| *ABCA1* | 2.5 | 2.9E-26 | 159 |

5'3' Frame 1 (SEQ ID NO: 44):

K K A K K S D T K N Y I S Y D F I Y Y E Met S R Met G H L E T E S Stop S V V A R D W G K G C Q C A W V L
W G V Met K Met F F R Stop I L V R V A C L C E Y T K N V C I I H Stop K S N F Met V Y K L Y L D K K L Y F
K K P S Stop C F T T S C S StopD T N P N I L S T D E N K F F D Stop R K C S I F S L S L F F F F F E I E S H
S V V Q A G V Q W H V L C S L Q P L P P G F K R V S C L S L P S S Stop D Y R H L P L C L A N F C I F S R
D G V S P C W P G W S R A P N V K Stop S A H F G L P K C W D Y R H E T P H P V H V L L I Met Q Stop C
S L Stop S Q T S K G Q R L A T Stop E K A S C Y K L E Y N Met T I W L Y Q V T W K N R D T Met F Y
I Stop L K G F R Q L H K H R P N F L L S G K L K F Stop V H Q T C G Y N H N N N N N I Y Stop S W A L
Y Stop Met L G S V L S H H I R S R C Y C Y L D F T D E V T E F T W R K S C E K Met C N V A Met I W F Q T
Y G L N Y W L Y W V W S R Stop Q T R Y V V I C H Met S N C Met P G N I Q L Y S E A K P G D V T L L P G
W Q W Q G A Stop V L H K Q Q Met H P L F R K N P A H S T S Stop P V L T F S H T W V L S F P L K
P Stop I R T Q H F L S T F P K L H F T L L Stop D C E L L K S I F L F Q K C L P A P K Q S A L E Met T
E Stop A H V L L Stop I L S L L Q T V Stop N V T G S R S H I L Stop P V V N F P C C R Q S A D S C T L T L
E Q Met P Q A L I A G S K E L R F H T G V A G G R S L P T F R T R T C P S P T R S R P A S Y T L A T E R S
Q R L S V C Met P G Stop L T V V L G P G E D L L R G A E G A L S L L A I F H G E Q S V T R T Met P D F K
K Q R G K W K Stop K A A E D S E L L F L I S F L E N Y G Q Q E G L T F Stop S V S L F A R E R E R E R E
R E I H F N Stop E T I H T I Stop N Stop P L Y L L R Stop G S H Y I A Q A G L K L L G S S D P P P L A S Q S
A G Met T G V S H R A R L N Stop P F Y F I Y L F Stop D R V L L L S P R L E C N G Met I S D H C N L R L P
G S N D S P A S A S Stop V A G I T G T C H H A H L F F S F F L S F F F F F Stop E R W G F T T L A R L V S
N S Stop P Q V I R P P H P L K V L G L Q V Stop A T V P G R T N H F K L T S S V A L S A F I T L C K H Y L L
F Stop N I F T P K E N L N P F N S D S P S S H P H S A P G D H Q S A F C L C G F T T S G Y F L Y Met E S
Y N I Stop P S V S G F L L L A Stop S F N V H P H W S I Y Q Y F I P V Y Y L F I F H C Met N T P Q L V
Y Stop F I N Stop Stop T L E L L P P F G Y C E Stop H C H E H L S A N Met S T R L Stop F I R V Y I Stop E
W S C W A R C Stop F D I Stop P F V A P S N C F P S G C T T L N F L Q Q C Met R V T L F L T C T H L S L
S S F L L F T K P V P H R L L F P L E Stop R V G E V A S L V E R L S K P P F L P F P Q I E Y G D Q E E E R
T G C H L P V V T K V H P L Q P L T R L R K T T L L A T S N A S V L T Q N I T L N F S T V T D R K G L G V E
G A S S G S A L R V S V Stop L S A Q L K I S E D T H R L V L P S P L R Stop R A G L P G P G W Q L
T Stop Met E R K R L P L H P L S P G L L P V T D P G L Q E L F T P T T A H Q R L T T P E P I S G P Q A C L
I L S A P I R R R G P S S L L L L Stop I T G R R E P F F L F F F F P G S R P R G S A L L P Q S A L P W N G
E N A D Met P L S P A A N S A P E L R E F S R R V E I A F P A R R G P I A S L L G R Q Met R R F S R L H G
Q P L P H N P R F F V G S Stop S I A A F E V V Stop T L L T R T A Q Stop A E L I F I P V C N R A K T P
L Met E K P E R Q E S A K H T K D W A V T G E N V S K S T G T A K R S G T F E A D A T G A G R W C V V
G E W E E T V E S L D L L L Stop V I R S H Q I F S S R R G K Stop S L C F A K L T L Met A T E Q S S G
G Met G A G R C W E A I V T T L V K S H G T S K A G I V T V G Met E R K G T S Stop E A F G R R I N S T L
L T G C V R Stop V R T A I R R G L Stop G F Stop P E W L E G H H F P Y L K Stop V A K R R E K E R S R G
I L Q R E Stop E F S F Stop H V A F E L Q E V H P C G C N T Q Stop T V G N Stop D L V S R R K V E Met R
S K G F I V D R E R N Stop Stop P K E K L Stop N K K I W A G H G G S C L Stop S Q H F G R P R Stop E D
C L S P G V Stop D Q P G Q H G E T P T L Q K L Q K L A G C G D T Y L Stop F Q L L G R L R W G D H L S L
G R S R L Q Stop A E I V P L H S N L G N I A R A R P C L K S K K K K R R F K Y R I L G R Stop K E D T E A
R C G G S C L Stop S Q H F G R Stop G G W I I Stop G Q E F K T S L A N Met V K P C F Y Stop K L S R H G
G G R L L I P A S R E A E V G E W L E H R R Q R L Q Stop A E I V P L H S S L G N R V R L C L K K K K K
K E D T E L A K Q T K K Y Q K D Met K N Stop K K A N Y D T V I E I R K Stop F Q E E E A G H C L C Met Y K
T V R H W L N K L Stop S I H L I E Y S H Stop N Y V A K L Y N C H K E Met F N A S F F P Q C I L E T L R L K
N S I Y A G H G G S R L Stop S Stop H F G R L R Q V D H E V R S L R P P W P Met Stop Stop N P V S T K
N T K L A R H G G R C L Stop S Q L L G R L R Q E N H L N L G G R C C S E Q R L C H C T P A Q V T Met R
D S I S KStop K K V Y I Y V C I Y Met Y I Y V Y I C I Y V C I Y V Y Met C V Y Met Y I C V Y Met Y I Y V Y I C V
Y Met C I Y V Y I C V Y Met C V Y Met C V Y Met C I Y V C I Y V Y Met C I Y V C I Y A Y I C V Y I C I Y Met C
V Y Met Y I Stop L Y H F Stop K L H MetStop L Q K G Met R R L G G S C L Stop S Q H F G R P R Q A D H L
R S G V Stop D Q P S Q Stop L L Y K I E Q F L Y F V K I Q K L A R C G S T C L Stop S H L L R R L R Q E N

FIG. 10A

P L N P R G G G C S E L R L H H C T T A W V T E Stop D T V S K K K K A Stop G N F Stop D E G T V L Y V
C Stop G N V Y T A L Y N Y P K S S Stop G R R P P L I L S Y A Q F L P P K K E E V K T Stop R Q K Stop N
P Q A D S P A P H P G P G S Stop R S T P D L I S Y V I S K L Q S L C G K A L Stop K S L S C S V L F Stop L
P V H A A P S H I P L A C S I D Q D P F T R T P L E L S A L K R D R N C L L R E L G F Stop D V S L A D A P
G Q I K P F L L Stop L G V Stop G V L S A A R P A T L K L E F L K F L F F I L F I F F Stop R L S L T L S S R L
E C N G Met L S A H C N L H L P G S S D S P A S A P G V A G I T G V Q H H A Q L I F V F L V E T G F H H V
G Q A G L E L L T S G D L P T S A S Q S A G I T G Met R H H A Q L N A L I L T R G G L L Met V P T S Q R C
P G D Stop Met A D Q S I L P G I Stop E G L N Q Stop R R E G Stop P R T T A R R R R D W E Q G P E Y
G Stop R P H L G L Stop N K T T N K Stop K T L E W V Q T K R K V E K L K T L R L K K G S G H G D S C
L Stop S Q H F E R P T Stop E N C L S P G V Q D Q P G Q H T E T L S L Q K I K N N Stop W D V V V H V C
G P S Y L G G Stop G G R I A Stop A Stop E V A A L V S H N H T T V V P P G Stop Q S E T V S K K K K G G
G R F Met R D L G S Stop L R I Stop H K Stop G N K P I P Y C P E G Stop I K E Stop N Y V G Met R A
S Met A Met D R K A A Q I TStop A V L Q C L G R N K L L L S P Y L F N S S K I L Stop T C
S Stop Met G Stop D N G L D T S Stop V P P S F K T Met I Stop S T S K L F N Q T Stop G N R S Y V I F S L
W N G C Q S H L F Stop L S S Stop F P F L H G F D Q I C L S C L Y D L D Stop V S L K Stop S Y L A D K
Y Stop L H F Stop V G R W Stop K F N Y L V L Met Stop A V L F C F V L F F E T E S R S V A R L E C S G V I
L A N C N L R L P G S S N S P A S A F R V A G T T C V P T T P G Stop F F I F S R D R V S P Y W P G W
S Stop S P D L V I C P P W P P E V L G L Stop G Stop A T Met P G P Stop C Stop F L L Y F I S I S F I L H
T Met V Q Stop R N H Stop A R S Q C D P V S S T G S T T Stop Stop Met Y G F G E R H L C R G F R C V V
H G P L S V P Q I I F R V S I R P KStop C S W Stop Y Stop A L F A F F H H H I D I S S D G G K F F A
P Stop Stop E S R Stop Stop H Q T V P V G I T F L T A L H L E G N S V P Q A G Met Q Stop S R L T A T S A
S W V Q A I L L P Q L P K Stop L G L Q V P A T T P G Stop F L Y F StopStop F H H V G Q A G L E L L A S G
D P P T L A F Q S A G I T G V S H H A Q P R C S Stop Stop N K N Y Stop F I K F Stop S L R A P F K N S V
A Stop N G K Stop E V L I K Y F C Y Met S K N S G C L E G K H Stop C D H Y S C E L N Stop P L Y S C N I
L F V Stop K N D Stop Q T G C S D F G I L Q L Q E H Stop Stop S K I V T S K Stop Q L A I F V P Met I K F E
L L A V A H A Y N P S T Stop G G Stop G G R S T Stop A Q E F E T S L G S L S K K K K K I S Q A W W H A
P A E V E G A L E P G R P R L Q Stop A Met I V P L H S S P G N R A R S C Q K K K K K K K E K K K Stop L
S S K T Q N C S D L A C G T K L D S F L I I K N S S D A I S G D V Q K C Q F L N I I E Stop N V P T F Stop K I
C I T Q Stop T N T F Q Met T K T Stop C Y K I Met H G Stop K V H Stop K C K Stop G Q V W W L Met P L I P
A F W E A E A G G S L E A R H L R P A W P T Stop Q D P I S K N N K S K R I S Q A W W H A R E V L A T W
E A T V G G W L E L R S L R L Q E A Met I V P L P S S L G D G V R P C F K N K T K K K E MetQ V R P Met K
Y N V Met K Y K K F I A Met V S N S Q C N Stop P L R Y Y V S G L Stop A Q T K P S Y P L Stop P A C I H T
D G L K Q L K I H K R S E N S L N Stop Stop H S T I E I C S C P T L T D T I Y S P P P L R R Y F V I F S L P L
R Met Y F V R L S Q T Y K N Stop Stop Stop S H H P L L T P F Stop T Q P A C T Q V K Y T A L L L T Q S L F
G G F F T R Met H V T F G A E D P G Q E D S F G R P V P C C R P H S V R R S T Y D L R S S D Q P A Q G
T S C Q F Q I G Stop V V F S L F S S L S C Y P S I F L S H Y P S I S L S F Q F P F F F L S S R D K E T H F I
C G P K T P A S V T D S G R Q S S L G V Stop S L W G R L P D Y S P T L H W C L I T T G Met P A L V I H P
H S L G D K S I A G T P A L A A H P H C S P G L L N A P R C P T R L L R A S T L S F L G F T S F T Met G N
L P P S I P P S S P L A C V L K N L K P L Q L T P D L K P K C L I F F C N T A W P Q Y K L D N D S K Stop P
E N G T F E F S I L Q V L D N S C H K Met G K W S E V P D V Q A F F Y T L V P P Stop S L L P Met Stop L I
P N L S S F S P F C S F G L H P K F R V L Stop I L L F Y G L I Stop P P P F S P G C S S P G Stop A R S Q F
S L S L C S P T L Stop S F Y H L P S S H L V Q L T V S F L D Stop L S P I C P T I S C Stop R D G Stop L
S Stop L H Q S R L V P G L P G Met S G C S D R P P V C P I C T A K R S P G G Q R S K V A F Q V P V G A
W E N T A G V S C G P Q R S A W Stop F Q A L N N S P Stop P L G L H L T P G C R I R S Stop V Q A T A R
P L P V T P L W T P S Y Stop S Q Q R R C G N H R L I S T W Stop T Q H S H Stop H L L D Q S V F S T G G
G Q A G F L C L P E S H R L S T N Met E P E F Q V R K P H S Q K P R L H P T R Stop C S A P R L W V L G
A K C Stop G L V Met S G N P H V P V T A V K Q K V N S L T N V I P Stop E D L Y K L L L G Y L F
I Stop Y StopT L A Y F V I R L Stop T N Stop G N H Y F S L L Y F S K N N F V T E F N I L C T T D L L
L Stop K Q S I S S K Q S I L N Y E Stop K L C Met L I L Q L Stop Y Stop S N F V Stop F Stop S Q N D V

FIG. 10B

P Stop Met P L Q L W V G S V Q T G T L K S Stop Met T A R P I L L K T F Q G K K K K K R G G W S Stop R
R S Q G Stop C S F F F I Stop P L P I S Stop R L G C F S S N I K T Q P S S W P I W Q Q P L D A L P
P Stop T Q R G Q K A V L F S I C I L L P N P L R T L E K A P K I R F Q P S N P T T G L N Stop P H L Q G V
Q Stop Stop S R G N I F L S C N Y L P P L Stop E K P Q P H L Q H T R T S K H L N R S G Q V F L Q D R L P
Q D L S S S A G N L V T G P R N A C S L G F L L S H V P S V P D P T G N Q T V Q L T Q E P L P E L L E L W
P K T L Stop L L P R C S R L S G Stop K L Met L P N R L R S L L D H H R C F G Stop L L Q Stop R G S L S
P S Stop Y R G Y P L H N T F F S R A C F P C L H N C C G Y Stop W P G C Stop T C Q N S P T L V P T W T
T F F Y T L F F S Y P Y L P S S L I R S R H F N Q I I C F P D C S W T T A T P H C R P F P Q F K A S F A S S
P C I S P P Stop S T S Met G H L Y S L L G N R S C T P Y H P I K T Stop S P L P H S Met P I S H P T A H F
K R I P Q H T L K G L K P V I T R L L Stop H G L L K P I N S P Y N S P I L P V Q K P D K S Y R L V Q D L C L
I N K I V L P Met H P I V P N P Y T L L S S I P P S H N P L F C S K Stop T Stop L T P Stop I L N P F P T P L S
I P Stop K T A L K A A P T L A L P N S S Q L F H Y T Q P K C R A V W S E F L H K S Q K H A L Stop P F C P
N N L T L L F Stop P S P H V C V W W L L L L Stop Y F Stop R P S K S H Y A Q L T L Y S S H N F Q N L F S
S S Y L T H I L S T P W L L Q L Y S T L F Stop D R V S L R L P G W H A V A Q S W L T A T S A S Q V P A I L
L P Q P L E Stop L G L Q V C A P H P A N F L Y F Stop Stop R W G F T Met L T K L V L N S Stop P K V I C P
S R P P K V L G L Q A Stop A T T P S L Y S L F A E S P T I T I V P G L D F N P A S H I I P D T T P D L H D Y
L S D P P G I H S I S P Y F L L S C S S P Stop S H L V Y Stop W Q F H Q A Stop S P F T G K G R L C Y T I F
H I Y P Stop G Y R S A P L H Y L S A S Q T H C L N S G P H S C K G T T C Q Y L Y Stop L Stop I C L S Y P
P P P C C Y Met G Stop K R F P H Y A R V L H H Stop C L F N K N S S Q G C F T S K G S W S H S L Q G P
S K G I R S H H S G Q R L C Stop Stop G S Stop R S S Stop H S N F C P S G P V F L L L I G H S H L L P
H Stop N F H V S I F S H T R Q Met V L G S R K I S P S S L T G P F Y S V V I S Stop P L P C R L Q A A S P
S L I T S H F I S I V K I C P E E N H F S V F I Y Y S T I P Q G L F R P L P F P T H Q A G E F A P A Q D W Q I
D F T D Met C R V R K L K Y L L V W V D T F T G W V Q A F P T G C E K A T T V I S S L L S D I I P P F S L A
T S I Q C E N R P A F I S Q I T Q A A S Q P L G I Stop W L L V L P Q N T T L K A L L K W I D L Q W Q G T L
R Y F H P D E V L F F T F I L I L I L V P D L Met P P S T S P Q L S P P H Y Q S H S L L A P F I I L L F F L R W
S L A L S P R L E C S G V I L A H C K L R L L G S H H S P A S A S Q V A G T R G A C H H A W L I F C I F S
R D G V S P C Stop P G W S P S P D L T I R P P Q P P K V L G L Q A Stop A T Met P G P L I L L Stop Q T T
A G F A F L F P P K S P R P R L T H C Stop K K R T L Y I F K R R V L F L P K S I W P G V Stop Q H K K T Q
G Stop T P K I R Q P S K Stop L C Stop T P L G T P Stop L D V L G P S N S Stop S F N T Y F S L S L I R T L
C L P S V Stop F L N S Y K T A S R P S T I I L Y D K Y S F Stop Q A H N I T P Y T Q I F L Q F N L S Y S R F
P C H P N P T Q S S P E K H R P L S L H T T P K N F R C L N T S P L F C F V F H T N I R R Stop E C Q A S
E S K L S H Q I P C D L H V Y I Q Met T Stop S N Stop R S T K E V K V A L T D D I P P L Stop F V P A P
R Stop L I P Y I L P P P L R Met Y F V H L S Q T Y K N Stop Stop Stop S Y H P L L T L F L D S A R L H P G
E I N S P V A 5'3' Frame 2 (SEQ ID NO: 45):

R R Q R S Q T Q K T I Y R Met I S F I Met K C P E W D I Stop R Q K V D L W L L E T G G R V A N V H G F C
G E Stop Stop K C S L G R F W Stop G L H V S V N I L K Met S A S Y T K R V I L W Y I N Y I L I K N Y I L K N
P L N V L P L V V A E T Q T Q I Y Stop V L Met K I N F L I K G S A P Y S L S L S F F F F L R Stop S L T L L S
R L E C S G T F S A H C N L C L P G S S E S P A S A S Q V A E I I G I C H Y A W L I F V F L V E Met G F H H
V G Q G G L E L L T S S D L P T S A S Q S A G I T G Met R H H T Q S Met F S Stop L C S D V V S S L K L Q
R D K D Stop P H E K R Q A A I N W S I I Stop Q F G C T K L L G K I E I P C S T F S Stop R G L G N C I N T
D L T S F Stop V G N Stop S S E S I R L V D T I I I T I T I F T R A G H C T E C L A V C Y R T T S E A G V I V
T W I L L Met R Stop L S S L G E K A V R K C V Met L L Stop S G S R P Met V L T T G S T G C G A D D K L
D Met S Stop S V I C P T V C L A I F S Y T Q R Q S L V Met Stop P S S L G G S G R E L K F C T N S R C I H
C S G R T Q L T P P P D P S Stop H S V T P G F Stop A F L S N H R Y V P N I S C L L F L N Y T S P S Y K I

FIG. 10C

V S S S K A S S S F R N V S L P L N S Q H W K Stop Q N E L Met S C S K F C H C Y K L C E Met S Q G V G
V I F C D L Stop L T F R A A G K A L I L V H Stop L W N K C H R P Stop L Q A P R S Stop D S I L G L L E A
E A F P L S G P G P A L P P R G P A Q P A T P W P Q S A H K G S V C V C R A D S Q W F W A Q A R T F S
E G R K G P S P S W P F S Met G S S Q Stop P G P C Q T S K N R E E S G S E R Q Q R T Q N C C F L F L
S Stop R I Met D S R K D S P F S L S V C L R E R E R E R E R E R Y I L I E R Q F T Q Y K T N H F I Y Stop D
R G L T I L P R L V S N S W A Q V I L L P W P P K V L G Stop Q V Stop A T V P G Stop T N H F I L F I Y F E
T E F C S C R P G W S A Met G Stop S R I T A T F A S R V Q T I L L L Q P P E Stop L G L Q A P A T Met P I
F F F L S F F L F F F F F R R D G V S P R W P G Stop S Q T P D L R Stop S A R P T L S K C W D Y R C E P
P C Q A E L T I L N Stop P V L W H L V H S Stop H C A N T T F C S K T F S P Q K K T Stop T H S T V I P H L
P T H T R P L V T I S L L S V S V D L P L Q D I S Y T W N R T I Y D L L C L A S F S W H N L S Met F I P I G A
Y I S T S F L F I T Y S Y S I V Stop I H H S W F T D L S I D E H W S C F H L L V I V N S T A Met N I Stop V Q
I Stop V P V Y N L L G F I S R S G V A G P D A N L I F N L L W H H Q T V S P V A A P L Stop I F S S N
V Stop E S P S S Stop R V P I C P F P L S Y F L Q S Q F P T D F S F P W S R G W E K L H L Stop Stop K D
Y P S L H S Y L F R K Stop N T V T R R R R G Q A A T S L W S L R Y T H Y S H Stop R D S V K L P
S Stop R P P T P R S S P R T S H Stop T F Q Q S Q I G R G S V W K V P A L A Q P C G Stop V F N F Q P S
L R S P K T P I A S S C P V P S A K G P A C P G L A G S Stop H E W R G S A S L S T H S R R G Y C R S Q
T R A F K S Y L H L Q Q P T S A Stop P R R S Q S A A P K L V Stop F C L L Q S G G A V L P A S C S C E S
Q V G G S L F S F F F F S R G V G L G A L L S Y L S L P Y P G Met G K Met R T C H S V R P R T V L Q N S
E S F P D G W R S R S L P A E V P S L P C W E D K Stop G A L A V S T A S P S L I T R D S L W A L S
P Stop L P L R W C R P C Stop P G R P S R Q S S F L F L S A I V Q K R L L W K S Q S A R S Q Q N T L K I
G Q S L G R T Stop V K A Q E Q Q S V Q E R S R L T Q P A Q E G G V W W E S G R R Q W K V Stop T C F
C K Stop Stop E V I R Y F Q A G E E N N L S V S Q S Stop L S W Q Q S R V A G G W G L G D V G K L L L P
L W Stop R V Met G P Q K L G Stop S R W E W K G R A Q A E R H L G G E S I A L Y Stop L D V Stop D
E Stop G Q Q S E E D F E V S S L S G W K D T T S P T Stop N R Stop Q K G E R K R E A E G F C K G N R
S S V F D Met W H L N C K K Y I P V D V I P S R Q L G I R I W C R E E K Stop R Stop D P K G L Stop W I G
R E I D D L K R N Y R I R R F G Q G T V A H A C N P S I L G D Q G R R I A Stop A Q E F E T S L G N Met V
R P R L Y K N C K N Stop P G V V T H T C N S S Y L G G Stop G G G I T Stop A W G G L G C S E L
R Stop C H C T P T W A T Stop Q E Q D P V S K V K K K K E D S S T E S W E G R K R T Q R P G V V A H A
C D P S T L D A E V G G S S E V R S S R P A Stop P T W Stop N P V S I K N Y P G Met V A G A C Stop F Q
L L E R L R Stop E N G L N I G G R G C S E L R L C H Y T P A W A T E Stop D S V S K K K K K K R T Q
S Stop Q N R Q R S I R K I Stop K I K K Q T T I L Stop Stop K Stop E N N S R K R K Q D I V Y V C T K
Q Stop D I G Stop I N Y K A F I Stop Stop N T A I K I Met L Q N Y I I A I K R C S Met H L F S P S A S Stop K
H S G Stop K I V Y Met L G T V A H V C N P S T L G G Stop G R W I T R S G V Stop D H P G Q C S E T L S
L P K I Q N Stop P G Met E A G A C N P S Y L G G Stop G R R I T Stop T W E A D V A V S R D C A T A L Q
P K Stop Q C E T P S Q N K K K Y I Y Met C V Y I C I Y Met C I Y V Y Met C V Y Met Y I C V Y I C I Y V Y I C I
Y Met C I Y V Y I C V Y Met Y I Y V Y I C V Y I C V Y I C V Y Met C V Y Met Y I C V Y Met C V Y Met R I Y V C
I Y V Y I C V C I C I Y N C T I F K N Y I C D C K K A Stop E G W V A H A C N P S T L G G Q G R L I T Stop G
Q E F E T S L A N N C Y T K Stop N N F C I L Stop K Y K N Stop P G V V A H V C S P T Y S G G Stop G R R
I P Stop T Q E A E V A V S Stop D C T T V L Q P G Stop Q S E T P S Q K K K R H E E T F R Met R E L F
Y Met F V E V Met Y T Q L C T I I Q N P H K G G D H P S Y C L Met P N F C L Q R K K K Stop K L K D R N E
I H R Q T A R R H T L G L V V K D R P L T Stop S V Met L S L N Y S H C V E K H C E N P C P V L F C S N Y
Q C Met Q P P V T Y P L L A Q S I K T L S R G P P Stop S C Q P L R G T G I A Y S G S S V F E T Stop V L
P Met L P A K Stop S P S F F N S V S K G F C L R L V L L H S N Stop N S L N F Y F L F Y L F F F R D Stop V
S L C H P G W S A Met A C S R L T A T S T S Q V Q V I L L P Q P L E Stop L G L Q V C S T T P S Stop F L Y
F Stop Stop R R G F T Met L A R L V S N S Stop P Q V I C P P R P P K V L G L Q A Stop G T Met P
S Stop Met P Stop F Stop Q E G D C Stop W Y P L H S V V L G I K W Q T R A Y C L E Y K K G S I S R E G K
D D P G P Q H G G G E T G S K A R S Met G K G H T W A S K T K P P T N K R P Stop N G S R Q K G K L R
N Stop K L Stop D Stop K R A L G Met V T H A Y N P N T L R G Q H R R I A Stop A Q E F K T S L D N I R R
P C L Y K K Stop K I I S G Met W W Y T S V V P A T W E A E V G G L L E P E R L R L W Stop A T I T P

FIG. 10D

L Stop S R L G N R A R L S Q K K K K G G E G L Stop G T L V A D L E Y D T N E E I N L F L I V Q R V
E Stop R N K T Met W E Stop E Q A W L W T G R Q L K Stop L E L F Y S V L G G I S C F S H H I C S T R P
R F C K H V P E W D E I Met D Stop I P L R F H L V L R L Stop Y K A H Q S S S T K H K V I G V Met L F S V
Y G Met D V N L I S F D C Q A S S H F F Met V L I K S V Stop A V F Met I W T R Stop A Stop S D H T W L I N
T N C I S K Stop A A G R N L I I W F Stop C E L F C F V L F C F L R Q S L A L S P G W S A V A Stop S W L T
A T S A S R V Q A I L L P Q P S E Stop L G L H V C P P H L A N F L F L V E I G F H H I G Q D G L D L L T
S Stop S A H L G L L K C W D Y R G K P P C P A L N V S S Y Y T S Y L Y H S F C I L W Y N R E T I R L G V
S V T Q F Q V L V L L L N R C Met A L G K G I Y A E V F D V Stop S Met D P Stop A Y P K Stop F S G Y
P Stop D Q N D V H G D I K P Y L P F F T I T L T F L L Met V G N S L H L D R N H G S S T K L Y Q W A L H S
S L P C T W R G I Q S P R L E C N D L G S L Q P L P P G F K R F S C L N F P S N Stop D Y R C L P P R L A
N F C I F S S F T Met L A R L V S N S W P Q V I H L P W P S K V L G L Q V Stop A T Met P S Q D V L D K I K
I I N L L N F D P Stop E H L L K I L W H E Met G S R K Y L Stop S T S A I C Q R T V V V L R E N I S V I I I V V
S Stop I N P F I H V I S F L F E R Met T D K L V V Q T L V F C S F K N I N K V K L L L Q S N N L Q Y L F
Q StopStop N L S F W Q W L Met P I I P A L R E A E A G G A L E L R S L R P A W A V S P K R K K K L A R H
G G Met H Q L R W K E H L S L G G Q G C S E P Stop L Y H C T P A Q A T E Q D L V K K K K K R K K K R K
N S F Q A K L R I V V I L H V V L S L T A S Stop Stop L K T L L Met L S V V Met F K N V N F Stop I L Stop N
K Met C Q H F R R F A Stop L S E P I L F K Stop P K H N V T K S C Met D K R C I E N A N E A R C G G S C
L Stop S Q H F G R Q R L E D H L R P G I Stop D Q P G Q H S K I L S L K I I R V R E L A R H G G Met R V K
S Stop L L G R L R W E D G L S L G V Stop G Y R K L Stop L C H C P P A W V Met E Stop D H V S K T K Q
K K K K C K L D Q Stop S I Met Stop Stop N T K N S L L W F Q I P S A I N L Stop D T T C Q A S E P K L S H
H I P C D L H V Y I Q Met A Stop S N Stop R S T K E V K I A L T D D I P P L R F V P A P P Stop L I R Y I L P
R P Stop E G T L Stop Y S P C P Stop E C T L Y A Y P K P I R T N D N P T T L C Stop L L F R L S P P A P
R Stop N I Q P C C S H K A C L V V S S H G C Met Stop H L V L K T Q D R R T P L G D Q C P V V A L T
P Stop G D P P Met I S G P Q T N Q P K E H L A N F K S G K W S F H S S P A F L A T L Q S S S L T T L Q S
P C P S N S R S F S S L V E I R R H I L S V D P K L Q R Q S R T R E D S L P L V F N H C G D A C L I I H P H
S I G V Stop S P R G C L P W S F T H I P L V T S Q L R G H L L W L L T H I A A Q G C S Met P P A A P P A F
S V P L P S L F S G L P P S L W A T F H P P F L L L L P Stop P V F S K T Stop N L F N S H L T Stop N L S V
L F S S A T P L G P N T N S T Met I P N S Q K T A L S S S P S Y K F Stop I I L V I K W A N G L R C L T S R H
S F T H W S L P S L C S Q C D S S Q I F L L S L L S V P S V S T P S S E S S E S F F S Met D S S D L P P S
P Q A A P R Q A E P G P N S H L A S A P P P Y N P F I T S P P H T W S S L Q F R S S T S S P R S A Q Q F
P V K E Met A D Y P D F I R A G W C L A F L E Stop V G V L T G P Q F V P S A P P R G L R V A R G A K L P
S K C L L V P G R T Q Q E C R A A H S A V H G D S R R Stop T T P L D P W A C I Stop L P A A E S E A E S
R Q P L G H S R S L L S G H P V T K V S K E D A V I T A Stop S P H G E H N T L T N T S L T S Q S S A L G
V D R Q V F C V Y Q N R T G Stop A Q T W N Q S S R Stop G N L T R R S P G C T P P G D A V R L G C G
C Stop E P S A R D S S Stop V G I P T F L S L L S N R R Stop T V L R Met Stop F L R K T C T N F Y Stop D
I Y L F N T E L W P T L Stop Stop D Y K Q I E E I T I S H F C I S Q K I I L L Q S S I Y C V L L I F Y C E S K A
F H Q N K V F Stop I Met S E N C V C Stop F C S C N I N Q T L C N S N H K Met Met C L K C P S S C G L A
V S R Q G P Stop N P E Stop L L D Q F Y Stop K H F K A K K K K K E V A G A E G V V K V N A P F S S S D
L S Q S V S V Stop A V F H Q I Stop K P S P V H G P F G N N P Stop Met L Y R P R P R G A R R P S Y S Q
Y A F Y Y P T R S G H Stop K K L Q K L D S S P Q T P Q Q D L I N L T F K V Y S N R V E A T Y F Stop V A I
T C L H C E R N P S H I S S T Q E L Q N T Stop I A A A R C S S R T A S P R I F L Q V L E I W S L G Q
G Met P A A W D S S Stop A Met S H L C Q T L L E I R L S N L P R S H S Q S C W N S G P R L S D S F P D
V L G L A A E N Stop C C P I A S E A S W T I T D A L G N S Y S E G E V C P L L N T E A T H S T I P S F Q G
P V S L A S I T V V G I D G Q A A K P V K T P Q L W C Q L G Q H S F I H S F L V I P T C P A P L L G Q D I L
T K L S A S L T V P G L Q P H L I A A L F P S S K P P S H P P L V S P H L N P Q V W D T S I P S L A T D H A
P L T I P L K P N H P Y P T Q C Q Y P I P Q H T L K G S H S T L Stop K D Stop S L L S L A C Y S Met A
F Stop S L Stop T L L T I P P F Y L S K N Q T S L T G Stop F R I C A L S T K L S C L C T P Stop C Q T H I P
S Y P Q Y L P P T T H Y S V L N K P S Stop P H K S Stop I L S P L P F P F L K K Q P Stop K L L P H Stop L
S L T H P N F F I T H S Q S A G L C G R N S Y T R A R S Met P C S L S V Q T T Stop P Y C F S L A L Met S

FIG. 10E

V C G G C C C F D T F R G P Q N H I Met L N S L S T V L I T S K I Y F L P H T Stop R I Y F P L P G S F S Y T
Q L F F E T E S H S V S Q A G Met Q W H N L G S L Q P P L P R F Q R F S C L S L W S S W D Y R C V P H
T R L I F C I F S R D G V S P C Stop P S W S Stop T P D L K Stop S A H L G L P K C W D Y R H E P P H P A
Y T H S L L S L P Q L P L F L A W T S I R P P T L F L I P H L T S Met T I S L I H L A F T P F P H I S F F P V P
H P D H T W F I D G S S T R P N R H S P A K A G Y A I L S S T S I L E A T A L P R S T T S Q Q A K L I A L T
R A L T L A K G L R V N I Y T D S K Y A F H I L H H H A V I W V E R G F L T Met Q G S F I I S A S L I K T L L
K A A L L P K E A G V I H C K G H Q K A S D P I T Q G N A Y A D K V A K E A A S I P T S V P Q G Q F F S F
L S V T P T Y S L I E T S T Y Q S F P T Q G K W F L D Q G K Y L L P A S Q A H S I L S S F H N L F R V G Y K
P L A H L L Stop P L I S F P S Stop K S V L K K I T S Q C S S T I L L S L R D C S G P F P S L H I K L G N L P
L P R T G K L T L L T C A E S G N Stop N T S W Y G Stop T L S L D G Y R P F P Q G V R R P P R S F L P F
C Q T Stop F L H L A L P P L Y S V K T D R P L L V K S P K Q L L S L L V F S G S W F Y L K T P P L R L
S Stop S G Stop I F S G K V P S D T F T L Met K S Y S L L L Y S F L F W F P I L C H P L P L P S Y L H H T I
N L T L S Stop P R L Stop S F F F F Stop D G V L L C P P G W S A V V Stop S W L T A S S A S W V H T I L L
P Q P P K Stop L G L E V P A T Met P G Stop F F V F L V E Met G F H H V S Q D G L H L L T S R S A H L S
L P K C W D Y R R E P L C P A L Stop S F F N K Q L L A L H F S F L Q N R Q G L D L L T A K K R G P C I F L
N E E C C F Y L N Q S G L V Y D N I K K L K D R P Q K F A N Q A N N Y A E P P W A L P N W Met S W V L P
I L S P L I P I F L F L L F G P C V F L L F S F S I H T K L H P G H Q Q S F Y T T N T P S N K P T I S P L I P K
S F F S L I S P T L G S H A T P I P L K A A P R N I A H Y L S I P P P K I F A A S T L H H Y F V L F F I L
I Stop E D R S V R P L S P S Stop A I K S P V T C T C T S R Stop P E A T E D P Q K
K Stop K Stop P Stop L Met T F H H C D L F L P H A N Stop Y H I F F P R P Stop E C T L Y T Y P K P I R T N
D N P T T L C Stop L S F W T Q P A C T Q V K Stop T A L L L 5'3' Frame 3 (SEQ ID NO: 46):

E G K E V R H K K L Y I V Stop F H L L Stop N V Q N G T S R D R K L I C G C Stop R L G E G L
P Met C Met G S V G S D E N V L Stop V D F G K G C Met S L Stop I Y Stop K C L H H T L K E Stop F Y G
I Stop I I S Stop Stop K I I F Stop K T L L Met F Y H Stop L Stop L R H K P K Y I K Y Stop Stop K Stop I
F Stop L K E V L H I L S L S L F F F F Stop D R V S L C C P G W S A V A R S L L T A T S A S R V Q A S L L P
Q P P K Stop L R L Stop A S A T Met P G Stop F L Y F Stop Stop R W G F T Met L A R V V S S S Stop R Q
V I C P L R P P K V L G L Q A Stop D T T P S P C S L N Y A V Met Stop S L V S N F K G T K T S H Met R K G
K L L Stop T G V Stop Y D N L A V P S Y L E K S R Y H V L H L V K G V Stop A T A Stop T Q T Stop L P F E
W E I K V L S P S D L W I Q S Stop Stop Q Stop Q Y L L E L G T V L N A W Q C V I A P H P K Q V L L L P G
F Y Stop Stop G N Stop V H L E K K L Stop E N V Stop C C Y D L V P D L W S Stop L L A L L G V E Q Met T
N Stop I C R N L S Y V Q L Y A W Q Y S V I L R G K A W Stop C D P P P W V A V A G S L S F A Q T A D A S
T V P E E P S S L H L L T R L N I Q S H L G F K L S S Q T I D T Y P T F P V Y F S Stop T T L H P P I R
L Stop A P Q K H L P L S E Met S P C P Stop T V S T G N D R Met S S C L A L N S V T A T N C V K C H R
E Stop E S Y F V T C S Stop L S V L Q A K R Stop F L Y T D F G T N A T G P N C R L Q G V E I P Y W G C
W R Q K P S H F Q D P D L P F P H A V P P S Q L H P G H R A L T K A Q C V Y A G L T H S G S G P R R G
P S Q R G G R G P L P P G H F P W G A V S N Q D H A R L Q K T E R K V E V K G S R G L R I A V S Y F F L
R E L W T A G R T H L L V C Q F V C E R E R E R E R E R D T F Stop L R D N S H N I K L T T L F I E I G V S
L Y C P G W S Q T P G L K Stop S S S L G L P K C W D D R C E P P C P A K L T I L F Y L F I L R Q S F A L V
A Q A G V Q W D D L G S L Q P S P P G F K R F S C F S L L S S W D Y R H L P P C P S F F F F L S F F F F
F F L G E Met G F H H V G Q A S L K L L T S G D P P A P P S Q S A G I T G V S H R A R P N Stop P F Stop I
D Q F C G T Stop C I H N I V Q T L P F V L K H F H P K R K L E P I Q Q Stop F P I F P P T L G P W Stop P S
V C F L S L W I Y H F R I F P I H G I V Q Y Met T F C V W L P S L G I I F Q C S S P L E H I S V L H S C L L P I
H I P L Y E Y T T V G L L I Y Q L Met N T G V A S T F W L L Stop I A L P Stop T F E C K Y E Y P F I I
Y Stop G L Y L G V E L L G Q Met L I Stop Y L T F C G T I K L F P Q W L H H F K F S P A Met Y E S H P L L

FIG. 10F

N V Y P F V P F L F P T F Y K A S S P Q T S L S P G V E G G R S C I S S R K T I Q A S I L T F S A N R I
R Stop P G G G E D R L P P P C G H Stop G T P T T A I N A T P Stop N Y P P S D L Q R L G P H P E H H I K
L F N S H R Stop E G A R C G R C Q L W L S P A G E C L T F S P A Stop D L R R H P S P R P A Q S P P L K
G R P A R A W L A A D Met N G E E A P P S P P T L A G V T A G H R P G P S R A I Y T Y N S P P A P D H A
G A N Q R P P S L S D S V C S N Q E A R S F Q P L A P V N H R S A G A F F P F F F F P G E S A S G L C S
P T S V C P T L E W G K C G H A T Q S G R E Q C S R T Q R V F Q T G G D R V P C P P R S H R F P A G K
T N E A L Stop P S P R P A P P S Stop P E I L C G L L V H S C L Stop G G V D L A N Q D G P V G R A H F Y
S C L Q S C K N A S Y G K A R A P G V S K T H Stop R L G S H W G E R E Stop K H R N S K A F R N V R
G Stop R N R R R K V V C G G R V G G D S G K F R L A S V S D K K S S D I F K Q E R K I I S L F R K V N S
H G N R A E Stop R G D G G W E Met L G S Y C Y H S G E E S W D L K S W D S H G G N G K E G H K L R
G I W E E N Q Stop H F I D W Met C E Met S E D S N Q K R T L R F L A Stop V A G R T P L P L P E I G S K
K E R E R E K Q R D F A K G I G V Q F L T C G I Stop I A R S T S L W Met Stop Y P V D S W E L G S G V E
K K S R D E I Q R V Y S G S G E K L Met T Stop R E I I E Stop E D L G R A R W L Met P V I P A F W E T K V
G G L L E P R S L R P A W A T W Stop D P D S T K T A K I S R V W Stop H I P V I P A T W E A E V G G S P
E P G E V Stop A A V S Stop D S A T A L Q P G Q H S K S K T L S Q K Stop K K K K K I Q V Q N L G K V E R
G H R G Q V W W L Met P V I P A L W T L R W V D H L R S G V Q D Q P S Q H G E T L F L L K I I Q A W W R
A P V N S S F S R G Stop G R R Met A Stop T Stop E A E V A V S Stop D C A T T L Q P G Q Q S E T L S Q
K K K K K K R G H R A S K T D K E V S E R Y E K L K K S K L R Y C N R N K K I I P G R G S R T L F Met Y V
Q N S K T L V K Stop I I K H S F D R I Q P L K L C C K T I Stop L P Stop R D V Q C I F F P P V H L R N T Q V
K K Stop Y I C W A R W L T S V I L A L W E A E A G G S R G Q E F E T T L A N V V K P C L Y Q K Y K I S P
A W R Q V P V I P A T W E A E A G E S L E P G R Q Met L Q Stop A E I V P L H S S P S D N A R L H L K I K
K S I Y I C V Y I Y V Y I C V Y Met Y I C V Y I C I Y V C I Y V Y Met C I Y V Y I C V Y Met C I Y V Y I C I
Y Met C I Y V C I Y V C I Y V Y I C V Y I C I Y V Y I C V Y I C V Y Met C V Y Met Y I Y V C V Y V Y I I V P F L K
I T Y V T A K R H E K A G W L Met P V I P A L W E A K A G Stop S P E V R S L R P A Stop P I I V I Q N R T I
F V F C K N T K I S Q V W Stop H Met S V V P L T Q E A E A G E S L E P K R R R L Q Stop A E I A P L Y Y S
L G D R V R H R L K K K K G Met R K L L G Stop G N C S I C L L R Stop C I H S S V Q L S K I L I R E E T T P
H I V L C P I S A S K E R R S K N L K T E Met K S T G R Q P G A T P W A W Stop L K I D P Stop P N Q L C Y
L Stop I T V I V W K S T V K I P V L F C S V L I T S A C S P Q S H T P C L L N R S R P F H A D P L R V V S
P Stop E G Q E L L T Q G A R F L R R E S C R C S R P N K A L P S L T R C L R G F V C G S S C Y T Q T R I
P Stop I F I F Y F I Y F F L E T E S H S V I Q A G V Q W H A L G S L Q P P P P R F K Stop F S C L S P W S S
W D Y R C A A P R P A N F C I F S R D G V S P C W P G W S R T P D L R Stop S A H L G L P K C W D Y R H
E A P C P A E C L N F N K R G T V D G T H F T A L S W G L N G R P E H T A W N I R R A Q S V E K G
R Met T Q D H S T E E A R L G A R P G V W V K A T P G P L K Q N H Q Q I K D P R Met G P D K K E
S Stop E T E N F K T E K G L W A W Stop L Met P I I P T L Stop E A N I G E L L E P R S S R P A W T T Y G
D P V S T K N K K Stop L V G C G G T R L W S Q L L G R L R W E D C L S L R G C G F G E P Q S H H C S P
A W V T E R D C L K K K K R G G K V Y E G P W Stop L T Stop N Met T Q Met R K Stop T Y S L L S R G L N
K G I K L C G N E S K H G Y G Q E G S S N N L S C S T V S W E E Stop A A S L T I F V Q L V Q D S V
N Met F L N G Met R Stop W I R Y L L G S T StopF Stop D Y D I K H I K A L Q P N I R Stop Stop E L C Y F Q
S Met E W Met S I S S L L I V K L V P I S S W F Stop S N L F K L S L Stop S G L G E L K V I I P
G Stop Stop I L I A F L S R P L V E I Stop L F G F N V S C F V L F C F V F Stop D R V S L C R Q A G V Q W
R D L G Stop L Q P P P P G F K Q F S C L S L P S S W D Y Met C A H H T W L I F Y F Stop Stop R Stop G F
T I L A R Met V L I S Stop P R D L P T L A S Stop S A G I I G V S H H A R P L Met L V L I I L H I Y I I H F A Y
Y G T I E K P L GStop E S V Stop P S F K Y W F Y Y L I D V W L W G K A F Met Q R F S Met C S P W T P E
R T P N N F Q G I H K T K Met Met F Met V I L S L I C L F S P S H Stop H F F Stop W W E I L C T L I G I T V
V A P N C T S G H Y I P H C P A L G G E F S P P G W N A Met I S A H C N L C L L G S S D S P A S T S Q V T
R I T G A C H H A W L I F V F L V V S P C W P G W S R T P G L R Stop S T Y L G L P K C W D Y R C E P P
C P A K Met F L I K Stop K L L I Y Stop I L I L K S T F Stop K F C G Met K W E V G S T Y K V L L L Y V K E Q
W L S Stop G K T L V Stop S L Stop L Stop A E L T P L F Met Stop Y P F C L K E Stop L T N W L F R L W Y
F A A S R T L I K Stop N C Y F K V T T C N I C S N D K I Stop A F G S G S C L Stop S Q H L G R L R R E E H

FIG. 10G

L S S G V Stop D Q P G Q S L Q K E K K N Stop P G Met V A C T S Stop G G R S T Stop A W E A K A A V S
H D C T T A L Q P R Q Q S K I L S K K K K K E K R K E K I A F K Q N S E L Stop Stop S C Met W
Y Stop A Stop Q L P N N Stop K L F Stop C Y Q W Stop C S K Met S I F K Y Y R I K C A N I L E D L H N S V
N Q Y F S N D Q N I Met L Q N H A W I K G A L K Met Q Met R P G V V A H A S N P S I L G G R G W R I
T Stop G Q A F E T S L A N I A R S Y L Stop K Stop Stop E Stop E N Stop P G Met V A C A Stop S L S Y L
G G Y G G R Met A Stop A Stop E F E V T G S Y D C A T A L Q P G Stop W S K T Met F Q K Q N K K K R N
A S Stop T N E V Stop C N E I Q K I H C Y G F K F P V Q L T F K I L R V R P L S P N Stop A I I S P V T
C Met Y T Y R W P E A T E D P Q K K Stop K Stop P Stop L Met T F H H Stop D L F L P H P N Stop Y D I F S
P A L K K V L C D I L P A L E N V L C T P I P N L Stop E L Met I I P P P F V D S F L D S A R L H P G E I Y S L
V A H T K P V W W F L H T D A C D I W C Stop R P R T G G L L W E T S A L L S P S L R E E I H L Stop S Q
V L R P T S P R N I L P I S N R V S G L F T L L Q P F L L P F N L P L S L P F N L P V L P I P V L F P
L Stop Stop R Stop G D T F Y L W T Q N S S V S H G L G K T V F P W C L I T V G T P A StopL F T H T P L V
S D H H G D A C L G H S P T F P W Stop Q V N C G D T C F G C S P T L Q P R A A Q C P P L P H P P S P C
L Y P L F S R V Y L L H Y G Q P S T L H S S F F S L S L C S Q K L K T S S T H T Stop P K T Stop V S Y F L L
Q H R L A P I Q T R Q Stop F Q I A R K R H F R V L H P T S S R Stop F L S Stop N G Q Met V Stop G
A Stop R P G I L L H I G P S L V S A P N V T H P K S F F F L S F L F L R S P P Q V P S P L N P S F L W T H
L T S P L L P R L L L A R L S Q V P I L T Stop P L L P H P I I L L S P P L L T P G P A Y S F V P R L A L P D L
P N N F L L K R W L T I L T S S E Q A G A W P S W N E W V F Stop Q A P S L S H L H R Q E V S G W P E E
Q S C L P S A C W C L G E H S R S V V R P T A Q C Met V I P G A E Q L P L T L G P A S D S R L Q N Q K L
S P G N R S A T P G H S S L D T Q L L K S A K K Met R Stop S P P D L H Met V N T T L S L T P P Stop P V
S L Q H W G W T G R F S V F T R I A Q A K H K H G T R V P G E E T S L A E A Q A A P H Q V Met Q C
A Stop A V G A R S Q V L G T R H E W E S P R S C H C C Q T E G K Q S Y E C N S L G R L V Q T F I R I S I
Y L I L N F G L L C D K T I N K L R K S L F L T S V F L K K Stop F C Y R V Q Y T V Y Y Stop S S I V K A K H
F I K T K Y F K L Stop V K I V Y V N F A A V I L I K L C V I L I T K Stop C A L N A P P A V G W Q C P D R D P
E I L N D C Stop T N S I K N I S R Q K K K K K R W L E L K A Stop S R L Met L L F L H L T S P N Q L A F R L
F F I K Y K N P A Q F Met A H L A T T L R C F T A L D P E G P E G R L I L N Met H F I T Q P A P D I R K S S
K N Stop I P A L K P H N R T Stop L T S P S R C T V I E Stop R Q H I S E L Q L L A S T V R E T P A T S P A
H K N F K T P E S Q R P G V P P G P P P P G S F F K C W K S G H W A K E C L Q P G I P P E P C P I C A R
P Y W K S D C P T Y P G A T P R A A G T L A Q D S L T P S Q Met F S A Stop R L K T D A A Q S P Q K P L
G P S Q Met L W V T L T V K G K S V P F L I Q R L P T P Q Y L L F K G L F P L P P Stop L L W V L Met A R L
L N L S K L P N S G A N L D N I L L Y T L FStop L S L P A Q L P Y Stop V K T F Stop P N Y L L P Stop L F L
D Y S H T S L P P F S P V Q S L L R I L P L Y L P T L I H K Y G T P L F P P W Q P I Met H P L P S H Stop N L
I T L T P L N A N I P S H S T L Stop K D P T A H F K R I K A C Y H S P A I A W P S K A Y K L S L Q F P H F T
C P K T R Q V L Q V S S G S V P Y Q Q N C L A Y A P H S A K P I Y P P I L N T S L P Q P I I L F Stop I N L A
D P I N P K S F P H S P F H S L K N S P K S C S H T S S P Stop L I P T F S L H T A K V Q G C V V G I L T Q
E P E A C P V A F L S K Q L D L T V L A Stop P S C L C V V A A A A L I L L E A L K I T L C S T H S L Q F
S Stop L P K S I F F L I P D A Y T F H S L A P S A I L N S F L R Q S L T P S P R L A C S G T I L A H C N L R
F P G S S D S P A S A S G V A G I T G V C P T P G Stop F F V F L V E Met G F H H V N Q A G L E L L
T Stop S D L P I S A S Q S A G I T G Met S H H T Q P I L T L C Stop V S H N Y H C S W P G L Q S G L P H Y
S Stop Y H T Stop P P Stop L S L Stop S T W H S L H F P I F P S F L F L T L I T L G L L Met A V P P G L I A I
H R Q R Q A Met L Y Y L P H L S L R L P L C P A P L P L S K P N S L P Stop L G P S L L Q R D Y V S I F I L
T L N Met P F I S S T T Met L L Y G L K E V S S L C K G P S S L V P L Stop Stop K L F S R L L Y F Q R K L E
S F T A R A I K R H Q I P S L R A T L Met L I R Stop L K K Q L A F Q L L S L R A S F S P S Y R S L P P T P S
L K L P R I N L F P H K A N G S W I K E N I S F Q P H R P I L F C R H F I T S S V Stop V T S R Stop P I S Y N
L S F H F H R E N L S Stop R K S L L S V H L L F Y Y P S G I V Q A P S L P Y T S S W G I C P C P G L A
N Stop L Y Stop H V P S Q E T K I P L G Met G R H F H W Met G T G L S H R V Stop E G H H G H F F P S V
R H N S S I Stop P C H L Y T V Stop K Q T G L Y Stop S N H P S S F S A S W Y L V A P G F T S K H H
P Stop G S L E V D R S S V A R Y P P I L S P Stop Stop S P I L Y F Y T H S Y S G S R S Y A T L Y L S P A I
S T T L S I S L S P S P V Y N P S F F F E Met E S C S V P Q A G V Q W C D L G S L Q A P P P G F T P F S C

FIG. 10H

L S L P S S W D Stop R C L P P C L A N F L Y F Stop Stop R W G F T Met L A R Met V S I S Stop P H D P P
T S A S Q S A G I T G V S H Y A R P S N P S L T N N C W L C I S L S S K I A K A S T Y S L L K K E D P V Y
F Stop T K S V V F T Stop I N L A W C Met T T Stop K N S R I D P K N S P T K Q I I Met L N P L G H S L I G
C P G S F Q F L V L Stop Y L F F S F S Y S D L V S S F C L V S Q F I Q N C I Q A I N N H S I R Q I L L L T S
P Q Y H P L Y P N L S S V Stop S L L L Stop V P Met P P Q S H S K Q P R E T S P I I S P Y H P Q K F S L P
Q H F T T I L F C F S Y Stop Y K K I G V S G L Stop V Q A K P S N P L Stop P A R V H P D D L K Q L K I H K
R S E S S L N Stop Stop H S T I V I C S C P T L T D T I Y S S P A L E N V L C T P I P N L Stop E L Met I I L P
P F A D S L F G L S P P A P R Stop N K Q P C C S 3'5' Frame 1 (SEQ ID NO: 47):

Stop A T G L F I S P G C R R A E S K K R V S K G W Stop D Y H Stop F L Stop V W D R C T K Y I L K G G G
R I Y G I S Stop R G A G T N H N G G Met S S V K A T F T S F V D L Q L L Q V I W Met Y T C R S Q G
I Stop W L S L D S E A Stop H S Y L L I L V Stop K T K Q N S G E V L R Q R K F L G V V W R D N G R C F S
G L L Stop V G L G W H G N L E Stop E R L N Stop R K I W V Stop G V I L W A C Stop K E Y L S Y R Met I V
D G L D A V L Y E L R N Stop T E G R H K V R I R E R E K Stop V L K D Stop E L E G P R T S N Stop G V P
K G V Q H N Y L L G W R I F G V Y P Stop V F L C C H T P G Q I D L G K N N T L R L K I Y R V L F
F Stop Q Stop V S R G L G D F G G K R N A K P A V V C Stop R R I R G P G I V A H A C N P S T L G
G Stop G G R I V R S G D G D H P G Stop H G E T P S L L K I Q K I S Q A W W Q A P L V P A T W E A E A G
E W C E P R R R S L Q Stop A K I T P L H S S L G D R A R L H L K K K R R I I N G A R R
E Stop D Stop Stop C G G D S W G E V E G G I R S G T R I R Met S I K V K N R T S S G Stop K Y R R V P C
H Stop R S I H F K R A L R V V F Stop G K T R S H Stop I P R G Stop E A A W V I Stop L I K A G L F S H C I
E V A R L N G G I Met S D R R E E Met T V V A F S H P V G K A C T H P V K V S T H T K R Y F S F L T R
H Met S V K S I C Q S W A G A N S P A Stop C V G K G R G L N N P Stop G I V E Stop Stop Met N T E
K Stop F S S G Q I F T Met E Met K Stop E V I R D G L A A C N L H G R G Y E Met T T E Stop N G P V R L E
G D I F L D P R T I C L V W E K I D T W K F Q Stop G S R W E Stop P I R R R K T G P E G Q K L E C Stop L
L L Stop L P Y Q H K R C P E Stop W D L Met P F D G P C S E Stop L Q L P L E V K Q P Stop E E F L L K R
H Stop Stop Stop R T L A Stop Stop G N L F Q P I Stop Q H G G G G Y E R H I Stop S Q Y K Y Stop H V V
P L Q E Stop G P E L R Q Stop V W L A E R Stop W S G A E R Stop P Q G Stop Met W K I V Stop H S L P L
P V N G D Stop A W W N C H Q Stop T K C D Q G E E Q E R R K Y G E Met E Stop Met P G G S E R Stop S
W R S G V V S G I Met W E A G L K S R P G T Met V I V G D S A K S E Y R L G V V A H A C N P S T L G G R
D G Q I T L G Q E F K T S L V N Met V K P H L Y Stop K Y K K L A G C G A H T C N P S Y S R G Stop G R R
I A G T W E A E V A V S Q D C A T A C Q P G R R S E T L S Q K R V E Y S Stop R S Q G V E S I C V R Y E E
E N R F W K L Stop E L Stop R V S Stop A Stop C D F E G L Stop K Y Q S S S S H H T Q T Stop G L
G Stop N S K V K L F G Q K G Y R A C F W L L C K N S D H T A L H F G C V Stop Stop K S W D E L G R A S
V G A A F R A V F Stop G Met E R G V G K G F R I Y G V S Stop V Y L E Q N N G L W E G G I E D R R V Y G
F G T Met G C I G K T I L L I R H R S Stop T N L Stop D L S G F W T G K Met G E L StopG E F I G F R R P C
Y S R R V I T G F N P F K V C C G I L L K C A V G W D I G I E W G K G D Stop V L Met G W Stop G V H D R
L P R R E Stop R C P I L V D Stop G G E I Q G E D A K E A L N W G K G R Q Stop G V A V V Q E Q S G K Q
I I W L K C L D L I R E L G R Stop G Stop L K K S V Stop K N V V Q V G T R V G E F Stop Q V Stop Q P G H
Q Y P Q Q L W R Q G K Q A L E K K V L W S G Stop P L Y Stop E G D R L P L H C K S Y P K H L Stop W S
K R L L R R L G S I S F Q P L S R E H L G R S Q R V L G Q S S S S S G S G S W V S W T V Stop F P V G S
G T D G T W L R R N P R L Q A F L G P V T R F P A L E E R S W G R R S W R N T W P L R F R C F E V L V
C W R C G W G F S H S G G K Stop L Q L R N Met L P L L Y Y C T P Stop R Stop G Stop L S P V V G F E G
W N L I F G A F S N V R S G L G N K Met H I E N K T A F W P L W V Stop G G K A S K G C C Q Met G H E L
G W V F I F D E K Q P K R Stop L I G R G Q Met K K K E H Stop P Stop L R L Q L Q P P L F F F F L
P Stop N V F N R I G L A V I Q D F R V P V W T L P T H S W R G I Stop G T S F C D Stop N Y T K F

FIG. 10I

D Stop Y Y S C K I N I H N F H S Stop F K I L C F D E Met L C F H N R R S V V H S I L N S V T K L F F E K Y
R S E K Stop Stop F P Q F V Y S L I T K Stop A K V Q Y Stop I N R Y P N K S L Y K S S Stop G I T F V R L F
T F C L T A V T G T W G F P L Met T S P Stop H L A P S T H S L G A L H H L V G C S L G F C E Stop G F L T
W N S G S Met F V L S L C D S G K H R K P A C P P P V L K T D W S R R C Stop Stop E C C V H H V E I R
R Stop L P H L L C Stop L Stop Stop L G V Q R G V T G S G R A V A W T Q L L I L Q P G V R C R P K G Q G
E L F S A W N H H A L R C G P H D T P A V F S Q A P T G T W K A T L L L W P P G D L L A V Q Met G Q T G
G L S E H P L I P G R P G T S L L Stop Stop S Q D S Q P S L Stop Q E I V G Q I G E S Stop S R N E T V S
W T R C E E G R Stop Stop K D Y R V G E Q R L S E N W D L A Q P G E E Q P G E K G G G Q Met S
P Stop K R R I Q R T R N L G W R P K E Q K G E K E E R F G Met S H I G S R D Stop G G T N V Stop K N A
W T S G T S D H L P I L Stop Q E L S R T C R Met E N S K V P F S G Y L E S L S S L Y W G Q A V L Q K K I
R H L G F R S G V S Stop R G F K F L R T Q A K G E E G G Met E G G R L P I V K E V N P R K E R V E A R
R R R V G Q R G A L S S P G L Q C G Stop A A K A G V P A I D L S P R E C G Stop Met T K A G I P V V I R
H Q W S V G E Stop S G R R P H S D Stop T P R E D C L P E S V T D A G V L G P Q I K C V S L S L L E R K
K N G N W K D R E I E G Stop Stop E R K I E G Stop Q E R L E K S E K T T Y P I Stop N W Q D V P W A G
W S E D L R S Stop V D L L T E Stop G R Q Q G T G L P K E S S C P G S S A P N V T C I R V K K P P N R L
C V S N K A V Y F T W V Q A G Stop V Stop K G V N K G W W D Y H Stop F L Stop V W D R R T K Y I L K G
R E N I T K Y L L K G G G E Y I V S V R V G Q E Q I S Met V E C H Q L R L F S L L L W I F S C F R P S V C I
H A G H R G Y D G L V W A Q R P D T Stop Y L K G Stop L H W E F E T I A Met N F L Y F I T L Y F I G L T C
I S F F F V L F L K H G L T P S P R L E G S G T I I A S C N L K L L S S S H P P T V A S Q V A K T S R A C H
H A W L I L L L L L F L E I G S C Y V G Q A G L K C L A S S D P P A S A S Q N A G I R G Met S H H T W P H
L H F Q C T F Y P C Met I L Stop H Y V L V I Stop K V L V H Stop V Met Q I F Stop N V G T F Y S I I F K
N Stop H F Stop T S P L I A S E E F L I I R K L S S L V P H A R S L Q F Stop V L L E S Y F F F S F F F F F F
F Stop Q D L A L L P G L E C S G T I Met A H C S L G L P G S S A P S T S A G A C H H A W L I F F F F L E R
L P R L V S N S Stop A Q V L L P P Q P P Stop V L G L Stop A Stop A T A K S S N F I I G T N I A S C Y F E V
T I L L Y Stop C S Stop S C K I P K S E Q P V C Q S F F Q T K R I L H E Stop R G Stop F S S Q
L Stop Stop S H Stop C F P S R Q P L F F D I Stop Q K Y F I S T S Y F P F H A T E F L K G A L K D Q N L I
N Stop Stop F L F Y Q E H L G W A W W L T P V I P A L W K A K V G G S P E A R S S R P A W P T
W Stop N Y Stop K Y K N Stop P G V V A G T C N P S Y L G S Stop G R R I A Stop T Q E A E V A V S R D H
C I P A W G T E F P S K C R A V R N V Met P T G T V W C Y Y R D S Y Q G A K N F P P S E
E Met S Met Stop W Stop K K A N K A Stop Y H H E H H F G L Met D T L K I I W G T L R G P W T T H R K P
L H K C L S P K P Y I Y Stop V V E P V L E T G S H Stop L L A Stop W F L Y C T I V C K Met N D I D Met K Y
N K N Stop H Stop G P G Met V A Y P Y N P S T S G G Q G G Q I T R S G D Q D H P G Q Y G E T L S L L K I
K N Stop P G V V G T H V V P A T R K A E A G E L L E P G R R R L Q L A K I T P L H S S L A T E R D S V S
K N K T K Q N K T A H I K T K Stop L N F Y Q R P T Stop K C N Stop Y L S A R Y D H F K L T Stop S R
S Stop R Q L K Q I Stop S K P Stop R N G N Stop L D N Q K R Stop D Stop H P F H R L K I T Stop L L L P Y
V W L K S F D V L Y I I V L K L G G T Stop E V S N P L S H P I Q E H V Y R I L D E L N K Y G E R S S L F L P
R H C R T A Q V I Stop A A F L S I A Met L A L I P T Stop F Y S F I Q P S G Q Stop G I G L F P H L C H I L S
Q L P R S L I N L P P P F F F F E T V S L C Y P G G T T V V Stop L W L T K A A T S Q A Q A I L P P Q P P
K Stop L G P Q T C T T T S H Stop L F F I F C R D R V S V C C P G W S Stop T P G L K Q F S Y V G L S K C
W D Y R H E S P C P E P F F S L K V F S F S T F L F V W T H S R V F Y L L V V L F Stop R P R C G L Y P Y
S G P C S Q S R L L R A V V L G H P S L L Y Stop L S P S Y I P G S Met L W S A I Stop S P G Q R C E V G T
I N S P P L V K I K A F S W A W C L Met P V I P A L W E A E V G R S P E V R S S R P A W P T W Stop N P V
S T K N T K I S W A W C C T P V I P A T P G A E A G E S L E P G R W R L Q Stop A E S Met P L H S S L D D
R V R L S L Stop K K I N K I K N K N L R N S S L S V A G R A A D K T P Stop T P S Stop R R K G F I W P G
A S A R L T S Q K P S S L S K Q F L S L L R A D N S K G V R V K G S Stop S I E Q A R G Met Stop L G A A
C T G N Stop N R T E Q D R D F H S A F P H N D C N L E I T Stop L I R S G V D L Stop L P G P G C G A G L
S A C G F H F C L Stop V F T S S F F G G R N W A Stop D N Met R G G L L P Y E D F G Stop L Y R A V Y T
L P Q Q T Y R T V P S S Stop K F P H A F F F F E T V S H S V T Q A V V Q W C N L S S L Q P P P L G F K G
F S C L S L L S K W D Y R H V L P H L A N F C I F T K Y K N C S I L Y N N Y W L G W S Q T P D L R Stop S

FIG. 10J

A C L G L P K C W D Y R H E P P S L L Met P F C S H I C N F Stop K W Y N Y I Y I Y T H I Y I H I Y T H I Y A
Y I H T Y I H I Y T Y I H T Y I H I Y T H I Y T H I Y T H I Y T Y I H I Y T H I Y T Y I Y I Y T H I Y I Y T H I Y T Y I
H T Y I H I Y T Y I Y I Y I H T Y I Y T F F Y F E Met E S R I V T W A G V Q W H N L C S L Q H L P P R F
K Stop F S C L S L P S S W D Y R H L P P C R A N F V F L V E T G F H Y I G Q G G L K L L T S Stop S T C L
S L P K C Stop D Y R R E P P C P A Y I L F F N L S V S K Met H W G K K D A L N I S L W Q L Y S F A
T Stop F Stop W L Y S I K Stop Met L Y N L F N Q C L T V L Y I H K Q C P A S S S W N Y F L I S I T V
S Stop F A F F Stop F F I S F Stop Y F F V C F A S S V S S F F F F F F L R Q S L T L L P R L E C S G T I S A
H C N L C L L C S S H S P T S A S R E A G I N R R P P P C L D N F Stop Stop K Q G F T Met L A R L V L N
S Stop P Q Met I H P P Q R P K C W D H R H E P P H L A S V S S F Y L P K I L Y L N L L F F F L L L R Q G L
A L A Met L P R L E C S G T I S A H C S L D L P R L R Stop S P H L S L P S S W N Y R Y V S P H P A N F C
S F C R V G V S P C C P G W S Q T P G L K Q S S Y L G L P K C W D Y R H E P P C P A Q I F L F Y N F S L
G H Q F L S R S T I N P L D L I S T F L L D T R S Stop F P T V Y W V L H P Q G C T S C N S N A T C Q K L N
S Y S L C K I P L L L S F S L L F A T Y F R Stop G K W C P S S H S G Stop K P Q S P L L I A V L T H L T H P
V N K V L L I L L P N A S Q L V P F L S I P T V T I P A F E V P Stop L F T R V V T I A S Q H L P A P I P P L L
C S V A Met R V N F A K Q R D Y F P L L L E N I Stop Stop L L I T Y R S K S K L S T V S S H S P T T H H L P
A P V A S A S N V P E R F A V P V L L L T F S P V T A Q S L V C F A D S W R S G F S I R G V F A R L Q T G
I K Met S S A Y W A V L V S K V Y T T S K A A Met D Stop E P T K N L G L Stop G R G W P W R R L K R L I
C L P S R E A Met G P R R A G N A I S T R L E N S L S S G A L F A A G L S G Met S A F S P F Q G R A
D Stop G R R A E P R G R L P G K K K K R K K G S R R P V I H R S K R L E G P R L L I G A D R I R Q A W G
P L I G S G V V R R W W A V V G V N S S Stop R P G S V T G S N P G E S G W R G R R F L S I H V S C Q P
G P G R P A L Stop R R G L G R T R R W V S S E I L S W A E S Stop T L T R R A E P E L A P S T P S P F L
S V T V E K F N V Met F W V R T E A L E V A R R V V L R S R V N G C S G C T L V T T G R W Q P V L S S S
W S P Y S I C G K G K N G G L D S L S T R D A T S P T L Y S R G K R S L W G T G F V K S R K E E R D K W
V H V K K R V T L I H C W R K F K V V Q P L G K Q F D G A T K G Stop I S N Stop H L A Q Q L H
S Stop I Stop T L I N Y K R V L I F A L K C S W Q C Y S Q Stop P K G G S N S S V H Q L I N Q Stop T N C G
V F I Q W N Met N R Stop Stop T G Met K Y Stop Y Met L Q W G Stop T L K D Y A K R R K P D T E G H I L Y
D S Met Y R K Y P E V V N P Q R Q K A D Stop W S P G A E C G W E D G E S L L N G F K F S F G V
K MetF Stop N K R Stop C L H N V Met N A L S A T E L V N L K W L V R P G T V A H T C N P S T L R G W G
G R I T Stop G Q E F E T S L A N V V K P H L S Stop K K K K K E R K K E K K R W A W W Q V P V I P A T Q
E A E A G E S F E P G R R R L Q StopS E I I P L H S S L G D K S K T L S Q N K Stop I K Stop N G Stop F S
R A R W L T P V I P A L W E A K G G G S L E P R S L R P A W A I Stop Stop D P Y L N K Stop S G Stop F Y
I V Stop I V S Q L K C I S L S L S L S L S L A N K L T D Stop K V S P S C C P Stop F S K K E I R N S N S E S
S A A F H F H F P L C F L K S G Met V L V T D C S P W K Met A R R E R A P S A P L R R S S P G P R T T V
S Q P G I H T L S L C E R S V A R V Stop L A G R D R V G E G Q V R V L K V G R L L P P A T P V W N L N S
L E P A I R A C G I C S K V S V Q E S A L C L Q H G K L T T G H K I Stop L L L P V T F H T V C S S D R
I Stop S K T Stop A H S V I S S A D C L G A G R H F Stop K R K Met L L R S S Q S Y R R V K C S L G K V D
R K C W V R I Y G L R G K L K T Q V Stop L N V K T G Q E V E Stop A G F F R N S G C I C C L C K T Stop A
P C H C H P G R R V T S P G F A S E Y N Stop I L P G I Q L D I Stop Q I T T Y L V C H L L H T Q Stop S
Q Stop L R P Stop V W N Q I I A T L H I F S Q L F L Q V N S V T S S V K S R Stop Q Stop H L L R Met W C D
N T L P S I Q Y S A Q L Stop Stop I L L L L L Stop L Y P Q V Stop W T Q N F N F P L K R K L G L C L C S C
L N P F N Stop Met Stop N Met V S R F F Q V T W Y S Q I V I L Y S S L Stop Q L A F S H V A S L C P F E
V Stop D Stop R L H H C I I K R T W T G C G V S C L Stop S Q H F G R P K W A D H L T L G A R D H P G Q
H G E T P S L L K I Q K L A R H S G R C L Stop S Q L L G R L R Q E T R L N P G G R G C S E Q R T C H C T
P A W T T E Stop D S I S K K K K K R E R E N Met E H F L Stop S K N L F S S V L N I F G F V S Q L Q L V V
K H Stop E G F L K Y N F L S R Y N L Y T I K L L F Stop C Met Met Q T F L V Y S Q R H A T L T K I Y L K N I
F I T P H R T H A H W Q P F P Q S L A T T D Q L S V S R C P I L D I S Stop Stop Met K S Y D I Stop F F V S
D F F A F

FIG. 10K

3'5' Frame 2 (SEQ ID NO: 48):

E Q Q G C L F H L G A G G L S P K R E S A K G G R I I I S S Y R F G I G V Q S T F S R A G E E Y Met V S V
S V G Q E Q I T Met V E C H Q L R L L S L L L W I F S C F R S S G C T R A G H R G F D G L A W T Q R P D
T P I F L Y Stop Y E K Q N K I V V K C Stop G S E N F W G W Y G E I Met G D V S R G C F E W D W G
G Met G T Stop S R R D Stop T E E R F G Y K G Stop Y C G L V R R S I C R I E Stop L L Met A W Met Q F
C Met N Stop E T K Q K E D T R S E Stop E K E K N R Y Stop R T K N W K D P G H P I R E C P R G F S I I I
C L V G E F L G S I L E F F Y V V I H Q A R L I Stop V K T T L F V Stop K Y T G S S F F S S E Stop V E A L A
I L E E R E Met Q S Q Q L F V K E G L E G R A Stop W L T P V I P A L W E A E V G G S Stop G Q E Met E T
I L A N Met V K P H L Y Stop K Y K K L A R H G G R H L Stop S Q L L G R L R Q E N G V N P G G G A C S E
P R S H H C T P A W G T E Q D S I S K K K E G L Stop T G L G E S E I D S V V E I A G E R Stop R V
A Stop D R E P E Stop E Stop V StopK Stop R I G L H Q G E S I G G Y L A T E D L S T S R E P Stop G W C
F E V K P G A T K Y Q E A E K L L G Stop F D Stop Stop R P V C F H T V Stop R W Q G Stop Met E E L C L
T E G K K Stop P W W P S H T L W E R P V P I Q Stop K C L P I P R G I L V S Stop L G T C Q Stop S Q F A
S P G Q G Q I P Q L D V Stop G R E G A Stop T I P E G Stop Stop N S R Stop T L R S D F L Q D R F S R W
K Stop N E R L Stop E Met G Stop R L V T Y T E E V Met K Stop R Q N R Met G L Stop G W K E I F S L I Q
E P F A L C G K R L I R G S F N E G V G G S D R Stop E G E K L A L R D R S W N A S C F F S Y L I S I S V A
L S D G I Stop C L L Met A L A V N D S S F L W K Stop S S L E K S F Y Stop R G T N D E G P L H S E E T S
F N P Y N S Met V V E D MetK G I F R V S I N I D T Stop S L C K S E G P S Stop G N E F G L L R G S G A G
Q S G S L K D R C G R Stop Y S I A C L C R Stop Met A I R P G G T A I N K P S V I R V R N R K E G N Met G
K W S E C Q V D Q R D S H G G Q V W Y Q E Stop C G R P D Stop S P G Q E Q W Stop L W E T Q Q R V S
I G W V W W L Met P V I P A L W E A E Met G R S L Stop V R S S R P A W L T W Stop N P I S T K N T K
N Stop P G V G H T P V I P A T P E A E A G E S L E P G K R R L Q Stop A K I V P L H A S L G D G V R L C L
K K E L S I A E G A R E W K V Y A S G Met R K K I D F G S Y E N C R E Stop V E H N V I L R A S K S I K A A
A A T T H R H E G Stop A K T V R S S C L D R K A T G H A S G S C V R I P T T Q P C T L A V C N E K V
G Met S Stop G E L V W E Q L L G L F F K E W K G E W G K D L G F Met G S A R F I Stop N R I Met G C G
R E V L R I G G Y Met G L A L W G A Stop A R Q F C Stop Stop G T D P E L T C K T C L V F G Q V K W G N
C K E S L Stop A L E G H A I A G E Stop Stop Q A L I L L K C A V G S F Stop S V L W D G I L A L S G V R V I
R F Stop W D G K G C Met I G C Q G G N R G V P Y L W I K V G R Y K G R Met R R R L Stop T G E K G G N
E V W L Stop S R N S Q G S R Stop F G Stop N V L T Stop Stop G S W A G R D N StopK R V Y K R Met L S
K L A P E L G S F D R F S S L A I N T H N S Y G G K G N R P L K R R Y C G V G S L C I K K G T D F P F T V
R V T Q S I C D G P R G F Stop G D W A A S V F S R Stop A E N I W E G V R E S W A R V P A A L G V A P
G Stop V G Q S D F Q Stop G L A Q Met G H G S G G I P G C R H S L A Q Stop P D F Q H L K K D P G G G
G P G G T P G R C D S G V L K F L C A G D V A G V S L T V E A S N C N S E I C C L Y S I T V H L E G E V
N Stop V L L W G L R A G I Stop F L E L F L Met S G A G W V I K C I L R I R R P S G P S G S R A V K H L R
V V A K W A Met N W A G F L Y L Met K N S L N A N Stop L G E V R Stop R K R S I N L D Y A F S S S H L F
F F F F C L E Met F L I E L V Stop Q S F R I S G S L S G H C Q P T A G G A F K A H H F V I R I T Q S L I N I
T A A K L T Y T I F T H N L K Y F V L Met K C F A F T I E D Q Stop Y T V Y Stop T L Stop Q N Y F L R N T E
V R N S D F L N L F I V L S Q S R P K F S I K Stop I D I L I K V C T S L P K E L H S Stop D C L P S V Stop Q
Q Stop Q E R G D S H S Stop R V P S T W L L A P T A Stop A H C I T W W G A A W A S A S E V S S P G T L
V P C L C L A C A I L V N T E N L P V H P Q C Stop R L T G Q G G V S E S V V F T Met W R S G G D Y R I F
F A D F S N W V S R E E Stop P G V A E R L P G L S F Stop F C S R E S D A G P R V K G S C S A P G I
T Met H C A V G R T T L L L C S P R H Q Q A L G R Q L C S S G H P E T S W R C R W D K L G A C Q N T H
S F Q E G Q A P A C S D E V R I V S H L F N R K L L G R S G R A S R G T K L Stop A G P G V R R G G D K
R I I G W G S R G Stop V R I G T W L S L A R S S L G R R G E V R Stop V H R K E G F R G L G T W G G D
R R N R K E R K K K D L G Stop V T L G A E T R E G P Met C K R Met P G R Q A P Q T I C P F Y D K N Y L
E L V G W R T R K C R F L A I W N H C R V C I G A K R C C R R K Stop D T Stop V L G Q V Stop V E E V L
S F Stop E H R L R E K K E E W R V E G C P Stop Stop R R Stop T R E K R G Stop R H G E G G W G S G G

FIG. 10L

H Stop A A L G C N V G E Q P K Q V S P Q L T C H Q G N V G E Stop P R Q A S P W Stop S D T N G V W V
N N Q A G V P T V I K H Q G K T V F P S P Stop L T L E F W V H R Stop N V S P Y L Y Stop R G K R T G I G
R T G R L K G S E R G R L K G S K K G W R R V K R P L T R F E I G K Met F L G L V G L R T Stop D H R W I
S S R S E G D N R A L V S Q R S P P V L G L Q H Q Met S H A S V Stop R N H Q T G F V Stop A T R L Y I S
P G C R R A E S K K E S T K G G G I I I S S Y R F G I G V Q S T F S R A G R I S Q S T F L R A G E N I S Y Q
L G W G R N K S Q W W N V I S Stop G Y F H F F C G S S V A S G H L Y V Y Met Q V T G
D Met Met A Stop F G L R G L T R S I L K V N C T G N L K P Stop Q Stop I F C I S L H Y T S L V Stop L A F L
F F L F C F Stop N Met V L L H H P G W R A V A Q S Stop L P V T S N S Stop A Q A I L P P Stop P P
K Stop L R L H A H A T Met P G Stop F S Y S Y Y F Stop R Stop D L A Met L A R L V S N A W P Q V I L Q P
L P P K Met L G L E A Stop A T T P G L I C I F N A P F I H A Stop F C N I Met F W S F E K Y W F T E L C K S
S K Met L A H F I L Stop Y L K I D I F E H H H Stop Stop H Q K S F Stop L L G S C Q A Stop Y H Met Q D H
Y N S E F C L K A I F S F L F S F F F F F D K I L L C C L G W S A V V Q S W L T A A L A S Q A Q V L L P P Q
L V H A T Met P G Stop F F F S F W R D C P G W S Q T P E L K C S S R L S L P K C W D Y R H E P L P K A
Q I L S L E Q I L Q V V T L K Stop Q F Y F I N V L E A A K Y Q S L N N Q F V S H S F K Q K G Y Y Met N K G
V N S A H N Y N D H T N V F P Q D N H C S L T Y S R S T L Stop V L P T S H F Met P Q N F Stop K V L L R I
K I Stop Stop I N N F Y F I K N I L A G H G G S H L Stop S Q H F G R P R Stop V D H L R P G V R D Q P G Q
H G E T T K N T K I S Q A W W Q A P V I L V T W E V E A G E S L E P R R Q R L Q Stop A E I I A F Q P G G
L N S P P S A G Q Stop G Met Stop C P L V Q F G A T T V I P I K V Q R I S H H Q K K C Q C D G E K R Q I R
L N I T Met N I I L V L W I P Stop K L F G V R S G V H G L H I E N L C I N A F P Q S H T S I K Stop Stop N Q
Y L K L G H T D S Stop P N G F S I V P Stop Y A K Stop Met I Stop I Stop S I I R T N I K G R A W W L T P I I
P A L Q E A K V G R S R G Q E I K T I L A N Met V K P Y L Y Stop K Stop K I S Q V W W A H Met Stop S Q L
L G R L R Q E N C L N P G G G G C S Stop P R S R H C T P A W R Q S E T L S Q K T K Q N K T K Q L T L K
P N N Stop I S T S G L L R N A I S I Y Q P G Met I T L S S P S P D H K D S L N R F D Q N H E E Met G T S L
T I K R D E I D I H S I D Stop K Stop H N S Y Y L Met F G Stop R A L Met C F I S Stop S Stop N Stop V E P
K R Y L I H Y L I P F R N Met F T E S W T S Stop T N Met V R E A A Y S S Q D T V E Q L K L F E L P S C
P Stop P C L L S F P H S F I P L F N P L D N K E Stop V Y F L I C V I F Stop V S Y Q G P S Stop T F P P L F
F F L R Q S R S V T Q A G L Q W C D C G S P K P Q P L R L K Q S S H L S L P S S W D H R R V P P H P T N
Y F L F F V E T G S P Y V V Q A G L E L L G S S N S P Met L A S Q S V G I I G Met S H H A Q S P F S V L K
F S V S Q L S F L S G P I L G S F I C W W F C F R G P G V A F T H T P G L A P S L A S S V L W S W V I L P
F S T D Stop A L L I F Q A V C S G L P F N P Q D N A V K W V P S T V P L L L K L R H S A G H G A S C
L Stop S Q H F G R P R W A D H L R S G V R D Q P G Q H G E T P S L L K I Q K L A G R G A A H L Stop S
Q L L Q G L R Q E N H L N L G G G G C S E P R A C H C T P A W Met T E Stop D S V S K K K Stop I
K Stop K I K I Stop G I L V Stop V Stop Q D E P Q T K P L R H R V K E G R A L F G R E H R Q D S R L K N R
A P Stop V S N S C P S Stop G L T T L R G S A Stop K G L D R L S K Q G V C D W G L H A L V I R T E Q N
R T G I F T V L F H T Met T V I Stop R Stop H N Stop L G Q G S I F N Y Q A Q G V A P G C L P V D F I S V F
K F L L L L S L E A E I G H K T I Stop G V V S S L Met R I L D N C T E L C I H Y L N K H I E Q F P H P K S F
L Met P F F F L R R C L T L S P R L Stop Y S G A I S A H C N L R L L G S R D S P A S A S Stop V S G T T
D Met C Y H T W L I F V F L Q N T K I V L F C I T I I G Stop A G L K L L T S G D Q P A L A S Q S A G I T
G Met S H P A F S C L F A V T Y V I F K N G T I I Y T Y T H T Y I Y I Y T H I Y T H I Y T H I Y T Y I H I Y T H I
Y T Y I H T Y I H T Y I H I Y I H I Y T Y I H I Y T H I Y T Y I H I Y T Y I H T Y I H I Y T H I Y I Y T H I Y T Y I Y T
H I Y I L F F I L R W S L A L S L G L E C S G T I S A H C N I C L P G S S D S P A S A S Q V A G I T G T C L H
A G L I L Y F W Stop R Q G F T T L A R V V S N S Stop P R D P P A S A S Q S A R I T D V S H R A Q H I Y Y
F L T Stop V F L R C T G G K K Met H Stop T S L Y G N Y I V L Q H N F N G C I L S N E C F I I Y L T N V L L
F C T Y I N N V L L P L P G I I F L F L L Q Y R S L L F F N F S Y L S D T S L S V L L A L C P L F F F F F
F Stop D R V S L C C P G W S V V A Q S Q L T A T S A S Y V Q A I L L P Q P L E K L E L T G A R H H A W I I
F N R N R V S P C W L G W S Stop T P D L R Stop S T H L S V Q S A G I T G Met S H H T W P L C P L S T F
P R F C T Stop I F F F F F Y F Stop D R V L L L L C C P G W S A V A L S Q L T A A Stop T S P G S G D P P
T S A S Q V A G I T G Met C H H T R L I F A V F V E S G S H H V A Q A G L K L L G S S N P P T L V S Q N A
G I T G Met S H R A L P K S S Y S I I S L Stop V I N F S P D P L Stop T L W I S S L L F F S T P D P N S Q L S

FIG. 10M

T G Y Y I H R D V L L A I Q Met P H V K N Stop T P I P F A K S L C F S L S L S F L L P I S G R G S G V L P A
T Q A R N L K V L F Stop L L S S L I S H I Q S I K C Y Stop F S S Q Met P L S L C P S F P F P P Stop L S Q L
L R S H D S S P E W Stop Q Stop L P N I S Q P P S P R Y S A L L P Stop E L T L R N R E I I F L S C L K I S
D D F L S L T E A S L N F P L S P P T L P P H T T F L R R L R Q P R T F L N A L L F L C F Y S R S P
Q Stop L P N L Stop C V L L T P G A L A F P Stop E A F L H D C R Q E Stop K Stop A L P T G P S W L A R S
T P P Q R Q L W T K S P Q R I S G Y E G G A G R G D G Stop S A S F V F P A G K R W D L G G Q G T R S
P P V W K T L Stop V L E H C S R P D Stop V A C P H F P H S R V G Q T E V G E Q S P E A D S P G K K K
K G K K A P A D L Stop F T G A R G W K D R A S Stop L E Q T E S D K L G G R Stop L A P A W S G A G G L
L Stop V Stop I A L E G P G L Stop P A V T P A R V G G E G G A S S P F Met S A A S Q A R A G R P F S G
G D W A G R G D G C L R R S Stop A G L K V K H S P A G L S Q S W H L P H R A P S Y L Stop L L K S
L Met Stop C S G Stop G P R R W R S L G G Stop F Y G V A L Met A V V G V P Stop Stop P Q G G G S L S
S P P P G H R I L F A E K V R Met E A W I V F L L E Met Q L L P P S T P G E R E V C G E L A L Stop K V G K
R K G T N G Y T L R R G Stop L S Y I A G E N L K W C S H W G N S L Met V P Q K V K Y Q I S I W P S N S T
P R Y K P Stop Stop I I N G Y S Y L H S N V H G S A I H N N Q K V E A T P V F I N Stop Stop I S K P T V V Y
S Y N G I Stop I G N K Q E Stop S T D I C S N G D E H Stop K I Met P R E G S Q T Q K V I Y C T I P C I G N I
L K W Stop I H R D R K Q T D G H Q G P S V G G K Met G N H C Stop Met G S S F L L G Stop K C F R T K G
S V C T Met L Stop Met H Stop V P Q N W S I Stop N G Stop F G L A R W L T P V I P A L Stop E G G A G G
S P E V R S L R L A W P T W Stop N P I S P K K K K K K E R K K K K D G H G G R C L Stop S Q L L R R L
K Q E N R L N P G G E G C S D P R S S H C T P A W A T R A K L C L K I N K Stop N K Met V S L A G H G G
S H L S S Q H F G R P R E E D H L S P G V Stop D Q P G Q Y S E T P I S I N K V V S F I L C E L S L
N Stop N V S L S L S L S L S L S Q T N Stop Q T K R Stop V L P A V H N S L R K K Stop E T A I L S P L L P
F T S T F L S V F Stop S L A W S W L L T A P H G K W P G G R G P L P P L Stop E G P R L G P E P
L Stop V S P A Y T H Stop A F V S A L W P G C S W L G G T A W G K G R S G S Stop K W E G F C L Q Q P
Q Y G I S T P W S L Q L G P V A F V P K S V Y K N Q R F A C S T E S Stop L Q V T K Y D S Y S L Stop H F
T Q F V A V T E F R A R H E L I L S F P V L T V Stop G Q G D I S E R G R C F Stop G A H N L I G G Stop S
V V Stop E K Stop T G N V G Y V S Met V Stop E E S L K P R C D Stop Met L R R V R R W S E L G S S G T
V D A S A V C A K L K L P A T A T Q G G G S H H Q A L P L S I T E Y C Q A Y S W T Y D R L R H I Stop F V I
C S T P S R A S S Stop D H R S G T R S Stop Q H Y T F S H S F F S K Stop T Q L P H Q Stop N P G N N N
T C F G C G A I T H C Q A F S T V P S S S K Y C Y C Y Y D C I H K S D G L R T L I S H S K G S Stop V C V Y
A V A Stop T P L T K C R T W Y L D F S K Stop L G T A K L S Y Y T P V Y S S L P F L Met W L V F V P L K F
E T R D Y I T A Stop L R E H G L G V V S H A C N P S T L G G R S G Q I T Stop R Stop E L E T T L A
N Met V K P H L Y Stop K Y K N Stop P G I V A D A Y N L S Y L G G Stop G R R L A Stop T R E A E V A V S
R E R A T A L Q P G Q Q S E T L S Q K K K K R E R E R I W S T S F N Q K I Y F H Q Y L I Y L G L C L S Y
N Stop W Stop N I K R V F Stop N I I F Y Q D I I Y I P Stop N Y S F S V Stop C R H F Stop Y I H R D Met Q P
L P K S T Stop R T F S S L P T E P Met H I G N P S P S L Stop Q P Q I N F L S L D V P F W T F H N
K Stop N H T I Y S F L C L T S L P S 3'5' Frame 3 (SEQ ID NO: 49):

S N R A V Y F T W V Q A G Stop V Q K E S Q Q R V V G L S L V L I G L G Stop V Y K V H S Q G R G K N I W
Y Q L A W G R N K S Q W W N V I S Stop G Y F H F F C G S S V A S G H L D V H V Q V T G D
L Met A Stop L G L R G L T L L S S Y I S Met K N K T K Stop W Stop S V E A A K I F G G G Met E R Stop W
A Met F L G A A L S G I G V A W E P R V G E I K L K K D L G I R G D I V G L L E G V F V V Stop N D
C Stop W P G C S F V Stop I E K L N R R K T Q G P N K R K R K I G I K G L R I G R T Q D I Q L G S A Q G G
S A Stop L F A W L A N F W G L S L S F F Met L S Y T R P D Stop F R Stop K Q H S S F K N I Q G P L F L A
V S K S R P W R F W R K E K C K A S S C L L K K D Stop R A G H S G S R L Stop S Q H F G R L R W A D R
E V R R W R P S W L T W Stop N P I S T K N T K N Stop P G Met V A G T S S P S Y L G G Stop G R

FIG. 10N

R Met V Stop T Q E A E L A V S Q D H T T A L Q P G G Q S K T P S Q K K K K D Y K R G Stop E R V R L I V
W W R Stop L G R G R G W H K I G N Q N K N E Y K S K E Stop D F I R V K V S E G T L P L K I Y P L Q E S
L K G G V L R Stop N Q E P L N T K R L R S C L G D L T N K G R S V F T L Y R G G K A K W R N Y V Stop Q
K G R N D R G G L L T P C G K G L Y P S S E S V Y P Y Q E V F Stop F P D S A H V S K V N L P V L G R G
K F P S L Met C R E G K G P E Q S L R D S R I V D E H Stop E V I F F R T D F H D G N E Met R G Y K R W A
S G L Stop P T R K R L Stop N D D R I E W A C E A G R R Y F P Stop S K N H L P C V G K D Stop Y V E V
S MetR E Stop V G V T D K K E K N W P Stop G T E V G Met L A A S L A T L S A Stop A L P Stop V Met G S
D A F Stop W P L Q Stop Met T P A S F G S K A A L R R V F I K E A L Met Met K D P C I V R K P L S T H I T
A W W W R I Stop K A Y L E S V Stop I L T R S P F A R V R A R V K A Met S L A C Stop E V V E R G R A V A
S R I D V E D S I A Stop P A F A G E W R L G L V E L P S I N Q V Stop S G Stop G T G K K E I W G N G V N
A R W I R E I V Met E V R C G I R N N V G G R I E V Q A R N N G N C G R L S K E Stop V Stop A G C G G S
C L Stop S Q H F G R P R W A D H F R S G V Q D Q L G Stop H G E T P S L L K I Q K I S R V W G T H
L Stop S Q L L Q R L R Q E N R W N L G S G G C S E P R L C H C Met P A W E T E Stop D S V S K K
S Stop V Stop L K E P G S G K Y Met R Q V Stop G R K Stop I L E V Met R T V E S E L S
I Met Stop F Stop G P L K V S K Q Q Q P P H T D Met R A R L K Q Stop G Q V V W T E R L Q G Met L L A L
V Stop E F R P H S P A L W L C V Met K K L G Stop V R E S Stop C G S S F Stop G C F L R N G K G S G E
R I Stop D L W G Q L G L F R T E Stop W V V G G R Y Stop G Stop E G I W V W H Y G V H R Q D N F V D K
A Q I L N Stop P V R L V W F L D R Stop N G G I V R R V Y R L Stop K A Met L Stop Q A S D N R L Stop S
F Stop S V L W D P F K V C C G Met G Y W H Stop V G Stop G Stop L G F N G Met V R G A Stop S V A K E
G I E V S H T C G L R W G D T R G G C E G G F E L G K R A A Met R C G C S P G T V R E A D N L V
K Met S Stop P N K G A G Q V G I T K K E C I K E C C P S W H Q S W G V L T G L A A W P S I P T T V Met E
A R E T G P Stop K E G I V E W V A S V L R R G Q T S P S L Stop E L P K A S V Met V Q E A S E A I G Q H
Q F S A A K P R T S G K E S E S L G P E F Q Q L W E W L L G K L D S L I S S R V W H R W D Met A Q E E S
Q A A G I P W P S D Q I S S T Stop R K I L G E A V L E E H L A A A I Q V F Stop S S C V L E Met W L G F L
S Q W R Q V I A T Q K Y V A S T L L L Y T L K V R L I K S C C G V Stop G L E S N F W S F F Stop C P E R V
G Stop Stop N A Y Stop E Stop D G L L A P L G L G R Stop S I Stop G L L P N G P Stop T G L G F Y
I Stop Stop K T A Stop T L T D W E R S D E E K G A L T L T T P S A P A T S F F F F F A L K C F Stop Stop N
W S S S H S G F Q G P C L D T A N P Q L E G H L R H I I L Stop L E L H K V Stop L I L Q L Q N Stop H T Q F
S L I I Stop N T L F Stop Stop N A L L S Q Stop K I S S T Q Y I E L C N K I I F Stop E I Q K Stop E I V I S S I
C L Stop S Y H K V G Q S S V L N K Stop I S StopStop K F V Q V F L R N Y I R K T V Y L L F D S S D R N V
G I P T H D E S L A L G S Stop H P Q P R R T A S P G G V Q P G L L R V R F P H L E L W F H V C A Stop P
V R F W Stop T Q K T C L S T P S A E D Stop L V K E V L V R V L C S P C G D Q A V I T A S S L L T L V T G
C P E R S D R E W P S G C L D S A S D S A A G S Q Met Q A Q G S R G V V Q R L E S P C T A L W A A R H
S C C V L P G T N R H L E G N F A P L A T R R P L G G A D G T N W G P V R T P T H S R K A R H Q P A
L Met K S G Stop S A I S L T G N C W A D R G E L V E E R N C K L D Q V Stop G G E V I K G L Stop G G G
A E A K Stop E L G P G S A W R G A A W G E G G R S D E S I E K K D S E D S E L G V E T E G T E R R E R
R K I W D E S H W E Q R L G R D Q C V K E C L D V R H L R P F A H F Met T R I I Stop N L Stop D G E L E
S A V F W L F G I I V E F V L G P S G V A E E N K T L R F Stop V R C E L K R F Stop V F E N T G Stop G R
R R R N G G W K V A H S E G G K P E K R E G R G T E K A G G A A G G I E Q P W A A Met W V S S Q S R
C P R N Stop L V T K G Met W V N D Q G R H P R G D Q T P Met E C G Stop I I R Q A S P Q Stop L N T K G
R L S S R V R D Stop R W S F G S T D K Met C L L I S T R E E K E R E L E G Q G D Stop R V V R E E
D StopR V A R K A G E E Stop K D H L P D L K L A R C S L G W L V Stop G P E I I G G S P H G V R A T T G
H W S P K G V L L S W V F S T K C H Met H P C E E T T K Q A L C E Q Q G C I F H L G A G G L S L K R S Q
Q R V V G L S L V L I G L G Stop A Y K V H S Q G Q G E Y H K V P S Stop G R G R I Y R I S Stop G G A G T
N L N G G Met S S V K A I F T S F V D L Q L L Q A I C Met Y T C R S Q G I Stop W L S L G S E A Stop H V V
S Stop R L I A L G I Stop N H S N E F F V F H Y I I L H W S N L H F F F F C F V F E T W S Y S I T Q A G G Q
W H N H S F L Stop P Q T P K L K P S S H R S L P S S Stop D F T R Met P P C L A N S L T L I I F R D R I L L
C W P G W S Q Met P G L K Stop S S S L C L P K C W D Stop R H E P P H L A S F A F S Met H L L SMet H
D F V T L C F G H L K S I G S L S Y A N L L K C W H I L F Y N I Stop K L T F L N I T T D S I R R V F N

FIG. 10O

Y Stop E A V K L S T T C K I T T I L S F A Stop K L F F L F F F L F F F F L T R S C S V A W A G V Q W Y N H
G S L Q P W P P R L K C S F H L S W C Met P P C L A N F F F L F G E T A Q A G L K L L S S S A P P A S A
S L S A G I I G Met S H C Q K L K F Y H W N K Y C K L L L Stop S N N F T L L Met F L K L Q N T K V Stop T
T S L S V I L S N K K D I T Stop I K G L I Q L T T I Met I T L Met F S L K T T T V L Stop H I A E V L Y K Y F L
L P I S C H R I F K R C S Stop G S K F N K L I I F I L S R T S W L G Met V A H T C N P S T L E G Q G R W I
T Stop G Q E F E T S L A N Met V K L L K I Q K L A R R G G R H L Stop S Stop L L G K L R Q E N R L N P G
G R G C S E P R S L H S S L G D Stop I P L Q V Q G S E E C N A H W Y S L V L L P Stop F L S R C K E F P
T I R R N V N V Met V K K G K Stop G L I S P Stop T S F W S Y G Y P E N Y L G Y A Q G S Met D Y T S K T
S A Stop Met P F P K A I H L L S S R T S T Stop N W V T L T P S L Met V S L L Y H S Met Q N E Stop Y R Y
E V Stop Stop E L T L R A G H G G L P L Stop S Q H F R R P R W A D H E V R R S R P S W P I W Stop N P I
S T K N K K L A R C G G H T C S P S Y S E G Stop G R R I A Stop T R E A E V A V S Q D H A T A L Q P G D
R A R L C L K K Q N K T K Q N S S H Stop N Q I I K F L P A A Y L E Met Q L V F I S Q V Stop S L Stop A H L
V Q I I K T A Stop T D L I K T Met K K W E L A Stop Q S K E Met R L T S I P Stop T E N N I T P I T L C L V E
E L Stop C A L Y H S L K T R W N L R G I Stop S I I S S H S G T C L Q N L G R V E Q I W Stop E K Q L I P P
K T L Stop N S S S Y L S C L P V H S H A C S H S H I V L F L Y S T L W T I R N R F I S S F V S Y S K S A T K
V P H K P S P P F F F F Stop D S L A L L P R R D Y S G V I V A H Q S R N L S G S S N P P T S A S Q V A G
T T D V Y H H I P L I I F Y F L Stop R Q G L R Met L S R L V L N S W A Q A I L L C W P L K V L G
L Stop A Stop V T Met P R A L F Q S Stop S F Q F L N F P F C L D P F Stop G L L F V G G F V L E A Q V W
P L P I L R A L L P V S P P P C C G P G S S F P S L L I E P F L Y S R Q Y A L V C H L I P R T T L Stop S G Y
H Q Q S P S C Stop N Stop G I Q L G Met V P H A C N P S T L G G R G G Q I T Stop G Q E F E T S L A
N Met V K P R L Y Stop K Y K N Stop L G V V L H T C N P S Y S R G Stop G R R I T Stop T W E V E V A V S
R E H A I A L Q P G Stop Q S E T Q S L K K N K Stop N K K Stop K F K E F Stop F E C S R T S R R Q N P L
D T E L K K E G L Y L A G S I G K T H V S K T E L P E Stop A I P V P L K G Stop Q L Stop G G P R E R V L I
D Stop A S K G Y V T G G C Met H W Stop L E Q N R T G Q G F S Q C F S T Q Stop L Stop F R D N I T
D Stop V R G R S L T T R P R V W R R A V C L W I S F L S L S F Y F F F L W R Q K L G I R Q Y E G W S P P
L Stop G F W I I V Q S C V Y I T S T N I Stop N S S L I L K V S S C L F F F Stop D G V S L C H P G C S T V V
Q S Q L T A T S A S W V Q G I L L P Q P P E Stop V G L Q T C A T T P G Stop F L Y F Y K I Q K L F Y F
V Stop Q L L A R L V S N S Stop P Q V I S L P W P P K V L G L Q A Stop A T Q P S H A F L Q S
H Met Stop F L K Met V Q L Y I H I H T H I Y T Y I H T Y I R I Y T H I Y T H I Y I Y T H I Y T H I Y T H I Y T H I
Y T Y I Y I Y T H I Y T Y I H I Y I H I Y T Y I H I Y T H I Y I Y T H I Y T Y I H I Y I H I Y T H I Y I Y F F L F Stop D
G V S H C H L G W S A V A Q S L L T A T S A S Q V Q V I L L P Q P P K Stop L G L Q A P A S Met P
G Stop F C I F G R D R V S L H W P G W S Q T P D L V I H L P Q P P K V L G L Q T Stop A T V P S I Y T I
F Stop P E C F Stop D A L G E K R C I E H L F Met A I I Stop F C N I I L Met A V F Y Q Met N A L Stop F
I Stop P Met S Y C F V H T Stop T Met S C F L F L E L F S Y F Y Y S I V V C F F L I F H I F L I L L C L F
C StopL C V L F F F F F F F F E T E S H S V A Q A G V Stop W H N L S S L Q P L P P Met F K P F S Y L S L S
R S W N Stop Q A P A T Met P G Stop F L I E T G F H H V G Stop A G L E L L T S D D P P T S A S K V L G S
Q A Stop A T T P G L C V L F L P S Q D S V L E S S F F F F T F E T G S C S C Y V A Q V G V Q W H Y L S S
L Q P R P P Q A Q V I P P P Q P P K Stop L E L Q V C V T T P G Stop F L Q F L Stop S R G L T Met L P R L
V S N S W A Q A I L L P W S P K Met L G L Q A Stop A T V P C P N L L I L Stop F L F R S S I S L P I H Y K P
F G S H L Y F S S R H Q I L I P N C L L G I T S T G Met Y F L Q F K C H Met S K T E L L F P L Q N P S A S L
F L S P F C Y L F Q V G E V V S F Q P L R L E T S K S S S D C C P H S S H T S S Q Stop S A I D S P P K C
L S A C A L P F H S H R D Y P S F Stop G P Met T L H Q S G N N S F P T S P S P H P P A T L L C C H E
S Stop L C E T E R L F S S P A Stop K Y L Met T S Y H L Q K Q V Stop T F H C L L P L S H H T P P S C A G
C V S L E R S Stop T L C C S C A F T H V L P S D C P I F S V F C Stop L L A L W L F H K R R F C T I A D R
N K N E L C L L G R P G Stop Q G L H H L K G S Y G L R A H K E S R V Met R E G L A V E T A K A P H L S S
Q Q G S D G T S A G R E R D L H P S G K L S E F W S T V R G R T E W H V R I F P I P G Stop G R L
R Stop E S R A P R P T P R E K K K K E K R L P P T C D S Q E Q E A G R T A P P D W S R Q N Q T S L G A
A D W L R R G Q A L V G C C R C K Stop L L K A R V C D R Q Stop P R R E W V E R E A L P L H S C Q L P
A R P G Q A G P L A E G T G Q D E A Met G V F G D L K L G Stop K L N T H P Q G Stop A R A G T F H T E

FIG. 10P

P L P I C D C Stop K V Stop C D V L G E D R G V G G R Stop E G S F T E S R Stop W L Stop W V Y L S D H
R E V A A C P L L L L V T V F Y L R K R Stop E W R L G Stop S F Y Stop R C N F S H P L L Q G K E K S V G
N W L C K K Stop E R G K G Q Met G T R Stop E E G D S H T L L E K I Stop S G A A T G E T V Stop W C H
K R L N I K L A S G P A T P L L D I N P N K L Stop T G T H I C T Q Met F Met A V L F T I T K R W K Q L Q C
S S I D K S V N Q L W C I H T Met E Y E Stop V I N R N E V L I Y A P Met G Met N I E R L C Q E K E A R H R
R S Y I V R F H V Stop E I S Stop S G K S T E T E S R L Met V T R G R V W V G R W G I T V E W V Q V F F
W G E N V L E Q K V V F A Q C Y E C T K C H R T G Q F K Met V S S A W H G G S H L Stop S Q H F E R V
G R A D H L R S G V Stop D Stop P G Q R G E T P S L L K K K K K R K K E R K K K Met G Met V A G A C N
P S Y S G G Stop S R R I V Stop T R E A K V A V I R D H P I A L Q P G R Q E Q N S V S K Stop I N K I K W L
V Stop P G T V A H T C H P S T L G G Q G R R I T Stop A Q E F E T S L G N I V R P L S Q Stop I K W L V L
Y C V N C L S I K Met Y L S L S L S L S L S R K Q T D R L K G E S F L L S I I L Stop E R N K K Q Q F Stop V
L C C L S L P L S S L F F E V W H G P G Y Stop L L P Met E N G Q E G E G P F R P S E K V L A W A Q N H
C E S A R H T H T E P L Stop A L C G Q G V A G W A G P R G G R A G P G P E S G K A S A S S N P
S Met E S Q L L G A C N Stop G L W H L F Q S Q C T R I S A L P A A R K V N Y R S Q N Met T P T P C D I S
H S L Stop Q Stop Q N L E Q D Met S S F C H F Q C Stop L F R G R E T F L K E E D A F E E L T I L Stop E
G E V Stop F R K S R Q E Met L G T Y L W F E R K A Stop N P G V T E C Stop D G S G G G V S W V L P E
Q W Met H L L F V Q N L S S L P L P P R E E G H I T R L C L Stop V Stop L N I A R H T V G H Met T D Y D I
S S L S S A P H P V E P V V K T I G L E P D H S N I T H F L T A F S P S E L S Y L I S K I Q V T I T P A S D V
V R Stop H T A K H S V Q C P A L V N I V I V I Met I V S T S L Met D S E L Stop F P T Q K E V R S V F Met Q
L P K P L Stop L N V E H G I S I F P S N L V Q P N C H I I L Q F I A A C L F S C G Stop S L S L Stop S L R L
E T T S L H N Stop E N Met D W V W C L Met P V I P A L W E A E V G R S L D V R S S R P P W P T
W Stop N P I S T K N T K I S Q A Stop W Q Met P I I S A T W E A E A G D S L E P G R Q R L Q Stop A E N V
P L H S S L D N R V R L Y L K K K K K E R E R E Y G A L P L I K K F I F I S T Stop Y I W V C V S A T T S G K
T L R G F F K I Stop F F I K I Stop F I Y H K I T L L V Y D A D I F S I F T E T C N P Y Q N L P K E H F H H S P
Q N P C T L A T L P P V S S N H R S T F C L Stop MetS H S G H F I I N E I I R Y I V F C V Stop L L C L L

FIG. 10Q

SEQUENCE LISTING

```
<160> NUMBER OF SEQ ID NOS: 49

<210> SEQ ID NO 1
<211> LENGTH: 16777
<212> TYPE: DNA
<213> ORGANISM: Homo sapiens
<220> FEATURE:
<221> NAME/KEY: exon
<222> LOCATION: (2001)..(2437)
<220> FEATURE:
<221> NAME/KEY: exon
<222> LOCATION: (9640)..(9872)
<220> FEATURE:
<221> NAME/KEY: exon
<222> LOCATION: (16460)..(16777)

<400> SEQUENCE: 1

cttcaaaaaa cagagaggaa agtggaagtg aaaggcagca gaggactcag aattgctgtt     60

tcttatttct ttcttagaga attatggaca gcaggaagga ctcacctttt agtctgtcag    120

tttgtttgcg agagagagag agagagagag agagagagag atacatttta attgagagac    180

aattcacaca atataaaact aaccacttta tttattgaga taggggtctc actatattgc    240

ccaggctggt ctcaaactcc tgggctcaag tgatcctcct cccttggcct cccaaagtgc    300

tgggatgaca ggtgtgagcc accgtgcccg gctaaactaa ccattttatt ttatttattt    360

attttgagac agagttttgc tcttgtcgcc caggctggag tgcaatggga tgatctcgga    420

tcactgcaac cttcgcctcc cgggttcaaa cgattctcct gcttcagcct cctgagtagc    480

tgggattaca ggcacctgcc accatgccca tctttttttt tctttctttc tttctttttt    540

tttttttttt taggagagat ggggtttcac cacgttggcc aggctagtct caaactcctg    600

acctcaggtg atccgcccgc cccaccctct caaagtgctg ggattacagg tgtgagccac    660

cgtgccaggc cgaactaacc attttaaatt gaccagttct gtggcactta gtgcattcat    720

aacattgtgc aaacactacc ttttgttcta aaacattttc accccaaaag aaaacttgaa    780

cccattcaac agtgattccc catcttccca cccacactcg gcccctggtg accatcagtc    840

tgctttctgt ctctgtggat ttaccacttc aggatatttc ctatacatgg aatcgtacaa    900

tatatgacct tctgtgtctg gcttccttct cttggcataa tctttcaatg ttcatcccca    960

ttggagcata tatcagtact tcattcctgt ttattaccta ttcatattcc attgtatgaa   1020

tacaccacag ttggtttact gatttatcaa ttgatgaaca ctggagttgc ttccaccttt   1080

tggttattgt gaatagcact gccatgaaca tttgagtgca aatatgagta cccgtttata   1140

atttattagg gtttatatct aggagtggag ttgctgggcc agatgctaat ttgatattta   1200

acctttttgtg gcaccatcaa actgtttccc cagtggctgc accactttaa atttctcca   1260
```

-continued

```
gcaatgtatg agagtcaccc tcttcttaac gtgtacccat ttgtcccttt cctctttcct   1320

actttttaca aagccagttc cccacagact tctctttccc ctggagtaga gggtgggaga   1380

agttgcatct ctagtagaaa gactatccaa gcctccattc ttacctttc cgcaaataga   1440

atacggtgac caggaggagg agaggacagg ctgccacctc cctgtggtca ctaaggtaca   1500

cccactacag ccattaacgc gactccgtaa aactaccctc ctagcgacct ccaacgcctc   1560

ggtcctcacc cagaacatca cattaaactt ttcaacagtc acagatagga aggggctcgg   1620

tgtggaaggt gccagctctg gctcagccct gcgggtgagt gtttaacttt cagcccagct   1680

taagatctcc gaagacaccc atcgcctcgt cctgcccagt cccctccgct aaagggccgg   1740

cctgcccggg cctggctggc agctgacatg aatggagagg aagcgcctcc ctctccaccc   1800

actctcgccg gggttactgc cggtcacaga cccgggcctt caagagctat ttacacctac   1860

aacagcccac cagcgcctga ccacgccgga gccaatcagc ggcccccaag cttgtctgat   1920

tctgtctgct ccaatcagga ggcgcggtcc ttccagcctc ttgctcctgt gaatcacagg   1980

tcggcgggag cctttttcc ttt ttt ttt ttt tcc cgg gga gtc ggc ctc ggg   2033
                      Phe Phe Phe Phe Ser Arg Gly Val Gly Leu Gly
                      1               5                   10

gct ctg ctc tcc tac ctc agt ctg ccc tac cct gga atg ggg aaa atg     2081
Ala Leu Leu Ser Tyr Leu Ser Leu Pro Tyr Pro Gly Met Gly Lys Met
            15                  20                  25

cgg aca tgc cac tca gtc cgg ccg cga aca gtg ctc cag aac tca gag     2129
Arg Thr Cys His Ser Val Arg Pro Arg Thr Val Leu Gln Asn Ser Glu
        30                  35                  40

agt ttt cca gac ggg tgg aga tcg cgt tcc ctg ccc gcc gag gtc cca     2177
Ser Phe Pro Asp Gly Trp Arg Ser Arg Ser Leu Pro Ala Glu Val Pro
    45                  50                  55

tcg ctt ccc tgc tgg gaa gac aaa tga ggc gct tta gcc gtc tcc acg     2225
Ser Leu Pro Cys Trp Glu Asp Lys     Gly Ala Leu Ala Val Ser Thr
60                  65                  70

gcc agc ccc tcc ctc ata acc cga gat tct ttg tgg gct ctt agt cca     2273
Ala Ser Pro Ser Leu Ile Thr Arg Asp Ser Leu Trp Ala Leu Ser Pro
75                  80                  85                  90

tag ctg cct ttg agg tgg tgt aga cct tgc taa cca gga cgg ccc agt     2321
    Leu Pro Leu Arg Trp Cys Arg Pro Cys     Pro Gly Arg Pro Ser
                    95                      100

agg cag agc tca ttt tta ttc ctg tct gca atc gtg caa aaa cgc ctc     2369
Arg Gln Ser Ser Phe Leu Phe Leu Ser Ala Ile Val Gln Lys Arg Leu
105                 110                 115                 120

tta tgg aaa agc cag agc gcc agg agt cag caa aac aca cta aag att     2417
Leu Trp Lys Ser Gln Ser Ala Arg Ser Gln Gln Asn Thr Leu Lys Ile
                125                 130                 135

ggg cag tca ctg ggg aga ac  gtgagtaaaa gcacaggaac agcaaagcgt        2467
Gly Gln Ser Leu Gly Arg Thr
            140

tcaggaacgt tcgaggctga cgcaaccggc gcaggaaggt ggtgtgtggt gggagagtgg   2527

gaggagacag tggaaagttt agacttgctt ctgtaagtga taagaagtca tcagatattt   2587

tcaagcagga gaggaaaata atctctctgt ttcgcaaagt taactctcat ggcaacagag   2647

cagagtagcg gggggatggg ggctgggaga tgttgggaag ctattgttac cactctggtg   2707

aagagtcatg ggacctcaaa agctgggata gtcacggtgg gaatggaaag gaagggcaca   2767

agctgagagg catttgggag gagaatcaat agcactttat tgactggatg tgtgagatga   2827

gtgaggacag caatcagaag aggactttga ggtttctagc ctgagtggct ggaaggacac   2887

cacttcccct acctgaaata ggtagcaaaa aggagagaga aagagagaag cagagggatt   2947
```

-continued

```
ttgcaaaggg aataggagtt cagtttttga catgtggcat ttgaattgca agaagtacat   3007
ccctgtggat gtaataccca gtagacagtt gggaattagg atctggtgtc gagaagaaaa   3067
gtagagatga gatccaaagg gtttatagtg gatcgggaga gaaattgatg acctaaagag   3127
aaattataga ataagaagat ttgggcaggg cacggtggct catgcctgta atcccagcat   3187
tttgggagac caaggtagga ggattgcttg agcccaggag tttgagacca gcctgggcaa   3247
catggtgaga ccccgactct acaaaaactg caaaaattac cgggtgtggt gacacatacc   3307
tgtaattcca gctacttggg aggctgaggt ggggggatca cctgagcctg gggaggtcta   3367
ggctgcagtg agctgagata gtgccactgc actccaacct gggcaacata gcaagagcaa   3427
gaccctgtct caaaagtaaa aaaaaaaaaa gaagattcaa gtacagaatc ttgggaaggt   3487
agaaagagga cacagaggcc aggtgtggtg gctcatgcct gtgatcccag cactttggac   3547
gctgaggtgg gtggatcatc tgaggtcagg agttcaagac cagcctagcc aacatggtga   3607
aaccctgttt ctattaaaaa ttatccaggc atggtggcgg gcgcctgtta attccagctt   3667
ctcgagaggc tgaggtagga gaatggcttg aacataggag gcagaggttg cagtgagctg   3727
agattgtgcc actacactcc agcctgggca acagagtgag actctgtctc aaaaaaaaaa   3787
aaaaaaaaaa agaggacaca gagctagcaa aacagacaaa gaagtatcag aaagatatga   3847
aaaattaaaa aaaagcaaac tacgatactg taatagaaat aagaaaataa ttccaggaag   3907
aggaagcagg acattgttta tgtatgtaca aaacagtaag acattggtta aataaattat   3967
aaagcattca tttgatagaa tacagccatt aaaattatgt tgcaaaacta tataattgcc   4027
ataaagagat gttcaatgca tctttttttcc cccagtgcat cttagaaaca ctcaggttaa   4087
aaaatagtat atatgctggg cacggtggct cacgtctgta atcctagcac tttgggaggc   4147
tgaggcaggt ggatcacgag gtcaggagtt tgagaccacc ctggccaatg tagtgaaacc   4207
ctgtctctac caaaaataca aaattagccc ggcatggagg caggtgcctg taatcccagc   4267
tacttgggag gctgaggcag gagaatcact tgaacctggg aggcagatgt tgcagtgagc   4327
agagattgtg ccactgcact ccagcccaag tgacaatgcg agactccatc tcaaaataaa   4387
aaaaagtata tatatatgtg tgtatatata tgtatatata tgtgtatata tgtatatatg   4447
tgtgtatata tgtatatatg tgtgtatata tgtatatatg tgtatatatg tatatatatg   4507
tgtatatatg tgtatatatg tgtatatatg tatatatatg tgtatatatg tgtgtatata   4567
tgtgtgtata tatgtgtata tatgtgtgta tatatgtata tatgtgtata tatgtgtgta   4627
tatatgcgta tatatgtgtg tatatatgta tatatatgtg tgtgtatatg tatatataat   4687
tgtaccattt ttaaaaatta catatgtgac tgcaaaaagg catgagaagg ctgggtggct   4747
catgcctgta atcccagcac tttgggaggc caaggcaggc tgatcacctg aggtcaggag   4807
tttgagacca gcctagccaa taattgttat acaaaataga acaatttttg tattttgtaa   4867
aaatacaaaa attagccagg tgtggtagca catgtctgta gtcccactta ctcaggaggc   4927
tgaggcagga gaatcccttg aacccaagag gcggaggttg cagtgagctg agattgcacc   4987
actgtactac agcctgggtg acagagtgag acaccgtctc aaaaaaaaaa aaggcatgag   5047
gaaactttta ggatgaggga actgttctat atgtttgttg aggtaatgta tacacagctc   5107
tgtacaatta tccaaaatcc tcataaggga ggagaccacc cctcatattg tcttatgccc   5167
aatttctgcc tccaaagaaa gaagaagtaa aaacttaaag acagaaatga aatccacagg   5227
cagacagccc ggcgccacac cctgggcctg gtagttaaag atcgacccct gacctaatca   5287
```

-continued

```
gttatgttat ctctaaatta cagtcattgt gtggaaaagc actgtgaaaa tccctgtcct   5347
gttctgttct gttctaatta ccagtgcatg cagcccccag tcacataccc cttgcttgct   5407
caatcgatca agaccctttc acgcggaccc ccttagagtt gtcagccctt aagagggaca   5467
ggaattgctt actcagggag ctcggttttt gagacgtgag tcttgccgat gctcccggcc   5527
aaataaagcc cttccttctt taactcggtg tctaaggggt tttgtctgcg gctcgtcctg   5587
ctacactcaa actagaattc cttaaatttt tattttttat tttatttatt ttttttttaga   5647
gactgagtct cactctgtca tccaggctgg agtgcaatgg catgctctcg gctcactgca   5707
acctccacct cccaggttca agtgattctc ctgcctcagc ccctggagta gctgggatta   5767
caggtgtgca gcaccacgcc cagctaattt ttgtattttt agtagagacg gggtttcacc   5827
atgttggcca ggctggtctc gaactcctga cctcaggtga tctgcccacc tcggcctccc   5887
aaagtgctgg gattacaggc atgaggcacc atgcccagct gaatgcctta attttaacaa   5947
gagggggact gttgatggta cccacttcac agcgttgtcc tggggattaa atggcagacc   6007
agagcatact gcctggaata taagaagggc tcaatcagta gagaagggaa ggatgaccca   6067
ggaccacagc acggaggagg cgagactggg agcaaggccc ggagtatggg taaaggccac   6127
acctgggcct ctaaaacaaa accaccaaca aataaaagac cctagaatgg gtccagacaa   6187
aaaggaaagt tgagaaactg aaaactttaa gactgaaaaa gggctctggg catggtgact   6247
catgcctata atcccaacac tttgagaggc caacatagga gaattgcttg agcccaggag   6307
ttcaagacca gcctggacaa catacggaga ccctgtctct acaaaaaata aaaaataatt   6367
agtgggatgt ggtggtacac gtctgtggtc ccagctactt gggaggctga ggtgggagga   6427
ttgcttgagc ctgagaggtt gcggctttgg tgagccacaa tcacaccact gtagtcccgc   6487
ctgggtaaca gagcgagact gtctcaaaaa aaaaaaaagg ggggggaagg tttatgaggg   6547
accttggtag ctgacttaga atatgacaca aatgaggaaa taaacctatt ccttattgtc   6607
cagagggttg aataaaggaa taaaactatg tgggaatgag agcaagcatg gctatggaca   6667
ggaaggcagc tcaaataact tgagctgttc tacagtgtct tgggaggaat aagctgcttc   6727
tctcaccata tttgttcaac tcgtccaaga ttctgtaaac atgttcctga atgggatgag   6787
ataatggatt agatacctct taggttccac ctagttttaa gactatgata taaagcacat   6847
caaagctctt caaccaaaca taaggtaata ggagttatgt tattttcagt ctatggaatg   6907
gatgtcaatc tcatctcttt tgattgtcaa gctagttccc atttcttcat ggttttgatc   6967
aaatctgttt aagctgtctt tatgatctgg actaggtgag cttaaagtga tcatacctgg   7027
ctgataaata ctaattgcat ttctaagtag gccgctggta gaaatttaat tatttggttt   7087
taatgtgagc tgttttgttt tgttttgttt tgtttttttga gacagagtct cgctctgtcg   7147
ccaggctgga gtgcagtggc gtgatcttgg ctaactgcaa cctccgcctc ccgggttcaa   7207
gcaattctcc tgcctcagcc ttccgagtag ctgggactac atgtgtgccc accacacctg   7267
gctaattttt tatttttagt agagataggg tttcaccata ttggccagga tggtcttgat   7327
ctcctgacct cgtgatctgc ccaccttggc ctcctgaagt gctgggatta taggggtaag   7387
ccaccatgcc cggcccttaa tgttagttct tattatactt catatctata tcattcattt   7447
tgcatactat ggtacaatag agaaaccatt aggctaggag tcagtgtgac ccagtttcaa   7507
gtactggttc tactacttaa tagatgtatg gctttgggga aaggcattta tgcagaggtt   7567
ttcgatgtgt agtccatgga cccctgagcg taccccaaat aattttcagg gtatccataa   7627
gaccaaaatg atgttcatgg tgatattaag ccttatttgc ctttttttcac catcacattg   7687
```

-continued

```
acatttcttc tgatggtggg aaattctttg caccttgata ggaatcacgg tagtagcacc   7747

aaactgtacc agtgggcatt acattcctca ctgccctgca cttggagggg aattcagtcc   7807

cccaggctgg aatgcaatga tctcggctca ctgcaacctc tgcctcctgg gttcaagcga   7867

ttctcctgcc tcaacttccc aagtaactag gattacaggt gcctgccacc acgcctggct   7927

aatttttgta tttttagtag tttcaccatg ttggccaggc tggtctcgaa ctcctggcct   7987

caggtgatcc acctaccttg gccttccaaa gtgctgggat tacaggtgtg agccaccatg   8047

cccagccaag atgttcttga taaaataaaa attattaatt tattaaattt tgatccttaa   8107

gagcaccttt taaaaattct gtggcatgaa atgggaagta ggaagtactt ataaagtact   8167

tctgctatat gtcaaagaac agtggttgtc ttgagggaaa acattagtgt gatcattata   8227

gttgtgagct gaattaaccc ctttattcat gtaatatcct ttttgtttga aagaatgact   8287

gacaaactgg ttgttcagac tttggtattt tgcagcttca agaacattaa taaagtaaaa   8347

ttgttacttc aaagtaacaa cttgcaatat ttgttccaat gataaaattt gagcttttgg   8407

cagtggctca tgcctataat cccagcactt agggaggctg aggcgggagg agcacttgag   8467

ctcaggagtt tgagaccagc ctgggcagtc tctccaaaaa gaaaaaaaaa attagccagg   8527

catggtggca tgcaccagct gaggtggaag gagcacttga gcctgggagg ccaaggctgc   8587

agtgagccat gattgtacca ctgcactcca gcccaggcaa cagagcaaga tcttgtcaaa   8647

aaaaaaaaaa aaagaaaaaa gaaaagaaaa aatagctttc aagcaaaact cagaattgta   8707

gtgatcttgc atgtggtact aagcttgaca gcttcctaat aattaaaaac tcttctgatg   8767

ctatcagtgg tgatgttcaa aaatgtcaat ttttaaatat tatagaataa aatgtgccaa   8827

cattttagaa gatttgcata actcagtgaa ccaatacttt tcaaatgacc aaaacataat   8887

gttacaaaat catgcatgga taaaaggtgc attgaaaatg caaatgaggc caggtgtggt   8947

ggctcatgcc tctaatccca gcattttggg aggcagaggc tggaggatca cttgaggcca   9007

ggcatttgag accagcctgg ccaacatagc aagatcctat ctctaaaaat aataagagta   9067

agagaattag ccaggcatgg tggcatgcgc gtgaagtctt agctacttgg gaggctacgg   9127

tgggaggatg gcttgagctt aggagtttga ggttacagga agctatgatt gtgccactgc   9187

cctccagcct gggtgatgga gtaagaccat gtttcaaaaa caaaacaaaa aaaaaagaaa   9247

tgcaagttag accaatgaag tataatgtaa tgaaatacaa aaaattcatt gctatggttt   9307

caaattccca gtgcaattaa cctttaagat actacgtgtc aggcctctga gcccaaacta   9367

agccatcata tcccctgtga cctgcatgta tacatacaga tggcctgaag caactgaaga   9427

tccacaaaag aagtgaaaat agccttaact gatgacattc caccattgag atttgttcct   9487

gccccaccct aactgatacg atatattctc cccgcccctt aagaaggtac tttgtgatat   9547

tctccctgcc cttgagaatg tactttgtac gcctatccca aacctataag aactaatgat   9607

aatcccacca ccctttgttg actccttttt ag a ctc agc ccg cct gca ccc agg   9661
                                      Leu Ser Pro Pro Ala Pro Arg
                                          145                 150

tga aat ata cag cct tgt tgc tca cac aaa gcc tgt ttg gtg gtt tct     9709
    Asn Ile Gln Pro Cys Cys Ser His Lys Ala Cys Leu Val Val Ser
                    155                 160                 165

tca cac gga tgc atg tga cat ttg gtg ctg aag acc cag gac agg agg     9757
Ser His Gly Cys Met     His Leu Val Leu Lys Thr Gln Asp Arg Arg
                170                     175                 180

act cct ttg gga gac cag tgc cct gtt gtc gcc ctc act ccg tga gga     9805
Thr Pro Leu Gly Asp Gln Cys Pro Val Val Ala Leu Thr Pro     Gly
```

-continued

```
            185                 190                     195

gat cca cct atg atc tca ggt cct cag acc aac cag ccc aag gaa cat     9853
Asp Pro Pro Met Ile Ser Gly Pro Gln Thr Asn Gln Pro Lys Glu His
            200                 205                 210

ctt gcc aat ttc aaa tcg g gtaagtggtc ttttcactct tctccagcct          9902
Leu Ala Asn Phe Lys Ser
        215

ttcttgctac ccttcaatct tcctctctca ctacccttca atctccctgt ccttccaatt   9962

cccgttcttt ttcctctcta gtagagataa ggagacacat tttatctgtg gacccaaaac  10022

tccagcgtca gtcacggact cgggaagaca gtcttccctt ggtgtttaat cactgtgggg  10082

acgcctgcct gattattcac ccacactcca ttggtgtctg atcaccacgg ggatgcctgc  10142

cttggtcatt cacccacatt cccttggtga caagtcaatt gcggggacac ctgctttggc  10202

tgctcaccca cattgcagcc cagggctgct caatgccccc cgctgcccca cccgccttct  10262

ccgtgcctct accctctctt ttctcgggtt tacctccttc actatgggca accttccacc  10322

ctccattcct ccttcttctc ccttagcctg tgttctcaaa aacttaaaac ctcttcaact  10382

cacacctgac ctaaaaccta agtgtcttat tttcttctgc aacaccgctt ggccccaata  10442

caaactcgac aatgattcca aatagccaga aaacggcact ttcgagttct ccatcctaca  10502

agttctagat aattcttgtc ataaaatggg caaatggtct gaggtgcctg acgtccaggc  10562

attcttttac acattggtcc ctccctagtc tctgctccca atgtgactca tcccaaatct  10622

ttcttctttc tctcctttct gttccttcgg tctccacccc aagttccgag tcctctgaat  10682

ccttcttttc tatggactca tctgacctcc ccccttctcc ccaggctgct cctcgccagg  10742

ctgagccagg tcccaattct cacttagcct ctgctccccc accctataat cctttttatca  10802

cctcccctcc tcacacctgg tccagcttac agtttcgttc ctcgactagc tctccccgat  10862

ctgcccaaca atttcctgtt aaagagatgg ctgactatcc tgacttcatc agagcaggct  10922

ggtgcctggc cttcctggaa tgagtgggtg ttctgacagg cccccagttt gtcccatctg  10982

caccgccaag aggtctccgg gtggccagag gagcaaagtt gccttccaag tgcctgttgg  11042

tgcctgggag aacacagcag gagtgtcgtg cggcccacag cgcagtgcat ggtgattcca  11102

ggcgctgaac aactcccctt gacccttggg cctgcatctg actcccggct gcagaatcag  11162

aagctgagtc caggcaaccg ctcggccact cccggtcact cctctctgga cacccagtta  11222

ctaaagtcag caaagaagat gcggtaatca ccgcctgatc tccacatggt gaacacaaca  11282

ctctcactaa cacctccttg accagtcagt cttcagcact gggggtggac aggcaggttt  11342

tctgtgttta ccagaatcgc acaggctaag cacaaacatg gaaccagagt tccaggtgag  11402

gaaacctcac tcgcagaagc ccaggctgca ccccaccagg tgatgcagtg cgcctaggct  11462

gtgggtgcta ggagccaagt gctagggact cgtcatgagt gggaatcccc acgttcctgt  11522

cactgctgtc aaacagaagg taaacagtct tacgaatgta attccttagg aagacttgta  11582

caaactttta ttaggatatc tatttattta atactgaact ttggcctact ttgtgataag  11642

actataaaca aattgaggaa atcactattt ctcacttctg tatttctcaa aaaataattt  11702

tgttacagag ttcaatatac tgtgtactac tgatcttcta ttgtgaaagc aaagcatttc  11762

atcaaaacaa agtattttaa attatgagtg aaaattgtgt atgttaattt tgcagctgta  11822

atattaatca aactttgtgt aattctaatc acaaaatgat gtgccttaaa tgcccctcca  11882

gctgtgggtt ggcagtgtcc agacagggac cctgaaatcc tgaatgactg ctagaccaat  11942

tctattaaaa acatttcaag gcaaaaaaaa aaaaaaaaga ggtggctgga gctgaaggcg  12002
```

-continued

```
tagtcaaggt taatgctcct ttttcttcat ctgacctctc ccaatcagtt agcgtttagg  12062
ctgtttttca tcaaatataa aaacccagcc cagttcatgg cccatttggc aacaaccctt  12122
agatgcttta ccgccctaga cccagagggg ccagaaggcc gtcttattct caatatgcat  12182
tttattaccc aacccgctcc ggacattaga aaaagctcca aaaattagat tccagccctc  12242
aaaccccaca acaggactta attaacctca ccttcaaggt gtacagtaat agagtagagg  12302
caacatattt ctgagttgca attacttgcc tccactgtga gagaaacccc agccacatct  12362
ccagcacaca agaacttcaa aacacctgaa tcgcagcggc caggtgttcc tccaggaccg  12422
cctcccccag gatctttctt caagtgctgg aaatctggtc actgggccaa ggaatgcctg  12482
cagcctggga ttcctcctga gccatgtccc atctgtgcca gaccctactg gaaatcagac  12542
tgtccaactt acccaggagc cactcccaga gctgctggaa ctctggccca agactctctg  12602
actccttccc agatgttctc ggcttagcgg ctgaaaactg atgctgccca atcgcctcag  12662
aagcctcttg gaccatcaca gatgctttgg gtaactctta cagtgaaggg gaagtctgtc  12722
cccttcttaa tacagaggct acccactcca caataccttc ttttcaaggg cctgtttccc  12782
ttgcctccat aactgttgtg ggtattgatg gccaggctgc taaacctgtc aaaactcccc  12842
aactctggtg ccaacttgga caacattctt ttatacactc ttttttagtt atccctacct  12902
gcccagctcc cttattaggt caagacattt taaccaaatt atctgcttcc ctgactgttc  12962
ctggactaca gccacacctc attgccgccc ttttccccag ttcaaagcct ccttcgcatc  13022
ctccccttgt atctccccac cttaatccac aagtatggga cacctctatt ccctccttgg  13082
caaccgatca tgcacccctt accatcccat taaaacctaa tcacccttac ccccactcaat  13142
gccaatatcc catcccacag cacactttaa aaggatccca cagcacactt taaaaggatt  13202
aaagcctgtt atcactcgcc tgctatagca tggccttcta aagcctataa actctcctta  13262
caattccccc attttacctg tccaaaaacc agacaagtct tacaggttag ttcaggatct  13322
gtgccttatc aacaaaattg tcttgcctat gcaccccata gtgccaaacc catataccct  13382
cctatcctca atacctccct cccacaaccc attattctgt tctaaataaa cctagctgac  13442
cccataaatc ctaaatcctt tccccactcc cctttccatt ccttaaaaaa cagccctaaa  13502
agctgctccc acactagctc tccctaactc atcccaactt tttcattaca cacagccaaa  13562
gtgcagggct gtgtggtcgg aattcttaca caagagccag aagcatgccc tgtagccttt  13622
ctgtccaaac aacttgacct tactgtttta gcctagccct catgtctgtg tgtggtggct  13682
gctgctgctt tgatactttt agaggccctc aaaatcacat tatgctcaac tcactctcta  13742
cagttctata acttccaaaa tctattttct tcctcatacc tgacgcatat actttccact  13802
ccctggctcc ttcagctata ctcaactctt ttttgagaca gagtctcact ccgtctccca  13862
ggctggcatg cagtggcaca atcttggctc actgcaacct ccgcttccca ggttccagcg  13922
attctcctgc ctcagcctct ggagtagctg ggattacagg tgtgtgcccc acacccggct  13982
aatttttttgt atttttagta gagatggggt ttcaccatgt taaccaagct ggtcttgaac  14042
tcctgaccta aagtgatctg cccatctcgg cctcccaaag tgctgggatt acaggcatga  14102
gccaccacac ccagcctata ctcactcttt gctgagtctc ccacaattac cattgttcct  14162
ggcctggact tcaatccggc ctcccacatt attcctgata ccacacctga cctccatgac  14222
tatctctctg atccacctgg cattcactcc atttccccat atttccttct ttcctgttcc  14282
tcaccctgat cacacttggt ttattgatgg cagttccacc aggcctaatc gccattcacc  14342
```

```
ggcaaaggca ggctatgcta tactatcttc cacatctatc cttgaggcta ccgctctgcc  14402

ccgctccact acctctcagc aagccaaact cattgcctta actcgggccc tcactcttgc  14462

aaagggacta cgtgtcaata tttatactga ctctaaatat gcctttcata tcctccacca  14522

ccatgctgtt atatgggttg aaagaggttt cctcactatg caagggtcct tcatcattag  14582

tgcctcttta ataaaaactc ttctcaaggc tgctttactt ccaaaggaag ctggagtcat  14642

tcactgcaag ggccatcaaa aggcatcaga tcccatcact cagggcaacg cttatgctga  14702

taaggtagct aaagaagcag ctagcattcc aacttctgtc cctcagggcc agtttttctc  14762

cttcttatcg gtcactccca cctactccct cattgaaact tccacgtatc aatcttttcc  14822

cacacaaggc aaatggttct tggatcaagg aaaatatctc cttccagcct cacaggccca  14882

ttctattctg tcgtcatttc ataacctctt ccgtgtaggt tacaagccgc tagcccatct  14942

cttataacct ctcatttcat ttccatcgtg aaaatctgtc ctgaagaaaa tcacttctca  15002

gtgttcatct actattctac tatccctcag ggattgttca ggccccttcc cttccctaca  15062

catcaagctg ggaatttgc ccctgcccag gactggcaaa ttgactttac tgacatgtgc  15122

cgagtcagga aactaaaata cctcttggta tgggtagaca ctttcactgg atgggtacag  15182

gcctttccca cagggtgtga gaaggccacc acggtcattt cttcccttct gtcagacata  15242

attcctccat ttagccttgc cacctctata cagtgtgaaa acagaccggc ctttattagt  15302

caaatcaccc aagcagcttc tcagcctctt ggtatttagt ggctcctggt tttacctcaa  15362

aacaccaccc ttaaggctct cttgaagtgg atagatcttc agtggcaagg taccctccga  15422

tactttcacc ctgatgaagt cctattcttt acttttatac tcattcttat tctggttccc  15482

gatcttatgc caccctctac ctctccccag ctatctccac cacactatca atctcactct  15542

ctcctagccc cgtttataat ccttcttttt tttttgagat ggagtcttgc tctgtccccc  15602

aggctggagt gcagtggtgt gatcttggct cactgcaagc tccgcctcct gggttcacac  15662

cattctcctg cctcagcctc ccaagtagct gggactagag gtgcctgcca ccatgcctgg  15722

ctaatttttt gtatttttag tagagatggg gtttcaccat gttagccagg atggtctcca  15782

tctcctgacc tcacgatccg cccacctcag cctcccaaag tgctgggatt acaggcgtga  15842

gccactatgc ccggccctct aatccttctt taacaaacaa ctgctggctt tgcatttctc  15902

tttcctccaa aatcgccaag gcctcgactt actcactgct aaaaaaagag gaccctgtat  15962

atttttaaac gaagagtgtt gtttttacct aaatcaatct ggcctggtgt atgacaacat  16022

aaaaaaactc aaggatagac cccaaaaatt cgccaaccaa gcaaataatt atgctgaacc  16082

cccttgggca ctccctaatt ggatgtcctg ggtccttcca attcttagtc ctttaatacc  16142

tatttttctc tttctcttat tcggaccttg tgtcttcctt ctgtttagtt tctcaattca  16202

tacaaaactg catccaggcc atcaacaatc attctatacg acaaatactc cttctaacaa  16262

gcccacaata tcaccccttta tacccaaatc tttcttcagt ttaatctctc ctactctagg  16322

ttcccatgcc accccaatcc cactcaaagc agccccgaga aacatcgccc attatctctc  16382

cataccaccc ccaaaaattt tcgctgcctc aacacttcac cactattttg ttttgttttt  16442

catactaata taagaag at  agg agt gtc agg cct ctg agt cca agc taa     16491
                   Asp Arg Ser Val Arg Pro Leu Ser Pro Ser
                           220                 225

gcc atc aaa tcc cct gtg acc tgc acg tgt aca tcc aga tga cct gaa    16539
Ala Ile Lys Ser Pro Val Thr Cys Thr Cys Thr Ser Arg     Pro Glu
        230                 235                 240

gca act gaa gat cca caa aag aag tga aag tag cct taa ctg atg aca    16587
```

-continued

```
Ala Thr Glu Asp Pro Gln Lys Lys     Lys     Pro     Leu Met Thr
        245                 250                         255

ttc cac cat tgt gat ttg ttc ctg ccc cac gct aac tga tac cat ata    16635
Phe His His Cys Asp Leu Phe Leu Pro His Ala Asn     Tyr His Ile
                260                 265                     270

ttc ttc ccc cgc cct tga gaa tgt act ttg tac acc tat ccc aaa cct    16683
Phe Phe Pro Arg Pro     Glu Cys Thr Leu Tyr Thr Tyr Pro Lys Pro
                275                 280                     285

ata aga act aat gat aat cct acc acc ctt tgc tga ctc tct ttt tgg    16731
Ile Arg Thr Asn Asp Asn Pro Thr Thr Leu Cys     Leu Ser Phe Trp
                290                 295                     300

act cag ccc gcc tgc acc cag gtg aaa taa aca gcc ctg ttg ctc a      16777
Thr Gln Pro Ala Cys Thr Gln Val Lys     Thr Ala Leu Leu Leu
                305                     310


<210> SEQ ID NO 2
<211> LENGTH: 10
<212> TYPE: DNA
<213> ORGANISM: Artificial Sequence
<220> FEATURE:
<223> OTHER INFORMATION: antisense oligonucleotide

<400> SEQUENCE: 2

acatgcatcc                                                            10


<210> SEQ ID NO 3
<211> LENGTH: 10
<212> TYPE: DNA
<213> ORGANISM: Artificial Sequence
<220> FEATURE:
<223> OTHER INFORMATION: antisense oligonucleotide

<400> SEQUENCE: 3

acttacccga                                                            10


<210> SEQ ID NO 4
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 4

ctccgtgagg agatccacct a                                               21


<210> SEQ ID NO 5
<211> LENGTH: 24
<212> TYPE: DNA
<213> ORGANISM: Artificial Sequence
<220> FEATURE:
<223> OTHER INFORMATION: antisense oligonucleotide

<400> SEQUENCE: 5

ctccgtgagg agatccacct actg                                            24


<210> SEQ ID NO 6
<211> LENGTH: 16
<212> TYPE: DNA
<213> ORGANISM: Artificial Sequence
<220> FEATURE:
<223> OTHER INFORMATION: Consensus promoter
<220> FEATURE:
<221> NAME/KEY: misc_feature
<222> LOCATION: (7)..(10)
<223> OTHER INFORMATION: n is a, c, g, or t
```

-continued

<400> SEQUENCE: 6
tramcynnnn tramcy 16

<210> SEQ ID NO 7
<211> LENGTH: 24
<212> TYPE: DNA
<213> ORGANISM: Homo sapiens

<400> SEQUENCE: 7
gcgatgaccg gcagtaaccc cggc 24

<210> SEQ ID NO 8
<211> LENGTH: 24
<212> TYPE: DNA
<213> ORGANISM: Mus musculus

<400> SEQUENCE: 8
acagtgaccg ccagtaaccc cagc 24

<210> SEQ ID NO 9
<211> LENGTH: 25
<212> TYPE: DNA
<213> ORGANISM: Homo sapiens

<400> SEQUENCE: 9
gtctgtgacc ggcagtaacc ccggc 25

<210> SEQ ID NO 10
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 10
tacacctatc ccaaacctat a 21

<210> SEQ ID NO 11
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 11
gagattcttt gtgggctctt a 21

<210> SEQ ID NO 12
<211> LENGTH: 21
<212> TYPE: DNA
<213> ORGANISM: Artificial Sequence
<220> FEATURE:
<223> OTHER INFORMATION: antisense oligonucleotide

<400> SEQUENCE: 12
cccacgctaa ctgataccat a 21

<210> SEQ ID NO 13
<211> LENGTH: 25
<212> TYPE: DNA
<213> ORGANISM: Artificial Sequence
<220> FEATURE:
<223> OTHER INFORMATION: siRNA

<400> SEQUENCE: 13
aaggaacauc uugccaauuu caaat 25

<210> SEQ ID NO 14
<211> LENGTH: 25
<212> TYPE: DNA
<213> ORGANISM: Artificial Sequence
<220> FEATURE:
<223> OTHER INFORMATION: siRNA

<400> SEQUENCE: 14
ugccccacgc uaacugauac cauat 25

<210> SEQ ID NO 15
<211> LENGTH: 10
<212> TYPE: DNA
<213> ORGANISM: Artificial Sequence
<220> FEATURE:
<223> OTHER INFORMATION: antisense oligonucleotide

<400> SEQUENCE: 15
tatacgcgca 10

<210> SEQ ID NO 16
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 16
aggggagtac gctagacttg tctga 25

<210> SEQ ID NO 17
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 17
ggcttgagct agagataaaa cagaa 25

<210> SEQ ID NO 18
<211> LENGTH: 25
<212> TYPE: DNA
<213> ORGANISM: Artificial Sequence
<220> FEATURE:
<223> OTHER INFORMATION: siRNA

<400> SEQUENCE: 18
gctattacaa catcacactg gccaa 25

<210> SEQ ID NO 19
<211> LENGTH: 21
<212> TYPE: DNA
<213> ORGANISM: Artificial Sequence
<220> FEATURE:
<223> OTHER INFORMATION: siRNA

<400> SEQUENCE: 19
ccagaggagg uacuacaaat t 21

<210> SEQ ID NO 20
<211> LENGTH: 25
<212> TYPE: DNA

<213> ORGANISM: Artificial Sequence
<220> FEATURE:
<223> OTHER INFORMATION: siRNA

<400> SEQUENCE: 20
cagcuuauca acaaccaaga cagtg 25

<210> SEQ ID NO 21
<211> LENGTH: 21
<212> TYPE: DNA
<213> ORGANISM: Artificial Sequence
<220> FEATURE:
<223> OTHER INFORMATION: siRNA

<400> SEQUENCE: 21
gccuuugaua uaccagaaut t 21

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22
ccacgctgct gaacatgct 19

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
tcgaacacct gctggatgac 20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
gggtgtgaac catgagaagt 20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
ccttccacga taccaaagtt 20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
ccaggagtca gcaaaacaca 20

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ctgggtcttc agcaccaaat 20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
tgcccacctc ttcggatatc 20

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
gatgtgccag cggtactcac t 21

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
gacgccaaga tgcacaagtc 20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
accagactgc ctaggtcgat 20

<210> SEQ ID NO 32
<211> LENGTH: 23
<212> TYPE: DNA
<213> ORGANISM: Artificial Sequence
<220> FEATURE:
<223> OTHER INFORMATION: primer

<400> SEQUENCE: 32
tcagcgaggc ggctttggag cag 23

<210> SEQ ID NO 33
<211> LENGTH: 21
<212> TYPE: DNA
<213> ORGANISM: Artificial Sequence
<220> FEATURE:

<223> OTHER INFORMATION: primer

<400> SEQUENCE: 33
catgtcttcg atgtcggtca g 21

<210> SEQ ID NO 34
<211> LENGTH: 19
<212> TYPE: DNA
<213> ORGANISM: Artificial Sequence
<220> FEATURE:
<223> OTHER INFORMATION: primer

<400> SEQUENCE: 34
cgctcctcca tcaatgaca 19

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
tgcgcaagac agcagattta 20

<210> SEQ ID NO 36
<211> LENGTH: 30
<212> TYPE: DNA
<213> ORGANISM: Artificial Sequence
<220> FEATURE:
<223> OTHER INFORMATION: primer

<400> SEQUENCE: 36
cctgactgaa aggctgcgtg agaagatatc 30

<210> SEQ ID NO 37
<211> LENGTH: 23
<212> TYPE: DNA
<213> ORGANISM: Artificial Sequence
<220> FEATURE:
<223> OTHER INFORMATION: primer

<400> SEQUENCE: 37
gggtagcagc aggctaagat gca 23

<210> SEQ ID NO 38
<211> LENGTH: 21
<212> TYPE: DNA
<213> ORGANISM: Artificial Sequence
<220> FEATURE:
<223> OTHER INFORMATION: primer

<400> SEQUENCE: 38
gatgtgggaa ttgttgccct t 21

<210> SEQ ID NO 39
<211> LENGTH: 23
<212> TYPE: DNA
<213> ORGANISM: Artificial Sequence
<220> FEATURE:
<223> OTHER INFORMATION: primer

<400> SEQUENCE: 39
attgtctctg ttccaacttc cag 23

<210> SEQ ID NO 40
<211> LENGTH: 22
<212> TYPE: DNA
<213> ORGANISM: Artificial Sequence
<220> FEATURE:
<223> OTHER INFORMATION: primer

<400> SEQUENCE: 40
aggctgtggg ctccatcgcc ta 22

<210> SEQ ID NO 41
<211> LENGTH: 23
<212> TYPE: DNA
<213> ORGANISM: Artificial Sequence
<220> FEATURE:
<223> OTHER INFORMATION: primer

<400> SEQUENCE: 41
agtcagtcca gtacatgaag cca 23

<210> SEQ ID NO 42
<211> LENGTH: 21
<212> TYPE: DNA
<213> ORGANISM: Artificial Sequence
<220> FEATURE:
<223> OTHER INFORMATION: primer

<400> SEQUENCE: 42
ggtaacgatg gtgtcgaggt c 21

<210> SEQ ID NO 43
<211> LENGTH: 24
<212> TYPE: DNA
<213> ORGANISM: Artificial Sequence
<220> FEATURE:
<223> OTHER INFORMATION: primer

<400> SEQUENCE: 43
ccagcattac agttcttgaa catg 24

<210> SEQ ID NO 44
<211> LENGTH: 5954
<212> TYPE: PRT
<213> ORGANISM: Homo sapiens

<400> SEQUENCE: 44

```
Lys Lys Ala Lys Lys Ser Asp Thr Lys Asn Tyr Ile Ser Tyr Asp Phe
1               5                   10                  15

Ile Tyr Tyr Glu Met Ser Arg Met Gly His Leu Glu Thr Glu Ser Ser
            20                  25                  30

Val Val Ala Arg Asp Trp Gly Lys Gly Cys Gln Cys Ala Trp Val Leu
        35                  40                  45

Trp Gly Val Met Lys Met Phe Phe Arg Ile Leu Val Arg Val Ala Cys
    50                  55                  60

Leu Cys Glu Tyr Thr Lys Asn Val Cys Ile Ile His Lys Ser Asn Phe
65                  70                  75                  80

Met Val Tyr Lys Leu Tyr Leu Asp Lys Lys Leu Tyr Phe Lys Lys Pro
                85                  90                  95

Ser Cys Phe Thr Thr Ser Cys Ser Asp Thr Asn Pro Asn Ile Leu Ser
            100                 105                 110

Thr Asp Glu Asn Lys Phe Phe Asp Arg Lys Cys Ser Ile Phe Ser Leu
        115                 120                 125
```

-continued

```
Ser Leu Phe Phe Phe Phe Phe Glu Ile Glu Ser His Ser Val Val Gln
    130                 135                 140

Ala Gly Val Gln Trp His Val Leu Cys Ser Leu Gln Pro Leu Pro Pro
145                 150                 155                 160

Gly Phe Lys Arg Val Ser Cys Leu Ser Leu Pro Ser Ser Asp Tyr Arg
                165                 170                 175

His Leu Pro Leu Cys Leu Ala Asn Phe Cys Ile Phe Ser Arg Asp Gly
            180                 185                 190

Val Ser Pro Cys Trp Pro Gly Trp Ser Arg Ala Pro Asn Val Lys Ser
        195                 200                 205

Ala His Phe Gly Leu Pro Lys Cys Trp Asp Tyr Arg His Glu Thr Pro
    210                 215                 220

His Pro Val His Val Leu Leu Ile Met Gln Cys Ser Leu Ser Gln Thr
225                 230                 235                 240

Ser Lys Gly Gln Arg Leu Ala Thr Glu Lys Ala Ser Cys Tyr Lys Leu
                245                 250                 255

Glu Tyr Asn Met Thr Ile Trp Leu Tyr Gln Val Thr Trp Lys Asn Arg
            260                 265                 270

Asp Thr Met Phe Tyr Ile Leu Lys Gly Phe Arg Gln Leu His Lys His
        275                 280                 285

Arg Pro Asn Phe Leu Leu Ser Gly Lys Leu Lys Phe Val His Gln Thr
    290                 295                 300

Cys Gly Tyr Asn His Asn Asn Asn Asn Asn Ile Tyr Ser Trp Ala Leu
305                 310                 315                 320

Tyr Met Leu Gly Ser Val Leu Ser His His Ile Arg Ser Arg Cys Tyr
                325                 330                 335

Cys Tyr Leu Asp Phe Thr Asp Glu Val Thr Glu Phe Thr Trp Arg Lys
            340                 345                 350

Ser Cys Glu Lys Met Cys Asn Val Ala Met Ile Trp Phe Gln Thr Tyr
        355                 360                 365

Gly Leu Asn Tyr Trp Leu Tyr Trp Val Trp Ser Arg Gln Thr Arg Tyr
    370                 375                 380

Val Val Ile Cys His Met Ser Asn Cys Met Pro Gly Asn Ile Gln Leu
385                 390                 395                 400

Tyr Ser Glu Ala Lys Pro Gly Asp Val Thr Leu Leu Pro Gly Trp Gln
                405                 410                 415

Trp Gln Gly Ala Val Leu His Lys Gln Gln Met His Pro Leu Phe Arg
            420                 425                 430

Lys Asn Pro Ala His Ser Thr Ser Pro Val Leu Thr Phe Ser His Thr
        435                 440                 445

Trp Val Leu Ser Phe Pro Leu Lys Pro Ile Arg Thr Gln His Phe Leu
    450                 455                 460

Ser Thr Phe Pro Lys Leu His Phe Thr Leu Leu Asp Cys Glu Leu Leu
465                 470                 475                 480

Lys Ser Ile Phe Leu Phe Gln Lys Cys Leu Pro Ala Pro Lys Gln Ser
                485                 490                 495

Ala Leu Glu Met Thr Glu Ala His Val Leu Leu Ile Leu Ser Leu Leu
            500                 505                 510

Gln Thr Val Asn Val Thr Gly Ser Arg Ser His Ile Leu Pro Val Val
        515                 520                 525

Asn Phe Pro Cys Cys Arg Gln Ser Ala Asp Ser Cys Thr Leu Thr Leu
    530                 535                 540

Glu Gln Met Pro Gln Ala Leu Ile Ala Gly Ser Lys Glu Leu Arg Phe
```

-continued 545 550 555 560

His Thr Gly Val Ala Gly Gly Arg Ser Leu Pro Thr Phe Arg Thr Arg
565 570 575

Thr Cys Pro Ser Pro Thr Arg Ser Arg Pro Ala Ser Tyr Thr Leu Ala
580 585 590

Thr Glu Arg Ser Gln Arg Leu Ser Val Cys Met Pro Gly Leu Thr Val
595 600 605

Val Leu Gly Pro Gly Glu Asp Leu Leu Arg Gly Ala Glu Gly Ala Leu
610 615 620

Ser Leu Leu Ala Ile Phe His Gly Glu Gln Ser Val Thr Arg Thr Met
625 630 635 640

Pro Asp Phe Lys Lys Gln Arg Gly Lys Trp Lys Lys Ala Ala Glu Asp
645 650 655

Ser Glu Leu Leu Phe Leu Ile Ser Phe Leu Glu Asn Tyr Gly Gln Gln
660 665 670

Glu Gly Leu Thr Phe Ser Val Ser Leu Phe Ala Arg Glu Arg Glu Arg
675 680 685

Glu Arg Glu Arg Glu Ile His Phe Asn Glu Thr Ile His Thr Ile Asn
690 695 700

Pro Leu Tyr Leu Leu Arg Gly Ser His Tyr Ile Ala Gln Ala Gly Leu
705 710 715 720

Lys Leu Leu Gly Ser Ser Asp Pro Pro Pro Leu Ala Ser Gln Ser Ala
725 730 735

Gly Met Thr Gly Val Ser His Arg Ala Arg Leu Asn Pro Phe Tyr Phe
740 745 750

Ile Tyr Leu Phe Asp Arg Val Leu Leu Leu Ser Pro Arg Leu Glu Cys
755 760 765

Asn Gly Met Ile Ser Asp His Cys Asn Leu Arg Leu Pro Gly Ser Asn
770 775 780

Asp Ser Pro Ala Ser Ala Ser Val Ala Gly Ile Thr Gly Thr Cys His
785 790 795 800

His Ala His Leu Phe Phe Ser Phe Phe Leu Ser Phe Phe Phe Phe Phe
805 810 815

Glu Arg Trp Gly Phe Thr Thr Leu Ala Arg Leu Val Ser Asn Ser Pro
820 825 830

Gln Val Ile Arg Pro Pro His Pro Leu Lys Val Leu Gly Leu Gln Val
835 840 845

Ala Thr Val Pro Gly Arg Thr Asn His Phe Lys Leu Thr Ser Ser Val
850 855 860

Ala Leu Ser Ala Phe Ile Thr Leu Cys Lys His Tyr Leu Leu Phe Asn
865 870 875 880

Ile Phe Thr Pro Lys Glu Asn Leu Asn Pro Phe Asn Ser Asp Ser Pro
885 890 895

Ser Ser His Pro His Ser Ala Pro Gly Asp His Gln Ser Ala Phe Cys
900 905 910

Leu Cys Gly Phe Thr Thr Ser Gly Tyr Phe Leu Tyr Met Glu Ser Tyr
915 920 925

Asn Ile Pro Ser Val Ser Gly Phe Leu Leu Leu Ala Ser Phe Asn Val
930 935 940

His Pro His Trp Ser Ile Tyr Gln Tyr Phe Ile Pro Val Tyr Tyr Leu
945 950 955 960

Phe Ile Phe His Cys Met Asn Thr Pro Gln Leu Val Tyr Phe Ile Asn
965 970 975

```
Thr Leu Glu Leu Leu Pro Pro Phe Gly Tyr Cys Glu His Cys His Glu
            980                 985                 990

His Leu Ser Ala Asn Met Ser Thr  Arg Leu Phe Ile Arg  Val Tyr Ile
        995                 1000                 1005

Glu Trp  Ser Cys Trp Ala Arg  Cys Phe Asp Ile Pro  Phe Val Ala
    1010                 1015                 1020

Pro Ser  Asn Cys Phe Pro Ser  Gly Cys Thr Thr Leu  Asn Phe Leu
    1025                 1030                 1035

Gln Gln  Cys Met Arg Val Thr  Leu Phe Leu Thr Cys  Thr His Leu
    1040                 1045                 1050

Ser Leu  Ser Ser Phe Leu Leu  Phe Thr Lys Pro Val  Pro His Arg
    1055                 1060                 1065

Leu Leu  Phe Pro Leu Glu Arg  Val Gly Glu Val Ala  Ser Leu Val
    1070                 1075                 1080

Glu Arg  Leu Ser Lys Pro Pro  Phe Leu Pro Phe Pro  Gln Ile Glu
    1085                 1090                 1095

Tyr Gly  Asp Gln Glu Glu Glu  Arg Thr Gly Cys His  Leu Pro Val
    1100                 1105                 1110

Val Thr  Lys Val His Pro Leu  Gln Pro Leu Thr Arg  Leu Arg Lys
    1115                 1120                 1125

Thr Thr  Leu Leu Ala Thr Ser  Asn Ala Ser Val Leu  Thr Gln Asn
    1130                 1135                 1140

Ile Thr  Leu Asn Phe Ser Thr  Val Thr Asp Arg Lys  Gly Leu Gly
    1145                 1150                 1155

Val Glu  Gly Ala Ser Ser Gly  Ser Ala Leu Arg Val  Ser Val Leu
    1160                 1165                 1170

Ser Ala  Gln Leu Lys Ile Ser  Glu Asp Thr His Arg  Leu Val Leu
    1175                 1180                 1185

Pro Ser  Pro Leu Arg Arg Ala  Gly Leu Pro Gly Pro  Gly Trp Gln
    1190                 1195                 1200

Leu Thr  Met Glu Arg Lys Arg  Leu Pro Leu His Pro  Leu Ser Pro
    1205                 1210                 1215

Gly Leu  Leu Pro Val Thr Asp  Pro Gly Leu Gln Glu  Leu Phe Thr
    1220                 1225                 1230

Pro Thr  Thr Ala His Gln Arg  Leu Thr Thr Pro Glu  Pro Ile Ser
    1235                 1240                 1245

Gly Pro  Gln Ala Cys Leu Ile  Leu Ser Ala Pro Ile  Arg Arg Arg
    1250                 1255                 1260

Gly Pro  Ser Ser Leu Leu Leu  Leu Ile Thr Gly Arg  Arg Glu Pro
    1265                 1270                 1275

Phe Phe  Leu Phe Phe Phe Phe  Pro Gly Ser Arg Pro  Arg Gly Ser
    1280                 1285                 1290

Ala Leu  Leu Pro Gln Ser Ala  Leu Pro Trp Asn Gly  Glu Asn Ala
    1295                 1300                 1305

Asp Met  Pro Leu Ser Pro Ala  Ala Asn Ser Ala Pro  Glu Leu Arg
    1310                 1315                 1320

Glu Phe  Ser Arg Arg Val Glu  Ile Ala Phe Pro Ala  Arg Arg Gly
    1325                 1330                 1335

Pro Ile  Ala Ser Leu Leu Gly  Arg Gln Met Arg Arg  Phe Ser Arg
    1340                 1345                 1350

Leu His  Gly Gln Pro Leu Pro  His Asn Pro Arg Phe  Phe Val Gly
    1355                 1360                 1365
```

-continued

```
Ser Ser  Ile Ala Ala Phe Glu  Val Val Thr Leu Leu  Thr Arg Thr
    1370                 1375                 1380

Ala Gln  Ala Glu Leu Ile Phe  Ile Pro Val Cys Asn  Arg Ala Lys
    1385                 1390                 1395

Thr Pro  Leu Met Glu Lys Pro  Glu Arg Gln Glu Ser  Ala Lys His
    1400                 1405                 1410

Thr Lys  Asp Trp Ala Val Thr  Gly Glu Asn Val Ser  Lys Ser Thr
    1415                 1420                 1425

Gly Thr  Ala Lys Arg Ser Gly  Thr Phe Glu Ala Asp  Ala Thr Gly
    1430                 1435                 1440

Ala Gly  Arg Trp Cys Val Val  Gly Glu Trp Glu Glu  Thr Val Glu
    1445                 1450                 1455

Ser Leu  Asp Leu Leu Leu Val  Ile Arg Ser His Gln  Ile Phe Ser
    1460                 1465                 1470

Ser Arg  Arg Gly Lys Ser Leu  Cys Phe Ala Lys Leu  Thr Leu Met
    1475                 1480                 1485

Ala Thr  Glu Gln Ser Ser Gly  Gly Met Gly Ala Gly  Arg Cys Trp
    1490                 1495                 1500

Glu Ala  Ile Val Thr Thr Leu  Val Lys Ser His Gly  Thr Ser Lys
    1505                 1510                 1515

Ala Gly  Ile Val Thr Val Gly  Met Glu Arg Lys Gly  Thr Ser Glu
    1520                 1525                 1530

Ala Phe  Gly Arg Arg Ile Asn  Ser Thr Leu Leu Thr  Gly Cys Val
    1535                 1540                 1545

Arg Val  Arg Thr Ala Ile Arg  Arg Gly Leu Gly Phe  Pro Glu Trp
    1550                 1555                 1560

Leu Glu  Gly His His Phe Pro  Tyr Leu Lys Val Ala  Lys Arg Arg
    1565                 1570                 1575

Glu Lys  Glu Arg Ser Arg Gly  Ile Leu Gln Arg Glu  Glu Phe Ser
    1580                 1585                 1590

Phe His  Val Ala Phe Glu Leu  Gln Glu Val His Pro  Cys Gly Cys
    1595                 1600                 1605

Asn Thr  Gln Thr Val Gly Asn  Asp Leu Val Ser Arg  Arg Lys Val
    1610                 1615                 1620

Glu Met  Arg Ser Lys Gly Phe  Ile Val Asp Arg Glu  Arg Asn Pro
    1625                 1630                 1635

Lys Glu  Lys Leu Asn Lys Lys  Ile Trp Ala Gly His  Gly Gly Ser
    1640                 1645                 1650

Cys Leu  Ser Gln His Phe Gly  Arg Pro Arg Glu Asp  Cys Leu Ser
    1655                 1660                 1665

Pro Gly  Val Asp Gln Pro Gly  Gln His Gly Glu Thr  Pro Thr Leu
    1670                 1675                 1680

Gln Lys  Leu Gln Lys Leu Ala  Gly Cys Gly Asp Thr  Tyr Leu Phe
    1685                 1690                 1695

Gln Leu  Leu Gly Arg Leu Arg  Trp Gly Asp His Leu  Ser Leu Gly
    1700                 1705                 1710

Arg Ser  Arg Leu Gln Ala Glu  Ile Val Pro Leu His  Ser Asn Leu
    1715                 1720                 1725

Gly Asn  Ile Ala Arg Ala Arg  Pro Cys Leu Lys Ser  Lys Lys Lys
    1730                 1735                 1740

Lys Arg  Arg Phe Lys Tyr Arg  Ile Leu Gly Arg Lys  Glu Asp Thr
    1745                 1750                 1755

Glu Ala  Arg Cys Gly Gly Ser  Cys Leu Ser Gln His  Phe Gly Arg
```

-continued

```
    1760                1765                1770

Gly Gly  Trp Ile Ile Gly Gln  Glu Phe Lys Thr Ser  Leu Ala Asn
    1775                1780                1785

Met Val  Lys Pro Cys Phe Tyr  Lys Leu Ser Arg His  Gly Gly Gly
    1790                1795                1800

Arg Leu  Leu Ile Pro Ala Ser  Arg Glu Ala Glu Val  Gly Glu Trp
    1805                1810                1815

Leu Glu  His Arg Arg Gln Arg  Leu Gln Ala Glu Ile  Val Pro Leu
    1820                1825                1830

His Ser  Ser Leu Gly Asn Arg  Val Arg Leu Cys Leu  Lys Lys Lys
    1835                1840                1845

Lys Lys  Lys Lys Glu Asp Thr  Glu Leu Ala Lys Gln  Thr Lys Lys
    1850                1855                1860

Tyr Gln  Lys Asp Met Lys Asn  Lys Lys Ala Asn Tyr  Asp Thr Val
    1865                1870                1875

Ile Glu  Ile Arg Lys Phe Gln  Glu Glu Glu Ala Gly  His Cys Leu
    1880                1885                1890

Cys Met  Tyr Lys Thr Val Arg  His Trp Leu Asn Lys  Leu Ser Ile
    1895                1900                1905

His Leu  Ile Glu Tyr Ser His  Asn Tyr Val Ala Lys  Leu Tyr Asn
    1910                1915                1920

Cys His  Lys Glu Met Phe Asn  Ala Ser Phe Phe Pro  Gln Cys Ile
    1925                1930                1935

Leu Glu  Thr Leu Arg Leu Lys  Asn Ser Ile Tyr Ala  Gly His Gly
    1940                1945                1950

Gly Ser  Arg Leu Ser His Phe  Gly Arg Leu Arg Gln  Val Asp His
    1955                1960                1965

Glu Val  Arg Ser Leu Arg Pro  Pro Trp Pro Met Asn  Pro Val Ser
    1970                1975                1980

Thr Lys  Asn Thr Lys Leu Ala  Arg His Gly Gly Arg  Cys Leu Ser
    1985                1990                1995

Gln Leu  Leu Gly Arg Leu Arg  Gln Glu Asn His Leu  Asn Leu Gly
    2000                2005                2010

Gly Arg  Cys Cys Ser Glu Gln  Arg Leu Cys His Cys  Thr Pro Ala
    2015                2020                2025

Gln Val  Thr Met Arg Asp Ser  Ile Ser Lys Lys Lys  Val Tyr Ile
    2030                2035                2040

Tyr Val  Cys Ile Tyr Met Tyr  Ile Tyr Val Tyr Ile  Cys Ile Tyr
    2045                2050                2055

Val Cys  Ile Tyr Val Tyr Met  Cys Val Tyr Met Tyr  Ile Cys Val
    2060                2065                2070

Tyr Met  Tyr Ile Tyr Val Tyr  Ile Cys Val Tyr Met  Cys Ile Tyr
    2075                2080                2085

Val Tyr  Ile Cys Val Tyr Met  Cys Val Tyr Met Cys  Val Tyr Met
    2090                2095                2100

Cys Ile  Tyr Val Cys Ile Tyr  Val Tyr Met Cys Ile  Tyr Val Cys
    2105                2110                2115

Ile Tyr  Ala Tyr Ile Cys Val  Tyr Ile Cys Ile Tyr  Met Cys Val
    2120                2125                2130

Tyr Met  Tyr Ile Leu Tyr His  Phe Lys Leu His Met  Leu Gln Lys
    2135                2140                2145

Gly Met  Arg Arg Leu Gly Gly  Ser Cys Leu Ser Gln  His Phe Gly
    2150                2155                2160
```

```
Arg Pro  Arg Gln Ala Asp His  Leu Arg Ser Gly Val  Asp Gln Pro
    2165                 2170                 2175

Ser Gln  Leu Leu Tyr Lys Ile  Glu Gln Phe Leu Tyr  Phe Val Lys
    2180                 2185                 2190

Ile Gln  Lys Leu Ala Arg Cys  Gly Ser Thr Cys Leu  Ser His Leu
    2195                 2200                 2205

Leu Arg  Arg Leu Arg Gln Glu  Asn Pro Leu Asn Pro  Arg Gly Gly
    2210                 2215                 2220

Gly Cys  Ser Glu Leu Arg Leu  His His Cys Thr Thr  Ala Trp Val
    2225                 2230                 2235

Thr Glu  Asp Thr Val Ser Lys  Lys Lys Lys Ala Gly  Asn Phe Asp
    2240                 2245                 2250

Glu Gly  Thr Val Leu Tyr Val  Cys Gly Asn Val Tyr  Thr Ala Leu
    2255                 2260                 2265

Tyr Asn  Tyr Pro Lys Ser Ser  Gly Arg Arg Pro Pro  Leu Ile Leu
    2270                 2275                 2280

Ser Tyr  Ala Gln Phe Leu Pro  Pro Lys Lys Glu Glu  Val Lys Thr
    2285                 2290                 2295

Arg Gln  Lys Asn Pro Gln Ala  Asp Ser Pro Ala Pro  His Pro Gly
    2300                 2305                 2310

Pro Gly  Ser Arg Ser Thr Pro  Asp Leu Ile Ser Tyr  Val Ile Ser
    2315                 2320                 2325

Lys Leu  Gln Ser Leu Cys Gly  Lys Ala Leu Lys Ser  Leu Ser Cys
    2330                 2335                 2340

Ser Val  Leu Phe Leu Pro Val  His Ala Ala Pro Ser  His Ile Pro
    2345                 2350                 2355

Leu Ala  Cys Ser Ile Asp Gln  Asp Pro Phe Thr Arg  Thr Pro Leu
    2360                 2365                 2370

Glu Leu  Ser Ala Leu Lys Arg  Asp Arg Asn Cys Leu  Leu Arg Glu
    2375                 2380                 2385

Leu Gly  Phe Asp Val Ser Leu  Ala Asp Ala Pro Gly  Gln Ile Lys
    2390                 2395                 2400

Pro Phe  Leu Leu Leu Gly Val  Gly Val Leu Ser Ala  Ala Arg Pro
    2405                 2410                 2415

Ala Thr  Leu Lys Leu Glu Phe  Leu Lys Phe Leu Phe  Phe Ile Leu
    2420                 2425                 2430

Phe Ile  Phe Phe Arg Leu Ser  Leu Thr Leu Ser Ser  Arg Leu Glu
    2435                 2440                 2445

Cys Asn  Gly Met Leu Ser Ala  His Cys Asn Leu His  Leu Pro Gly
    2450                 2455                 2460

Ser Ser  Asp Ser Pro Ala Ser  Ala Pro Gly Val Ala  Gly Ile Thr
    2465                 2470                 2475

Gly Val  Gln His His Ala Gln  Leu Ile Phe Val Phe  Leu Val Glu
    2480                 2485                 2490

Thr Gly  Phe His His Val Gly  Gln Ala Gly Leu Glu  Leu Leu Thr
    2495                 2500                 2505

Ser Gly  Asp Leu Pro Thr Ser  Ala Ser Gln Ser Ala  Gly Ile Thr
    2510                 2515                 2520

Gly Met  Arg His His Ala Gln  Leu Asn Ala Leu Ile  Leu Thr Arg
    2525                 2530                 2535

Gly Gly  Leu Leu Met Val Pro  Thr Ser Gln Arg Cys  Pro Gly Asp
    2540                 2545                 2550
```

-continued

```
Met Ala  Asp Gln Ser Ile Leu  Pro Gly Ile Glu Gly  Leu Asn Gln
    2555                 2560                 2565

Arg Arg  Glu Gly Pro Arg Thr  Thr Ala Arg Arg Arg  Arg Asp Trp
    2570                 2575                 2580

Glu Gln  Gly Pro Glu Tyr Gly  Arg Pro His Leu Gly  Leu Asn Lys
    2585                 2590                 2595

Thr Thr  Asn Lys Lys Thr Leu  Glu Trp Val Gln Thr  Lys Arg Lys
    2600                 2605                 2610

Val Glu  Lys Leu Lys Thr Leu  Arg Leu Lys Lys Gly  Ser Gly His
    2615                 2620                 2625

Gly Asp  Ser Cys Leu Ser Gln  His Phe Glu Arg Pro  Thr Glu Asn
    2630                 2635                 2640

Cys Leu  Ser Pro Gly Val Gln  Asp Gln Pro Gly Gln  His Thr Glu
    2645                 2650                 2655

Thr Leu  Ser Leu Gln Lys Ile  Lys Asn Asn Trp Asp  Val Val Val
    2660                 2665                 2670

His Val  Cys Gly Pro Ser Tyr  Leu Gly Gly Gly Gly  Arg Ile Ala
    2675                 2680                 2685

Ala Glu  Val Ala Ala Leu Val  Ser His Asn His Thr  Thr Val Val
    2690                 2695                 2700

Pro Pro  Gly Gln Ser Glu Thr  Val Ser Lys Lys Lys  Lys Gly Gly
    2705                 2710                 2715

Gly Arg  Phe Met Arg Asp Leu  Gly Ser Leu Arg Ile  His Lys Gly
    2720                 2725                 2730

Asn Lys  Pro Ile Pro Tyr Cys  Pro Glu Gly Ile Lys  Glu Asn Tyr
    2735                 2740                 2745

Val Gly  Met Arg Ala Ser Met  Ala Met Asp Arg Lys  Ala Ala Gln
    2750                 2755                 2760

Ile Thr  Ala Val Leu Gln Cys  Leu Gly Arg Asn Lys  Leu Leu Leu
    2765                 2770                 2775

Ser Pro  Tyr Leu Phe Asn Ser  Ser Lys Ile Leu Thr  Cys Ser Met
    2780                 2785                 2790

Gly Asp  Asn Gly Leu Asp Thr  Ser Val Pro Pro Ser  Phe Lys Thr
    2795                 2800                 2805

Met Ile  Ser Thr Ser Lys Leu  Phe Asn Gln Thr Gly  Asn Arg Ser
    2810                 2815                 2820

Tyr Val  Ile Phe Ser Leu Trp  Asn Gly Cys Gln Ser  His Leu Phe
    2825                 2830                 2835

Leu Ser  Ser Phe Pro Phe Leu  His Gly Phe Asp Gln  Ile Cys Leu
    2840                 2845                 2850

Ser Cys  Leu Tyr Asp Leu Asp  Val Ser Leu Lys Ser  Tyr Leu Ala
    2855                 2860                 2865

Asp Lys  Tyr Leu His Phe Val  Gly Arg Trp Lys Phe  Asn Tyr Leu
    2870                 2875                 2880

Val Leu  Met Ala Val Leu Phe  Cys Phe Val Leu Phe  Phe Glu Thr
    2885                 2890                 2895

Glu Ser  Arg Ser Val Ala Arg  Leu Glu Cys Ser Gly  Val Ile Leu
    2900                 2905                 2910

Ala Asn  Cys Asn Leu Arg Leu  Pro Gly Ser Ser Asn  Ser Pro Ala
    2915                 2920                 2925

Ser Ala  Phe Arg Val Ala Gly  Thr Thr Cys Val Pro  Thr Thr Pro
    2930                 2935                 2940

Gly Phe  Phe Ile Phe Ser Arg  Asp Arg Val Ser Pro  Tyr Trp Pro
```

```
    2945                2950                2955

Gly Trp  Ser Ser Pro Asp Leu  Val Ile Cys Pro Pro  Trp Pro Pro
    2960                2965                2970

Glu Val  Leu Gly Leu Gly Ala  Thr Met Pro Gly Pro  Cys Phe Leu
    2975                2980                2985

Leu Tyr  Phe Ile Ser Ile Ser  Phe Ile Leu His Thr  Met Val Gln
    2990                2995                3000

Arg Asn  His Ala Arg Ser Gln  Cys Asp Pro Val Ser  Ser Thr Gly
    3005                3010                3015

Ser Thr  Thr Met Tyr Gly Phe  Gly Glu Arg His Leu  Cys Arg Gly
    3020                3025                3030

Phe Arg  Cys Val Val His Gly  Pro Leu Ser Val Pro  Gln Ile Ile
    3035                3040                3045

Phe Arg  Val Ser Ile Arg Pro  Lys Cys Ser Trp Tyr  Ala Leu Phe
    3050                3055                3060

Ala Phe  Phe His His His Ile  Asp Ile Ser Ser Asp  Gly Gly Lys
    3065                3070                3075

Phe Phe  Ala Pro Glu Ser Arg  His Gln Thr Val Pro  Val Gly Ile
    3080                3085                3090

Thr Phe  Leu Thr Ala Leu His  Leu Glu Gly Asn Ser  Val Pro Gln
    3095                3100                3105

Ala Gly  Met Gln Ser Arg Leu  Thr Ala Thr Ser Ala  Ser Trp Val
    3110                3115                3120

Gln Ala  Ile Leu Leu Pro Gln  Leu Pro Lys Leu Gly  Leu Gln Val
    3125                3130                3135

Pro Ala  Thr Thr Pro Gly Phe  Leu Tyr Phe Phe His  His Val Gly
    3140                3145                3150

Gln Ala  Gly Leu Glu Leu Leu  Ala Ser Gly Asp Pro  Pro Thr Leu
    3155                3160                3165

Ala Phe  Gln Ser Ala Gly Ile  Thr Gly Val Ser His  His Ala Gln
    3170                3175                3180

Pro Arg  Cys Ser Asn Lys Asn  Tyr Phe Ile Lys Phe  Ser Leu Arg
    3185                3190                3195

Ala Pro  Phe Lys Asn Ser Val  Ala Asn Gly Lys Glu  Val Leu Ile
    3200                3205                3210

Lys Tyr  Phe Cys Tyr Met Ser  Lys Asn Ser Gly Cys  Leu Glu Gly
    3215                3220                3225

Lys His  Cys Asp His Tyr Ser  Cys Glu Leu Asn Pro  Leu Tyr Ser
    3230                3235                3240

Cys Asn  Ile Leu Phe Val Lys  Asn Asp Gln Thr Gly  Cys Ser Asp
    3245                3250                3255

Phe Gly  Ile Leu Gln Leu Gln  Glu His Ser Lys Ile  Val Thr Ser
    3260                3265                3270

Lys Gln  Leu Ala Ile Phe Val  Pro Met Ile Lys Phe  Glu Leu Leu
    3275                3280                3285

Ala Val  Ala His Ala Tyr Asn  Pro Ser Thr Gly Gly  Gly Gly Arg
    3290                3295                3300

Ser Thr  Ala Gln Glu Phe Glu  Thr Ser Leu Gly Ser  Leu Ser Lys
    3305                3310                3315

Lys Lys  Lys Lys Ile Ser Gln  Ala Trp Trp His Ala  Pro Ala Glu
    3320                3325                3330

Val Glu  Gly Ala Leu Glu Pro  Gly Arg Pro Arg Leu  Gln Ala Met
    3335                3340                3345
```

-continued

```
Ile Val Pro Leu His Ser Ser Pro Gly Asn Arg Ala Arg Ser Cys
    3350                3355                3360

Gln Lys Lys Lys Lys Lys Lys Lys Glu Lys Lys Lys Leu Ser Ser
    3365                3370                3375

Lys Thr Gln Asn Cys Ser Asp Leu Ala Cys Gly Thr Lys Leu Asp
    3380                3385                3390

Ser Phe Leu Ile Ile Lys Asn Ser Ser Asp Ala Ile Ser Gly Asp
    3395                3400                3405

Val Gln Lys Cys Gln Phe Leu Asn Ile Ile Glu Asn Val Pro Thr
    3410                3415                3420

Phe Lys Ile Cys Ile Thr Gln Thr Asn Thr Phe Gln Met Thr Lys
    3425                3430                3435

Thr Cys Tyr Lys Ile Met His Gly Lys Val His Lys Cys Lys Gly
    3440                3445                3450

Gln Val Trp Trp Leu Met Pro Leu Ile Pro Ala Phe Trp Glu Ala
    3455                3460                3465

Glu Ala Gly Gly Ser Leu Glu Ala Arg His Leu Arg Pro Ala Trp
    3470                3475                3480

Pro Thr Gln Asp Pro Ile Ser Lys Asn Asn Lys Ser Lys Arg Ile
    3485                3490                3495

Ser Gln Ala Trp Trp His Ala Arg Glu Val Leu Ala Thr Trp Glu
    3500                3505                3510

Ala Thr Val Gly Gly Trp Leu Glu Leu Arg Ser Leu Arg Leu Gln
    3515                3520                3525

Glu Ala Met Ile Val Pro Leu Pro Ser Ser Leu Gly Asp Gly Val
    3530                3535                3540

Arg Pro Cys Phe Lys Asn Lys Thr Lys Lys Lys Glu Met Gln Val
    3545                3550                3555

Arg Pro Met Lys Tyr Asn Val Met Lys Tyr Lys Lys Phe Ile Ala
    3560                3565                3570

Met Val Ser Asn Ser Gln Cys Asn Pro Leu Arg Tyr Tyr Val Ser
    3575                3580                3585

Gly Leu Ala Gln Thr Lys Pro Ser Tyr Pro Leu Pro Ala Cys Ile
    3590                3595                3600

His Thr Asp Gly Leu Lys Gln Leu Lys Ile His Lys Arg Ser Glu
    3605                3610                3615

Asn Ser Leu Asn His Ser Thr Ile Glu Ile Cys Ser Cys Pro Thr
    3620                3625                3630

Leu Thr Asp Thr Ile Tyr Ser Pro Pro Pro Leu Arg Arg Tyr Phe
    3635                3640                3645

Val Ile Phe Ser Leu Pro Leu Arg Met Tyr Phe Val Arg Leu Ser
    3650                3655                3660

Gln Thr Tyr Lys Asn Ser His His Pro Leu Leu Thr Pro Phe Thr
    3665                3670                3675

Gln Pro Ala Cys Thr Gln Val Lys Tyr Thr Ala Leu Leu Leu Thr
    3680                3685                3690

Gln Ser Leu Phe Gly Gly Phe Phe Thr Arg Met His Val Thr Phe
    3695                3700                3705

Gly Ala Glu Asp Pro Gly Gln Glu Asp Ser Phe Gly Arg Pro Val
    3710                3715                3720

Pro Cys Cys Arg Pro His Ser Val Arg Arg Ser Thr Tyr Asp Leu
    3725                3730                3735
```

```
Arg Ser  Ser Asp Gln Pro Ala  Gln Gly Thr Ser Cys  Gln Phe Gln
    3740                 3745                 3750

Ile Gly  Val Val Phe Ser Leu  Phe Ser Ser Leu Ser  Cys Tyr Pro
    3755                 3760                 3765

Ser Ile  Phe Leu Ser His Tyr  Pro Ser Ile Ser Leu  Ser Phe Gln
    3770                 3775                 3780

Phe Pro  Phe Phe Phe Leu Ser  Ser Arg Asp Lys Glu  Thr His Phe
    3785                 3790                 3795

Ile Cys  Gly Pro Lys Thr Pro  Ala Ser Val Thr Asp  Ser Gly Arg
    3800                 3805                 3810

Gln Ser  Ser Leu Gly Val Ser  Leu Trp Gly Arg Leu  Pro Asp Tyr
    3815                 3820                 3825

Ser Pro  Thr Leu His Trp Cys  Leu Ile Thr Thr Gly  Met Pro Ala
    3830                 3835                 3840

Leu Val  Ile His Pro His Ser  Leu Gly Asp Lys Ser  Ile Ala Gly
    3845                 3850                 3855

Thr Pro  Ala Leu Ala Ala His  Pro His Cys Ser Pro  Gly Leu Leu
    3860                 3865                 3870

Asn Ala  Pro Arg Cys Pro Thr  Arg Leu Leu Arg Ala  Ser Thr Leu
    3875                 3880                 3885

Ser Phe  Leu Gly Phe Thr Ser  Phe Thr Met Gly Asn  Leu Pro Pro
    3890                 3895                 3900

Ser Ile  Pro Pro Ser Ser Pro  Leu Ala Cys Val Leu  Lys Asn Leu
    3905                 3910                 3915

Lys Pro  Leu Gln Leu Thr Pro  Asp Leu Lys Pro Lys  Cys Leu Ile
    3920                 3925                 3930

Phe Phe  Cys Asn Thr Ala Trp  Pro Gln Tyr Lys Leu  Asp Asn Asp
    3935                 3940                 3945

Ser Lys  Pro Glu Asn Gly Thr  Phe Glu Phe Ser Ile  Leu Gln Val
    3950                 3955                 3960

Leu Asp  Asn Ser Cys His Lys  Met Gly Lys Trp Ser  Glu Val Pro
    3965                 3970                 3975

Asp Val  Gln Ala Phe Phe Tyr  Thr Leu Val Pro Pro  Ser Leu Leu
    3980                 3985                 3990

Pro Met  Leu Ile Pro Asn Leu  Ser Ser Phe Ser Pro  Phe Cys Ser
    3995                 4000                 4005

Phe Gly  Leu His Pro Lys Phe  Arg Val Leu Ile Leu  Leu Phe Tyr
    4010                 4015                 4020

Gly Leu  Ile Pro Pro Pro Phe  Ser Pro Gly Cys Ser  Ser Pro Gly
    4025                 4030                 4035

Ala Arg  Ser Gln Phe Ser Leu  Ser Leu Cys Ser Pro  Thr Leu Ser
    4040                 4045                 4050

Phe Tyr  His Leu Pro Ser Ser  His Leu Val Gln Leu  Thr Val Ser
    4055                 4060                 4065

Phe Leu  Asp Leu Ser Pro Ile  Cys Pro Thr Ile Ser  Cys Arg Asp
    4070                 4075                 4080

Gly Leu  Ser Leu His Gln Ser  Arg Leu Val Pro Gly  Leu Pro Gly
    4085                 4090                 4095

Met Ser  Gly Cys Ser Asp Arg  Pro Pro Val Cys Pro  Ile Cys Thr
    4100                 4105                 4110

Ala Lys  Arg Ser Pro Gly Gly  Gln Arg Ser Lys Val  Ala Phe Gln
    4115                 4120                 4125

Val Pro  Val Gly Ala Trp Glu  Asn Thr Ala Gly Val  Ser Cys Gly
```

-continued

```
    4130                4135                4140

Pro Gln  Arg Ser Ala Trp Phe  Gln Ala Leu Asn Asn  Ser Pro Pro
    4145                4150                4155

Leu Gly  Leu His Leu Thr Pro  Gly Cys Arg Ile Arg  Ser Val Gln
    4160                4165                4170

Ala Thr  Ala Arg Pro Leu Pro  Val Thr Pro Leu Trp  Thr Pro Ser
    4175                4180                4185

Tyr Ser  Gln Gln Arg Arg Cys  Gly Asn His Arg Leu  Ile Ser Thr
    4190                4195                4200

Trp Thr  Gln His Ser His His  Leu Leu Asp Gln Ser  Val Phe Ser
    4205                4210                4215

Thr Gly  Gly Gly Gln Ala Gly  Phe Leu Cys Leu Pro  Glu Ser His
    4220                4225                4230

Arg Leu  Ser Thr Asn Met Glu  Pro Glu Phe Gln Val  Arg Lys Pro
    4235                4240                4245

His Ser  Gln Lys Pro Arg Leu  His Pro Thr Arg Cys  Ser Ala Pro
    4250                4255                4260

Arg Leu  Trp Val Leu Gly Ala  Lys Cys Gly Leu Val  Met Ser Gly
    4265                4270                4275

Asn Pro  His Val Pro Val Thr  Ala Val Lys Gln Lys  Val Asn Ser
    4280                4285                4290

Leu Thr  Asn Val Ile Pro Glu  Asp Leu Tyr Lys Leu  Leu Leu Gly
    4295                4300                4305

Tyr Leu  Phe Ile Tyr Thr Leu  Ala Tyr Phe Val Ile  Arg Leu Thr
    4310                4315                4320

Asn Gly  Asn His Tyr Phe Ser  Leu Leu Tyr Phe Ser  Lys Asn Asn
    4325                4330                4335

Phe Val  Thr Glu Phe Asn Ile  Leu Cys Thr Thr Asp  Leu Leu Leu
    4340                4345                4350

Lys Gln  Ser Ile Ser Ser Lys  Gln Ser Ile Leu Asn  Tyr Glu Lys
    4355                4360                4365

Leu Cys  Met Leu Ile Leu Gln  Leu Tyr Ser Asn Phe  Val Phe Ser
    4370                4375                4380

Gln Asn  Asp Val Pro Met Pro  Leu Gln Leu Trp Val  Gly Ser Val
    4385                4390                4395

Gln Thr  Gly Thr Leu Lys Ser  Met Thr Ala Arg Pro  Ile Leu Leu
    4400                4405                4410

Lys Thr  Phe Gln Gly Lys Lys  Lys Lys Lys Arg Gly  Gly Trp Ser
    4415                4420                4425

Arg Arg  Ser Gln Gly Cys Ser  Phe Phe Phe Ile Pro  Leu Pro Ile
    4430                4435                4440

Ser Arg  Leu Gly Cys Phe Ser  Ser Asn Ile Lys Thr  Gln Pro Ser
    4445                4450                4455

Ser Trp  Pro Ile Trp Gln Gln  Pro Leu Asp Ala Leu  Pro Pro Thr
    4460                4465                4470

Gln Arg  Gly Gln Lys Ala Val  Leu Phe Ser Ile Cys  Ile Leu Leu
    4475                4480                4485

Pro Asn  Pro Leu Arg Thr Leu  Glu Lys Ala Pro Lys  Ile Arg Phe
    4490                4495                4500

Gln Pro  Ser Asn Pro Thr Thr  Gly Leu Asn Pro His  Leu Gln Gly
    4505                4510                4515

Val Gln  Ser Arg Gly Asn Ile  Phe Leu Ser Cys Asn  Tyr Leu Pro
    4520                4525                4530
```

-continued

```
Pro Leu  Glu Lys Pro Gln Pro  His Leu Gln His Thr  Arg Thr Ser
    4535                 4540                 4545

Lys His  Leu Asn Arg Ser Gly  Gln Val Phe Leu Gln  Asp Arg Leu
    4550                 4555                 4560

Pro Gln  Asp Leu Ser Ser Ser  Ala Gly Asn Leu Val  Thr Gly Pro
    4565                 4570                 4575

Arg Asn  Ala Cys Ser Leu Gly  Phe Leu Leu Ser His  Val Pro Ser
    4580                 4585                 4590

Val Pro  Asp Pro Thr Gly Asn  Gln Thr Val Gln Leu  Thr Gln Glu
    4595                 4600                 4605

Pro Leu  Pro Glu Leu Leu Glu  Leu Trp Pro Lys Thr  Leu Leu Leu
    4610                 4615                 4620

Pro Arg  Cys Ser Arg Leu Ser  Gly Lys Leu Met Leu  Pro Asn Arg
    4625                 4630                 4635

Leu Arg  Ser Leu Leu Asp His  His Arg Cys Phe Gly  Leu Leu Gln
    4640                 4645                 4650

Arg Gly  Ser Leu Ser Pro Ser  Tyr Arg Gly Tyr Pro  Leu His Asn
    4655                 4660                 4665

Thr Phe  Phe Ser Arg Ala Cys  Phe Pro Cys Leu His  Asn Cys Cys
    4670                 4675                 4680

Gly Tyr  Trp Pro Gly Cys Thr  Cys Gln Asn Ser Pro  Thr Leu Val
    4685                 4690                 4695

Pro Thr  Trp Thr Thr Phe Phe  Tyr Thr Leu Phe Phe  Ser Tyr Pro
    4700                 4705                 4710

Tyr Leu  Pro Ser Ser Leu Ile  Arg Ser Arg His Phe  Asn Gln Ile
    4715                 4720                 4725

Ile Cys  Phe Pro Asp Cys Ser  Trp Thr Thr Ala Thr  Pro His Cys
    4730                 4735                 4740

Arg Pro  Phe Pro Gln Phe Lys  Ala Ser Phe Ala Ser  Ser Pro Cys
    4745                 4750                 4755

Ile Ser  Pro Pro Ser Thr Ser  Met Gly His Leu Tyr  Ser Leu Leu
    4760                 4765                 4770

Gly Asn  Arg Ser Cys Thr Pro  Tyr His Pro Ile Lys  Thr Ser Pro
    4775                 4780                 4785

Leu Pro  His Ser Met Pro Ile  Ser His Pro Thr Ala  His Phe Lys
    4790                 4795                 4800

Arg Ile  Pro Gln His Thr Leu  Lys Gly Leu Lys Pro  Val Ile Thr
    4805                 4810                 4815

Arg Leu  Leu His Gly Leu Leu  Lys Pro Ile Asn Ser  Pro Tyr Asn
    4820                 4825                 4830

Ser Pro  Ile Leu Pro Val Gln  Lys Pro Asp Lys Ser  Tyr Arg Leu
    4835                 4840                 4845

Val Gln  Asp Leu Cys Leu Ile  Asn Lys Ile Val Leu  Pro Met His
    4850                 4855                 4860

Pro Ile  Val Pro Asn Pro Tyr  Thr Leu Leu Ser Ser  Ile Pro Pro
    4865                 4870                 4875

Ser His  Asn Pro Leu Phe Cys  Ser Lys Thr Leu Thr  Pro Ile Leu
    4880                 4885                 4890

Asn Pro  Phe Pro Thr Pro Leu  Ser Ile Pro Lys Thr  Ala Leu Lys
    4895                 4900                 4905

Ala Ala  Pro Thr Leu Ala Leu  Pro Asn Ser Ser Gln  Leu Phe His
    4910                 4915                 4920
```

-continued

```
Tyr Thr  Gln Pro Lys Cys Arg  Ala Val Trp Ser Glu  Phe Leu His
    4925                 4930                 4935

Lys Ser  Gln Lys His Ala Leu  Pro Phe Cys Pro Asn  Asn Leu Thr
    4940                 4945                 4950

Leu Leu  Phe Pro Ser Pro His  Val Cys Val Trp Trp  Leu Leu Leu
    4955                 4960                 4965

Leu Tyr  Phe Arg Pro Ser Lys  Ser His Tyr Ala Gln  Leu Thr Leu
    4970                 4975                 4980

Tyr Ser  Ser His Asn Phe Gln  Asn Leu Phe Ser Ser  Ser Tyr Leu
    4985                 4990                 4995

Thr His  Ile Leu Ser Thr Pro  Trp Leu Leu Gln Leu  Tyr Ser Thr
    5000                 5005                 5010

Leu Phe  Asp Arg Val Ser Leu  Arg Leu Pro Gly Trp  His Ala Val
    5015                 5020                 5025

Ala Gln  Ser Trp Leu Thr Ala  Thr Ser Ala Ser Gln  Val Pro Ala
    5030                 5035                 5040

Ile Leu  Leu Pro Gln Pro Leu  Glu Leu Gly Leu Gln  Val Cys Ala
    5045                 5050                 5055

Pro His  Pro Ala Asn Phe Leu  Tyr Phe Arg Trp Gly  Phe Thr Met
    5060                 5065                 5070

Leu Thr  Lys Leu Val Leu Asn  Ser Pro Lys Val Ile  Cys Pro Ser
    5075                 5080                 5085

Arg Pro  Pro Lys Val Leu Gly  Leu Gln Ala Ala Thr  Thr Pro Ser
    5090                 5095                 5100

Leu Tyr  Ser Leu Phe Ala Glu  Ser Pro Thr Ile Thr  Ile Val Pro
    5105                 5110                 5115

Gly Leu  Asp Phe Asn Pro Ala  Ser His Ile Ile Pro  Asp Thr Thr
    5120                 5125                 5130

Pro Asp  Leu His Asp Tyr Leu  Ser Asp Pro Pro Gly  Ile His Ser
    5135                 5140                 5145

Ile Ser  Pro Tyr Phe Leu Leu  Ser Cys Ser Ser Pro  Ser His Leu
    5150                 5155                 5160

Val Tyr  Trp Gln Phe His Gln  Ala Ser Pro Phe Thr  Gly Lys Gly
    5165                 5170                 5175

Arg Leu  Cys Tyr Thr Ile Phe  His Ile Tyr Pro Gly  Tyr Arg Ser
    5180                 5185                 5190

Ala Pro  Leu His Tyr Leu Ser  Ala Ser Gln Thr His  Cys Leu Asn
    5195                 5200                 5205

Ser Gly  Pro His Ser Cys Lys  Gly Thr Thr Cys Gln  Tyr Leu Tyr
    5210                 5215                 5220

Leu Ile  Cys Leu Ser Tyr Pro  Pro Pro Pro Cys Cys  Tyr Met Gly
    5225                 5230                 5235

Lys Arg  Phe Pro His Tyr Ala  Arg Val Leu His His  Cys Leu Phe
    5240                 5245                 5250

Asn Lys  Asn Ser Ser Gln Gly  Cys Phe Thr Ser Lys  Gly Ser Trp
    5255                 5260                 5265

Ser His  Ser Leu Gln Gly Pro  Ser Lys Gly Ile Arg  Ser His His
    5270                 5275                 5280

Ser Gly  Gln Arg Leu Cys Gly  Ser Arg Ser Ser His  Ser Asn Phe
    5285                 5290                 5295

Cys Pro  Ser Gly Pro Val Phe  Leu Leu Leu Ile Gly  His Ser His
    5300                 5305                 5310

Leu Leu  Pro His Asn Phe His  Val Ser Ile Phe Ser  His Thr Arg
```

```
    5315                5320                5325

Gln Met  Val Leu Gly Ser Arg  Lys Ile Ser Pro Ser  Ser Leu Thr
    5330                5335                5340

Gly Pro  Phe Tyr Ser Val Val  Ile Ser Pro Leu Pro  Cys Arg Leu
    5345                5350                5355

Gln Ala  Ala Ser Pro Ser Leu  Ile Thr Ser His Phe  Ile Ser Ile
    5360                5365                5370

Val Lys  Ile Cys Pro Glu Glu  Asn His Phe Ser Val  Phe Ile Tyr
    5375                5380                5385

Tyr Ser  Thr Ile Pro Gln Gly  Leu Phe Arg Pro Leu  Pro Phe Pro
    5390                5395                5400

Thr His  Gln Ala Gly Glu Phe  Ala Pro Ala Gln Asp  Trp Gln Ile
    5405                5410                5415

Asp Phe  Thr Asp Met Cys Arg  Val Arg Lys Leu Lys  Tyr Leu Leu
    5420                5425                5430

Val Trp  Val Asp Thr Phe Thr  Gly Trp Val Gln Ala  Phe Pro Thr
    5435                5440                5445

Gly Cys  Glu Lys Ala Thr Thr  Val Ile Ser Ser Leu  Leu Ser Asp
    5450                5455                5460

Ile Ile  Pro Pro Phe Ser Leu  Ala Thr Ser Ile Gln  Cys Glu Asn
    5465                5470                5475

Arg Pro  Ala Phe Ile Ser Gln  Ile Thr Gln Ala Ala  Ser Gln Pro
    5480                5485                5490

Leu Gly  Ile Trp Leu Leu Val  Leu Pro Gln Asn Thr  Thr Leu Lys
    5495                5500                5505

Ala Leu  Leu Lys Trp Ile Asp  Leu Gln Trp Gln Gly  Thr Leu Arg
    5510                5515                5520

Tyr Phe  His Pro Asp Glu Val  Leu Phe Phe Thr Phe  Ile Leu Ile
    5525                5530                5535

Leu Ile  Leu Val Pro Asp Leu  Met Pro Pro Ser Thr  Ser Pro Gln
    5540                5545                5550

Leu Ser  Pro Pro His Tyr Gln  Ser His Ser Leu Leu  Ala Pro Phe
    5555                5560                5565

Ile Ile  Leu Leu Phe Phe Leu  Arg Trp Ser Leu Ala  Leu Ser Pro
    5570                5575                5580

Arg Leu  Glu Cys Ser Gly Val  Ile Leu Ala His Cys  Lys Leu Arg
    5585                5590                5595

Leu Leu  Gly Ser His His Ser  Pro Ala Ser Ala Ser  Gln Val Ala
    5600                5605                5610

Gly Thr  Arg Gly Ala Cys His  His Ala Trp Leu Ile  Phe Cys Ile
    5615                5620                5625

Phe Ser  Arg Asp Gly Val Ser  Pro Cys Pro Gly Trp  Ser Pro Ser
    5630                5635                5640

Pro Asp  Leu Thr Ile Arg Pro  Pro Gln Pro Pro Lys  Val Leu Gly
    5645                5650                5655

Leu Gln  Ala Ala Thr Met Pro  Gly Pro Leu Ile Leu  Leu Gln Thr
    5660                5665                5670

Thr Ala  Gly Phe Ala Phe Leu  Phe Pro Pro Lys Ser  Pro Arg Pro
    5675                5680                5685

Arg Leu  Thr His Cys Lys Lys  Arg Thr Leu Tyr Ile  Phe Lys Arg
    5690                5695                5700

Arg Val  Leu Phe Leu Pro Lys  Ser Ile Trp Pro Gly  Val Gln His
    5705                5710                5715
```

-continued

Lys Lys Thr Gln Gly Thr Pro Lys Ile Arg Gln Pro Ser Lys Leu
5720 5725 5730

Cys Thr Pro Leu Gly Thr Pro Leu Asp Val Leu Gly Pro Ser Asn
5735 5740 5745

Ser Ser Phe Asn Thr Tyr Phe Ser Leu Ser Leu Ile Arg Thr Leu
5750 5755 5760

Cys Leu Pro Ser Val Phe Leu Asn Ser Tyr Lys Thr Ala Ser Arg
5765 5770 5775

Pro Ser Thr Ile Ile Leu Tyr Asp Lys Tyr Ser Phe Gln Ala His
5780 5785 5790

Asn Ile Thr Pro Tyr Thr Gln Ile Phe Leu Gln Phe Asn Leu Ser
5795 5800 5805

Tyr Ser Arg Phe Pro Cys His Pro Asn Pro Thr Gln Ser Ser Pro
5810 5815 5820

Glu Lys His Arg Pro Leu Ser Leu His Thr Thr Pro Lys Asn Phe
5825 5830 5835

Arg Cys Leu Asn Thr Ser Pro Leu Phe Cys Phe Val Phe His Thr
5840 5845 5850

Asn Ile Arg Arg Glu Cys Gln Ala Ser Glu Ser Lys Leu Ser His
5855 5860 5865

Gln Ile Pro Cys Asp Leu His Val Tyr Ile Gln Met Thr Ser Asn
5870 5875 5880

Arg Ser Thr Lys Glu Val Lys Val Ala Leu Thr Asp Asp Ile Pro
5885 5890 5895

Pro Leu Phe Val Pro Ala Pro Arg Leu Ile Pro Tyr Ile Leu Pro
5900 5905 5910

Pro Pro Leu Arg Met Tyr Phe Val His Leu Ser Gln Thr Tyr Lys
5915 5920 5925

Asn Ser Tyr His Pro Leu Leu Thr Leu Phe Leu Asp Ser Ala Arg
5930 5935 5940

Leu His Pro Gly Glu Ile Asn Ser Pro Val Ala
5945 5950

<210> SEQ ID NO 45
<211> LENGTH: 6005
<212> TYPE: PRT
<213> ORGANISM: Homo sapiens

<400> SEQUENCE: 45

Arg Arg Gln Arg Ser Gln Thr Gln Lys Thr Ile Tyr Arg Met Ile Ser
1 5 10 15

Phe Ile Met Lys Cys Pro Glu Trp Asp Ile Arg Gln Lys Val Asp Leu
20 25 30

Trp Leu Leu Glu Thr Gly Gly Arg Val Ala Asn Val His Gly Phe Cys
35 40 45

Gly Glu Lys Cys Ser Leu Gly Arg Phe Trp Gly Leu His Val Ser Val
50 55 60

Asn Ile Leu Lys Met Ser Ala Ser Tyr Thr Lys Arg Val Ile Leu Trp
65 70 75 80

Tyr Ile Asn Tyr Ile Leu Ile Lys Asn Tyr Ile Leu Lys Asn Pro Leu
85 90 95

Asn Val Leu Pro Leu Val Val Ala Glu Thr Gln Thr Gln Ile Tyr Val
100 105 110

Leu Met Lys Ile Asn Phe Leu Ile Lys Gly Ser Ala Pro Tyr Ser Leu

```
        115                 120                 125

Ser Leu Ser Phe Phe Phe Phe Leu Arg Ser Leu Thr Leu Leu Ser Arg
    130                 135                 140

Leu Glu Cys Ser Gly Thr Phe Ser Ala His Cys Asn Leu Cys Leu Pro
145                 150                 155                 160

Gly Ser Ser Glu Ser Pro Ala Ser Ala Ser Gln Val Ala Glu Ile Ile
                165                 170                 175

Gly Ile Cys His Tyr Ala Trp Leu Ile Phe Val Phe Leu Val Glu Met
            180                 185                 190

Gly Phe His His Val Gly Gln Gly Gly Leu Glu Leu Leu Thr Ser Ser
        195                 200                 205

Asp Leu Pro Thr Ser Ala Ser Gln Ser Ala Gly Ile Thr Gly Met Arg
    210                 215                 220

His His Thr Gln Ser Met Phe Ser Leu Cys Ser Asp Val Val Ser Ser
225                 230                 235                 240

Leu Lys Leu Gln Arg Asp Lys Asp Pro His Glu Lys Arg Gln Ala Ala
                245                 250                 255

Ile Asn Trp Ser Ile Ile Gln Phe Gly Cys Thr Lys Leu Leu Gly Lys
            260                 265                 270

Ile Glu Ile Pro Cys Ser Thr Phe Ser Arg Gly Leu Gly Asn Cys Ile
        275                 280                 285

Asn Thr Asp Leu Thr Ser Phe Val Gly Asn Ser Ser Glu Ser Ile Arg
    290                 295                 300

Leu Val Asp Thr Ile Ile Ile Thr Ile Thr Ile Phe Thr Arg Ala Gly
305                 310                 315                 320

His Cys Thr Glu Cys Leu Ala Val Cys Tyr Arg Thr Thr Ser Glu Ala
                325                 330                 335

Gly Val Ile Val Thr Trp Ile Leu Leu Met Arg Leu Ser Ser Leu Gly
            340                 345                 350

Glu Lys Ala Val Arg Lys Cys Val Met Leu Leu Ser Gly Ser Arg Pro
        355                 360                 365

Met Val Leu Thr Thr Gly Ser Thr Gly Cys Gly Ala Asp Asp Lys Leu
    370                 375                 380

Asp Met Ser Ser Val Ile Cys Pro Thr Val Cys Leu Ala Ile Phe Ser
385                 390                 395                 400

Tyr Thr Gln Arg Gln Ser Leu Val Met Pro Ser Ser Leu Gly Gly Ser
                405                 410                 415

Gly Arg Glu Leu Lys Phe Cys Thr Asn Ser Arg Cys Ile His Cys Ser
            420                 425                 430

Gly Arg Thr Gln Leu Thr Pro Pro Pro Asp Pro Ser His Ser Val Thr
        435                 440                 445

Pro Gly Phe Ala Phe Leu Ser Asn His Arg Tyr Val Pro Asn Ile Ser
    450                 455                 460

Cys Leu Leu Phe Leu Asn Tyr Thr Ser Pro Ser Tyr Lys Ile Val Ser
465                 470                 475                 480

Ser Ser Lys Ala Ser Ser Ser Phe Arg Asn Val Ser Leu Pro Leu Asn
                485                 490                 495

Ser Gln His Trp Lys Gln Asn Glu Leu Met Ser Cys Ser Lys Phe Cys
            500                 505                 510

His Cys Tyr Lys Leu Cys Glu Met Ser Gln Gly Val Gly Val Ile Phe
        515                 520                 525

Cys Asp Leu Leu Thr Phe Arg Ala Ala Gly Lys Ala Leu Ile Leu Val
    530                 535                 540
```

-continued

```
His Leu Trp Asn Lys Cys His Arg Pro Leu Gln Ala Pro Arg Ser Asp
545                 550                 555                 560

Ser Ile Leu Gly Leu Leu Glu Ala Glu Ala Phe Pro Leu Ser Gly Pro
                565                 570                 575

Gly Pro Ala Leu Pro Pro Arg Gly Pro Ala Gln Pro Ala Thr Pro Trp
            580                 585                 590

Pro Gln Ser Ala His Lys Gly Ser Val Cys Val Cys Arg Ala Asp Ser
        595                 600                 605

Gln Trp Phe Trp Ala Gln Ala Arg Thr Phe Ser Glu Gly Arg Lys Gly
    610                 615                 620

Pro Ser Pro Ser Trp Pro Phe Ser Met Gly Ser Ser Gln Pro Gly Pro
625                 630                 635                 640

Cys Gln Thr Ser Lys Asn Arg Glu Glu Ser Gly Ser Glu Arg Gln Gln
                645                 650                 655

Arg Thr Gln Asn Cys Cys Phe Leu Phe Leu Ser Arg Ile Met Asp Ser
            660                 665                 670

Arg Lys Asp Ser Pro Phe Ser Leu Ser Val Cys Leu Arg Glu Arg Glu
        675                 680                 685

Arg Glu Arg Glu Arg Glu Arg Tyr Ile Leu Ile Glu Arg Gln Phe Thr
    690                 695                 700

Gln Tyr Lys Thr Asn His Phe Ile Tyr Asp Arg Gly Leu Thr Ile Leu
705                 710                 715                 720

Pro Arg Leu Val Ser Asn Ser Trp Ala Gln Val Ile Leu Leu Pro Trp
                725                 730                 735

Pro Pro Lys Val Leu Gly Gln Val Ala Thr Val Pro Gly Thr Asn His
            740                 745                 750

Phe Ile Leu Phe Ile Tyr Phe Glu Thr Glu Phe Cys Ser Cys Arg Pro
        755                 760                 765

Gly Trp Ser Ala Met Gly Ser Arg Ile Thr Ala Thr Phe Ala Ser Arg
    770                 775                 780

Val Gln Thr Ile Leu Leu Leu Gln Pro Pro Glu Leu Gly Leu Gln Ala
785                 790                 795                 800

Pro Ala Thr Met Pro Ile Phe Phe Phe Leu Ser Phe Phe Leu Phe Phe
                805                 810                 815

Phe Phe Phe Arg Arg Asp Gly Val Ser Pro Arg Trp Pro Gly Ser Gln
            820                 825                 830

Thr Pro Asp Leu Arg Ser Ala Arg Pro Thr Leu Ser Lys Cys Trp Asp
        835                 840                 845

Tyr Arg Cys Glu Pro Pro Cys Gln Ala Glu Leu Thr Ile Leu Asn Pro
    850                 855                 860

Val Leu Trp His Leu Val His Ser His Cys Ala Asn Thr Thr Phe Cys
865                 870                 875                 880

Ser Lys Thr Phe Ser Pro Gln Lys Lys Thr Thr His Ser Thr Val Ile
                885                 890                 895

Pro His Leu Pro Thr His Thr Arg Pro Leu Val Thr Ile Ser Leu Leu
            900                 905                 910

Ser Val Ser Val Asp Leu Pro Leu Gln Asp Ile Ser Tyr Thr Trp Asn
        915                 920                 925

Arg Thr Ile Tyr Asp Leu Leu Cys Leu Ala Ser Phe Ser Trp His Asn
    930                 935                 940

Leu Ser Met Phe Ile Pro Ile Gly Ala Tyr Ile Ser Thr Ser Phe Leu
945                 950                 955                 960
```

-continued

```
Phe Ile Thr Tyr Ser Tyr Ser Ile Val Ile His His Ser Trp Phe Thr
                965                 970                 975

Asp Leu Ser Ile Asp Glu His Trp Ser Cys Phe His Leu Leu Val Ile
            980                 985                 990

Val Asn Ser Thr Ala Met Asn Ile  Val Gln Ile Val Pro  Val Tyr Asn
        995                 1000                1005

Leu Leu  Gly Phe Ile Ser Arg  Ser Gly Val Ala Gly  Pro Asp Ala
    1010                1015                1020

Asn Leu  Ile Phe Asn Leu Leu  Trp His His Gln Thr  Val Ser Pro
    1025                1030                1035

Val Ala  Ala Pro Leu Ile Phe  Ser Ser Asn Val Glu  Ser Pro Ser
    1040                1045                1050

Ser Arg  Val Pro Ile Cys Pro  Phe Pro Leu Ser Tyr  Phe Leu Gln
    1055                1060                1065

Ser Gln  Phe Pro Thr Asp Phe  Ser Phe Pro Trp Ser  Arg Gly Trp
    1070                1075                1080

Glu Lys  Leu His Leu Lys Asp  Tyr Pro Ser Leu His  Ser Tyr Leu
    1085                1090                1095

Phe Arg  Lys Asn Thr Val Thr  Arg Arg Arg Arg Gly  Gln Ala Ala
    1100                1105                1110

Thr Ser  Leu Trp Ser Leu Arg  Tyr Thr His Tyr Ser  His Arg Asp
    1115                1120                1125

Ser Val  Lys Leu Pro Ser Arg  Pro Pro Thr Pro Arg  Ser Ser Pro
    1130                1135                1140

Arg Thr  Ser His Thr Phe Gln  Gln Ser Gln Ile Gly  Arg Gly Ser
    1145                1150                1155

Val Trp  Lys Val Pro Ala Leu  Ala Gln Pro Cys Gly  Val Phe Asn
    1160                1165                1170

Phe Gln  Pro Ser Leu Arg Ser  Pro Lys Thr Pro Ile  Ala Ser Ser
    1175                1180                1185

Cys Pro  Val Pro Ser Ala Lys  Gly Pro Ala Cys Pro  Gly Leu Ala
    1190                1195                1200

Gly Ser  His Glu Trp Arg Gly  Ser Ala Ser Leu Ser  Thr His Ser
    1205                1210                1215

Arg Arg  Gly Tyr Cys Arg Ser  Gln Thr Arg Ala Phe  Lys Ser Tyr
    1220                1225                1230

Leu His  Leu Gln Gln Pro Thr  Ser Ala Pro Arg Arg  Ser Gln Ser
    1235                1240                1245

Ala Ala  Pro Lys Leu Val Phe  Cys Leu Leu Gln Ser  Gly Gly Ala
    1250                1255                1260

Val Leu  Pro Ala Ser Cys Ser  Cys Glu Ser Gln Val  Gly Gly Ser
    1265                1270                1275

Leu Phe  Ser Phe Phe Phe Phe  Ser Arg Gly Val Gly  Leu Gly Ala
    1280                1285                1290

Leu Leu  Ser Tyr Leu Ser Leu  Pro Tyr Pro Gly Met  Gly Lys Met
    1295                1300                1305

Arg Thr  Cys His Ser Val Arg  Pro Arg Thr Val Leu  Gln Asn Ser
    1310                1315                1320

Glu Ser  Phe Pro Asp Gly Trp  Arg Ser Arg Ser Leu  Pro Ala Glu
    1325                1330                1335

Val Pro  Ser Leu Pro Cys Trp  Glu Asp Lys Gly Ala  Leu Ala Val
    1340                1345                1350

Ser Thr  Ala Ser Pro Ser Leu  Ile Thr Arg Asp Ser  Leu Trp Ala
```

```
    1355                1360                1365

Leu Ser  Pro Leu Pro Leu Arg  Trp Cys Arg Pro Cys  Pro Gly Arg
    1370                1375                1380

Pro Ser  Arg Gln Ser Ser Phe  Leu Phe Leu Ser Ala  Ile Val Gln
    1385                1390                1395

Lys Arg  Leu Leu Trp Lys Ser  Gln Ser Ala Arg Ser  Gln Gln Asn
    1400                1405                1410

Thr Leu  Lys Ile Gly Gln Ser  Leu Gly Arg Thr Val  Lys Ala Gln
    1415                1420                1425

Glu Gln  Gln Ser Val Gln Glu  Arg Ser Arg Leu Thr  Gln Pro Ala
    1430                1435                1440

Gln Glu  Gly Gly Val Trp Trp  Glu Ser Gly Arg Arg  Gln Trp Lys
    1445                1450                1455

Val Thr  Cys Phe Cys Lys Glu  Val Ile Arg Tyr Phe  Gln Ala Gly
    1460                1465                1470

Glu Glu  Asn Asn Leu Ser Val  Ser Gln Ser Leu Ser  Trp Gln Gln
    1475                1480                1485

Ser Arg  Val Ala Gly Gly Trp  Gly Leu Gly Asp Val  Gly Lys Leu
    1490                1495                1500

Leu Leu  Pro Leu Trp Arg Val  Met Gly Pro Gln Lys  Leu Gly Ser
    1505                1510                1515

Arg Trp  Glu Trp Lys Gly Arg  Ala Gln Ala Glu Arg  His Leu Gly
    1520                1525                1530

Gly Glu  Ser Ile Ala Leu Tyr  Leu Asp Val Asp Glu  Gly Gln Gln
    1535                1540                1545

Ser Glu  Glu Asp Phe Glu Val  Ser Ser Leu Ser Gly  Trp Lys Asp
    1550                1555                1560

Thr Thr  Ser Pro Thr Asn Arg  Gln Lys Gly Glu Arg  Lys Arg Glu
    1565                1570                1575

Ala Glu  Gly Phe Cys Lys Gly  Asn Arg Ser Ser Val  Phe Asp Met
    1580                1585                1590

Trp His  Leu Asn Cys Lys Lys  Tyr Ile Pro Val Asp  Val Ile Pro
    1595                1600                1605

Ser Arg  Gln Leu Gly Ile Arg  Ile Trp Cys Arg Glu  Glu Lys Arg
    1610                1615                1620

Asp Pro  Lys Gly Leu Trp Ile  Gly Arg Glu Ile Asp  Asp Leu Lys
    1625                1630                1635

Arg Asn  Tyr Arg Ile Arg Arg  Phe Gly Gln Gly Thr  Val Ala His
    1640                1645                1650

Ala Cys  Asn Pro Ser Ile Leu  Gly Asp Gln Gly Arg  Arg Ile Ala
    1655                1660                1665

Ala Gln  Glu Phe Glu Thr Ser  Leu Gly Asn Met Val  Arg Pro Arg
    1670                1675                1680

Leu Tyr  Lys Asn Cys Lys Asn  Pro Gly Val Val Thr  His Thr Cys
    1685                1690                1695

Asn Ser  Ser Tyr Leu Gly Gly  Gly Gly Gly Ile Thr  Ala Trp Gly
    1700                1705                1710

Gly Leu  Gly Cys Ser Glu Leu  Arg Cys His Cys Thr  Pro Thr Trp
    1715                1720                1725

Ala Thr  Gln Glu Gln Asp Pro  Val Ser Lys Val Lys  Lys Lys Lys
    1730                1735                1740

Glu Asp  Ser Ser Thr Glu Ser  Trp Glu Gly Arg Lys  Arg Thr Gln
    1745                1750                1755
```

-continued

```
Arg Pro  Gly Val Val Ala His  Ala Cys Asp Pro Ser  Thr Leu Asp
    1760                 1765                 1770

Ala Glu  Val Gly Gly Ser Ser  Glu Val Arg Ser Ser  Arg Pro Ala
    1775                 1780                 1785

Pro Thr  Trp Asn Pro Val Ser  Ile Lys Asn Tyr Pro  Gly Met Val
    1790                 1795                 1800

Ala Gly  Ala Cys Phe Gln Leu  Leu Glu Arg Leu Arg  Glu Asn Gly
    1805                 1810                 1815

Leu Asn  Ile Gly Gly Arg Gly  Cys Ser Glu Leu Arg  Leu Cys His
    1820                 1825                 1830

Tyr Thr  Pro Ala Trp Ala Thr  Glu Asp Ser Val Ser  Lys Lys Lys
    1835                 1840                 1845

Lys Lys  Lys Lys Arg Thr Gln  Ser Gln Asn Arg Gln  Arg Ser Ile
    1850                 1855                 1860

Arg Lys  Ile Lys Ile Lys Lys  Lys Gln Thr Thr Ile  Leu Lys Glu
    1865                 1870                 1875

Asn Asn  Ser Arg Lys Arg Lys  Gln Asp Ile Val Tyr  Val Cys Thr
    1880                 1885                 1890

Lys Gln  Asp Ile Gly Ile Asn  Tyr Lys Ala Phe Ile  Asn Thr Ala
    1895                 1900                 1905

Ile Lys  Ile Met Leu Gln Asn  Tyr Ile Ile Ala Ile  Lys Arg Cys
    1910                 1915                 1920

Ser Met  His Leu Phe Ser Pro  Ser Ala Ser Lys His  Ser Gly Lys
    1925                 1930                 1935

Ile Val  Tyr Met Leu Gly Thr  Val Ala His Val Cys  Asn Pro Ser
    1940                 1945                 1950

Thr Leu  Gly Gly Gly Arg Trp  Ile Thr Arg Ser Gly  Val Asp His
    1955                 1960                 1965

Pro Gly  Gln Cys Ser Glu Thr  Leu Ser Leu Pro Lys  Ile Gln Asn
    1970                 1975                 1980

Pro Gly  Met Glu Ala Gly Ala  Cys Asn Pro Ser Tyr  Leu Gly Gly
    1985                 1990                 1995

Gly Arg  Arg Ile Thr Thr Trp  Glu Ala Asp Val Ala  Val Ser Arg
    2000                 2005                 2010

Asp Cys  Ala Thr Ala Leu Gln  Pro Lys Gln Cys Glu  Thr Pro Ser
    2015                 2020                 2025

Gln Asn  Lys Lys Lys Tyr Ile  Tyr Met Cys Val Tyr  Ile Cys Ile
    2030                 2035                 2040

Tyr Met  Cys Ile Tyr Val Tyr  Met Cys Val Tyr Met  Tyr Ile Cys
    2045                 2050                 2055

Val Tyr  Ile Cys Ile Tyr Val  Tyr Ile Cys Ile Tyr  Met Cys Ile
    2060                 2065                 2070

Tyr Val  Tyr Ile Cys Val Tyr  Met Tyr Ile Tyr Val  Tyr Ile Cys
    2075                 2080                 2085

Val Tyr  Ile Cys Val Tyr Ile  Cys Val Tyr Met Cys  Val Tyr Met
    2090                 2095                 2100

Tyr Ile  Cys Val Tyr Met Cys  Val Tyr Met Arg Ile  Tyr Val Cys
    2105                 2110                 2115

Ile Tyr  Val Tyr Ile Cys Val  Cys Ile Cys Ile Tyr  Asn Cys Thr
    2120                 2125                 2130

Ile Phe  Lys Asn Tyr Ile Cys  Asp Cys Lys Lys Ala  Glu Gly Trp
    2135                 2140                 2145
```

-continued

```
Val Ala  His Ala Cys Asn Pro  Ser Thr Leu Gly Gly  Gln Gly Arg
    2150                 2155                 2160

Leu Ile  Thr Gly Gln Glu Phe  Glu Thr Ser Leu Ala  Asn Asn Cys
    2165                 2170                 2175

Tyr Thr  Lys Asn Asn Phe Cys  Ile Leu Lys Tyr Lys  Asn Pro Gly
    2180                 2185                 2190

Val Val  Ala His Val Cys Ser  Pro Thr Tyr Ser Gly  Gly Gly Arg
    2195                 2200                 2205

Arg Ile  Pro Thr Gln Glu Ala  Glu Val Ala Val Ser  Asp Cys Thr
    2210                 2215                 2220

Thr Val  Leu Gln Pro Gly Gln  Ser Glu Thr Pro Ser  Gln Lys Lys
    2225                 2230                 2235

Lys Arg  His Glu Glu Thr Phe  Arg Met Arg Glu Leu  Phe Tyr Met
    2240                 2245                 2250

Phe Val  Glu Val Met Tyr Thr  Gln Leu Cys Thr Ile  Ile Gln Asn
    2255                 2260                 2265

Pro His  Lys Gly Gly Asp His  Pro Ser Tyr Cys Leu  Met Pro Asn
    2270                 2275                 2280

Phe Cys  Leu Gln Arg Lys Lys  Lys Lys Leu Lys Asp  Arg Asn Glu
    2285                 2290                 2295

Ile His  Arg Gln Thr Ala Arg  Arg His Thr Leu Gly  Leu Val Val
    2300                 2305                 2310

Lys Asp  Arg Pro Leu Thr Ser  Val Met Leu Ser Leu  Asn Tyr Ser
    2315                 2320                 2325

His Cys  Val Glu Lys His Cys  Glu Asn Pro Cys Pro  Val Leu Phe
    2330                 2335                 2340

Cys Ser  Asn Tyr Gln Cys Met  Gln Pro Pro Val Thr  Tyr Pro Leu
    2345                 2350                 2355

Leu Ala  Gln Ser Ile Lys Thr  Leu Ser Arg Gly Pro  Pro Ser Cys
    2360                 2365                 2370

Gln Pro  Leu Arg Gly Thr Gly  Ile Ala Tyr Ser Gly  Ser Ser Val
    2375                 2380                 2385

Phe Glu  Thr Val Leu Pro Met  Leu Pro Ala Lys Ser  Pro Ser Phe
    2390                 2395                 2400

Phe Asn  Ser Val Ser Lys Gly  Phe Cys Leu Arg Leu  Val Leu Leu
    2405                 2410                 2415

His Ser  Asn Asn Ser Leu Asn  Phe Tyr Phe Leu Phe  Tyr Leu Phe
    2420                 2425                 2430

Phe Phe  Arg Asp Val Ser Leu  Cys His Pro Gly Trp  Ser Ala Met
    2435                 2440                 2445

Ala Cys  Ser Arg Leu Thr Ala  Thr Ser Thr Ser Gln  Val Gln Val
    2450                 2455                 2460

Ile Leu  Leu Pro Gln Pro Leu  Glu Leu Gly Leu Gln  Val Cys Ser
    2465                 2470                 2475

Thr Thr  Pro Ser Phe Leu Tyr  Phe Arg Arg Gly Phe  Thr Met Leu
    2480                 2485                 2490

Ala Arg  Leu Val Ser Asn Ser  Pro Gln Val Ile Cys  Pro Pro Arg
    2495                 2500                 2505

Pro Pro  Lys Val Leu Gly Leu  Gln Ala Gly Thr Met  Pro Ser Met
    2510                 2515                 2520

Pro Phe  Gln Glu Gly Asp Cys  Trp Tyr Pro Leu His  Ser Val Val
    2525                 2530                 2535

Leu Gly  Ile Lys Trp Gln Thr  Arg Ala Tyr Cys Leu  Glu Tyr Lys
```

```
    2540                2545                2550

Lys Gly  Ser Ile Ser Arg Glu  Gly Lys Asp Asp Pro  Gly Pro Gln
    2555                2560                2565

His Gly  Gly Gly Glu Thr Gly  Ser Lys Ala Arg Ser  Met Gly Lys
    2570                2575                2580

Gly His  Thr Trp Ala Ser Lys  Thr Lys Pro Pro Thr  Asn Lys Arg
    2585                2590                2595

Pro Asn  Gly Ser Arg Gln Lys  Gly Lys Leu Arg Asn  Lys Leu Asp
    2600                2605                2610

Lys Arg  Ala Leu Gly Met Val  Thr His Ala Tyr Asn  Pro Asn Thr
    2615                2620                2625

Leu Arg  Gly Gln His Arg Arg  Ile Ala Ala Gln Glu  Phe Lys Thr
    2630                2635                2640

Ser Leu  Asp Asn Ile Arg Arg  Pro Cys Leu Tyr Lys  Lys Lys Ile
    2645                2650                2655

Ile Ser  Gly Met Trp Trp Tyr  Thr Ser Val Val Pro  Ala Thr Trp
    2660                2665                2670

Glu Ala  Glu Val Gly Gly Leu  Leu Glu Pro Glu Arg  Leu Arg Leu
    2675                2680                2685

Trp Ala  Thr Ile Thr Pro Leu  Ser Arg Leu Gly Asn  Arg Ala Arg
    2690                2695                2700

Leu Ser  Gln Lys Lys Lys Lys  Gly Gly Glu Gly Leu  Gly Thr Leu
    2705                2710                2715

Val Ala  Asp Leu Glu Tyr Asp  Thr Asn Glu Glu Ile  Asn Leu Phe
    2720                2725                2730

Leu Ile  Val Gln Arg Val Glu  Arg Asn Lys Thr Met  Trp Glu Glu
    2735                2740                2745

Gln Ala  Trp Leu Trp Thr Gly  Arg Gln Leu Lys Leu  Glu Leu Phe
    2750                2755                2760

Tyr Ser  Val Leu Gly Gly Ile  Ser Cys Phe Ser His  His Ile Cys
    2765                2770                2775

Ser Thr  Arg Pro Arg Phe Cys  Lys His Val Pro Glu  Trp Asp Glu
    2780                2785                2790

Ile Met  Asp Ile Pro Leu Arg  Phe His Leu Val Leu  Arg Leu Tyr
    2795                2800                2805

Lys Ala  His Gln Ser Ser Ser  Thr Lys His Lys Val  Ile Gly Val
    2810                2815                2820

Met Leu  Phe Ser Val Tyr Gly  Met Asp Val Asn Leu  Ile Ser Phe
    2825                2830                2835

Asp Cys  Gln Ala Ser Ser His  Phe Phe Met Val Leu  Ile Lys Ser
    2840                2845                2850

Val Ala  Val Phe Met Ile Trp  Thr Arg Ala Ser Asp  His Thr Trp
    2855                2860                2865

Leu Ile  Asn Thr Asn Cys Ile  Ser Lys Ala Ala Gly  Arg Asn Leu
    2870                2875                2880

Ile Ile  Trp Phe Cys Glu Leu  Phe Cys Phe Val Leu  Phe Cys Phe
    2885                2890                2895

Leu Arg  Gln Ser Leu Ala Leu  Ser Pro Gly Trp Ser  Ala Val Ala
    2900                2905                2910

Ser Trp  Leu Thr Ala Thr Ser  Ala Ser Arg Val Gln  Ala Ile Leu
    2915                2920                2925

Leu Pro  Gln Pro Ser Glu Leu  Gly Leu His Val Cys  Pro Pro His
    2930                2935                2940
```

-continued

```
Leu Ala Asn Phe Leu Phe Leu Val Glu Ile Gly Phe His His Ile
    2945                2950                2955

Gly Gln Asp Gly Leu Asp Leu Leu Thr Ser Ser Ala His Leu Gly
    2960                2965                2970

Leu Leu Lys Cys Trp Asp Tyr Arg Gly Lys Pro Pro Cys Pro Ala
    2975                2980                2985

Leu Asn Val Ser Ser Tyr Tyr Thr Ser Tyr Leu Tyr His Ser Phe
    2990                2995                3000

Cys Ile Leu Trp Tyr Asn Arg Glu Thr Ile Arg Leu Gly Val Ser
    3005                3010                3015

Val Thr Gln Phe Gln Val Leu Val Leu Leu Leu Asn Arg Cys Met
    3020                3025                3030

Ala Leu Gly Lys Gly Ile Tyr Ala Glu Val Phe Asp Val Ser Met
    3035                3040                3045

Asp Pro Ala Tyr Pro Lys Phe Ser Gly Tyr Pro Asp Gln Asn Asp
    3050                3055                3060

Val His Gly Asp Ile Lys Pro Tyr Leu Pro Phe Phe Thr Ile Thr
    3065                3070                3075

Leu Thr Phe Leu Leu Met Val Gly Asn Ser Leu His Leu Asp Arg
    3080                3085                3090

Asn His Gly Ser Ser Thr Lys Leu Tyr Gln Trp Ala Leu His Ser
    3095                3100                3105

Ser Leu Pro Cys Thr Trp Arg Gly Ile Gln Ser Pro Arg Leu Glu
    3110                3115                3120

Cys Asn Asp Leu Gly Ser Leu Gln Pro Leu Pro Pro Gly Phe Lys
    3125                3130                3135

Arg Phe Ser Cys Leu Asn Phe Pro Ser Asn Asp Tyr Arg Cys Leu
    3140                3145                3150

Pro Pro Arg Leu Ala Asn Phe Cys Ile Phe Ser Ser Phe Thr Met
    3155                3160                3165

Leu Ala Arg Leu Val Ser Asn Ser Trp Pro Gln Val Ile His Leu
    3170                3175                3180

Pro Trp Pro Ser Lys Val Leu Gly Leu Gln Val Ala Thr Met Pro
    3185                3190                3195

Ser Gln Asp Val Leu Asp Lys Ile Lys Ile Ile Asn Leu Leu Asn
    3200                3205                3210

Phe Asp Pro Glu His Leu Leu Lys Ile Leu Trp His Glu Met Gly
    3215                3220                3225

Ser Arg Lys Tyr Leu Ser Thr Ser Ala Ile Cys Gln Arg Thr Val
    3230                3235                3240

Val Val Leu Arg Glu Asn Ile Ser Val Ile Ile Ile Val Val Ser
    3245                3250                3255

Ile Asn Pro Phe Ile His Val Ile Ser Phe Leu Phe Glu Arg Met
    3260                3265                3270

Thr Asp Lys Leu Val Val Gln Thr Leu Val Phe Cys Ser Phe Lys
    3275                3280                3285

Asn Ile Asn Lys Val Lys Leu Leu Leu Gln Ser Asn Asn Leu Gln
    3290                3295                3300

Tyr Leu Phe Gln Asn Leu Ser Phe Trp Gln Trp Leu Met Pro Ile
    3305                3310                3315

Ile Pro Ala Leu Arg Glu Ala Glu Ala Gly Gly Ala Leu Glu Leu
    3320                3325                3330
```

-continued

Arg Ser Leu Arg Pro Ala Trp Ala Val Ser Pro Lys Arg Lys Lys
3335 3340 3345

Lys Leu Ala Arg His Gly Gly Met His Gln Leu Arg Trp Lys Glu
3350 3355 3360

His Leu Ser Leu Gly Gly Gln Gly Cys Ser Glu Pro Leu Tyr His
3365 3370 3375

Cys Thr Pro Ala Gln Ala Thr Glu Gln Asp Leu Val Lys Lys Lys
3380 3385 3390

Lys Lys Arg Lys Lys Lys Arg Lys Asn Ser Phe Gln Ala Lys Leu
3395 3400 3405

Arg Ile Val Val Ile Leu His Val Val Leu Ser Leu Thr Ala Ser
3410 3415 3420

Leu Lys Thr Leu Leu Met Leu Ser Val Val Met Phe Lys Asn Val
3425 3430 3435

Asn Phe Ile Leu Asn Lys Met Cys Gln His Phe Arg Arg Phe Ala
3440 3445 3450

Leu Ser Glu Pro Ile Leu Phe Lys Pro Lys His Asn Val Thr Lys
3455 3460 3465

Ser Cys Met Asp Lys Arg Cys Ile Glu Asn Ala Asn Glu Ala Arg
3470 3475 3480

Cys Gly Gly Ser Cys Leu Ser Gln His Phe Gly Arg Gln Arg Leu
3485 3490 3495

Glu Asp His Leu Arg Pro Gly Ile Asp Gln Pro Gly Gln His Ser
3500 3505 3510

Lys Ile Leu Ser Leu Lys Ile Ile Arg Val Arg Glu Leu Ala Arg
3515 3520 3525

His Gly Gly Met Arg Val Lys Ser Leu Leu Gly Arg Leu Arg Trp
3530 3535 3540

Glu Asp Gly Leu Ser Leu Gly Val Gly Tyr Arg Lys Leu Leu Cys
3545 3550 3555

His Cys Pro Pro Ala Trp Val Met Glu Asp His Val Ser Lys Thr
3560 3565 3570

Lys Gln Lys Lys Lys Lys Cys Lys Leu Asp Gln Ser Ile Met Asn
3575 3580 3585

Thr Lys Asn Ser Leu Leu Trp Phe Gln Ile Pro Ser Ala Ile Asn
3590 3595 3600

Leu Asp Thr Thr Cys Gln Ala Ser Glu Pro Lys Leu Ser His His
3605 3610 3615

Ile Pro Cys Asp Leu His Val Tyr Ile Gln Met Ala Ser Asn Arg
3620 3625 3630

Ser Thr Lys Glu Val Lys Ile Ala Leu Thr Asp Asp Ile Pro Pro
3635 3640 3645

Leu Arg Phe Val Pro Ala Pro Pro Leu Ile Arg Tyr Ile Leu Pro
3650 3655 3660

Arg Pro Glu Gly Thr Leu Tyr Ser Pro Cys Pro Glu Cys Thr Leu
3665 3670 3675

Tyr Ala Tyr Pro Lys Pro Ile Arg Thr Asn Asp Asn Pro Thr Thr
3680 3685 3690

Leu Cys Leu Leu Phe Arg Leu Ser Pro Pro Ala Pro Arg Asn Ile
3695 3700 3705

Gln Pro Cys Cys Ser His Lys Ala Cys Leu Val Val Ser Ser His
3710 3715 3720

Gly Cys Met His Leu Val Leu Lys Thr Gln Asp Arg Arg Thr Pro

```
    3725                3730                3735

Leu Gly  Asp Gln Cys Pro Val  Val Ala Leu Thr Pro  Gly Asp Pro
    3740                3745                3750

Pro Met  Ile Ser Gly Pro Gln  Thr Asn Gln Pro Lys  Glu His Leu
    3755                3760                3765

Ala Asn  Phe Lys Ser Gly Lys  Trp Ser Phe His Ser  Ser Pro Ala
    3770                3775                3780

Phe Leu  Ala Thr Leu Gln Ser  Ser Ser Leu Thr Thr  Leu Gln Ser
    3785                3790                3795

Pro Cys  Pro Ser Asn Ser Arg  Ser Phe Ser Ser Leu  Val Glu Ile
    3800                3805                3810

Arg Arg  His Ile Leu Ser Val  Asp Pro Lys Leu Gln  Arg Gln Ser
    3815                3820                3825

Arg Thr  Arg Glu Asp Ser Leu  Pro Leu Val Phe Asn  His Cys Gly
    3830                3835                3840

Asp Ala  Cys Leu Ile Ile His  Pro His Ser Ile Gly  Val Ser Pro
    3845                3850                3855

Arg Gly  Cys Leu Pro Trp Ser  Phe Thr His Ile Pro  Leu Val Thr
    3860                3865                3870

Ser Gln  Leu Arg Gly His Leu  Leu Trp Leu Leu Thr  His Ile Ala
    3875                3880                3885

Ala Gln  Gly Cys Ser Met Pro  Pro Ala Ala Pro Pro  Ala Phe Ser
    3890                3895                3900

Val Pro  Leu Pro Ser Leu Phe  Ser Gly Leu Pro Pro  Ser Leu Trp
    3905                3910                3915

Ala Thr  Phe His Pro Pro Phe  Leu Leu Leu Leu Pro  Pro Val Phe
    3920                3925                3930

Ser Lys  Thr Asn Leu Phe Asn  Ser His Leu Thr Asn  Leu Ser Val
    3935                3940                3945

Leu Phe  Ser Ser Ala Thr Pro  Leu Gly Pro Asn Thr  Asn Ser Thr
    3950                3955                3960

Met Ile  Pro Asn Ser Gln Lys  Thr Ala Leu Ser Ser  Ser Pro Ser
    3965                3970                3975

Tyr Lys  Phe Ile Ile Leu Val  Ile Lys Trp Ala Asn  Gly Leu Arg
    3980                3985                3990

Cys Leu  Thr Ser Arg His Ser  Phe Thr His Trp Ser  Leu Pro Ser
    3995                4000                4005

Leu Cys  Ser Gln Cys Asp Ser  Ser Gln Ile Phe Leu  Leu Ser Leu
    4010                4015                4020

Leu Ser  Val Pro Ser Val Ser  Thr Pro Ser Ser Glu  Ser Ser Glu
    4025                4030                4035

Ser Phe  Phe Ser Met Asp Ser  Ser Asp Leu Pro Pro  Ser Pro Gln
    4040                4045                4050

Ala Ala  Pro Arg Gln Ala Glu  Pro Gly Pro Asn Ser  His Leu Ala
    4055                4060                4065

Ser Ala  Pro Pro Pro Tyr Asn  Pro Phe Ile Thr Ser  Pro Pro His
    4070                4075                4080

Thr Trp  Ser Ser Leu Gln Phe  Arg Ser Ser Thr Ser  Ser Pro Arg
    4085                4090                4095

Ser Ala  Gln Gln Phe Pro Val  Lys Glu Met Ala Asp  Tyr Pro Asp
    4100                4105                4110

Phe Ile  Arg Ala Gly Trp Cys  Leu Ala Phe Leu Glu  Val Gly Val
    4115                4120                4125
```

```
Leu Thr  Gly Pro Gln Phe Val  Pro Ser Ala Pro Pro  Arg Gly Leu
    4130                 4135                 4140

Arg Val  Ala Arg Gly Ala Lys  Leu Pro Ser Lys Cys  Leu Leu Val
    4145                 4150                 4155

Pro Gly  Arg Thr Gln Gln Glu  Cys Arg Ala Ala His  Ser Ala Val
    4160                 4165                 4170

His Gly  Asp Ser Arg Arg Thr  Thr Pro Leu Asp Pro  Trp Ala Cys
    4175                 4180                 4185

Ile Leu  Pro Ala Ala Glu Ser  Glu Ala Glu Ser Arg  Gln Pro Leu
    4190                 4195                 4200

Gly His  Ser Arg Ser Leu Leu  Ser Gly His Pro Val  Thr Lys Val
    4205                 4210                 4215

Ser Lys  Glu Asp Ala Val Ile  Thr Ala Ser Pro His  Gly Glu His
    4220                 4225                 4230

Asn Thr  Leu Thr Asn Thr Ser  Leu Thr Ser Gln Ser  Ser Ala Leu
    4235                 4240                 4245

Gly Val  Asp Arg Gln Val Phe  Cys Val Tyr Gln Asn  Arg Thr Gly
    4250                 4255                 4260

Ala Gln  Thr Trp Asn Gln Ser  Ser Arg Gly Asn Leu  Thr Arg Arg
    4265                 4270                 4275

Ser Pro  Gly Cys Thr Pro Pro  Gly Asp Ala Val Arg  Leu Gly Cys
    4280                 4285                 4290

Gly Cys  Glu Pro Ser Ala Arg  Asp Ser Ser Val Gly  Ile Pro Thr
    4295                 4300                 4305

Phe Leu  Ser Leu Leu Ser Asn  Arg Arg Thr Val Leu  Arg Met Phe
    4310                 4315                 4320

Leu Arg  Lys Thr Cys Thr Asn  Phe Tyr Asp Ile Tyr  Leu Phe Asn
    4325                 4330                 4335

Thr Glu  Leu Trp Pro Thr Leu  Asp Tyr Lys Gln Ile  Glu Glu Ile
    4340                 4345                 4350

Thr Ile  Ser His Phe Cys Ile  Ser Gln Lys Ile Ile  Leu Leu Gln
    4355                 4360                 4365

Ser Ser  Ile Tyr Cys Val Leu  Leu Ile Phe Tyr Cys  Glu Ser Lys
    4370                 4375                 4380

Ala Phe  His Gln Asn Lys Val  Phe Ile Met Ser Glu  Asn Cys Val
    4385                 4390                 4395

Cys Phe  Cys Ser Cys Asn Ile  Asn Gln Thr Leu Cys  Asn Ser Asn
    4400                 4405                 4410

His Lys  Met Met Cys Leu Lys  Cys Pro Ser Ser Cys  Gly Leu Ala
    4415                 4420                 4425

Val Ser  Arg Gln Gly Pro Asn  Pro Glu Leu Leu Asp  Gln Phe Tyr
    4430                 4435                 4440

Lys His  Phe Lys Ala Lys Lys  Lys Lys Lys Glu Val  Ala Gly Ala
    4445                 4450                 4455

Glu Gly  Val Val Lys Val Asn  Ala Pro Phe Ser Ser  Ser Asp Leu
    4460                 4465                 4470

Ser Gln  Ser Val Ser Val Ala  Val Phe His Gln Ile  Lys Pro Ser
    4475                 4480                 4485

Pro Val  His Gly Pro Phe Gly  Asn Asn Pro Met Leu  Tyr Arg Pro
    4490                 4495                 4500

Arg Pro  Arg Gly Ala Arg Arg  Pro Ser Tyr Ser Gln  Tyr Ala Phe
    4505                 4510                 4515
```

-continued

```
Tyr Tyr Pro Thr Arg Ser Gly His Lys Lys Leu Gln Lys Leu Asp
    4520                4525                4530

Ser Ser Pro Gln Thr Pro Gln Gln Asp Leu Ile Asn Leu Thr Phe
    4535                4540                4545

Lys Val Tyr Ser Asn Arg Val Glu Ala Thr Tyr Phe Val Ala Ile
    4550                4555                4560

Thr Cys Leu His Cys Glu Arg Asn Pro Ser His Ile Ser Ser Thr
    4565                4570                4575

Gln Glu Leu Gln Asn Thr Ile Ala Ala Ala Arg Cys Ser Ser Arg
    4580                4585                4590

Thr Ala Ser Pro Arg Ile Phe Leu Gln Val Leu Glu Ile Trp Ser
    4595                4600                4605

Leu Gly Gln Gly Met Pro Ala Ala Trp Asp Ser Ser Ala Met Ser
    4610                4615                4620

His Leu Cys Gln Thr Leu Leu Glu Ile Arg Leu Ser Asn Leu Pro
    4625                4630                4635

Arg Ser His Ser Gln Ser Cys Trp Asn Ser Gly Pro Arg Leu Ser
    4640                4645                4650

Asp Ser Phe Pro Asp Val Leu Gly Leu Ala Ala Glu Asn Cys Cys
    4655                4660                4665

Pro Ile Ala Ser Glu Ala Ser Trp Thr Ile Thr Asp Ala Leu Gly
    4670                4675                4680

Asn Ser Tyr Ser Glu Gly Glu Val Cys Pro Leu Leu Asn Thr Glu
    4685                4690                4695

Ala Thr His Ser Thr Ile Pro Ser Phe Gln Gly Pro Val Ser Leu
    4700                4705                4710

Ala Ser Ile Thr Val Val Gly Ile Asp Gly Gln Ala Ala Lys Pro
    4715                4720                4725

Val Lys Thr Pro Gln Leu Trp Cys Gln Leu Gly Gln His Ser Phe
    4730                4735                4740

Ile His Ser Phe Leu Val Ile Pro Thr Cys Pro Ala Pro Leu Leu
    4745                4750                4755

Gly Gln Asp Ile Leu Thr Lys Leu Ser Ala Ser Leu Thr Val Pro
    4760                4765                4770

Gly Leu Gln Pro His Leu Ile Ala Ala Leu Phe Pro Ser Ser Lys
    4775                4780                4785

Pro Pro Ser His Pro Pro Leu Val Ser Pro His Leu Asn Pro Gln
    4790                4795                4800

Val Trp Asp Thr Ser Ile Pro Ser Leu Ala Thr Asp His Ala Pro
    4805                4810                4815

Leu Thr Ile Pro Leu Lys Pro Asn His Pro Tyr Pro Thr Gln Cys
    4820                4825                4830

Gln Tyr Pro Ile Pro Gln His Thr Leu Lys Gly Ser His Ser Thr
    4835                4840                4845

Leu Lys Asp Ser Leu Leu Ser Leu Ala Cys Tyr Ser Met Ala Phe
    4850                4855                4860

Ser Leu Thr Leu Leu Thr Ile Pro Pro Phe Tyr Leu Ser Lys Asn
    4865                4870                4875

Gln Thr Ser Leu Thr Gly Phe Arg Ile Cys Ala Leu Ser Thr Lys
    4880                4885                4890

Leu Ser Cys Leu Cys Thr Pro Cys Gln Thr His Ile Pro Ser Tyr
    4895                4900                4905

Pro Gln Tyr Leu Pro Pro Thr Thr His Tyr Ser Val Leu Asn Lys
```

-continued

```
    4910                4915                4920

Pro Ser  Pro His Lys Ser Ile  Leu Ser Pro Leu Pro  Phe Pro Phe
    4925                4930                4935

Leu Lys  Lys Gln Pro Lys Leu  Leu Pro His Leu Ser  Leu Thr His
    4940                4945                4950

Pro Asn  Phe Phe Ile Thr His  Ser Gln Ser Ala Gly  Leu Cys Gly
    4955                4960                4965

Arg Asn  Ser Tyr Thr Arg Ala  Arg Ser Met Pro Cys  Ser Leu Ser
    4970                4975                4980

Val Gln  Thr Thr Pro Tyr Cys  Phe Ser Leu Ala Leu  Met Ser Val
    4985                4990                4995

Cys Gly  Gly Cys Cys Cys Phe  Asp Thr Phe Arg Gly  Pro Gln Asn
    5000                5005                5010

His Ile  Met Leu Asn Ser Leu  Ser Thr Val Leu Ile  Thr Ser Lys
    5015                5020                5025

Ile Tyr  Phe Leu Pro His Thr  Arg Ile Tyr Phe Pro  Leu Pro Gly
    5030                5035                5040

Ser Phe  Ser Tyr Thr Gln Leu  Phe Phe Glu Thr Glu  Ser His Ser
    5045                5050                5055

Val Ser  Gln Ala Gly Met Gln  Trp His Asn Leu Gly  Ser Leu Gln
    5060                5065                5070

Pro Pro  Leu Pro Arg Phe Gln  Arg Phe Ser Cys Leu  Ser Leu Trp
    5075                5080                5085

Ser Ser  Trp Asp Tyr Arg Cys  Val Pro His Thr Arg  Leu Ile Phe
    5090                5095                5100

Cys Ile  Phe Ser Arg Asp Gly  Val Ser Pro Cys Pro  Ser Trp Ser
    5105                5110                5115

Thr Pro  Asp Leu Lys Ser Ala  His Leu Gly Leu Pro  Lys Cys Trp
    5120                5125                5130

Asp Tyr  Arg His Glu Pro Pro  His Pro Ala Tyr Thr  His Ser Leu
    5135                5140                5145

Leu Ser  Leu Pro Gln Leu Pro  Leu Phe Leu Ala Trp  Thr Ser Ile
    5150                5155                5160

Arg Pro  Pro Thr Leu Phe Leu  Ile Pro His Leu Thr  Ser Met Thr
    5165                5170                5175

Ile Ser  Leu Ile His Leu Ala  Phe Thr Pro Phe Pro  His Ile Ser
    5180                5185                5190

Phe Phe  Pro Val Pro His Pro  Asp His Thr Trp Phe  Ile Asp Gly
    5195                5200                5205

Ser Ser  Thr Arg Pro Asn Arg  His Ser Pro Ala Lys  Ala Gly Tyr
    5210                5215                5220

Ala Ile  Leu Ser Ser Thr Ser  Ile Leu Glu Ala Thr  Ala Leu Pro
    5225                5230                5235

Arg Ser  Thr Thr Ser Gln Gln  Ala Lys Leu Ile Ala  Leu Thr Arg
    5240                5245                5250

Ala Leu  Thr Leu Ala Lys Gly  Leu Arg Val Asn Ile  Tyr Thr Asp
    5255                5260                5265

Ser Lys  Tyr Ala Phe His Ile  Leu His His His Ala  Val Ile Trp
    5270                5275                5280

Val Glu  Arg Gly Phe Leu Thr  Met Gln Gly Ser Phe  Ile Ile Ser
    5285                5290                5295

Ala Ser  Leu Ile Lys Thr Leu  Leu Lys Ala Ala Leu  Leu Pro Lys
    5300                5305                5310
```

-continued

```
Glu Ala Gly Val Ile His Cys Lys Gly His Gln Lys Ala Ser Asp
    5315                5320                5325

Pro Ile Thr Gln Gly Asn Ala Tyr Ala Asp Lys Val Ala Lys Glu
    5330                5335                5340

Ala Ala Ser Ile Pro Thr Ser Val Pro Gln Gly Gln Phe Phe Ser
    5345                5350                5355

Phe Leu Ser Val Thr Pro Thr Tyr Ser Leu Ile Glu Thr Ser Thr
    5360                5365                5370

Tyr Gln Ser Phe Pro Thr Gln Gly Lys Trp Phe Leu Asp Gln Gly
    5375                5380                5385

Lys Tyr Leu Leu Pro Ala Ser Gln Ala His Ser Ile Leu Ser Ser
    5390                5395                5400

Phe His Asn Leu Phe Arg Val Gly Tyr Lys Pro Leu Ala His Leu
    5405                5410                5415

Leu Pro Leu Ile Ser Phe Pro Ser Lys Ser Val Leu Lys Lys Ile
    5420                5425                5430

Thr Ser Gln Cys Ser Ser Thr Ile Leu Leu Ser Leu Arg Asp Cys
    5435                5440                5445

Ser Gly Pro Phe Pro Ser Leu His Ile Lys Leu Gly Asn Leu Pro
    5450                5455                5460

Leu Pro Arg Thr Gly Lys Leu Thr Leu Leu Thr Cys Ala Glu Ser
    5465                5470                5475

Gly Asn Asn Thr Ser Trp Tyr Gly Thr Leu Ser Leu Asp Gly Tyr
    5480                5485                5490

Arg Pro Phe Pro Gln Gly Val Arg Arg Pro Pro Arg Ser Phe Leu
    5495                5500                5505

Pro Phe Cys Gln Thr Phe Leu His Leu Ala Leu Pro Pro Leu Tyr
    5510                5515                5520

Ser Val Lys Thr Asp Arg Pro Leu Leu Val Lys Ser Pro Lys Gln
    5525                5530                5535

Leu Leu Ser Leu Leu Val Phe Ser Gly Ser Trp Phe Tyr Leu Lys
    5540                5545                5550

Thr Pro Pro Leu Arg Leu Ser Ser Gly Ile Phe Ser Gly Lys Val
    5555                5560                5565

Pro Ser Asp Thr Phe Thr Leu Met Lys Ser Tyr Ser Leu Leu Leu
    5570                5575                5580

Tyr Ser Phe Leu Phe Trp Phe Pro Ile Leu Cys His Pro Leu Pro
    5585                5590                5595

Leu Pro Ser Tyr Leu His His Thr Ile Asn Leu Thr Leu Ser Pro
    5600                5605                5610

Arg Leu Ser Phe Phe Phe Phe Asp Gly Val Leu Leu Cys Pro Pro
    5615                5620                5625

Gly Trp Ser Ala Val Val Ser Trp Leu Thr Ala Ser Ser Ala Ser
    5630                5635                5640

Trp Val His Thr Ile Leu Leu Pro Gln Pro Pro Lys Leu Gly Leu
    5645                5650                5655

Glu Val Pro Ala Thr Met Pro Gly Phe Phe Val Phe Leu Val Glu
    5660                5665                5670

Met Gly Phe His His Val Ser Gln Asp Gly Leu His Leu Leu Thr
    5675                5680                5685

Ser Arg Ser Ala His Leu Ser Leu Pro Lys Cys Trp Asp Tyr Arg
    5690                5695                5700
```

-continued

```
Arg Glu  Pro Leu Cys Pro Ala  Leu Ser Phe Phe Asn  Lys Gln Leu
    5705                 5710                 5715

Leu Ala  Leu His Phe Ser Phe  Leu Gln Asn Arg Gln  Gly Leu Asp
    5720                 5725                 5730

Leu Leu  Thr Ala Lys Lys Arg  Gly Pro Cys Ile Phe  Leu Asn Glu
    5735                 5740                 5745

Glu Cys  Cys Phe Tyr Leu Asn  Gln Ser Gly Leu Val  Tyr Asp Asn
    5750                 5755                 5760

Ile Lys  Lys Leu Lys Asp Arg  Pro Gln Lys Phe Ala  Asn Gln Ala
    5765                 5770                 5775

Asn Asn  Tyr Ala Glu Pro Pro  Trp Ala Leu Pro Asn  Trp Met Ser
    5780                 5785                 5790

Trp Val  Leu Pro Ile Leu Ser  Pro Leu Ile Pro Ile  Phe Leu Phe
    5795                 5800                 5805

Leu Leu  Phe Gly Pro Cys Val  Phe Leu Leu Phe Ser  Phe Ser Ile
    5810                 5815                 5820

His Thr  Lys Leu His Pro Gly  His Gln Gln Ser Phe  Tyr Thr Thr
    5825                 5830                 5835

Asn Thr  Pro Ser Asn Lys Pro  Thr Ile Ser Pro Leu  Ile Pro Lys
    5840                 5845                 5850

Ser Phe  Phe Ser Leu Ile Ser  Pro Thr Leu Gly Ser  His Ala Thr
    5855                 5860                 5865

Pro Ile  Pro Leu Lys Ala Ala  Pro Arg Asn Ile Ala  His Tyr Leu
    5870                 5875                 5880

Ser Ile  Pro Pro Pro Lys Ile  Phe Ala Ala Ser Thr  Leu His His
    5885                 5890                 5895

Tyr Phe  Val Leu Phe Phe Ile  Leu Ile Glu Asp Arg  Ser Val Arg
    5900                 5905                 5910

Pro Leu  Ser Pro Ser Ala Ile  Lys Ser Pro Val Thr  Cys Thr Cys
    5915                 5920                 5925

Thr Ser  Arg Pro Glu Ala Thr  Glu Asp Pro Gln Lys  Lys Lys Pro
    5930                 5935                 5940

Leu Met  Thr Phe His His Cys  Asp Leu Phe Leu Pro  His Ala Asn
    5945                 5950                 5955

Tyr His  Ile Phe Phe Pro Arg  Pro Glu Cys Thr Leu  Tyr Thr Tyr
    5960                 5965                 5970

Pro Lys  Pro Ile Arg Thr Asn  Asp Asn Pro Thr Thr  Leu Cys Leu
    5975                 5980                 5985

Ser Phe  Trp Thr Gln Pro Ala  Cys Thr Gln Val Lys  Thr Ala Leu
    5990                 5995                 6000

Leu Leu
    6005


<210> SEQ ID NO 46
<211> LENGTH: 6003
<212> TYPE: PRT
<213> ORGANISM: Homo sapiens

<400> SEQUENCE: 46

Glu Gly Lys Glu Val Arg His Lys Lys Leu Tyr Ile Val Phe His Leu
1               5                   10                  15

Leu Asn Val Gln Asn Gly Thr Ser Arg Asp Arg Lys Leu Ile Cys Gly
            20                  25                  30

Cys Arg Leu Gly Glu Gly Leu Pro Met Cys Met Gly Ser Val Gly Ser
        35                  40                  45
```

-continued

```
Asp Glu Asn Val Leu Val Asp Phe Gly Lys Gly Cys Met Ser Leu Ile
    50                  55                  60

Tyr Lys Cys Leu His His Thr Leu Lys Glu Phe Tyr Gly Ile Ile Ile
65                  70                  75                  80

Ser Lys Ile Ile Phe Lys Thr Leu Leu Met Phe Tyr His Leu Leu Arg
                85                  90                  95

His Lys Pro Lys Tyr Ile Lys Tyr Lys Ile Phe Leu Lys Glu Val Leu
            100                 105                 110

His Ile Leu Ser Leu Ser Leu Phe Phe Phe Phe Asp Arg Val Ser Leu
        115                 120                 125

Cys Cys Pro Gly Trp Ser Ala Val Ala Arg Ser Leu Leu Thr Ala Thr
    130                 135                 140

Ser Ala Ser Arg Val Gln Ala Ser Leu Leu Pro Gln Pro Pro Lys Leu
145                 150                 155                 160

Arg Leu Ala Ser Ala Thr Met Pro Gly Phe Leu Tyr Phe Arg Trp Gly
                165                 170                 175

Phe Thr Met Leu Ala Arg Val Val Ser Ser Ser Arg Gln Val Ile Cys
            180                 185                 190

Pro Leu Arg Pro Pro Lys Val Leu Gly Leu Gln Ala Asp Thr Thr Pro
        195                 200                 205

Ser Pro Cys Ser Leu Asn Tyr Ala Val Met Ser Leu Val Ser Asn Phe
    210                 215                 220

Lys Gly Thr Lys Thr Ser His Met Arg Lys Gly Lys Leu Leu Thr Gly
225                 230                 235                 240

Val Tyr Asp Asn Leu Ala Val Pro Ser Tyr Leu Glu Lys Ser Arg Tyr
                245                 250                 255

His Val Leu His Leu Val Lys Gly Val Ala Thr Ala Thr Gln Thr Leu
            260                 265                 270

Pro Phe Glu Trp Glu Ile Lys Val Leu Ser Pro Ser Asp Leu Trp Ile
        275                 280                 285

Gln Ser Gln Gln Tyr Leu Leu Glu Leu Gly Thr Val Leu Asn Ala Trp
    290                 295                 300

Gln Cys Val Ile Ala Pro His Pro Lys Gln Val Leu Leu Leu Pro Gly
305                 310                 315                 320

Phe Tyr Gly Asn Val His Leu Glu Lys Lys Leu Glu Asn Val Cys Cys
                325                 330                 335

Tyr Asp Leu Val Pro Asp Leu Trp Ser Leu Leu Ala Leu Leu Gly Val
            340                 345                 350

Glu Gln Met Thr Asn Ile Cys Arg Asn Leu Ser Tyr Val Gln Leu Tyr
        355                 360                 365

Ala Trp Gln Tyr Ser Val Ile Leu Arg Gly Lys Ala Trp Cys Asp Pro
    370                 375                 380

Pro Pro Trp Val Ala Val Ala Gly Ser Leu Ser Phe Ala Gln Thr Ala
385                 390                 395                 400

Asp Ala Ser Thr Val Pro Glu Glu Pro Ser Ser Leu His Leu Leu Thr
                405                 410                 415

Arg Leu Asn Ile Gln Ser His Leu Gly Phe Lys Leu Ser Ser Gln Thr
            420                 425                 430

Ile Asp Thr Tyr Pro Thr Phe Pro Val Tyr Phe Ser Thr Thr Leu His
        435                 440                 445

Pro Pro Ile Arg Leu Ala Pro Gln Lys His Leu Pro Leu Ser Glu Met
    450                 455                 460
```

-continued

```
Ser Pro Cys Pro Thr Val Ser Thr Gly Asn Asp Arg Met Ser Ser Cys
465                 470                 475                 480

Leu Ala Leu Asn Ser Val Thr Ala Thr Asn Cys Val Lys Cys His Arg
                485                 490                 495

Glu Glu Ser Tyr Phe Val Thr Cys Ser Leu Ser Val Leu Gln Ala Lys
            500                 505                 510

Arg Phe Leu Tyr Thr Asp Phe Gly Thr Asn Ala Thr Gly Pro Asn Cys
        515                 520                 525

Arg Leu Gln Gly Val Glu Ile Pro Tyr Trp Gly Cys Trp Arg Gln Lys
    530                 535                 540

Pro Ser His Phe Gln Asp Pro Asp Leu Pro Phe Pro His Ala Val Pro
545                 550                 555                 560

Pro Ser Gln Leu His Pro Gly His Arg Ala Leu Thr Lys Ala Gln Cys
                565                 570                 575

Val Tyr Ala Gly Leu Thr His Ser Gly Ser Gly Pro Arg Arg Gly Pro
            580                 585                 590

Ser Gln Arg Gly Gly Arg Gly Pro Leu Pro Pro Gly His Phe Pro Trp
        595                 600                 605

Gly Ala Val Ser Asn Gln Asp His Ala Arg Leu Gln Lys Thr Glu Arg
    610                 615                 620

Lys Val Glu Val Lys Gly Ser Arg Gly Leu Arg Ile Ala Val Ser Tyr
625                 630                 635                 640

Phe Phe Leu Arg Glu Leu Trp Thr Ala Gly Arg Thr His Leu Leu Val
                645                 650                 655

Cys Gln Phe Val Cys Glu Arg Glu Arg Glu Arg Glu Arg Glu Arg Asp
            660                 665                 670

Thr Phe Leu Arg Asp Asn Ser His Asn Ile Lys Leu Thr Thr Leu Phe
        675                 680                 685

Ile Glu Ile Gly Val Ser Leu Tyr Cys Pro Gly Trp Ser Gln Thr Pro
    690                 695                 700

Gly Leu Lys Ser Ser Ser Leu Gly Leu Pro Lys Cys Trp Asp Asp Arg
705                 710                 715                 720

Cys Glu Pro Pro Cys Pro Ala Lys Leu Thr Ile Leu Phe Tyr Leu Phe
                725                 730                 735

Ile Leu Arg Gln Ser Phe Ala Leu Val Ala Gln Ala Gly Val Gln Trp
            740                 745                 750

Asp Asp Leu Gly Ser Leu Gln Pro Ser Pro Pro Gly Phe Lys Arg Phe
        755                 760                 765

Ser Cys Phe Ser Leu Leu Ser Ser Trp Asp Tyr Arg His Leu Pro Pro
    770                 775                 780

Cys Pro Ser Phe Phe Phe Phe Leu Ser Phe Phe Phe Phe Phe Phe Leu
785                 790                 795                 800

Gly Glu Met Gly Phe His His Val Gly Gln Ala Ser Leu Lys Leu Leu
                805                 810                 815

Thr Ser Gly Asp Pro Pro Ala Pro Pro Ser Gln Ser Ala Gly Ile Thr
            820                 825                 830

Gly Val Ser His Arg Ala Arg Pro Asn Pro Phe Ile Asp Gln Phe Cys
        835                 840                 845

Gly Thr Cys Ile His Asn Ile Val Gln Thr Leu Pro Phe Val Leu Lys
    850                 855                 860

His Phe His Pro Lys Arg Lys Leu Glu Pro Ile Gln Gln Phe Pro Ile
865                 870                 875                 880

Phe Pro Pro Thr Leu Gly Pro Trp Pro Ser Val Cys Phe Leu Ser Leu
```

```
                885                 890                 895

Trp Ile Tyr His Phe Arg Ile Phe Pro Ile His Gly Ile Val Gln Tyr
            900                 905                 910

Met Thr Phe Cys Val Trp Leu Pro Ser Leu Gly Ile Ile Phe Gln Cys
        915                 920                 925

Ser Ser Pro Leu Glu His Ile Ser Val Leu His Ser Cys Leu Leu Pro
    930                 935                 940

Ile His Ile Pro Leu Tyr Glu Tyr Thr Thr Val Gly Leu Leu Ile Tyr
945                 950                 955                 960

Gln Leu Met Asn Thr Gly Val Ala Ser Thr Phe Trp Leu Leu Ile Ala
                965                 970                 975

Leu Pro Thr Phe Glu Cys Lys Tyr Glu Tyr Pro Phe Ile Ile Tyr Gly
            980                 985                 990

Leu Tyr Leu Gly Val Glu Leu Leu  Gly Gln Met Leu Ile  Tyr Leu Thr
        995                 1000                1005

Phe Cys  Gly Thr Ile Lys Leu  Phe Pro Gln Trp Leu  His His Phe
    1010                1015                1020

Lys Phe  Ser Pro Ala Met Tyr  Glu Ser His Pro Leu  Leu Asn Val
    1025                1030                1035

Tyr Pro  Phe Val Pro Phe Leu  Phe Pro Thr Phe Tyr  Lys Ala Ser
    1040                1045                1050

Ser Pro  Gln Thr Ser Leu Ser  Pro Gly Val Glu Gly  Gly Arg Ser
    1055                1060                1065

Cys Ile  Ser Ser Arg Lys Thr  Ile Gln Ala Ser Ile  Leu Thr Phe
    1070                1075                1080

Ser Ala  Asn Arg Ile Arg Pro  Gly Gly Gly Glu Asp  Arg Leu Pro
    1085                1090                1095

Pro Pro  Cys Gly His Gly Thr  Pro Thr Thr Ala Ile  Asn Ala Thr
    1100                1105                1110

Pro Asn  Tyr Pro Pro Ser Asp  Leu Gln Arg Leu Gly  Pro His Pro
    1115                1120                1125

Glu His  His Ile Lys Leu Phe  Asn Ser His Arg Glu  Gly Ala Arg
    1130                1135                1140

Cys Gly  Arg Cys Gln Leu Trp  Leu Ser Pro Ala Gly  Glu Cys Leu
    1145                1150                1155

Thr Phe  Ser Pro Ala Asp Leu  Arg Arg His Pro Ser  Pro Arg Pro
    1160                1165                1170

Ala Gln  Ser Pro Pro Leu Lys  Gly Arg Pro Ala Arg  Ala Trp Leu
    1175                1180                1185

Ala Ala  Asp Met Asn Gly Glu  Glu Ala Pro Pro Ser  Pro Pro Thr
    1190                1195                1200

Leu Ala  Gly Val Thr Ala Gly  His Arg Pro Gly Pro  Ser Arg Ala
    1205                1210                1215

Ile Tyr  Thr Tyr Asn Ser Pro  Pro Ala Pro Asp His  Ala Gly Ala
    1220                1225                1230

Asn Gln  Arg Pro Pro Ser Leu  Ser Asp Ser Val Cys  Ser Asn Gln
    1235                1240                1245

Glu Ala  Arg Ser Phe Gln Pro  Leu Ala Pro Val Asn  His Arg Ser
    1250                1255                1260

Ala Gly  Ala Phe Phe Pro Phe  Phe Phe Phe Pro Gly  Glu Ser Ala
    1265                1270                1275

Ser Gly  Leu Cys Ser Pro Thr  Ser Val Cys Pro Thr  Leu Glu Trp
    1280                1285                1290
```

-continued

```
Gly Lys  Cys Gly His Ala Thr  Gln Ser Gly Arg Glu  Gln Cys Ser
    1295                 1300                 1305

Arg Thr  Gln Arg Val Phe Gln  Thr Gly Gly Asp Arg  Val Pro Cys
    1310                 1315                 1320

Pro Pro  Arg Ser His Arg Phe  Pro Ala Gly Lys Thr  Asn Glu Ala
    1325                 1330                 1335

Leu Pro  Ser Pro Arg Pro Ala  Pro Pro Ser Pro Glu  Ile Leu Cys
    1340                 1345                 1350

Gly Leu  Leu Val His Ser Cys  Leu Gly Gly Val Asp  Leu Ala Asn
    1355                 1360                 1365

Gln Asp  Gly Pro Val Gly Arg  Ala His Phe Tyr Ser  Cys Leu Gln
    1370                 1375                 1380

Ser Cys  Lys Asn Ala Ser Tyr  Gly Lys Ala Arg Ala  Pro Gly Val
    1385                 1390                 1395

Ser Lys  Thr His Arg Leu Gly  Ser His Trp Gly Glu  Arg Glu Lys
    1400                 1405                 1410

His Arg  Asn Ser Lys Ala Phe  Arg Asn Val Arg Gly  Arg Asn Arg
    1415                 1420                 1425

Arg Arg  Lys Val Val Cys Gly  Gly Arg Val Gly Gly  Asp Ser Gly
    1430                 1435                 1440

Lys Phe  Arg Leu Ala Ser Val  Ser Asp Lys Lys Ser  Ser Asp Ile
    1445                 1450                 1455

Phe Lys  Gln Glu Arg Lys Ile  Ile Ser Leu Phe Arg  Lys Val Asn
    1460                 1465                 1470

Ser His  Gly Asn Arg Ala Glu  Arg Gly Asp Gly Gly  Trp Glu Met
    1475                 1480                 1485

Leu Gly  Ser Tyr Cys Tyr His  Ser Gly Glu Glu Ser  Trp Asp Leu
    1490                 1495                 1500

Lys Ser  Trp Asp Ser His Gly  Gly Asn Gly Lys Glu  Gly His Lys
    1505                 1510                 1515

Leu Arg  Gly Ile Trp Glu Glu  Asn Gln His Phe Ile  Asp Trp Met
    1520                 1525                 1530

Cys Glu  Met Ser Glu Asp Ser  Asn Gln Lys Arg Thr  Leu Arg Phe
    1535                 1540                 1545

Leu Ala  Val Ala Gly Arg Thr  Pro Leu Pro Leu Pro  Glu Ile Gly
    1550                 1555                 1560

Ser Lys  Lys Glu Arg Glu Arg  Glu Lys Gln Arg Asp  Phe Ala Lys
    1565                 1570                 1575

Gly Ile  Gly Val Gln Phe Leu  Thr Cys Gly Ile Ile  Ala Arg Ser
    1580                 1585                 1590

Thr Ser  Leu Trp Met Tyr Pro  Val Asp Ser Trp Glu  Leu Gly Ser
    1595                 1600                 1605

Gly Val  Glu Lys Lys Ser Arg  Asp Glu Ile Gln Arg  Val Tyr Ser
    1610                 1615                 1620

Gly Ser  Gly Glu Lys Leu Met  Thr Arg Glu Ile Ile  Glu Glu Asp
    1625                 1630                 1635

Leu Gly  Arg Ala Arg Trp Leu  Met Pro Val Ile Pro  Ala Phe Trp
    1640                 1645                 1650

Glu Thr  Lys Val Gly Gly Leu  Leu Glu Pro Arg Ser  Leu Arg Pro
    1655                 1660                 1665

Ala Trp  Ala Thr Trp Asp Pro  Asp Ser Thr Lys Thr  Ala Lys Ile
    1670                 1675                 1680
```

Ser Arg Val Trp His Ile Pro Val Ile Pro Ala Thr Trp Glu Ala
1685 1690 1695

Glu Val Gly Gly Ser Pro Glu Pro Gly Glu Val Ala Ala Val Ser
1700 1705 1710

Asp Ser Ala Thr Ala Leu Gln Pro Gly Gln His Ser Lys Ser Lys
1715 1720 1725

Thr Leu Ser Gln Lys Lys Lys Lys Lys Lys Ile Gln Val Gln Asn
1730 1735 1740

Leu Gly Lys Val Glu Arg Gly His Arg Gly Gln Val Trp Trp Leu
1745 1750 1755

Met Pro Val Ile Pro Ala Leu Trp Thr Leu Arg Trp Val Asp His
1760 1765 1770

Leu Arg Ser Gly Val Gln Asp Gln Pro Ser Gln His Gly Glu Thr
1775 1780 1785

Leu Phe Leu Leu Lys Ile Ile Gln Ala Trp Trp Arg Ala Pro Val
1790 1795 1800

Asn Ser Ser Phe Ser Arg Gly Gly Arg Arg Met Ala Thr Glu Ala
1805 1810 1815

Glu Val Ala Val Ser Asp Cys Ala Thr Thr Leu Gln Pro Gly Gln
1820 1825 1830

Gln Ser Glu Thr Leu Ser Gln Lys Lys Lys Lys Lys Lys Arg Gly
1835 1840 1845

His Arg Ala Ser Lys Thr Asp Lys Glu Val Ser Glu Arg Tyr Glu
1850 1855 1860

Lys Leu Lys Lys Ser Lys Leu Arg Tyr Cys Asn Arg Asn Lys Lys
1865 1870 1875

Ile Ile Pro Gly Arg Gly Ser Arg Thr Leu Phe Met Tyr Val Gln
1880 1885 1890

Asn Ser Lys Thr Leu Val Lys Ile Ile Lys His Ser Phe Asp Arg
1895 1900 1905

Ile Gln Pro Leu Lys Leu Cys Cys Lys Thr Ile Leu Pro Arg Asp
1910 1915 1920

Val Gln Cys Ile Phe Phe Pro Pro Val His Leu Arg Asn Thr Gln
1925 1930 1935

Val Lys Lys Tyr Ile Cys Trp Ala Arg Trp Leu Thr Ser Val Ile
1940 1945 1950

Leu Ala Leu Trp Glu Ala Glu Ala Gly Gly Ser Arg Gly Gln Glu
1955 1960 1965

Phe Glu Thr Thr Leu Ala Asn Val Val Lys Pro Cys Leu Tyr Gln
1970 1975 1980

Lys Tyr Lys Ile Ser Pro Ala Trp Arg Gln Val Pro Val Ile Pro
1985 1990 1995

Ala Thr Trp Glu Ala Glu Ala Gly Glu Ser Leu Glu Pro Gly Arg
2000 2005 2010

Gln Met Leu Gln Ala Glu Ile Val Pro Leu His Ser Ser Pro Ser
2015 2020 2025

Asp Asn Ala Arg Leu His Leu Lys Ile Lys Lys Ser Ile Tyr Ile
2030 2035 2040

Cys Val Tyr Ile Tyr Val Tyr Ile Cys Val Tyr Met Tyr Ile Cys
2045 2050 2055

Val Tyr Ile Cys Ile Tyr Val Cys Ile Tyr Val Tyr Met Cys Ile
2060 2065 2070

Tyr Val Tyr Ile Cys Val Tyr Met Cys Ile Tyr Val Tyr Ile Cys

```
    2075                2080                2085

Ile Tyr  Met Cys Ile Tyr Val  Cys Ile Tyr Val Cys  Ile Tyr Val
    2090                2095                2100

Tyr Ile  Cys Val Tyr Ile Cys  Ile Tyr Val Tyr Ile  Cys Val Tyr
    2105                2110                2115

Ile Cys  Val Tyr Met Cys Val  Tyr Met Tyr Ile Tyr  Val Cys Val
    2120                2125                2130

Tyr Val  Tyr Ile Ile Val Pro  Phe Leu Lys Ile Thr  Tyr Val Thr
    2135                2140                2145

Ala Lys  Arg His Glu Lys Ala  Gly Trp Leu Met Pro  Val Ile Pro
    2150                2155                2160

Ala Leu  Trp Glu Ala Lys Ala  Gly Ser Pro Glu Val  Arg Ser Leu
    2165                2170                2175

Arg Pro  Ala Pro Ile Ile Val  Ile Gln Asn Arg Thr  Ile Phe Val
    2180                2185                2190

Phe Cys  Lys Asn Thr Lys Ile  Ser Gln Val Trp His  Met Ser Val
    2195                2200                2205

Val Pro  Leu Thr Gln Glu Ala  Glu Ala Gly Glu Ser  Leu Glu Pro
    2210                2215                2220

Lys Arg  Arg Arg Leu Gln Ala  Glu Ile Ala Pro Leu  Tyr Tyr Ser
    2225                2230                2235

Leu Gly  Asp Arg Val Arg His  Arg Leu Lys Lys Lys  Lys Gly Met
    2240                2245                2250

Arg Lys  Leu Leu Gly Gly Asn  Cys Ser Ile Cys Leu  Leu Arg Cys
    2255                2260                2265

Ile His  Ser Ser Val Gln Leu  Ser Lys Ile Leu Ile  Arg Glu Glu
    2270                2275                2280

Thr Thr  Pro His Ile Val Leu  Cys Pro Ile Ser Ala  Ser Lys Glu
    2285                2290                2295

Arg Arg  Ser Lys Asn Leu Lys  Thr Glu Met Lys Ser  Thr Gly Arg
    2300                2305                2310

Gln Pro  Gly Ala Thr Pro Trp  Ala Trp Leu Lys Ile  Asp Pro Pro
    2315                2320                2325

Asn Gln  Leu Cys Tyr Leu Ile  Thr Val Ile Val Trp  Lys Ser Thr
    2330                2335                2340

Val Lys  Ile Pro Val Leu Phe  Cys Ser Val Leu Ile  Thr Ser Ala
    2345                2350                2355

Cys Ser  Pro Gln Ser His Thr  Pro Cys Leu Leu Asn  Arg Ser Arg
    2360                2365                2370

Pro Phe  His Ala Asp Pro Leu  Arg Val Val Ser Pro  Glu Gly Gln
    2375                2380                2385

Glu Leu  Leu Thr Gln Gly Ala  Arg Phe Leu Arg Arg  Glu Ser Cys
    2390                2395                2400

Arg Cys  Ser Arg Pro Asn Lys  Ala Leu Pro Ser Leu  Thr Arg Cys
    2405                2410                2415

Leu Arg  Gly Phe Val Cys Gly  Ser Ser Cys Tyr Thr  Gln Thr Arg
    2420                2425                2430

Ile Pro  Ile Phe Ile Phe Tyr  Phe Ile Tyr Phe Phe  Leu Glu Thr
    2435                2440                2445

Glu Ser  His Ser Val Ile Gln  Ala Gly Val Gln Trp  His Ala Leu
    2450                2455                2460

Gly Ser  Leu Gln Pro Pro Pro  Pro Arg Phe Lys Phe  Ser Cys Leu
    2465                2470                2475
```

```
Ser Pro Trp Ser Ser Trp Asp Tyr Arg Cys Ala Ala Pro Arg Pro
    2480                2485                2490

Ala Asn Phe Cys Ile Phe Ser Arg Asp Gly Val Ser Pro Cys Trp
    2495                2500                2505

Pro Gly Trp Ser Arg Thr Pro Asp Leu Arg Ser Ala His Leu Gly
    2510                2515                2520

Leu Pro Lys Cys Trp Asp Tyr Arg His Glu Ala Pro Cys Pro Ala
    2525                2530                2535

Glu Cys Leu Asn Phe Asn Lys Arg Gly Thr Val Asp Gly Thr His
    2540                2545                2550

Phe Thr Ala Leu Ser Trp Gly Leu Asn Gly Arg Pro Glu His Thr
    2555                2560                2565

Ala Trp Asn Ile Arg Arg Ala Gln Ser Val Glu Lys Gly Arg Met
    2570                2575                2580

Thr Gln Asp His Ser Thr Glu Glu Ala Arg Leu Gly Ala Arg Pro
    2585                2590                2595

Gly Val Trp Val Lys Ala Thr Pro Gly Pro Leu Lys Gln Asn His
    2600                2605                2610

Gln Gln Ile Lys Asp Pro Arg Met Gly Pro Asp Lys Lys Glu Ser
    2615                2620                2625

Glu Thr Glu Asn Phe Lys Thr Glu Lys Gly Leu Trp Ala Trp Leu
    2630                2635                2640

Met Pro Ile Ile Pro Thr Leu Glu Ala Asn Ile Gly Glu Leu Leu
    2645                2650                2655

Glu Pro Arg Ser Ser Arg Pro Ala Trp Thr Thr Tyr Gly Asp Pro
    2660                2665                2670

Val Ser Thr Lys Asn Lys Lys Leu Val Gly Cys Gly Gly Thr Arg
    2675                2680                2685

Leu Trp Ser Gln Leu Leu Gly Arg Leu Arg Trp Glu Asp Cys Leu
    2690                2695                2700

Ser Leu Arg Gly Cys Gly Phe Gly Glu Pro Gln Ser His His Cys
    2705                2710                2715

Ser Pro Ala Trp Val Thr Glu Arg Asp Cys Leu Lys Lys Lys Lys
    2720                2725                2730

Arg Gly Gly Lys Val Tyr Glu Gly Pro Trp Leu Thr Asn Met Thr
    2735                2740                2745

Gln Met Arg Lys Thr Tyr Ser Leu Leu Ser Arg Gly Leu Asn Lys
    2750                2755                2760

Gly Ile Lys Leu Cys Gly Asn Glu Ser Lys His Gly Tyr Gly Gln
    2765                2770                2775

Glu Gly Ser Ser Asn Asn Leu Ser Cys Ser Thr Val Ser Trp Glu
    2780                2785                2790

Glu Ala Ala Ser Leu Thr Ile Phe Val Gln Leu Val Gln Asp Ser
    2795                2800                2805

Val Asn Met Phe Leu Asn Gly Met Arg Trp Ile Arg Tyr Leu Leu
    2810                2815                2820

Gly Ser Thr Phe Asp Tyr Asp Ile Lys His Ile Lys Ala Leu Gln
    2825                2830                2835

Pro Asn Ile Arg Glu Leu Cys Tyr Phe Gln Ser Met Glu Trp Met
    2840                2845                2850

Ser Ile Ser Ser Leu Leu Ile Val Lys Leu Val Pro Ile Ser Ser
    2855                2860                2865
```

-continued

```
Trp Phe  Ser Asn Leu Phe Lys  Leu Ser Leu Ser Gly  Leu Gly Glu
    2870                 2875                 2880

Leu Lys  Val Ile Ile Pro Gly  Ile Leu Ile Ala Phe  Leu Ser Arg
    2885                 2890                 2895

Pro Leu  Val Glu Ile Leu Phe  Gly Phe Asn Val Ser  Cys Phe Val
    2900                 2905                 2910

Leu Phe  Cys Phe Val Phe Asp  Arg Val Ser Leu Cys  Arg Gln Ala
    2915                 2920                 2925

Gly Val  Gln Trp Arg Asp Leu  Gly Leu Gln Pro Pro  Pro Pro Gly
    2930                 2935                 2940

Phe Lys  Gln Phe Ser Cys Leu  Ser Leu Pro Ser Ser  Trp Asp Tyr
    2945                 2950                 2955

Met Cys  Ala His His Thr Trp  Leu Ile Phe Tyr Phe  Arg Gly Phe
    2960                 2965                 2970

Thr Ile  Leu Ala Arg Met Val  Leu Ile Ser Pro Arg  Asp Leu Pro
    2975                 2980                 2985

Thr Leu  Ala Ser Ser Ala Gly  Ile Ile Gly Val Ser  His His Ala
    2990                 2995                 3000

Arg Pro  Leu Met Leu Val Leu  Ile Ile Leu His Ile  Tyr Ile Ile
    3005                 3010                 3015

His Phe  Ala Tyr Tyr Gly Thr  Ile Glu Lys Pro Leu  Gly Glu Ser
    3020                 3025                 3030

Val Pro  Ser Phe Lys Tyr Trp  Phe Tyr Tyr Leu Ile  Asp Val Trp
    3035                 3040                 3045

Leu Trp  Gly Lys Ala Phe Met  Gln Arg Phe Ser Met  Cys Ser Pro
    3050                 3055                 3060

Trp Thr  Pro Glu Arg Thr Pro  Asn Asn Phe Gln Gly  Ile His Lys
    3065                 3070                 3075

Thr Lys  Met Met Phe Met Val  Ile Leu Ser Leu Ile  Cys Leu Phe
    3080                 3085                 3090

Ser Pro  Ser His His Phe Phe  Trp Trp Glu Ile Leu  Cys Thr Leu
    3095                 3100                 3105

Ile Gly  Ile Thr Val Val Ala  Pro Asn Cys Thr Ser  Gly His Tyr
    3110                 3115                 3120

Ile Pro  His Cys Pro Ala Leu  Gly Gly Glu Phe Ser  Pro Pro Gly
    3125                 3130                 3135

Trp Asn  Ala Met Ile Ser Ala  His Cys Asn Leu Cys  Leu Leu Gly
    3140                 3145                 3150

Ser Ser  Asp Ser Pro Ala Ser  Thr Ser Gln Val Thr  Arg Ile Thr
    3155                 3160                 3165

Gly Ala  Cys His His Ala Trp  Leu Ile Phe Val Phe  Leu Val Val
    3170                 3175                 3180

Ser Pro  Cys Trp Pro Gly Trp  Ser Arg Thr Pro Gly  Leu Arg Ser
    3185                 3190                 3195

Thr Tyr  Leu Gly Leu Pro Lys  Cys Trp Asp Tyr Arg  Cys Glu Pro
    3200                 3205                 3210

Pro Cys  Pro Ala Lys Met Phe  Leu Ile Lys Lys Leu  Leu Ile Tyr
    3215                 3220                 3225

Ile Leu  Ile Leu Lys Ser Thr  Phe Lys Phe Cys Gly  Met Lys Trp
    3230                 3235                 3240

Glu Val  Gly Ser Thr Tyr Lys  Val Leu Leu Leu Tyr  Val Lys Glu
    3245                 3250                 3255

Gln Trp  Leu Ser Gly Lys Thr  Leu Val Ser Leu Leu  Ala Glu Leu
```

```
    3260                3265                3270

Thr Pro  Leu Phe Met Tyr Pro  Phe Cys Leu Lys Glu  Leu Thr Asn
    3275                3280                3285

Trp Leu  Phe Arg Leu Trp Tyr  Phe Ala Ala Ser Arg  Thr Leu Ile
    3290                3295                3300

Lys Asn  Cys Tyr Phe Lys Val  Thr Thr Cys Asn Ile  Cys Ser Asn
    3305                3310                3315

Asp Lys  Ile Ala Phe Gly Ser  Gly Ser Cys Leu Ser  Gln His Leu
    3320                3325                3330

Gly Arg  Leu Arg Arg Glu Glu  His Leu Ser Ser Gly  Val Asp Gln
    3335                3340                3345

Pro Gly  Gln Ser Leu Gln Lys  Glu Lys Lys Asn Pro  Gly Met Val
    3350                3355                3360

Ala Cys  Thr Ser Gly Gly Arg  Ser Thr Ala Trp Glu  Ala Lys Ala
    3365                3370                3375

Ala Val  Ser His Asp Cys Thr  Thr Ala Leu Gln Pro  Arg Gln Gln
    3380                3385                3390

Ser Lys  Ile Leu Ser Lys Lys  Lys Lys Lys Glu Lys  Arg Lys Glu
    3395                3400                3405

Lys Ile  Ala Phe Lys Gln Asn  Ser Glu Leu Ser Cys  Met Trp Tyr
    3410                3415                3420

Ala Gln  Leu Pro Asn Asn Lys  Leu Phe Cys Tyr Gln  Trp Cys Ser
    3425                3430                3435

Lys Met  Ser Ile Phe Lys Tyr  Tyr Arg Ile Lys Cys  Ala Asn Ile
    3440                3445                3450

Leu Glu  Asp Leu His Asn Ser  Val Asn Gln Tyr Phe  Ser Asn Asp
    3455                3460                3465

Gln Asn  Ile Met Leu Gln Asn  His Ala Trp Ile Lys  Gly Ala Leu
    3470                3475                3480

Lys Met  Gln Met Arg Pro Gly  Val Val Ala His Ala  Ser Asn Pro
    3485                3490                3495

Ser Ile  Leu Gly Gly Arg Gly  Trp Arg Ile Thr Gly  Gln Ala Phe
    3500                3505                3510

Glu Thr  Ser Leu Ala Asn Ile  Ala Arg Ser Tyr Leu  Lys Glu Glu
    3515                3520                3525

Asn Pro  Gly Met Val Ala Cys  Ala Ser Leu Ser Tyr  Leu Gly Gly
    3530                3535                3540

Tyr Gly  Gly Arg Met Ala Ala  Glu Phe Glu Val Thr  Gly Ser Tyr
    3545                3550                3555

Asp Cys  Ala Thr Ala Leu Gln  Pro Gly Trp Ser Lys  Thr Met Phe
    3560                3565                3570

Gln Lys  Gln Asn Lys Lys Lys  Arg Asn Ala Ser Thr  Asn Glu Val
    3575                3580                3585

Cys Asn  Glu Ile Gln Lys Ile  His Cys Tyr Gly Phe  Lys Phe Pro
    3590                3595                3600

Val Gln  Leu Thr Phe Lys Ile  Leu Arg Val Arg Pro  Leu Ser Pro
    3605                3610                3615

Asn Ala  Ile Ile Ser Pro Val  Thr Cys Met Tyr Thr  Tyr Arg Trp
    3620                3625                3630

Pro Glu  Ala Thr Glu Asp Pro  Gln Lys Lys Lys Pro  Leu Met Thr
    3635                3640                3645

Phe His  His Asp Leu Phe Leu  Pro His Pro Asn Tyr  Asp Ile Phe
    3650                3655                3660
```

-continued

```
Ser Pro  Ala Leu Lys Lys Val  Leu Cys Asp Ile Leu  Pro Ala Leu
    3665                 3670                 3675

Glu Asn  Val Leu Cys Thr Pro  Ile Pro Asn Leu Glu  Leu Met Ile
    3680                 3685                 3690

Ile Pro  Pro Pro Phe Val Asp  Ser Phe Leu Asp Ser  Ala Arg Leu
    3695                 3700                 3705

His Pro  Gly Glu Ile Tyr Ser  Leu Val Ala His Thr  Lys Pro Val
    3710                 3715                 3720

Trp Trp  Phe Leu His Thr Asp  Ala Cys Asp Ile Trp  Cys Arg Pro
    3725                 3730                 3735

Arg Thr  Gly Gly Leu Leu Trp  Glu Thr Ser Ala Leu  Leu Ser Pro
    3740                 3745                 3750

Ser Leu  Arg Glu Glu Ile His  Leu Ser Gln Val Leu  Arg Pro Thr
    3755                 3760                 3765

Ser Pro  Arg Asn Ile Leu Pro  Ile Ser Asn Arg Val  Ser Gly Leu
    3770                 3775                 3780

Phe Thr  Leu Leu Gln Pro Phe  Leu Leu Pro Phe Asn  Leu Pro Leu
    3785                 3790                 3795

Ser Leu  Pro Phe Asn Leu Pro  Val Leu Pro Ile Pro  Val Leu Phe
    3800                 3805                 3810

Pro Leu  Arg Gly Asp Thr Phe  Tyr Leu Trp Thr Gln  Asn Ser Ser
    3815                 3820                 3825

Val Ser  His Gly Leu Gly Lys  Thr Val Phe Pro Trp  Cys Leu Ile
    3830                 3835                 3840

Thr Val  Gly Thr Pro Ala Leu  Phe Thr His Thr Pro  Leu Val Ser
    3845                 3850                 3855

Asp His  His Gly Asp Ala Cys  Leu Gly His Ser Pro  Thr Phe Pro
    3860                 3865                 3870

Trp Gln  Val Asn Cys Gly Asp  Thr Cys Phe Gly Cys  Ser Pro Thr
    3875                 3880                 3885

Leu Gln  Pro Arg Ala Ala Gln  Cys Pro Pro Leu Pro  His Pro Pro
    3890                 3895                 3900

Ser Pro  Cys Leu Tyr Pro Leu  Phe Ser Arg Val Tyr  Leu Leu His
    3905                 3910                 3915

Tyr Gly  Gln Pro Ser Thr Leu  His Ser Ser Phe Phe  Ser Leu Ser
    3920                 3925                 3930

Leu Cys  Ser Gln Lys Leu Lys  Thr Ser Ser Thr His  Thr Pro Lys
    3935                 3940                 3945

Thr Val  Ser Tyr Phe Leu Leu  Gln His Arg Leu Ala  Pro Ile Gln
    3950                 3955                 3960

Thr Arg  Gln Phe Gln Ile Ala  Arg Lys Arg His Phe  Arg Val Leu
    3965                 3970                 3975

His Pro  Thr Ser Ser Arg Phe  Leu Ser Asn Gly Gln  Met Val Gly
    3980                 3985                 3990

Ala Arg  Pro Gly Ile Leu Leu  His Ile Gly Pro Ser  Leu Val Ser
    3995                 4000                 4005

Ala Pro  Asn Val Thr His Pro  Lys Ser Phe Phe Phe  Leu Ser Phe
    4010                 4015                 4020

Leu Phe  Leu Arg Ser Pro Pro  Gln Val Pro Ser Pro  Leu Asn Pro
    4025                 4030                 4035

Ser Phe  Leu Trp Thr His Leu  Thr Ser Pro Leu Leu  Pro Arg Leu
    4040                 4045                 4050
```

-continued

```
Leu Leu Ala Arg Leu Ser Gln Val Pro Ile Leu Thr Pro Leu Leu
    4055                4060                4065

Pro His Pro Ile Ile Leu Leu Ser Pro Pro Leu Leu Thr Pro Gly
    4070                4075                4080

Pro Ala Tyr Ser Phe Val Pro Arg Leu Ala Leu Pro Asp Leu Pro
    4085                4090                4095

Asn Asn Phe Leu Leu Lys Arg Trp Leu Thr Ile Leu Thr Ser Ser
    4100                4105                4110

Glu Gln Ala Gly Ala Trp Pro Ser Trp Asn Glu Trp Val Phe Gln
    4115                4120                4125

Ala Pro Ser Leu Ser His Leu His Arg Gln Glu Val Ser Gly Trp
    4130                4135                4140

Pro Glu Glu Gln Ser Cys Leu Pro Ser Ala Cys Trp Cys Leu Gly
    4145                4150                4155

Glu His Ser Arg Ser Val Val Arg Pro Thr Ala Gln Cys Met Val
    4160                4165                4170

Ile Pro Gly Ala Glu Gln Leu Pro Leu Thr Leu Gly Pro Ala Ser
    4175                4180                4185

Asp Ser Arg Leu Gln Asn Gln Lys Leu Ser Pro Gly Asn Arg Ser
    4190                4195                4200

Ala Thr Pro Gly His Ser Ser Leu Asp Thr Gln Leu Leu Lys Ser
    4205                4210                4215

Ala Lys Lys Met Arg Ser Pro Pro Asp Leu His Met Val Asn Thr
    4220                4225                4230

Thr Leu Ser Leu Thr Pro Pro Pro Val Ser Leu Gln His Trp Gly
    4235                4240                4245

Trp Thr Gly Arg Phe Ser Val Phe Thr Arg Ile Ala Gln Ala Lys
    4250                4255                4260

His Lys His Gly Thr Arg Val Pro Gly Glu Glu Thr Ser Leu Ala
    4265                4270                4275

Glu Ala Gln Ala Ala Pro His Gln Val Met Gln Cys Ala Ala Val
    4280                4285                4290

Gly Ala Arg Ser Gln Val Leu Gly Thr Arg His Glu Trp Glu Ser
    4295                4300                4305

Pro Arg Ser Cys His Cys Cys Gln Thr Glu Gly Lys Gln Ser Tyr
    4310                4315                4320

Glu Cys Asn Ser Leu Gly Arg Leu Val Gln Thr Phe Ile Arg Ile
    4325                4330                4335

Ser Ile Tyr Leu Ile Leu Asn Phe Gly Leu Leu Cys Asp Lys Thr
    4340                4345                4350

Ile Asn Lys Leu Arg Lys Ser Leu Phe Leu Thr Ser Val Phe Leu
    4355                4360                4365

Lys Lys Phe Cys Tyr Arg Val Gln Tyr Thr Val Tyr Tyr Ser Ser
    4370                4375                4380

Ile Val Lys Ala Lys His Phe Ile Lys Thr Lys Tyr Phe Lys Leu
    4385                4390                4395

Val Lys Ile Val Tyr Val Asn Phe Ala Ala Val Ile Leu Ile Lys
    4400                4405                4410

Leu Cys Val Ile Leu Ile Thr Lys Cys Ala Leu Asn Ala Pro Pro
    4415                4420                4425

Ala Val Gly Trp Gln Cys Pro Asp Arg Asp Pro Glu Ile Leu Asn
    4430                4435                4440

Asp Cys Thr Asn Ser Ile Lys Asn Ile Ser Arg Gln Lys Lys Lys
```

-continued

```
    4445                4450                4455

Lys Lys  Arg Trp Leu Glu Leu  Lys Ala Ser Arg Leu  Met Leu Leu
    4460                4465                4470

Phe Leu  His Leu Thr Ser Pro  Asn Gln Leu Ala Phe  Arg Leu Phe
    4475                4480                4485

Phe Ile  Lys Tyr Lys Asn Pro  Ala Gln Phe Met Ala  His Leu Ala
    4490                4495                4500

Thr Thr  Leu Arg Cys Phe Thr  Ala Leu Asp Pro Glu  Gly Pro Glu
    4505                4510                4515

Gly Arg  Leu Ile Leu Asn Met  His Phe Ile Thr Gln  Pro Ala Pro
    4520                4525                4530

Asp Ile  Arg Lys Ser Ser Lys  Asn Ile Pro Ala Leu  Lys Pro His
    4535                4540                4545

Asn Arg  Thr Leu Thr Ser Pro  Ser Arg Cys Thr Val  Ile Glu Arg
    4550                4555                4560

Gln His  Ile Ser Glu Leu Gln  Leu Leu Ala Ser Thr  Val Arg Glu
    4565                4570                4575

Thr Pro  Ala Thr Ser Pro Ala  His Lys Asn Phe Lys  Thr Pro Glu
    4580                4585                4590

Ser Gln  Arg Pro Gly Val Pro  Pro Gly Pro Pro Pro  Pro Gly Ser
    4595                4600                4605

Phe Phe  Lys Cys Trp Lys Ser  Gly His Trp Ala Lys  Glu Cys Leu
    4610                4615                4620

Gln Pro  Gly Ile Pro Pro Glu  Pro Cys Pro Ile Cys  Ala Arg Pro
    4625                4630                4635

Tyr Trp  Lys Ser Asp Cys Pro  Thr Tyr Pro Gly Ala  Thr Pro Arg
    4640                4645                4650

Ala Ala  Gly Thr Leu Ala Gln  Asp Ser Leu Thr Pro  Ser Gln Met
    4655                4660                4665

Phe Ser  Ala Arg Leu Lys Thr  Asp Ala Ala Gln Ser  Pro Gln Lys
    4670                4675                4680

Pro Leu  Gly Pro Ser Gln Met  Leu Trp Val Thr Leu  Thr Val Lys
    4685                4690                4695

Gly Lys  Ser Val Pro Phe Leu  Ile Gln Arg Leu Pro  Thr Pro Gln
    4700                4705                4710

Tyr Leu  Leu Phe Lys Gly Leu  Phe Pro Leu Pro Pro  Leu Leu Trp
    4715                4720                4725

Val Leu  Met Ala Arg Leu Leu  Asn Leu Ser Lys Leu  Pro Asn Ser
    4730                4735                4740

Gly Ala  Asn Leu Asp Asn Ile  Leu Leu Tyr Thr Leu  Phe Leu Ser
    4745                4750                4755

Leu Pro  Ala Gln Leu Pro Tyr  Val Lys Thr Phe Pro  Asn Tyr Leu
    4760                4765                4770

Leu Pro  Leu Phe Leu Asp Tyr  Ser His Thr Ser Leu  Pro Pro Phe
    4775                4780                4785

Ser Pro  Val Gln Ser Leu Leu  Arg Ile Leu Pro Leu  Tyr Leu Pro
    4790                4795                4800

Thr Leu  Ile His Lys Tyr Gly  Thr Pro Leu Phe Pro  Pro Trp Gln
    4805                4810                4815

Pro Ile  Met His Pro Leu Pro  Ser His Asn Leu Ile  Thr Leu Thr
    4820                4825                4830

Pro Leu  Asn Ala Asn Ile Pro  Ser His Ser Thr Leu  Lys Asp Pro
    4835                4840                4845
```

```
Thr Ala His Phe Lys Arg Ile Lys Ala Cys Tyr His Ser Pro Ala
    4850                4855                4860

Ile Ala Trp Pro Ser Lys Ala Tyr Lys Leu Ser Leu Gln Phe Pro
    4865                4870                4875

His Phe Thr Cys Pro Lys Thr Arg Gln Val Leu Gln Val Ser Ser
    4880                4885                4890

Gly Ser Val Pro Tyr Gln Gln Asn Cys Leu Ala Tyr Ala Pro His
    4895                4900                4905

Ser Ala Lys Pro Ile Tyr Pro Pro Ile Leu Asn Thr Ser Leu Pro
    4910                4915                4920

Gln Pro Ile Ile Leu Phe Ile Asn Leu Ala Asp Pro Ile Asn Pro
    4925                4930                4935

Lys Ser Phe Pro His Ser Pro Phe His Ser Leu Lys Asn Ser Pro
    4940                4945                4950

Lys Ser Cys Ser His Thr Ser Ser Pro Leu Ile Pro Thr Phe Ser
    4955                4960                4965

Leu His Thr Ala Lys Val Gln Gly Cys Val Val Gly Ile Leu Thr
    4970                4975                4980

Gln Glu Pro Glu Ala Cys Pro Val Ala Phe Leu Ser Lys Gln Leu
    4985                4990                4995

Asp Leu Thr Val Leu Ala Pro Ser Cys Leu Cys Val Val Ala Ala
    5000                5005                5010

Ala Ala Leu Ile Leu Leu Glu Ala Leu Lys Ile Thr Leu Cys Ser
    5015                5020                5025

Thr His Ser Leu Gln Phe Ser Leu Pro Lys Ser Ile Phe Phe Leu
    5030                5035                5040

Ile Pro Asp Ala Tyr Thr Phe His Ser Leu Ala Pro Ser Ala Ile
    5045                5050                5055

Leu Asn Ser Phe Leu Arg Gln Ser Leu Thr Pro Ser Pro Arg Leu
    5060                5065                5070

Ala Cys Ser Gly Thr Ile Leu Ala His Cys Asn Leu Arg Phe Pro
    5075                5080                5085

Gly Ser Ser Asp Ser Pro Ala Ser Ala Ser Gly Val Ala Gly Ile
    5090                5095                5100

Thr Gly Val Cys Pro Thr Pro Gly Phe Phe Val Phe Leu Val Glu
    5105                5110                5115

Met Gly Phe His His Val Asn Gln Ala Gly Leu Glu Leu Leu Thr
    5120                5125                5130

Ser Asp Leu Pro Ile Ser Ala Ser Gln Ser Ala Gly Ile Thr Gly
    5135                5140                5145

Met Ser His His Thr Gln Pro Ile Leu Thr Leu Cys Val Ser His
    5150                5155                5160

Asn Tyr His Cys Ser Trp Pro Gly Leu Gln Ser Gly Leu Pro His
    5165                5170                5175

Tyr Ser Tyr His Thr Pro Pro Leu Ser Leu Ser Thr Trp His Ser
    5180                5185                5190

Leu His Phe Pro Ile Phe Pro Ser Phe Leu Phe Leu Thr Leu Ile
    5195                5200                5205

Thr Leu Gly Leu Leu Met Ala Val Pro Pro Gly Leu Ile Ala Ile
    5210                5215                5220

His Arg Gln Arg Gln Ala Met Leu Tyr Tyr Leu Pro His Leu Ser
    5225                5230                5235
```

-continued

```
Leu Arg  Leu Pro Leu Cys Pro  Ala Pro Leu Pro Leu  Ser Lys Pro
    5240                 5245                 5250

Asn Ser  Leu Pro Leu Gly Pro  Ser Leu Leu Gln Arg  Asp Tyr Val
    5255                 5260                 5265

Ser Ile  Phe Ile Leu Thr Leu  Asn Met Pro Phe Ile  Ser Ser Thr
    5270                 5275                 5280

Thr Met  Leu Leu Tyr Gly Leu  Lys Glu Val Ser Ser  Leu Cys Lys
    5285                 5290                 5295

Gly Pro  Ser Ser Leu Val Pro  Leu Lys Leu Phe Ser  Arg Leu Leu
    5300                 5305                 5310

Tyr Phe  Gln Arg Lys Leu Glu  Ser Phe Thr Ala Arg  Ala Ile Lys
    5315                 5320                 5325

Arg His  Gln Ile Pro Ser Leu  Arg Ala Thr Leu Met  Leu Ile Arg
    5330                 5335                 5340

Leu Lys  Lys Gln Leu Ala Phe  Gln Leu Leu Ser Leu  Arg Ala Ser
    5345                 5350                 5355

Phe Ser  Pro Ser Tyr Arg Ser  Leu Pro Pro Thr Pro  Ser Leu Lys
    5360                 5365                 5370

Leu Pro  Arg Ile Asn Leu Phe  Pro His Lys Ala Asn  Gly Ser Trp
    5375                 5380                 5385

Ile Lys  Glu Asn Ile Ser Phe  Gln Pro His Arg Pro  Ile Leu Phe
    5390                 5395                 5400

Cys Arg  His Phe Ile Thr Ser  Ser Val Val Thr Ser  Arg Pro Ile
    5405                 5410                 5415

Ser Tyr  Asn Leu Ser Phe His  Phe His Arg Glu Asn  Leu Ser Arg
    5420                 5425                 5430

Lys Ser  Leu Leu Ser Val His  Leu Leu Phe Tyr Tyr  Pro Ser Gly
    5435                 5440                 5445

Ile Val  Gln Ala Pro Ser Leu  Pro Tyr Thr Ser Ser  Trp Gly Ile
    5450                 5455                 5460

Cys Pro  Cys Pro Gly Leu Ala  Asn Leu Tyr His Val  Pro Ser Gln
    5465                 5470                 5475

Glu Thr  Lys Ile Pro Leu Gly  Met Gly Arg His Phe  His Trp Met
    5480                 5485                 5490

Gly Thr  Gly Leu Ser His Arg  Val Glu Gly His His  Gly His Phe
    5495                 5500                 5505

Phe Pro  Ser Val Arg His Asn  Ser Ser Ile Pro Cys  His Leu Tyr
    5510                 5515                 5520

Thr Val  Lys Gln Thr Gly Leu  Tyr Ser Asn His Pro  Ser Ser Phe
    5525                 5530                 5535

Ser Ala  Ser Trp Tyr Leu Val  Ala Pro Gly Phe Thr  Ser Lys His
    5540                 5545                 5550

His Pro  Gly Ser Leu Glu Val  Asp Arg Ser Ser Val  Ala Arg Tyr
    5555                 5560                 5565

Pro Pro  Ile Leu Ser Pro Ser  Pro Ile Leu Tyr Phe  Tyr Thr His
    5570                 5575                 5580

Ser Tyr  Ser Gly Ser Arg Ser  Tyr Ala Thr Leu Tyr  Leu Ser Pro
    5585                 5590                 5595

Ala Ile  Ser Thr Thr Leu Ser  Ile Ser Leu Ser Pro  Ser Pro Val
    5600                 5605                 5610

Tyr Asn  Pro Ser Phe Phe Phe  Glu Met Glu Ser Cys  Ser Val Pro
    5615                 5620                 5625

Gln Ala  Gly Val Gln Trp Cys  Asp Leu Gly Ser Leu  Gln Ala Pro
```

```
    5630                5635                5640

Pro Pro  Gly Phe Thr Pro Phe  Ser Cys Leu Ser Leu  Pro Ser Ser
    5645                5650                5655

Trp Asp  Arg Cys Leu Pro Pro  Cys Leu Ala Asn Phe  Leu Tyr Phe
    5660                5665                5670

Arg Trp  Gly Phe Thr Met Leu  Ala Arg Met Val Ser  Ile Ser Pro
    5675                5680                5685

His Asp  Pro Pro Thr Ser Ala  Ser Gln Ser Ala Gly  Ile Thr Gly
    5690                5695                5700

Val Ser  His Tyr Ala Arg Pro  Ser Asn Pro Ser Leu  Thr Asn Asn
    5705                5710                5715

Cys Trp  Leu Cys Ile Ser Leu  Ser Ser Lys Ile Ala  Lys Ala Ser
    5720                5725                5730

Thr Tyr  Ser Leu Leu Lys Lys  Glu Asp Pro Val Tyr  Phe Thr Lys
    5735                5740                5745

Ser Val  Val Phe Thr Ile Asn  Leu Ala Trp Cys Met  Thr Thr Lys
    5750                5755                5760

Asn Ser  Arg Ile Asp Pro Lys  Asn Ser Pro Thr Lys  Gln Ile Ile
    5765                5770                5775

Met Leu  Asn Pro Leu Gly His  Ser Leu Ile Gly Cys  Pro Gly Ser
    5780                5785                5790

Phe Gln  Phe Leu Val Leu Tyr  Leu Phe Phe Ser Phe  Ser Tyr Ser
    5795                5800                5805

Asp Leu  Val Ser Ser Phe Cys  Leu Val Ser Gln Phe  Ile Gln Asn
    5810                5815                5820

Cys Ile  Gln Ala Ile Asn Asn  His Ser Ile Arg Gln  Ile Leu Leu
    5825                5830                5835

Leu Thr  Ser Pro Gln Tyr His  Pro Leu Tyr Pro Asn  Leu Ser Ser
    5840                5845                5850

Val Ser  Leu Leu Leu Val Pro  Met Pro Pro Gln Ser  His Ser Lys
    5855                5860                5865

Gln Pro  Arg Glu Thr Ser Pro  Ile Ile Ser Pro Tyr  His Pro Gln
    5870                5875                5880

Lys Phe  Ser Leu Pro Gln His  Phe Thr Thr Ile Leu  Phe Cys Phe
    5885                5890                5895

Ser Tyr  Tyr Lys Lys Ile Gly  Val Ser Gly Leu Val  Gln Ala Lys
    5900                5905                5910

Pro Ser  Asn Pro Leu Pro Ala  Arg Val His Pro Asp  Asp Leu Lys
    5915                5920                5925

Gln Leu  Lys Ile His Lys Arg  Ser Glu Ser Ser Leu  Asn His Ser
    5930                5935                5940

Thr Ile  Val Ile Cys Ser Cys  Pro Thr Leu Thr Asp  Thr Ile Tyr
    5945                5950                5955

Ser Ser  Pro Ala Leu Glu Asn  Val Leu Cys Thr Pro  Ile Pro Asn
    5960                5965                5970

Leu Glu  Leu Met Ile Ile Leu  Pro Pro Phe Ala Asp  Ser Leu Phe
    5975                5980                5985

Gly Leu  Ser Pro Pro Ala Pro  Arg Asn Lys Gln Pro  Cys Cys Ser
    5990                5995                6000
```

<210> SEQ ID NO 47
<211> LENGTH: 5952
<212> TYPE: PRT
<213> ORGANISM: Homo sapiens

<400> SEQUENCE: 47

Ala Thr Gly Leu Phe Ile Ser Pro Gly Cys Arg Arg Ala Glu Ser Lys
1               5                   10                  15

Lys Arg Val Ser Lys Gly Trp Asp Tyr His Phe Leu Val Trp Asp Arg
            20                  25                  30

Cys Thr Lys Tyr Ile Leu Lys Gly Gly Gly Arg Ile Tyr Gly Ile Ser
        35                  40                  45

Arg Gly Ala Gly Thr Asn His Asn Gly Gly Met Ser Ser Val Lys Ala
    50                  55                  60

Thr Phe Thr Ser Phe Val Asp Leu Gln Leu Leu Gln Val Ile Trp Met
65                  70                  75                  80

Tyr Thr Cys Arg Ser Gln Gly Ile Trp Leu Ser Leu Asp Ser Glu Ala
                85                  90                  95

His Ser Tyr Leu Leu Ile Leu Val Lys Thr Lys Gln Asn Ser Gly Glu
            100                 105                 110

Val Leu Arg Gln Arg Lys Phe Leu Gly Val Val Trp Arg Asp Asn Gly
        115                 120                 125

Arg Cys Phe Ser Gly Leu Leu Val Gly Leu Gly Trp His Gly Asn Leu
    130                 135                 140

Glu Glu Arg Leu Asn Arg Lys Ile Trp Val Gly Val Ile Leu Trp Ala
145                 150                 155                 160

Cys Lys Glu Tyr Leu Ser Tyr Arg Met Ile Val Asp Gly Leu Asp Ala
                165                 170                 175

Val Leu Tyr Glu Leu Arg Asn Thr Glu Gly Arg His Lys Val Arg Ile
            180                 185                 190

Arg Glu Arg Glu Lys Val Leu Lys Asp Glu Leu Glu Gly Pro Arg Thr
        195                 200                 205

Ser Asn Gly Val Pro Lys Gly Val Gln His Asn Tyr Leu Leu Gly Trp
    210                 215                 220

Arg Ile Phe Gly Val Tyr Pro Val Phe Leu Cys Cys His Thr Pro Gly
225                 230                 235                 240

Gln Ile Asp Leu Gly Lys Asn Asn Thr Leu Arg Leu Lys Ile Tyr Arg
                245                 250                 255

Val Leu Phe Phe Gln Val Ser Arg Gly Leu Gly Asp Phe Gly Gly Lys
            260                 265                 270

Arg Asn Ala Lys Pro Ala Val Val Cys Arg Arg Ile Arg Gly Pro Gly
        275                 280                 285

Ile Val Ala His Ala Cys Asn Pro Ser Thr Leu Gly Gly Gly Gly Arg
    290                 295                 300

Ile Val Arg Ser Gly Asp Gly Asp His Pro Gly His Gly Glu Thr Pro
305                 310                 315                 320

Ser Leu Leu Lys Ile Gln Lys Ile Ser Gln Ala Trp Trp Gln Ala Pro
                325                 330                 335

Leu Val Pro Ala Thr Trp Glu Ala Glu Ala Gly Glu Trp Cys Glu Pro
            340                 345                 350

Arg Arg Arg Ser Leu Gln Ala Lys Ile Thr Pro Leu His Ser Ser Leu
        355                 360                 365

Gly Asp Arg Ala Arg Leu His Leu Lys Lys Lys Arg Arg Ile Ile Asn
    370                 375                 380

Gly Ala Arg Arg Glu Asp Cys Gly Gly Asp Ser Trp Gly Glu Val Glu
385                 390                 395                 400

Gly Gly Ile Arg Ser Gly Thr Arg Ile Arg Met Ser Ile Lys Val Lys

-continued

```
                405                 410                 415

Asn Arg Thr Ser Ser Gly Lys Tyr Arg Arg Val Pro Cys His Arg Ser
            420                 425                 430

Ile His Phe Lys Arg Ala Leu Arg Val Val Phe Gly Lys Thr Arg Ser
        435                 440                 445

His Ile Pro Arg Gly Glu Ala Ala Trp Val Ile Leu Ile Lys Ala Gly
    450                 455                 460

Leu Phe Ser His Cys Ile Glu Val Ala Arg Leu Asn Gly Gly Ile Met
465                 470                 475                 480

Ser Asp Arg Arg Glu Glu Met Thr Val Val Ala Phe Ser His Pro Val
                485                 490                 495

Gly Lys Ala Cys Thr His Pro Val Lys Val Ser Thr His Thr Lys Arg
            500                 505                 510

Tyr Phe Ser Phe Leu Thr Arg His Met Ser Val Lys Ser Ile Cys Gln
        515                 520                 525

Ser Trp Ala Gly Ala Asn Ser Pro Ala Cys Val Gly Lys Gly Arg Gly
    530                 535                 540

Leu Asn Asn Pro Gly Ile Val Glu Met Asn Thr Glu Lys Phe Ser Ser
545                 550                 555                 560

Gly Gln Ile Phe Thr Met Glu Met Lys Glu Val Ile Arg Asp Gly Leu
                565                 570                 575

Ala Ala Cys Asn Leu His Gly Arg Gly Tyr Glu Met Thr Thr Glu Asn
            580                 585                 590

Gly Pro Val Arg Leu Glu Gly Asp Ile Phe Leu Asp Pro Arg Thr Ile
        595                 600                 605

Cys Leu Val Trp Glu Lys Ile Asp Thr Trp Lys Phe Gln Gly Ser Arg
    610                 615                 620

Trp Glu Pro Ile Arg Arg Arg Lys Thr Gly Pro Glu Gly Gln Lys Leu
625                 630                 635                 640

Glu Cys Leu Leu Leu Leu Pro Tyr Gln His Lys Arg Cys Pro Glu Trp
                645                 650                 655

Asp Leu Met Pro Phe Asp Gly Pro Cys Ser Glu Leu Gln Leu Pro Leu
            660                 665                 670

Glu Val Lys Gln Pro Glu Glu Phe Leu Leu Lys Arg His Arg Thr Leu
        675                 680                 685

Ala Gly Asn Leu Phe Gln Pro Ile Gln His Gly Gly Gly Gly Tyr Glu
    690                 695                 700

Arg His Ile Ser Gln Tyr Lys Tyr His Val Val Pro Leu Gln Glu Gly
705                 710                 715                 720

Pro Glu Leu Arg Gln Val Trp Leu Ala Glu Arg Trp Ser Gly Ala Glu
                725                 730                 735

Arg Pro Gln Gly Met Trp Lys Ile Val His Ser Leu Pro Leu Pro Val
            740                 745                 750

Asn Gly Asp Ala Trp Trp Asn Cys His Gln Thr Lys Cys Asp Gln Gly
        755                 760                 765

Glu Glu Gln Glu Arg Arg Lys Tyr Gly Glu Met Glu Met Pro Gly Gly
    770                 775                 780

Ser Glu Arg Ser Trp Arg Ser Gly Val Val Ser Gly Ile Met Trp Glu
785                 790                 795                 800

Ala Gly Leu Lys Ser Arg Pro Gly Thr Met Val Ile Val Gly Asp Ser
                805                 810                 815

Ala Lys Ser Glu Tyr Arg Leu Gly Val Val Ala His Ala Cys Asn Pro
            820                 825                 830
```

-continued

Ser Thr Leu Gly Gly Arg Asp Gly Gln Ile Thr Leu Gly Gln Glu Phe
835 840 845

Lys Thr Ser Leu Val Asn Met Val Lys Pro His Leu Tyr Lys Tyr Lys
850 855 860

Lys Leu Ala Gly Cys Gly Ala His Thr Cys Asn Pro Ser Tyr Ser Arg
865 870 875 880

Gly Gly Arg Arg Ile Ala Gly Thr Trp Glu Ala Glu Val Ala Val Ser
885 890 895

Gln Asp Cys Ala Thr Ala Cys Gln Pro Gly Arg Arg Ser Glu Thr Leu
900 905 910

Ser Gln Lys Arg Val Glu Tyr Ser Arg Ser Gln Gly Val Glu Ser Ile
915 920 925

Cys Val Arg Tyr Glu Glu Glu Asn Arg Phe Trp Lys Leu Glu Leu Arg
930 935 940

Val Ser Ala Cys Asp Phe Glu Gly Leu Lys Tyr Gln Ser Ser Ser Ser
945 950 955 960

His His Thr Gln Thr Gly Leu Gly Asn Ser Lys Val Lys Leu Phe Gly
965 970 975

Gln Lys Gly Tyr Arg Ala Cys Phe Trp Leu Leu Cys Lys Asn Ser Asp
980 985 990

His Thr Ala Leu His Phe Gly Cys Val Lys Ser Trp Asp Glu Leu Gly
995 1000 1005

Arg Ala Ser Val Gly Ala Ala Phe Arg Ala Val Phe Gly Met Glu
1010 1015 1020

Arg Gly Val Gly Lys Gly Phe Arg Ile Tyr Gly Val Ser Val Tyr
1025 1030 1035

Leu Glu Gln Asn Asn Gly Leu Trp Glu Gly Gly Ile Glu Asp Arg
1040 1045 1050

Arg Val Tyr Gly Phe Gly Thr Met Gly Cys Ile Gly Lys Thr Ile
1055 1060 1065

Leu Leu Ile Arg His Arg Ser Thr Asn Leu Asp Leu Ser Gly Phe
1070 1075 1080

Trp Thr Gly Lys Met Gly Glu Leu Gly Glu Phe Ile Gly Phe Arg
1085 1090 1095

Arg Pro Cys Tyr Ser Arg Arg Val Ile Thr Gly Phe Asn Pro Phe
1100 1105 1110

Lys Val Cys Cys Gly Ile Leu Leu Lys Cys Ala Val Gly Trp Asp
1115 1120 1125

Ile Gly Ile Glu Trp Gly Lys Gly Asp Val Leu Met Gly Trp Gly
1130 1135 1140

Val His Asp Arg Leu Pro Arg Arg Glu Arg Cys Pro Ile Leu Val
1145 1150 1155

Asp Gly Gly Glu Ile Gln Gly Glu Asp Ala Lys Glu Ala Leu Asn
1160 1165 1170

Trp Gly Lys Gly Arg Gln Gly Val Ala Val Val Gln Glu Gln Ser
1175 1180 1185

Gly Lys Gln Ile Ile Trp Leu Lys Cys Leu Asp Leu Ile Arg Glu
1190 1195 1200

Leu Gly Arg Gly Leu Lys Lys Ser Val Lys Asn Val Val Gln Val
1205 1210 1215

Gly Thr Arg Val Gly Glu Phe Gln Val Gln Pro Gly His Gln Tyr
1220 1225 1230

-continued

```
Pro Gln  Gln Leu Trp Arg Gln  Gly Lys Gln Ala Leu  Glu Lys Lys
    1235                 1240                 1245

Val Leu  Trp Ser Gly Pro Leu  Tyr Glu Gly Asp Arg  Leu Pro Leu
    1250                 1255                 1260

His Cys  Lys Ser Tyr Pro Lys  His Leu Trp Ser Lys  Arg Leu Leu
    1265                 1270                 1275

Arg Arg  Leu Gly Ser Ile Ser  Phe Gln Pro Leu Ser  Arg Glu His
    1280                 1285                 1290

Leu Gly  Arg Ser Gln Arg Val  Leu Gly Gln Ser Ser  Ser Ser Ser
    1295                 1300                 1305

Gly Ser  Gly Ser Trp Val Ser  Trp Thr Val Phe Pro  Val Gly Ser
    1310                 1315                 1320

Gly Thr  Asp Gly Thr Trp Leu  Arg Arg Asn Pro Arg  Leu Gln Ala
    1325                 1330                 1335

Phe Leu  Gly Pro Val Thr Arg  Phe Pro Ala Leu Glu  Glu Arg Ser
    1340                 1345                 1350

Trp Gly  Arg Arg Ser Trp Arg  Asn Thr Trp Pro Leu  Arg Phe Arg
    1355                 1360                 1365

Cys Phe  Glu Val Leu Val Cys  Trp Arg Cys Gly Trp  Gly Phe Ser
    1370                 1375                 1380

His Ser  Gly Gly Lys Leu Gln  Leu Arg Asn Met Leu  Pro Leu Leu
    1385                 1390                 1395

Tyr Tyr  Cys Thr Pro Arg Gly  Leu Ser Pro Val Val  Gly Phe Glu
    1400                 1405                 1410

Gly Trp  Asn Leu Ile Phe Gly  Ala Phe Ser Asn Val  Arg Ser Gly
    1415                 1420                 1425

Leu Gly  Asn Lys Met His Ile  Glu Asn Lys Thr Ala  Phe Trp Pro
    1430                 1435                 1440

Leu Trp  Val Gly Gly Lys Ala  Ser Lys Gly Cys Cys  Gln Met Gly
    1445                 1450                 1455

His Glu  Leu Gly Trp Val Phe  Ile Phe Asp Glu Lys  Gln Pro Lys
    1460                 1465                 1470

Arg Leu  Ile Gly Arg Gly Gln  Met Lys Lys Lys Glu  His Pro Leu
    1475                 1480                 1485

Arg Leu  Gln Leu Gln Pro Pro  Leu Phe Phe Phe Phe  Leu Pro Asn
    1490                 1495                 1500

Val Phe  Asn Arg Ile Gly Leu  Ala Val Ile Gln Asp  Phe Arg Val
    1505                 1510                 1515

Pro Val  Trp Thr Leu Pro Thr  His Ser Trp Arg Gly  Ile Gly Thr
    1520                 1525                 1530

Ser Phe  Cys Asp Asn Tyr Thr  Lys Phe Asp Tyr Tyr  Ser Cys Lys
    1535                 1540                 1545

Ile Asn  Ile His Asn Phe His  Ser Phe Lys Ile Leu  Cys Phe Asp
    1550                 1555                 1560

Glu Met  Leu Cys Phe His Asn  Arg Arg Ser Val Val  His Ser Ile
    1565                 1570                 1575

Leu Asn  Ser Val Thr Lys Leu  Phe Phe Glu Lys Tyr  Arg Ser Glu
    1580                 1585                 1590

Lys Phe  Pro Gln Phe Val Tyr  Ser Leu Ile Thr Lys  Ala Lys Val
    1595                 1600                 1605

Gln Tyr  Ile Asn Arg Tyr Pro  Asn Lys Ser Leu Tyr  Lys Ser Ser
    1610                 1615                 1620

Gly Ile  Thr Phe Val Arg Leu  Phe Thr Phe Cys Leu  Thr Ala Val
```

```
1625                1630                1635

Thr Gly Thr Trp Gly Phe Pro Leu Met Thr Ser Pro His Leu Ala
    1640                1645                1650

Pro Ser Thr His Ser Leu Gly Ala Leu His His Leu Val Gly Cys
    1655                1660                1665

Ser Leu Gly Phe Cys Glu Gly Phe Leu Thr Trp Asn Ser Gly Ser
    1670                1675                1680

Met Phe Val Leu Ser Leu Cys Asp Ser Gly Lys His Arg Lys Pro
    1685                1690                1695

Ala Cys Pro Pro Pro Val Leu Lys Thr Asp Trp Ser Arg Arg Cys
    1700                1705                1710

Glu Cys Cys Val His His Val Glu Ile Arg Arg Leu Pro His Leu
    1715                1720                1725

Leu Cys Leu Leu Gly Val Gln Arg Gly Val Thr Gly Ser Gly Arg
    1730                1735                1740

Ala Val Ala Trp Thr Gln Leu Leu Ile Leu Gln Pro Gly Val Arg
    1745                1750                1755

Cys Arg Pro Lys Gly Gln Gly Glu Leu Phe Ser Ala Trp Asn His
    1760                1765                1770

His Ala Leu Arg Cys Gly Pro His Asp Thr Pro Ala Val Phe Ser
    1775                1780                1785

Gln Ala Pro Thr Gly Thr Trp Lys Ala Thr Leu Leu Leu Trp Pro
    1790                1795                1800

Pro Gly Asp Leu Leu Ala Val Gln Met Gly Gln Thr Gly Gly Leu
    1805                1810                1815

Ser Glu His Pro Leu Ile Pro Gly Arg Pro Gly Thr Ser Leu Leu
    1820                1825                1830

Ser Gln Asp Ser Gln Pro Ser Leu Gln Glu Ile Val Gly Gln Ile
    1835                1840                1845

Gly Glu Ser Ser Arg Asn Glu Thr Val Ser Trp Thr Arg Cys Glu
    1850                1855                1860

Glu Gly Arg Lys Asp Tyr Arg Val Gly Glu Gln Arg Leu Ser Glu
    1865                1870                1875

Asn Trp Asp Leu Ala Gln Pro Gly Glu Glu Gln Pro Gly Glu Lys
    1880                1885                1890

Gly Gly Gly Gln Met Ser Pro Lys Arg Arg Ile Gln Arg Thr Arg
    1895                1900                1905

Asn Leu Gly Trp Arg Pro Lys Glu Gln Lys Gly Glu Lys Glu Glu
    1910                1915                1920

Arg Phe Gly Met Ser His Ile Gly Ser Arg Asp Gly Gly Thr Asn
    1925                1930                1935

Val Lys Asn Ala Trp Thr Ser Gly Thr Ser Asp His Leu Pro Ile
    1940                1945                1950

Leu Gln Glu Leu Ser Arg Thr Cys Arg Met Glu Asn Ser Lys Val
    1955                1960                1965

Pro Phe Ser Gly Tyr Leu Glu Ser Leu Ser Ser Leu Tyr Trp Gly
    1970                1975                1980

Gln Ala Val Leu Gln Lys Lys Ile Arg His Leu Gly Phe Arg Ser
    1985                1990                1995

Gly Val Ser Arg Gly Phe Lys Phe Leu Arg Thr Gln Ala Lys Gly
    2000                2005                2010

Glu Glu Gly Gly Met Glu Gly Gly Arg Leu Pro Ile Val Lys Glu
    2015                2020                2025
```

-continued

```
Val Asn  Pro Arg Lys Glu Arg  Val Glu Ala Arg Arg  Arg Arg Val
    2030                 2035                 2040

Gly Gln  Arg Gly Ala Leu Ser  Ser Pro Gly Leu Gln  Cys Gly Ala
    2045                 2050                 2055

Ala Lys  Ala Gly Val Pro Ala  Ile Asp Leu Ser Pro  Arg Glu Cys
    2060                 2065                 2070

Gly Met  Thr Lys Ala Gly Ile  Pro Val Val Ile Arg  His Gln Trp
    2075                 2080                 2085

Ser Val  Gly Glu Ser Gly Arg  Arg Pro His Ser Asp  Thr Pro Arg
    2090                 2095                 2100

Glu Asp  Cys Leu Pro Glu Ser  Val Thr Asp Ala Gly  Val Leu Gly
    2105                 2110                 2115

Pro Gln  Ile Lys Cys Val Ser  Leu Ser Leu Leu Glu  Arg Lys Lys
    2120                 2125                 2130

Asn Gly  Asn Trp Lys Asp Arg  Glu Ile Glu Gly Glu  Arg Lys Ile
    2135                 2140                 2145

Glu Gly  Gln Glu Arg Leu Glu  Lys Ser Glu Lys Thr  Thr Tyr Pro
    2150                 2155                 2160

Ile Asn  Trp Gln Asp Val Pro  Trp Ala Gly Trp Ser  Glu Asp Leu
    2165                 2170                 2175

Arg Ser  Val Asp Leu Leu Thr  Glu Gly Arg Gln Gln  Gly Thr Gly
    2180                 2185                 2190

Leu Pro  Lys Glu Ser Ser Cys  Pro Gly Ser Ser Ala  Pro Asn Val
    2195                 2200                 2205

Thr Cys  Ile Arg Val Lys Lys  Pro Pro Asn Arg Leu  Cys Val Ser
    2210                 2215                 2220

Asn Lys  Ala Val Tyr Phe Thr  Trp Val Gln Ala Gly  Val Lys Gly
    2225                 2230                 2235

Val Asn  Lys Gly Trp Trp Asp  Tyr His Phe Leu Val  Trp Asp Arg
    2240                 2245                 2250

Arg Thr  Lys Tyr Ile Leu Lys  Gly Arg Glu Asn Ile  Thr Lys Tyr
    2255                 2260                 2265

Leu Leu  Lys Gly Gly Gly Glu  Tyr Ile Val Ser Val  Arg Val Gly
    2270                 2275                 2280

Gln Glu  Gln Ile Ser Met Val  Glu Cys His Gln Leu  Arg Leu Phe
    2285                 2290                 2295

Ser Leu  Leu Leu Trp Ile Phe  Ser Cys Phe Arg Pro  Ser Val Cys
    2300                 2305                 2310

Ile His  Ala Gly His Arg Gly  Tyr Asp Gly Leu Val  Trp Ala Gln
    2315                 2320                 2325

Arg Pro  Asp Thr Tyr Leu Lys  Gly Leu His Trp Glu  Phe Glu Thr
    2330                 2335                 2340

Ile Ala  Met Asn Phe Leu Tyr  Phe Ile Thr Leu Tyr  Phe Ile Gly
    2345                 2350                 2355

Leu Thr  Cys Ile Ser Phe Phe  Phe Val Leu Phe Leu  Lys His Gly
    2360                 2365                 2370

Leu Thr  Pro Ser Pro Arg Leu  Glu Gly Ser Gly Thr  Ile Ile Ala
    2375                 2380                 2385

Ser Cys  Asn Leu Lys Leu Leu  Ser Ser Ser His Pro  Pro Thr Val
    2390                 2395                 2400

Ala Ser  Gln Val Ala Lys Thr  Ser Arg Ala Cys His  His Ala Trp
    2405                 2410                 2415
```

```
Leu Ile  Leu Leu Leu Leu Leu  Phe Leu Glu Ile Gly  Ser Cys Tyr
    2420                 2425                 2430

Val Gly  Gln Ala Gly Leu Lys  Cys Leu Ala Ser Ser  Asp Pro Pro
    2435                 2440                 2445

Ala Ser  Ala Ser Gln Asn Ala  Gly Ile Arg Gly Met  Ser His His
    2450                 2455                 2460

Thr Trp  Pro His Leu His Phe  Gln Cys Thr Phe Tyr  Pro Cys Met
    2465                 2470                 2475

Ile Leu  His Tyr Val Leu Val  Ile Lys Val Leu Val  His Val Met
    2480                 2485                 2490

Gln Ile  Phe Asn Val Gly Thr  Phe Tyr Ser Ile Ile  Phe Lys Asn
    2495                 2500                 2505

His Phe  Thr Ser Pro Leu Ile  Ala Ser Glu Glu Phe  Leu Ile Ile
    2510                 2515                 2520

Arg Lys  Leu Ser Ser Leu Val  Pro His Ala Arg Ser  Leu Gln Phe
    2525                 2530                 2535

Val Leu  Leu Glu Ser Tyr Phe  Phe Phe Ser Phe Phe  Phe Phe Phe
    2540                 2545                 2550

Phe Phe  Gln Asp Leu Ala Leu  Leu Pro Gly Leu Glu  Cys Ser Gly
    2555                 2560                 2565

Thr Ile  Met Ala His Cys Ser  Leu Gly Leu Pro Gly  Ser Ser Ala
    2570                 2575                 2580

Pro Ser  Thr Ser Ala Gly Ala  Cys His His Ala Trp  Leu Ile Phe
    2585                 2590                 2595

Phe Phe  Phe Leu Glu Arg Leu  Pro Arg Leu Val Ser  Asn Ser Ala
    2600                 2605                 2610

Gln Val  Leu Leu Pro Pro Gln  Pro Pro Val Leu Gly  Leu Ala Ala
    2615                 2620                 2625

Thr Ala  Lys Ser Ser Asn Phe  Ile Ile Gly Thr Asn  Ile Ala Ser
    2630                 2635                 2640

Cys Tyr  Phe Glu Val Thr Ile  Leu Leu Tyr Cys Ser  Ser Cys Lys
    2645                 2650                 2655

Ile Pro  Lys Ser Glu Gln Pro  Val Cys Gln Ser Phe  Phe Gln Thr
    2660                 2665                 2670

Lys Arg  Ile Leu His Glu Arg  Gly Phe Ser Ser Gln  Leu Ser His
    2675                 2680                 2685

Cys Phe  Pro Ser Arg Gln Pro  Leu Phe Phe Asp Ile  Gln Lys Tyr
    2690                 2695                 2700

Phe Ile  Ser Thr Ser Tyr Phe  Pro Phe His Ala Thr  Glu Phe Leu
    2705                 2710                 2715

Lys Gly  Ala Leu Lys Asp Gln  Asn Leu Ile Asn Phe  Leu Phe Tyr
    2720                 2725                 2730

Gln Glu  His Leu Gly Trp Ala  Trp Trp Leu Thr Pro  Val Ile Pro
    2735                 2740                 2745

Ala Leu  Trp Lys Ala Lys Val  Gly Gly Ser Pro Glu  Ala Arg Ser
    2750                 2755                 2760

Ser Arg  Pro Ala Trp Pro Thr  Trp Asn Tyr Lys Tyr  Lys Asn Pro
    2765                 2770                 2775

Gly Val  Val Ala Gly Thr Cys  Asn Pro Ser Tyr Leu  Gly Ser Gly
    2780                 2785                 2790

Arg Arg  Ile Ala Thr Gln Glu  Ala Glu Val Ala Val  Ser Arg Asp
    2795                 2800                 2805

His Cys  Ile Pro Ala Trp Gly  Thr Glu Phe Pro Ser  Lys Cys Arg
```

2810 2815 2820

Ala Val Arg Asn Val Met Pro Thr Gly Thr Val Trp Cys Tyr Tyr
2825 2830 2835

Arg Asp Ser Tyr Gln Gly Ala Lys Asn Phe Pro Pro Ser Glu Glu
2840 2845 2850

Met Ser Met Trp Lys Lys Ala Asn Lys Ala Tyr His His Glu His
2855 2860 2865

His Phe Gly Leu Met Asp Thr Leu Lys Ile Ile Trp Gly Thr Leu
2870 2875 2880

Arg Gly Pro Trp Thr Thr His Arg Lys Pro Leu His Lys Cys Leu
2885 2890 2895

Ser Pro Lys Pro Tyr Ile Tyr Val Val Glu Pro Val Leu Glu Thr
2900 2905 2910

Gly Ser His Leu Leu Ala Trp Phe Leu Tyr Cys Thr Ile Val Cys
2915 2920 2925

Lys Met Asn Asp Ile Asp Met Lys Tyr Asn Lys Asn His Gly Pro
2930 2935 2940

Gly Met Val Ala Tyr Pro Tyr Asn Pro Ser Thr Ser Gly Gly Gln
2945 2950 2955

Gly Gly Gln Ile Thr Arg Ser Gly Asp Gln Asp His Pro Gly Gln
2960 2965 2970

Tyr Gly Glu Thr Leu Ser Leu Leu Lys Ile Lys Asn Pro Gly Val
2975 2980 2985

Val Gly Thr His Val Val Pro Ala Thr Arg Lys Ala Glu Ala Gly
2990 2995 3000

Glu Leu Leu Glu Pro Gly Arg Arg Arg Leu Gln Leu Ala Lys Ile
3005 3010 3015

Thr Pro Leu His Ser Ser Leu Ala Thr Glu Arg Asp Ser Val Ser
3020 3025 3030

Lys Asn Lys Thr Lys Gln Asn Lys Thr Ala His Ile Lys Thr Lys
3035 3040 3045

Leu Asn Phe Tyr Gln Arg Pro Thr Lys Cys Asn Tyr Leu Ser Ala
3050 3055 3060

Arg Tyr Asp His Phe Lys Leu Thr Ser Arg Ser Arg Gln Leu Lys
3065 3070 3075

Gln Ile Ser Lys Pro Arg Asn Gly Asn Leu Asp Asn Gln Lys Arg
3080 3085 3090

Asp His Pro Phe His Arg Leu Lys Ile Thr Leu Leu Leu Pro Tyr
3095 3100 3105

Val Trp Leu Lys Ser Phe Asp Val Leu Tyr Ile Ile Val Leu Lys
3110 3115 3120

Leu Gly Gly Thr Glu Val Ser Asn Pro Leu Ser His Pro Ile Gln
3125 3130 3135

Glu His Val Tyr Arg Ile Leu Asp Glu Leu Asn Lys Tyr Gly Glu
3140 3145 3150

Arg Ser Ser Leu Phe Leu Pro Arg His Cys Arg Thr Ala Gln Val
3155 3160 3165

Ile Ala Ala Phe Leu Ser Ile Ala Met Leu Ala Leu Ile Pro Thr
3170 3175 3180

Phe Tyr Ser Phe Ile Gln Pro Ser Gly Gln Gly Ile Gly Leu Phe
3185 3190 3195

Pro His Leu Cys His Ile Leu Ser Gln Leu Pro Arg Ser Leu Ile
3200 3205 3210

-continued

```
Asn Leu Pro Pro Pro Phe Phe Phe Phe Glu Thr Val Ser Leu Cys
    3215                3220                3225

Tyr Pro Gly Gly Thr Thr Val Val Leu Trp Leu Thr Lys Ala Ala
    3230                3235                3240

Thr Ser Gln Ala Gln Ala Ile Leu Pro Pro Gln Pro Pro Lys Leu
    3245                3250                3255

Gly Pro Gln Thr Cys Thr Thr Thr Ser His Leu Phe Phe Ile Phe
    3260                3265                3270

Cys Arg Asp Arg Val Ser Val Cys Cys Pro Gly Trp Ser Thr Pro
    3275                3280                3285

Gly Leu Lys Gln Phe Ser Tyr Val Gly Leu Ser Lys Cys Trp Asp
    3290                3295                3300

Tyr Arg His Glu Ser Pro Cys Pro Glu Pro Phe Phe Ser Leu Lys
    3305                3310                3315

Val Phe Ser Phe Ser Thr Phe Leu Phe Val Trp Thr His Ser Arg
    3320                3325                3330

Val Phe Tyr Leu Leu Val Val Leu Phe Arg Pro Arg Cys Gly Leu
    3335                3340                3345

Tyr Pro Tyr Ser Gly Pro Cys Ser Gln Ser Arg Leu Leu Arg Ala
    3350                3355                3360

Val Val Leu Gly His Pro Ser Leu Leu Tyr Leu Ser Pro Ser Tyr
    3365                3370                3375

Ile Pro Gly Ser Met Leu Trp Ser Ala Ile Ser Pro Gly Gln Arg
    3380                3385                3390

Cys Glu Val Gly Thr Ile Asn Ser Pro Pro Leu Val Lys Ile Lys
    3395                3400                3405

Ala Phe Ser Trp Ala Trp Cys Leu Met Pro Val Ile Pro Ala Leu
    3410                3415                3420

Trp Glu Ala Glu Val Gly Arg Ser Pro Glu Val Arg Ser Ser Arg
    3425                3430                3435

Pro Ala Trp Pro Thr Trp Asn Pro Val Ser Thr Lys Asn Thr Lys
    3440                3445                3450

Ile Ser Trp Ala Trp Cys Cys Thr Pro Val Ile Pro Ala Thr Pro
    3455                3460                3465

Gly Ala Glu Ala Gly Glu Ser Leu Glu Pro Gly Arg Trp Arg Leu
    3470                3475                3480

Gln Ala Glu Ser Met Pro Leu His Ser Ser Leu Asp Asp Arg Val
    3485                3490                3495

Arg Leu Ser Leu Lys Lys Ile Asn Lys Ile Lys Asn Lys Asn Leu
    3500                3505                3510

Arg Asn Ser Ser Leu Ser Val Ala Gly Arg Ala Ala Asp Lys Thr
    3515                3520                3525

Pro Thr Pro Ser Arg Arg Lys Gly Phe Ile Trp Pro Gly Ala Ser
    3530                3535                3540

Ala Arg Leu Thr Ser Gln Lys Pro Ser Ser Leu Ser Lys Gln Phe
    3545                3550                3555

Leu Ser Leu Leu Arg Ala Asp Asn Ser Lys Gly Val Arg Val Lys
    3560                3565                3570

Gly Ser Ser Ile Glu Gln Ala Arg Gly Met Leu Gly Ala Ala Cys
    3575                3580                3585

Thr Gly Asn Asn Arg Thr Glu Gln Asp Arg Asp Phe His Ser Ala
    3590                3595                3600
```

-continued

```
Phe Pro  His Asn Asp Cys Asn  Leu Glu Ile Thr Leu  Ile Arg Ser
    3605                 3610                 3615

Gly Val  Asp Leu Leu Pro Gly  Pro Gly Cys Gly Ala  Gly Leu Ser
    3620                 3625                 3630

Ala Cys  Gly Phe His Phe Cys  Leu Val Phe Thr Ser  Ser Phe Phe
    3635                 3640                 3645

Gly Gly  Arg Asn Trp Ala Asp  Asn Met Arg Gly Gly  Leu Leu Pro
    3650                 3655                 3660

Tyr Glu  Asp Phe Gly Leu Tyr  Arg Ala Val Tyr Thr  Leu Pro Gln
    3665                 3670                 3675

Gln Thr  Tyr Arg Thr Val Pro  Ser Ser Lys Phe Pro  His Ala Phe
    3680                 3685                 3690

Phe Phe  Phe Glu Thr Val Ser  His Ser Val Thr Gln  Ala Val Val
    3695                 3700                 3705

Gln Trp  Cys Asn Leu Ser Ser  Leu Gln Pro Pro Pro  Leu Gly Phe
    3710                 3715                 3720

Lys Gly  Phe Ser Cys Leu Ser  Leu Leu Ser Lys Trp  Asp Tyr Arg
    3725                 3730                 3735

His Val  Leu Pro His Leu Ala  Asn Phe Cys Ile Phe  Thr Lys Tyr
    3740                 3745                 3750

Lys Asn  Cys Ser Ile Leu Tyr  Asn Asn Tyr Trp Leu  Gly Trp Ser
    3755                 3760                 3765

Gln Thr  Pro Asp Leu Arg Ser  Ala Cys Leu Gly Leu  Pro Lys Cys
    3770                 3775                 3780

Trp Asp  Tyr Arg His Glu Pro  Pro Ser Leu Leu Met  Pro Phe Cys
    3785                 3790                 3795

Ser His  Ile Cys Asn Phe Lys  Trp Tyr Asn Tyr Ile  Tyr Ile Tyr
    3800                 3805                 3810

Thr His  Ile Tyr Ile His Ile  Tyr Thr His Ile Tyr  Ala Tyr Ile
    3815                 3820                 3825

His Thr  Tyr Ile His Ile Tyr  Thr Tyr Ile His Thr  Tyr Ile His
    3830                 3835                 3840

Ile Tyr  Thr His Ile Tyr Thr  His Ile Tyr Thr His  Ile Tyr Thr
    3845                 3850                 3855

Tyr Ile  His Ile Tyr Thr His  Ile Tyr Thr Tyr Ile  Tyr Ile Tyr
    3860                 3865                 3870

Thr His  Ile Tyr Ile Tyr Thr  His Ile Tyr Thr Tyr  Ile His Thr
    3875                 3880                 3885

Tyr Ile  His Ile Tyr Thr Tyr  Ile Tyr Ile Tyr Ile  His Thr Tyr
    3890                 3895                 3900

Ile Tyr  Thr Phe Phe Tyr Phe  Glu Met Glu Ser Arg  Ile Val Thr
    3905                 3910                 3915

Trp Ala  Gly Val Gln Trp His  Asn Leu Cys Ser Leu  Gln His Leu
    3920                 3925                 3930

Pro Pro  Arg Phe Lys Phe Ser  Cys Leu Ser Leu Pro  Ser Ser Trp
    3935                 3940                 3945

Asp Tyr  Arg His Leu Pro Pro  Cys Arg Ala Asn Phe  Val Phe Leu
    3950                 3955                 3960

Val Glu  Thr Gly Phe His Tyr  Ile Gly Gln Gly Gly  Leu Lys Leu
    3965                 3970                 3975

Leu Thr  Ser Ser Thr Cys Leu  Ser Leu Pro Lys Cys  Asp Tyr Arg
    3980                 3985                 3990

Arg Glu  Pro Pro Cys Pro Ala  Tyr Ile Leu Phe Phe  Asn Leu Ser
```

```
    3995                4000                4005

Val Ser  Lys Met His Trp Gly  Lys Lys Asp Ala Leu  Asn Ile Ser
    4010                4015                4020

Leu Trp  Gln Leu Tyr Ser Phe  Ala Thr Phe Trp Leu  Tyr Ser Ile
    4025                4030                4035

Lys Met  Leu Tyr Asn Leu Phe  Asn Gln Cys Leu Thr  Val Leu Tyr
    4040                4045                4050

Ile His  Lys Gln Cys Pro Ala  Ser Ser Ser Trp Asn  Tyr Phe Leu
    4055                4060                4065

Ile Ser  Ile Thr Val Ser Phe  Ala Phe Phe Phe Phe  Ile Ser Phe
    4070                4075                4080

Tyr Phe  Phe Val Cys Phe Ala  Ser Ser Val Ser Ser  Phe Phe Phe
    4085                4090                4095

Phe Phe  Phe Leu Arg Gln Ser  Leu Thr Leu Leu Pro  Arg Leu Glu
    4100                4105                4110

Cys Ser  Gly Thr Ile Ser Ala  His Cys Asn Leu Cys  Leu Leu Cys
    4115                4120                4125

Ser Ser  His Ser Pro Thr Ser  Ala Ser Arg Glu Ala  Gly Ile Asn
    4130                4135                4140

Arg Arg  Pro Pro Pro Cys Leu  Asp Asn Phe Lys Gln  Gly Phe Thr
    4145                4150                4155

Met Leu  Ala Arg Leu Val Leu  Asn Ser Pro Gln Met  Ile His Pro
    4160                4165                4170

Pro Gln  Arg Pro Lys Cys Trp  Asp His Arg His Glu  Pro Pro His
    4175                4180                4185

Leu Ala  Ser Val Ser Ser Phe  Tyr Leu Pro Lys Ile  Leu Tyr Leu
    4190                4195                4200

Asn Leu  Leu Phe Phe Phe Leu  Leu Leu Arg Gln Gly  Leu Ala Leu
    4205                4210                4215

Ala Met  Leu Pro Arg Leu Glu  Cys Ser Gly Thr Ile  Ser Ala His
    4220                4225                4230

Cys Ser  Leu Asp Leu Pro Arg  Leu Arg Ser Pro His  Leu Ser Leu
    4235                4240                4245

Pro Ser  Ser Trp Asn Tyr Arg  Tyr Val Ser Pro His  Pro Ala Asn
    4250                4255                4260

Phe Cys  Ser Phe Cys Arg Val  Gly Val Ser Pro Cys  Cys Pro Gly
    4265                4270                4275

Trp Ser  Gln Thr Pro Gly Leu  Lys Gln Ser Ser Tyr  Leu Gly Leu
    4280                4285                4290

Pro Lys  Cys Trp Asp Tyr Arg  His Glu Pro Pro Cys  Pro Ala Gln
    4295                4300                4305

Ile Phe  Leu Phe Tyr Asn Phe  Ser Leu Gly His Gln  Phe Leu Ser
    4310                4315                4320

Arg Ser  Thr Ile Asn Pro Leu  Asp Leu Ile Ser Thr  Phe Leu Leu
    4325                4330                4335

Asp Thr  Arg Ser Phe Pro Thr  Val Tyr Trp Val Leu  His Pro Gln
    4340                4345                4350

Gly Cys  Thr Ser Cys Asn Ser  Asn Ala Thr Cys Gln  Lys Leu Asn
    4355                4360                4365

Ser Tyr  Ser Leu Cys Lys Ile  Pro Leu Leu Leu Ser  Phe Ser Leu
    4370                4375                4380

Leu Phe  Ala Thr Tyr Phe Arg  Gly Lys Trp Cys Pro  Ser Ser His
    4385                4390                4395
```

-continued

```
Ser Gly  Lys Pro Gln Ser Pro  Leu Leu Ile Ala Val  Leu Thr His
    4400                 4405                 4410

Leu Thr  His Pro Val Asn Lys  Val Leu Leu Ile Leu  Leu Pro Asn
    4415                 4420                 4425

Ala Ser  Gln Leu Val Pro Phe  Leu Ser Ile Pro Thr  Val Thr Ile
    4430                 4435                 4440

Pro Ala  Phe Glu Val Pro Leu  Phe Thr Arg Val Val  Thr Ile Ala
    4445                 4450                 4455

Ser Gln  His Leu Pro Ala Pro  Ile Pro Pro Leu Leu  Cys Ser Val
    4460                 4465                 4470

Ala Met  Arg Val Asn Phe Ala  Lys Gln Arg Asp Tyr  Phe Pro Leu
    4475                 4480                 4485

Leu Leu  Glu Asn Ile Leu Leu  Ile Thr Tyr Arg Ser  Lys Ser Lys
    4490                 4495                 4500

Leu Ser  Thr Val Ser Ser His  Ser Pro Thr Thr His  His Leu Pro
    4505                 4510                 4515

Ala Pro  Val Ala Ser Ala Ser  Asn Val Pro Glu Arg  Phe Ala Val
    4520                 4525                 4530

Pro Val  Leu Leu Leu Thr Phe  Ser Pro Val Thr Ala  Gln Ser Leu
    4535                 4540                 4545

Val Cys  Phe Ala Asp Ser Trp  Arg Ser Gly Phe Ser  Ile Arg Gly
    4550                 4555                 4560

Val Phe  Ala Arg Leu Gln Thr  Gly Ile Lys Met Ser  Ser Ala Tyr
    4565                 4570                 4575

Trp Ala  Val Leu Val Ser Lys  Val Tyr Thr Thr Ser  Lys Ala Ala
    4580                 4585                 4590

Met Asp  Glu Pro Thr Lys Asn  Leu Gly Leu Gly Arg  Gly Trp Pro
    4595                 4600                 4605

Trp Arg  Arg Leu Lys Arg Leu  Ile Cys Leu Pro Ser  Arg Glu Ala
    4610                 4615                 4620

Met Gly  Pro Arg Arg Ala Gly  Asn Ala Ile Ser Thr  Arg Leu Glu
    4625                 4630                 4635

Asn Ser  Leu Ser Ser Gly Ala  Leu Phe Ala Ala Gly  Leu Ser Gly
    4640                 4645                 4650

Met Ser  Ala Phe Ser Pro Phe  Gln Gly Arg Ala Asp  Gly Arg Arg
    4655                 4660                 4665

Ala Glu  Pro Arg Gly Arg Leu  Pro Gly Lys Lys Lys  Lys Arg Lys
    4670                 4675                 4680

Lys Gly  Ser Arg Arg Pro Val  Ile His Arg Ser Lys  Arg Leu Glu
    4685                 4690                 4695

Gly Pro  Arg Leu Leu Ile Gly  Ala Asp Arg Ile Arg  Gln Ala Trp
    4700                 4705                 4710

Gly Pro  Leu Ile Gly Ser Gly  Val Val Arg Arg Trp  Trp Ala Val
    4715                 4720                 4725

Val Gly  Val Asn Ser Ser Arg  Pro Gly Ser Val Thr  Gly Ser Asn
    4730                 4735                 4740

Pro Gly  Glu Ser Gly Trp Arg  Gly Arg Arg Phe Leu  Ser Ile His
    4745                 4750                 4755

Val Ser  Cys Gln Pro Gly Pro  Gly Arg Pro Ala Leu  Arg Arg Gly
    4760                 4765                 4770

Leu Gly  Arg Thr Arg Arg Trp  Val Ser Ser Glu Ile  Leu Ser Trp
    4775                 4780                 4785
```

Ala Glu Ser Thr Leu Thr Arg Arg Ala Glu Pro Glu Leu Ala Pro
4790 4795 4800

Ser Thr Pro Ser Pro Phe Leu Ser Val Thr Val Glu Lys Phe Asn
4805 4810 4815

Val Met Phe Trp Val Arg Thr Glu Ala Leu Glu Val Ala Arg Arg
4820 4825 4830

Val Val Leu Arg Ser Arg Val Asn Gly Cys Ser Gly Cys Thr Leu
4835 4840 4845

Val Thr Thr Gly Arg Trp Gln Pro Val Leu Ser Ser Ser Trp Ser
4850 4855 4860

Pro Tyr Ser Ile Cys Gly Lys Gly Lys Asn Gly Gly Leu Asp Ser
4865 4870 4875

Leu Ser Thr Arg Asp Ala Thr Ser Pro Thr Leu Tyr Ser Arg Gly
4880 4885 4890

Lys Arg Ser Leu Trp Gly Thr Gly Phe Val Lys Ser Arg Lys Glu
4895 4900 4905

Glu Arg Asp Lys Trp Val His Val Lys Lys Arg Val Thr Leu Ile
4910 4915 4920

His Cys Trp Arg Lys Phe Lys Val Val Gln Pro Leu Gly Lys Gln
4925 4930 4935

Phe Asp Gly Ala Thr Lys Gly Ile Ser Asn His Leu Ala Gln Gln
4940 4945 4950

Leu His Ser Ile Thr Leu Ile Asn Tyr Lys Arg Val Leu Ile Phe
4955 4960 4965

Ala Leu Lys Cys Ser Trp Gln Cys Tyr Ser Gln Pro Lys Gly Gly
4970 4975 4980

Ser Asn Ser Ser Val His Gln Leu Ile Asn Gln Thr Asn Cys Gly
4985 4990 4995

Val Phe Ile Gln Trp Asn Met Asn Arg Thr Gly Met Lys Tyr Tyr
5000 5005 5010

Met Leu Gln Trp Gly Thr Leu Lys Asp Tyr Ala Lys Arg Arg Lys
5015 5020 5025

Pro Asp Thr Glu Gly His Ile Leu Tyr Asp Ser Met Tyr Arg Lys
5030 5035 5040

Tyr Pro Glu Val Val Asn Pro Gln Arg Gln Lys Ala Asp Trp Ser
5045 5050 5055

Pro Gly Ala Glu Cys Gly Trp Glu Asp Gly Glu Ser Leu Leu Asn
5060 5065 5070

Gly Phe Lys Phe Ser Phe Gly Val Lys Met Phe Asn Lys Arg Cys
5075 5080 5085

Leu His Asn Val Met Asn Ala Leu Ser Ala Thr Glu Leu Val Asn
5090 5095 5100

Leu Lys Trp Leu Val Arg Pro Gly Thr Val Ala His Thr Cys Asn
5105 5110 5115

Pro Ser Thr Leu Arg Gly Trp Gly Gly Arg Ile Thr Gly Gln Glu
5120 5125 5130

Phe Glu Thr Ser Leu Ala Asn Val Val Lys Pro His Leu Ser Lys
5135 5140 5145

Lys Lys Lys Lys Glu Arg Lys Lys Glu Lys Lys Arg Trp Ala Trp
5150 5155 5160

Trp Gln Val Pro Val Ile Pro Ala Thr Gln Glu Ala Glu Ala Gly
5165 5170 5175

Glu Ser Phe Glu Pro Gly Arg Arg Arg Leu Gln Ser Glu Ile Ile

-continued

```
    5180                5185                5190

Pro Leu His Ser Ser Leu Gly Asp Lys Ser Lys Thr Leu Ser Gln
    5195                5200                5205

Asn Lys Ile Lys Asn Gly Phe Ser Arg Ala Arg Trp Leu Thr Pro
    5210                5215                5220

Val Ile Pro Ala Leu Trp Glu Ala Lys Gly Gly Gly Ser Leu Glu
    5225                5230                5235

Pro Arg Ser Leu Arg Pro Ala Trp Ala Ile Asp Pro Tyr Leu Asn
    5240                5245                5250

Lys Ser Gly Phe Tyr Ile Val Ile Val Ser Gln Leu Lys Cys Ile
    5255                5260                5265

Ser Leu Ser Leu Ser Leu Ser Leu Ser Leu Ala Asn Lys Leu Thr
    5270                5275                5280

Asp Lys Val Ser Pro Ser Cys Cys Pro Phe Ser Lys Lys Glu Ile
    5285                5290                5295

Arg Asn Ser Asn Ser Glu Ser Ser Ala Ala Phe His Phe His Phe
    5300                5305                5310

Pro Leu Cys Phe Leu Lys Ser Gly Met Val Leu Val Thr Asp Cys
    5315                5320                5325

Ser Pro Trp Lys Met Ala Arg Arg Glu Arg Ala Pro Ser Ala Pro
    5330                5335                5340

Leu Arg Arg Ser Ser Pro Gly Pro Arg Thr Thr Val Ser Gln Pro
    5345                5350                5355

Gly Ile His Thr Leu Ser Leu Cys Glu Arg Ser Val Ala Arg Val
    5360                5365                5370

Leu Ala Gly Arg Asp Arg Val Gly Glu Gly Gln Val Arg Val Leu
    5375                5380                5385

Lys Val Gly Arg Leu Leu Pro Pro Ala Thr Pro Val Trp Asn Leu
    5390                5395                5400

Asn Ser Leu Glu Pro Ala Ile Arg Ala Cys Gly Ile Cys Ser Lys
    5405                5410                5415

Val Ser Val Gln Glu Ser Ala Leu Cys Leu Gln His Gly Lys Leu
    5420                5425                5430

Thr Thr Gly His Lys Ile Leu Leu Leu Pro Val Thr Phe His Thr
    5435                5440                5445

Val Cys Ser Ser Asp Arg Ile Ser Lys Thr Ala His Ser Val Ile
    5450                5455                5460

Ser Ser Ala Asp Cys Leu Gly Ala Gly Arg His Phe Lys Arg Lys
    5465                5470                5475

Met Leu Leu Arg Ser Ser Gln Ser Tyr Arg Arg Val Lys Cys Ser
    5480                5485                5490

Leu Gly Lys Val Asp Arg Lys Cys Trp Val Arg Ile Tyr Gly Leu
    5495                5500                5505

Arg Gly Lys Leu Lys Thr Gln Val Leu Asn Val Lys Thr Gly Gln
    5510                5515                5520

Glu Val Glu Ala Gly Phe Phe Arg Asn Ser Gly Cys Ile Cys Cys
    5525                5530                5535

Leu Cys Lys Thr Ala Pro Cys His Cys His Pro Gly Arg Arg Val
    5540                5545                5550

Thr Ser Pro Gly Phe Ala Ser Glu Tyr Asn Ile Leu Pro Gly Ile
    5555                5560                5565

Gln Leu Asp Ile Gln Ile Thr Thr Tyr Leu Val Cys His Leu Leu
    5570                5575                5580
```

His Thr Gln Ser Gln Leu Arg Pro Val Trp Asn Gln Ile Ile Ala
5585 5590 5595

Thr Leu His Ile Phe Ser Gln Leu Phe Leu Gln Val Asn Ser Val
5600 5605 5610

Thr Ser Ser Val Lys Ser Arg Gln His Leu Leu Arg Met Trp Cys
5615 5620 5625

Asp Asn Thr Leu Pro Ser Ile Gln Tyr Ser Ala Gln Leu Ile Leu
5630 5635 5640

Leu Leu Leu Leu Leu Tyr Pro Gln Val Trp Thr Gln Asn Phe Asn
5645 5650 5655

Phe Pro Leu Lys Arg Lys Leu Gly Leu Cys Leu Cys Ser Cys Leu
5660 5665 5670

Asn Pro Phe Asn Met Asn Met Val Ser Arg Phe Phe Gln Val Thr
5675 5680 5685

Trp Tyr Ser Gln Ile Val Ile Leu Tyr Ser Ser Leu Gln Leu Ala
5690 5695 5700

Phe Ser His Val Ala Ser Leu Cys Pro Phe Glu Val Asp Arg Leu
5705 5710 5715

His His Cys Ile Ile Lys Arg Thr Trp Thr Gly Cys Gly Val Ser
5720 5725 5730

Cys Leu Ser Gln His Phe Gly Arg Pro Lys Trp Ala Asp His Leu
5735 5740 5745

Thr Leu Gly Ala Arg Asp His Pro Gly Gln His Gly Glu Thr Pro
5750 5755 5760

Ser Leu Leu Lys Ile Gln Lys Leu Ala Arg His Ser Gly Arg Cys
5765 5770 5775

Leu Ser Gln Leu Leu Gly Arg Leu Arg Gln Glu Thr Arg Leu Asn
5780 5785 5790

Pro Gly Gly Arg Gly Cys Ser Glu Gln Arg Thr Cys His Cys Thr
5795 5800 5805

Pro Ala Trp Thr Thr Glu Asp Ser Ile Ser Lys Lys Lys Lys Lys
5810 5815 5820

Arg Glu Arg Glu Asn Met Glu His Phe Leu Ser Lys Asn Leu Phe
5825 5830 5835

Ser Ser Val Leu Asn Ile Phe Gly Phe Val Ser Gln Leu Gln Leu
5840 5845 5850

Val Val Lys His Glu Gly Phe Leu Lys Tyr Asn Phe Leu Ser Arg
5855 5860 5865

Tyr Asn Leu Tyr Thr Ile Lys Leu Leu Phe Cys Met Met Gln Thr
5870 5875 5880

Phe Leu Val Tyr Ser Gln Arg His Ala Thr Leu Thr Lys Ile Tyr
5885 5890 5895

Leu Lys Asn Ile Phe Ile Thr Pro His Arg Thr His Ala His Trp
5900 5905 5910

Gln Pro Phe Pro Gln Ser Leu Ala Thr Thr Asp Gln Leu Ser Val
5915 5920 5925

Ser Arg Cys Pro Ile Leu Asp Ile Ser Met Lys Ser Tyr Asp Ile
5930 5935 5940

Phe Phe Val Ser Asp Phe Phe Ala Phe
5945 5950

<210> SEQ ID NO 48
<211> LENGTH: 5962

<212> TYPE: PRT
<213> ORGANISM: Homo sapiens

<400> SEQUENCE: 48

```
Glu Gln Gln Gly Cys Leu Phe His Leu Gly Ala Gly Gly Leu Ser Pro
1               5                   10                  15

Lys Arg Glu Ser Ala Lys Gly Gly Arg Ile Ile Ile Ser Ser Tyr Arg
            20                  25                  30

Phe Gly Ile Gly Val Gln Ser Thr Phe Ser Arg Ala Gly Glu Glu Tyr
        35                  40                  45

Met Val Ser Val Ser Val Gly Gln Glu Gln Ile Thr Met Val Glu Cys
    50                  55                  60

His Gln Leu Arg Leu Leu Ser Leu Leu Leu Trp Ile Phe Ser Cys Phe
65                  70                  75                  80

Arg Ser Ser Gly Cys Thr Arg Ala Gly His Arg Gly Phe Asp Gly Leu
                85                  90                  95

Ala Trp Thr Gln Arg Pro Asp Thr Pro Ile Phe Leu Tyr Tyr Glu Lys
            100                 105                 110

Gln Asn Lys Ile Val Val Lys Cys Gly Ser Glu Asn Phe Trp Gly Trp
        115                 120                 125

Tyr Gly Glu Ile Met Gly Asp Val Ser Arg Gly Cys Phe Glu Trp Asp
    130                 135                 140

Trp Gly Gly Met Gly Thr Ser Arg Arg Asp Thr Glu Glu Arg Phe Gly
145                 150                 155                 160

Tyr Lys Gly Tyr Cys Gly Leu Val Arg Arg Ser Ile Cys Arg Ile Glu
                165                 170                 175

Leu Leu Met Ala Trp Met Gln Phe Cys Met Asn Glu Thr Lys Gln Lys
            180                 185                 190

Glu Asp Thr Arg Ser Glu Glu Lys Glu Lys Asn Arg Tyr Arg Thr Lys
        195                 200                 205

Asn Trp Lys Asp Pro Gly His Pro Ile Arg Glu Cys Pro Arg Gly Phe
    210                 215                 220

Ser Ile Ile Ile Cys Leu Val Gly Glu Phe Leu Gly Ser Ile Leu Glu
225                 230                 235                 240

Phe Phe Tyr Val Val Ile His Gln Ala Arg Leu Ile Val Lys Thr Thr
                245                 250                 255

Leu Phe Val Lys Tyr Thr Gly Ser Ser Phe Phe Ser Ser Glu Val Glu
            260                 265                 270

Ala Leu Ala Ile Leu Glu Glu Arg Glu Met Gln Ser Gln Gln Leu Phe
        275                 280                 285

Val Lys Glu Gly Leu Glu Gly Arg Ala Trp Leu Thr Pro Val Ile Pro
    290                 295                 300

Ala Leu Trp Glu Ala Glu Val Gly Gly Ser Gly Gln Glu Met Glu Thr
305                 310                 315                 320

Ile Leu Ala Asn Met Val Lys Pro His Leu Tyr Lys Tyr Lys Lys Leu
                325                 330                 335

Ala Arg His Gly Gly Arg His Leu Ser Gln Leu Leu Gly Arg Leu Arg
            340                 345                 350

Gln Glu Asn Gly Val Asn Pro Gly Gly Gly Ala Cys Ser Glu Pro Arg
        355                 360                 365

Ser His His Cys Thr Pro Ala Trp Gly Thr Glu Gln Asp Ser Ile Ser
    370                 375                 380

Lys Lys Lys Glu Gly Leu Thr Gly Leu Gly Glu Ser Glu Ile Asp Ser
385                 390                 395                 400
```

-continued

```
Val Val Glu Ile Ala Gly Glu Arg Arg Val Ala Asp Arg Glu Pro Glu
                405                 410                 415

Glu Val Lys Arg Ile Gly Leu His Gln Gly Glu Ser Ile Gly Gly Tyr
            420                 425                 430

Leu Ala Thr Glu Asp Leu Ser Thr Ser Arg Glu Pro Gly Trp Cys Phe
        435                 440                 445

Glu Val Lys Pro Gly Ala Thr Lys Tyr Gln Glu Ala Glu Lys Leu Leu
    450                 455                 460

Gly Phe Asp Arg Pro Val Cys Phe His Thr Val Arg Trp Gln Gly Met
465                 470                 475                 480

Glu Glu Leu Cys Leu Thr Glu Gly Lys Lys Pro Trp Trp Pro Ser His
                485                 490                 495

Thr Leu Trp Glu Arg Pro Val Pro Ile Gln Lys Cys Leu Pro Ile Pro
            500                 505                 510

Arg Gly Ile Leu Val Ser Leu Gly Thr Cys Gln Ser Gln Phe Ala Ser
        515                 520                 525

Pro Gly Gln Gly Gln Ile Pro Gln Leu Asp Val Gly Arg Glu Gly Ala
    530                 535                 540

Thr Ile Pro Glu Gly Asn Ser Arg Thr Leu Arg Ser Asp Phe Leu Gln
545                 550                 555                 560

Asp Arg Phe Ser Arg Trp Lys Asn Glu Arg Leu Glu Met Gly Arg Leu
                565                 570                 575

Val Thr Tyr Thr Glu Glu Val Met Lys Arg Gln Asn Arg Met Gly Leu
            580                 585                 590

Gly Trp Lys Glu Ile Phe Ser Leu Ile Gln Glu Pro Phe Ala Leu Cys
        595                 600                 605

Gly Lys Arg Leu Ile Arg Gly Ser Phe Asn Glu Gly Val Gly Gly Ser
    610                 615                 620

Asp Arg Glu Gly Glu Lys Leu Ala Leu Arg Asp Arg Ser Trp Asn Ala
625                 630                 635                 640

Ser Cys Phe Phe Ser Tyr Leu Ile Ser Ile Ser Val Ala Leu Ser Asp
                645                 650                 655

Gly Ile Cys Leu Leu Met Ala Leu Ala Val Asn Asp Ser Ser Phe Leu
            660                 665                 670

Trp Lys Ser Ser Leu Glu Lys Ser Phe Tyr Arg Gly Thr Asn Asp Glu
        675                 680                 685

Gly Pro Leu His Ser Glu Glu Thr Ser Phe Asn Pro Tyr Asn Ser Met
    690                 695                 700

Val Val Glu Asp Met Lys Gly Ile Phe Arg Val Ser Ile Asn Ile Asp
705                 710                 715                 720

Thr Ser Leu Cys Lys Ser Glu Gly Pro Ser Gly Asn Glu Phe Gly Leu
                725                 730                 735

Leu Arg Gly Ser Gly Ala Gly Gln Ser Gly Ser Leu Lys Asp Arg Cys
            740                 745                 750

Gly Arg Tyr Ser Ile Ala Cys Leu Cys Arg Met Ala Ile Arg Pro Gly
        755                 760                 765

Gly Thr Ala Ile Asn Lys Pro Ser Val Ile Arg Val Arg Asn Arg Lys
    770                 775                 780

Glu Gly Asn Met Gly Lys Trp Ser Glu Cys Gln Val Asp Gln Arg Asp
785                 790                 795                 800

Ser His Gly Gly Gln Val Trp Tyr Gln Glu Cys Gly Arg Pro Asp Ser
                805                 810                 815
```

-continued

```
Pro Gly Gln Glu Gln Trp Leu Trp Glu Thr Gln Gln Arg Val Ser Ile
            820                 825                 830

Gly Trp Val Trp Trp Leu Met Pro Val Ile Pro Ala Leu Trp Glu Ala
        835                 840                 845

Glu Met Gly Arg Ser Leu Val Arg Ser Ser Arg Pro Ala Trp Leu Thr
    850                 855                 860

Trp Asn Pro Ile Ser Thr Lys Asn Thr Lys Asn Pro Gly Val Gly His
865                 870                 875                 880

Thr Pro Val Ile Pro Ala Thr Pro Glu Ala Glu Ala Gly Glu Ser Leu
                885                 890                 895

Glu Pro Gly Lys Arg Arg Leu Gln Ala Lys Ile Val Pro Leu His Ala
            900                 905                 910

Ser Leu Gly Asp Gly Val Arg Leu Cys Leu Lys Lys Glu Leu Ser Ile
        915                 920                 925

Ala Glu Gly Ala Arg Glu Trp Lys Val Tyr Ala Ser Gly Met Arg Lys
    930                 935                 940

Lys Ile Asp Phe Gly Ser Tyr Glu Asn Cys Arg Glu Val Glu His Asn
945                 950                 955                 960

Val Ile Leu Arg Ala Ser Lys Ser Ile Lys Ala Ala Ala Ala Thr Thr
                965                 970                 975

His Arg His Glu Gly Ala Lys Thr Val Arg Ser Ser Cys Leu Asp Arg
            980                 985                 990

Lys Ala Thr Gly His Ala Ser Gly  Ser Cys Val Arg Ile  Pro Thr Thr
        995                 1000                 1005

Gln Pro  Cys Thr Leu Ala Val  Cys Asn Glu Lys Val  Gly Met Ser
    1010                 1015                 1020

Gly Glu  Leu Val Trp Glu Gln  Leu Leu Gly Leu Phe  Phe Lys Glu
    1025                 1030                 1035

Trp Lys  Gly Glu Trp Gly Lys  Asp Leu Gly Phe Met  Gly Ser Ala
    1040                 1045                 1050

Arg Phe  Ile Asn Arg Ile Met  Gly Cys Gly Arg Glu  Val Leu Arg
    1055                 1060                 1065

Ile Gly  Gly Tyr Met Gly Leu  Ala Leu Trp Gly Ala  Ala Arg Gln
    1070                 1075                 1080

Phe Cys  Gly Thr Asp Pro Glu  Leu Thr Cys Lys Thr  Cys Leu Val
    1085                 1090                 1095

Phe Gly  Gln Val Lys Trp Gly  Asn Cys Lys Glu Ser  Leu Ala Leu
    1100                 1105                 1110

Glu Gly  His Ala Ile Ala Gly  Glu Gln Ala Leu Ile  Leu Leu Lys
    1115                 1120                 1125

Cys Ala  Val Gly Ser Phe Ser  Val Leu Trp Asp Gly  Ile Leu Ala
    1130                 1135                 1140

Leu Ser  Gly Val Arg Val Ile  Arg Phe Trp Asp Gly  Lys Gly Cys
    1145                 1150                 1155

Met Ile  Gly Cys Gln Gly Gly  Asn Arg Gly Val Pro  Tyr Leu Trp
    1160                 1165                 1170

Ile Lys  Val Gly Arg Tyr Lys  Gly Arg Met Arg Arg  Arg Leu Thr
    1175                 1180                 1185

Gly Glu  Lys Gly Gly Asn Glu  Val Trp Leu Ser Arg  Asn Ser Gln
    1190                 1195                 1200

Gly Ser  Arg Phe Gly Asn Val  Leu Thr Gly Ser Trp  Ala Gly Arg
    1205                 1210                 1215

Asp Asn  Lys Arg Val Tyr Lys  Arg Met Leu Ser Lys  Leu Ala Pro
```

-continued

```
    1220                1225                1230

Glu Leu  Gly Ser Phe Asp Arg  Phe Ser Ser Leu Ala  Ile Asn Thr
    1235                1240                1245

His Asn  Ser Tyr Gly Gly Lys  Gly Asn Arg Pro Leu  Lys Arg Arg
    1250                1255                1260

Tyr Cys  Gly Val Gly Ser Leu  Cys Ile Lys Lys Gly  Thr Asp Phe
    1265                1270                1275

Pro Phe  Thr Val Arg Val Thr  Gln Ser Ile Cys Asp  Gly Pro Arg
    1280                1285                1290

Gly Phe  Gly Asp Trp Ala Ala  Ser Val Phe Ser Arg  Ala Glu Asn
    1295                1300                1305

Ile Trp  Glu Gly Val Arg Glu  Ser Trp Ala Arg Val  Pro Ala Ala
    1310                1315                1320

Leu Gly  Val Ala Pro Gly Val  Gly Gln Ser Asp Phe  Gln Gly Leu
    1325                1330                1335

Ala Gln  Met Gly His Gly Ser  Gly Gly Ile Pro Gly  Cys Arg His
    1340                1345                1350

Ser Leu  Ala Gln Pro Asp Phe  Gln His Leu Lys Lys  Asp Pro Gly
    1355                1360                1365

Gly Gly  Gly Pro Gly Gly Thr  Pro Gly Arg Cys Asp  Ser Gly Val
    1370                1375                1380

Leu Lys  Phe Leu Cys Ala Gly  Asp Val Ala Gly Val  Ser Leu Thr
    1385                1390                1395

Val Glu  Ala Ser Asn Cys Asn  Ser Glu Ile Cys Cys  Leu Tyr Ser
    1400                1405                1410

Ile Thr  Val His Leu Glu Gly  Glu Val Asn Val Leu  Leu Trp Gly
    1415                1420                1425

Leu Arg  Ala Gly Ile Phe Leu  Glu Leu Phe Leu Met  Ser Gly Ala
    1430                1435                1440

Gly Trp  Val Ile Lys Cys Ile  Leu Arg Ile Arg Arg  Pro Ser Gly
    1445                1450                1455

Pro Ser  Gly Ser Arg Ala Val  Lys His Leu Arg Val  Val Ala Lys
    1460                1465                1470

Trp Ala  Met Asn Trp Ala Gly  Phe Leu Tyr Leu Met  Lys Asn Ser
    1475                1480                1485

Leu Asn  Ala Asn Leu Gly Glu  Val Arg Arg Lys Arg  Ser Ile Asn
    1490                1495                1500

Leu Asp  Tyr Ala Phe Ser Ser  Ser His Leu Phe Phe  Phe Phe Phe
    1505                1510                1515

Cys Leu  Glu Met Phe Leu Ile  Glu Leu Val Gln Ser  Phe Arg Ile
    1520                1525                1530

Ser Gly  Ser Leu Ser Gly His  Cys Gln Pro Thr Ala  Gly Gly Ala
    1535                1540                1545

Phe Lys  Ala His His Phe Val  Ile Arg Ile Thr Gln  Ser Leu Ile
    1550                1555                1560

Asn Ile  Thr Ala Ala Lys Leu  Thr Tyr Thr Ile Phe  Thr His Asn
    1565                1570                1575

Leu Lys  Tyr Phe Val Leu Met  Lys Cys Phe Ala Phe  Thr Ile Glu
    1580                1585                1590

Asp Gln  Tyr Thr Val Tyr Thr  Leu Gln Asn Tyr Phe  Leu Arg Asn
    1595                1600                1605

Thr Glu  Val Arg Asn Ser Asp  Phe Leu Asn Leu Phe  Ile Val Leu
    1610                1615                1620
```

-continued

```
Ser Gln  Ser Arg Pro Lys Phe  Ser Ile Lys Ile Asp  Ile Leu Ile
    1625                 1630                 1635

Lys Val  Cys Thr Ser Leu Pro  Lys Glu Leu His Ser  Asp Cys Leu
    1640                 1645                 1650

Pro Ser  Val Gln Gln Gln Glu  Arg Gly Asp Ser His  Ser Arg Val
    1655                 1660                 1665

Pro Ser  Thr Trp Leu Leu Ala  Pro Thr Ala Ala His  Cys Ile Thr
    1670                 1675                 1680

Trp Trp  Gly Ala Ala Trp Ala  Ser Ala Ser Glu Val  Ser Ser Pro
    1685                 1690                 1695

Gly Thr  Leu Val Pro Cys Leu  Cys Leu Ala Cys Ala  Ile Leu Val
    1700                 1705                 1710

Asn Thr  Glu Asn Leu Pro Val  His Pro Gln Cys Arg  Leu Thr Gly
    1715                 1720                 1725

Gln Gly  Gly Val Ser Glu Ser  Val Val Phe Thr Met  Trp Arg Ser
    1730                 1735                 1740

Gly Gly  Asp Tyr Arg Ile Phe  Phe Ala Asp Phe Ser  Asn Trp Val
    1745                 1750                 1755

Ser Arg  Glu Glu Pro Gly Val  Ala Glu Arg Leu Pro  Gly Leu Ser
    1760                 1765                 1770

Phe Phe  Cys Ser Arg Glu Ser  Asp Ala Gly Pro Arg  Val Lys Gly
    1775                 1780                 1785

Ser Cys  Ser Ala Pro Gly Ile  Thr Met His Cys Ala  Val Gly Arg
    1790                 1795                 1800

Thr Thr  Leu Leu Leu Cys Ser  Pro Arg His Gln Gln  Ala Leu Gly
    1805                 1810                 1815

Arg Gln  Leu Cys Ser Ser Gly  His Pro Glu Thr Ser  Trp Arg Cys
    1820                 1825                 1830

Arg Trp  Asp Lys Leu Gly Ala  Cys Gln Asn Thr His  Ser Phe Gln
    1835                 1840                 1845

Glu Gly  Gln Ala Pro Ala Cys  Ser Asp Glu Val Arg  Ile Val Ser
    1850                 1855                 1860

His Leu  Phe Asn Arg Lys Leu  Leu Gly Arg Ser Gly  Arg Ala Ser
    1865                 1870                 1875

Arg Gly  Thr Lys Leu Ala Gly  Pro Gly Val Arg Arg  Gly Gly Asp
    1880                 1885                 1890

Lys Arg  Ile Ile Gly Trp Gly  Ser Arg Gly Val Arg  Ile Gly Thr
    1895                 1900                 1905

Trp Leu  Ser Leu Ala Arg Ser  Ser Leu Gly Arg Arg  Gly Glu Val
    1910                 1915                 1920

Arg Val  His Arg Lys Glu Gly  Phe Arg Gly Leu Gly  Thr Trp Gly
    1925                 1930                 1935

Gly Asp  Arg Arg Asn Arg Lys  Glu Arg Lys Lys Lys  Asp Leu Gly
    1940                 1945                 1950

Val Thr  Leu Gly Ala Glu Thr  Arg Glu Gly Pro Met  Cys Lys Arg
    1955                 1960                 1965

Met Pro  Gly Arg Gln Ala Pro  Gln Thr Ile Cys Pro  Phe Tyr Asp
    1970                 1975                 1980

Lys Asn  Tyr Leu Glu Leu Val  Gly Trp Arg Thr Arg  Lys Cys Arg
    1985                 1990                 1995

Phe Leu  Ala Ile Trp Asn His  Cys Arg Val Cys Ile  Gly Ala Lys
    2000                 2005                 2010
```

-continued

```
Arg Cys  Cys Arg Arg Lys Asp  Thr Val Leu Gly Gln  Val Val Glu
    2015                 2020                 2025

Glu Val  Leu Ser Phe Glu His  Arg Leu Arg Glu Lys  Lys Glu Glu
    2030                 2035                 2040

Trp Arg  Val Glu Gly Cys Pro  Arg Arg Thr Arg Glu  Lys Arg Gly
    2045                 2050                 2055

Arg His  Gly Glu Gly Gly Trp  Gly Ser Gly Gly His  Ala Ala Leu
    2060                 2065                 2070

Gly Cys  Asn Val Gly Glu Gln  Pro Lys Gln Val Ser  Pro Gln Leu
    2075                 2080                 2085

Thr Cys  His Gln Gly Asn Val  Gly Glu Pro Arg Gln  Ala Ser Pro
    2090                 2095                 2100

Trp Ser  Asp Thr Asn Gly Val  Trp Val Asn Asn Gln  Ala Gly Val
    2105                 2110                 2115

Pro Thr  Val Ile Lys His Gln  Gly Lys Thr Val Phe  Pro Ser Pro
    2120                 2125                 2130

Leu Thr  Leu Glu Phe Trp Val  His Arg Asn Val Ser  Pro Tyr Leu
    2135                 2140                 2145

Tyr Arg  Gly Lys Arg Thr Gly  Ile Gly Arg Thr Gly  Arg Leu Lys
    2150                 2155                 2160

Gly Ser  Glu Arg Gly Arg Leu  Lys Gly Ser Lys Lys  Gly Trp Arg
    2165                 2170                 2175

Arg Val  Lys Arg Pro Leu Thr  Arg Phe Glu Ile Gly  Lys Met Phe
    2180                 2185                 2190

Leu Gly  Leu Val Gly Leu Arg  Thr Asp His Arg Trp  Ile Ser Ser
    2195                 2200                 2205

Arg Ser  Glu Gly Asp Asn Arg  Ala Leu Val Ser Gln  Arg Ser Pro
    2210                 2215                 2220

Pro Val  Leu Gly Leu Gln His  Gln Met Ser His Ala  Ser Val Arg
    2225                 2230                 2235

Asn His  Gln Thr Gly Phe Val  Ala Thr Arg Leu Tyr  Ile Ser Pro
    2240                 2245                 2250

Gly Cys  Arg Arg Ala Glu Ser  Lys Lys Glu Ser Thr  Lys Gly Gly
    2255                 2260                 2265

Gly Ile  Ile Ile Ser Ser Tyr  Arg Phe Gly Ile Gly  Val Gln Ser
    2270                 2275                 2280

Thr Phe  Ser Arg Ala Gly Arg  Ile Ser Gln Ser Thr  Phe Leu Arg
    2285                 2290                 2295

Ala Gly  Glu Asn Ile Ser Tyr  Gln Leu Gly Trp Gly  Arg Asn Lys
    2300                 2305                 2310

Ser Gln  Trp Trp Asn Val Ile  Ser Gly Tyr Phe His  Phe Phe Cys
    2315                 2320                 2325

Gly Ser  Ser Val Ala Ser Gly  His Leu Tyr Val Tyr  Met Gln Val
    2330                 2335                 2340

Thr Gly  Asp Met Met Ala Phe  Gly Leu Arg Gly Leu  Thr Arg Ser
    2345                 2350                 2355

Ile Leu  Lys Val Asn Cys Thr  Gly Asn Leu Lys Pro  Gln Ile Phe
    2360                 2365                 2370

Cys Ile  Ser Leu His Tyr Thr  Ser Leu Val Leu Ala  Phe Leu Phe
    2375                 2380                 2385

Phe Leu  Phe Cys Phe Asn Met  Val Leu Leu His His  Pro Gly Trp
    2390                 2395                 2400

Arg Ala  Val Ala Gln Ser Leu  Pro Val Thr Ser Asn  Ser Ala Gln
```

```
    2405                2410                2415

Ala Ile  Leu Pro Pro Pro Pro  Lys Leu Arg Leu His  Ala His Ala
    2420                2425                2430

Thr Met  Pro Gly Phe Ser Tyr  Ser Tyr Tyr Phe Arg  Asp Leu Ala
    2435                2440                2445

Met Leu  Ala Arg Leu Val Ser  Asn Ala Trp Pro Gln  Val Ile Leu
    2450                2455                2460

Gln Pro  Leu Pro Pro Lys Met  Leu Gly Leu Glu Ala  Ala Thr Thr
    2465                2470                2475

Pro Gly  Leu Ile Cys Ile Phe  Asn Ala Pro Phe Ile  His Ala Phe
    2480                2485                2490

Cys Asn  Ile Met Phe Trp Ser  Phe Glu Lys Tyr Trp  Phe Thr Glu
    2495                2500                2505

Leu Cys  Lys Ser Ser Lys Met  Leu Ala His Phe Ile  Leu Tyr Leu
    2510                2515                2520

Lys Ile  Asp Ile Phe Glu His  His His His Gln Lys  Ser Phe Leu
    2525                2530                2535

Leu Gly  Ser Cys Gln Ala Tyr  His Met Gln Asp His  Tyr Asn Ser
    2540                2545                2550

Glu Phe  Cys Leu Lys Ala Ile  Phe Ser Phe Leu Phe  Ser Phe Phe
    2555                2560                2565

Phe Phe  Phe Asp Lys Ile Leu  Leu Cys Cys Leu Gly  Trp Ser Ala
    2570                2575                2580

Val Val  Gln Ser Trp Leu Thr  Ala Ala Leu Ala Ser  Gln Ala Gln
    2585                2590                2595

Val Leu  Leu Pro Pro Gln Leu  Val His Ala Thr Met  Pro Gly Phe
    2600                2605                2610

Phe Phe  Ser Phe Trp Arg Asp  Cys Pro Gly Trp Ser  Gln Thr Pro
    2615                2620                2625

Glu Leu  Lys Cys Ser Ser Arg  Leu Ser Leu Pro Lys  Cys Trp Asp
    2630                2635                2640

Tyr Arg  His Glu Pro Leu Pro  Lys Ala Gln Ile Leu  Ser Leu Glu
    2645                2650                2655

Gln Ile  Leu Gln Val Val Thr  Leu Lys Gln Phe Tyr  Phe Ile Asn
    2660                2665                2670

Val Leu  Glu Ala Ala Lys Tyr  Gln Ser Leu Asn Asn  Gln Phe Val
    2675                2680                2685

Ser His  Ser Phe Lys Gln Lys  Gly Tyr Tyr Met Asn  Lys Gly Val
    2690                2695                2700

Asn Ser  Ala His Asn Tyr Asn  Asp His Thr Asn Val  Phe Pro Gln
    2705                2710                2715

Asp Asn  His Cys Ser Leu Thr  Tyr Ser Arg Ser Thr  Leu Val Leu
    2720                2725                2730

Pro Thr  Ser His Phe Met Pro  Gln Asn Phe Lys Val  Leu Leu Arg
    2735                2740                2745

Ile Lys  Ile Ile Asn Asn Phe  Tyr Phe Ile Lys Asn  Ile Leu Ala
    2750                2755                2760

Gly His  Gly Gly Ser His Leu  Ser Gln His Phe Gly  Arg Pro Arg
    2765                2770                2775

Val Asp  His Leu Arg Pro Gly  Val Arg Asp Gln Pro  Gly Gln His
    2780                2785                2790

Gly Glu  Thr Thr Lys Asn Thr  Lys Ile Ser Gln Ala  Trp Trp Gln
    2795                2800                2805
```

-continued

```
Ala Pro  Val Ile Leu Val Thr  Trp Glu Val Glu Ala  Gly Glu Ser
    2810                 2815                 2820

Leu Glu  Pro Arg Arg Gln Arg  Leu Gln Ala Glu Ile  Ile Ala Phe
    2825                 2830                 2835

Gln Pro  Gly Gly Leu Asn Ser  Pro Pro Ser Ala Gly  Gln Gly Met
    2840                 2845                 2850

Cys Pro  Leu Val Gln Phe Gly  Ala Thr Thr Val Ile  Pro Ile Lys
    2855                 2860                 2865

Val Gln  Arg Ile Ser His His  Gln Lys Lys Cys Gln  Cys Asp Gly
    2870                 2875                 2880

Glu Lys  Arg Gln Ile Arg Leu  Asn Ile Thr Met Asn  Ile Ile Leu
    2885                 2890                 2895

Val Leu  Trp Ile Pro Lys Leu  Phe Gly Val Arg Ser  Gly Val His
    2900                 2905                 2910

Gly Leu  His Ile Glu Asn Leu  Cys Ile Asn Ala Phe  Pro Gln Ser
    2915                 2920                 2925

His Thr  Ser Ile Lys Asn Gln  Tyr Leu Lys Leu Gly  His Thr Asp
    2930                 2935                 2940

Ser Pro  Asn Gly Phe Ser Ile  Val Pro Tyr Ala Lys  Met Ile Ile
    2945                 2950                 2955

Ser Ile  Ile Arg Thr Asn Ile  Lys Gly Arg Ala Trp  Trp Leu Thr
    2960                 2965                 2970

Pro Ile  Ile Pro Ala Leu Gln  Glu Ala Lys Val Gly  Arg Ser Arg
    2975                 2980                 2985

Gly Gln  Glu Ile Lys Thr Ile  Leu Ala Asn Met Val  Lys Pro Tyr
    2990                 2995                 3000

Leu Tyr  Lys Lys Ile Ser Gln  Val Trp Trp Ala His  Met Ser Gln
    3005                 3010                 3015

Leu Leu  Gly Arg Leu Arg Gln  Glu Asn Cys Leu Asn  Pro Gly Gly
    3020                 3025                 3030

Gly Gly  Cys Ser Pro Arg Ser  Arg His Cys Thr Pro  Ala Trp Arg
    3035                 3040                 3045

Gln Ser  Glu Thr Leu Ser Gln  Lys Thr Lys Gln Asn  Lys Thr Lys
    3050                 3055                 3060

Gln Leu  Thr Leu Lys Pro Asn  Asn Ile Ser Thr Ser  Gly Leu Leu
    3065                 3070                 3075

Arg Asn  Ala Ile Ser Ile Tyr  Gln Pro Gly Met Ile  Thr Leu Ser
    3080                 3085                 3090

Ser Pro  Ser Pro Asp His Lys  Asp Ser Leu Asn Arg  Phe Asp Gln
    3095                 3100                 3105

Asn His  Glu Glu Met Gly Thr  Ser Leu Thr Ile Lys  Arg Asp Glu
    3110                 3115                 3120

Ile Asp  Ile His Ser Ile Asp  Lys His Asn Ser Tyr  Tyr Leu Met
    3125                 3130                 3135

Phe Gly  Arg Ala Leu Met Cys  Phe Ile Ser Ser Asn  Val Glu Pro
    3140                 3145                 3150

Lys Arg  Tyr Leu Ile His Tyr  Leu Ile Pro Phe Arg  Asn Met Phe
    3155                 3160                 3165

Thr Glu  Ser Trp Thr Ser Thr  Asn Met Val Arg Glu  Ala Ala Tyr
    3170                 3175                 3180

Ser Ser  Gln Asp Thr Val Glu  Gln Leu Lys Leu Phe  Glu Leu Pro
    3185                 3190                 3195
```

-continued

Ser Cys Pro Pro Cys Leu Leu Ser Phe Pro His Ser Phe Ile Pro
3200 3205 3210

Leu Phe Asn Pro Leu Asp Asn Lys Glu Val Tyr Phe Leu Ile Cys
3215 3220 3225

Val Ile Phe Val Ser Tyr Gln Gly Pro Ser Thr Phe Pro Pro Leu
3230 3235 3240

Phe Phe Phe Leu Arg Gln Ser Arg Ser Val Thr Gln Ala Gly Leu
3245 3250 3255

Gln Trp Cys Asp Cys Gly Ser Pro Lys Pro Gln Pro Leu Arg Leu
3260 3265 3270

Lys Gln Ser Ser His Leu Ser Leu Pro Ser Ser Trp Asp His Arg
3275 3280 3285

Arg Val Pro Pro His Pro Thr Asn Tyr Phe Leu Phe Phe Val Glu
3290 3295 3300

Thr Gly Ser Pro Tyr Val Val Gln Ala Gly Leu Glu Leu Leu Gly
3305 3310 3315

Ser Ser Asn Ser Pro Met Leu Ala Ser Gln Ser Val Gly Ile Ile
3320 3325 3330

Gly Met Ser His His Ala Gln Ser Pro Phe Ser Val Leu Lys Phe
3335 3340 3345

Ser Val Ser Gln Leu Ser Phe Leu Ser Gly Pro Ile Leu Gly Ser
3350 3355 3360

Phe Ile Cys Trp Trp Phe Cys Phe Arg Gly Pro Gly Val Ala Phe
3365 3370 3375

Thr His Thr Pro Gly Leu Ala Pro Ser Leu Ala Ser Ser Val Leu
3380 3385 3390

Trp Ser Trp Val Ile Leu Pro Phe Ser Thr Asp Ala Leu Leu Ile
3395 3400 3405

Phe Gln Ala Val Cys Ser Gly Leu Pro Phe Asn Pro Gln Asp Asn
3410 3415 3420

Ala Val Lys Trp Val Pro Ser Thr Val Pro Leu Leu Leu Lys Leu
3425 3430 3435

Arg His Ser Ala Gly His Gly Ala Ser Cys Leu Ser Gln His Phe
3440 3445 3450

Gly Arg Pro Arg Trp Ala Asp His Leu Arg Ser Gly Val Arg Asp
3455 3460 3465

Gln Pro Gly Gln His Gly Glu Thr Pro Ser Leu Leu Lys Ile Gln
3470 3475 3480

Lys Leu Ala Gly Arg Gly Ala Ala His Leu Ser Gln Leu Leu Gln
3485 3490 3495

Gly Leu Arg Gln Glu Asn His Leu Asn Leu Gly Gly Gly Gly Cys
3500 3505 3510

Ser Glu Pro Arg Ala Cys His Cys Thr Pro Ala Trp Met Thr Glu
3515 3520 3525

Asp Ser Val Ser Lys Lys Lys Ile Lys Lys Ile Lys Ile Gly Ile
3530 3535 3540

Leu Val Val Gln Asp Glu Pro Gln Thr Lys Pro Leu Arg His Arg
3545 3550 3555

Val Lys Glu Gly Arg Ala Leu Phe Gly Arg Glu His Arg Gln Asp
3560 3565 3570

Ser Arg Leu Lys Asn Arg Ala Pro Val Ser Asn Ser Cys Pro Ser
3575 3580 3585

Gly Leu Thr Thr Leu Arg Gly Ser Ala Lys Gly Leu Asp Arg Leu

-continued

```
    3590                3595                3600

Ser Lys  Gln Gly Val Cys Asp  Trp Gly Leu His Ala  Leu Val Ile
    3605                3610                3615

Arg Thr  Glu Gln Asn Arg Thr  Gly Ile Phe Thr Val  Leu Phe His
    3620                3625                3630

Thr Met  Thr Val Ile Arg His  Asn Leu Gly Gln Gly  Ser Ile Phe
    3635                3640                3645

Asn Tyr  Gln Ala Gln Gly Val  Ala Pro Gly Cys Leu  Pro Val Asp
    3650                3655                3660

Phe Ile  Ser Val Phe Lys Phe  Leu Leu Leu Leu Ser  Leu Glu Ala
    3665                3670                3675

Glu Ile  Gly His Lys Thr Ile  Gly Val Val Ser Ser  Leu Met Arg
    3680                3685                3690

Ile Leu  Asp Asn Cys Thr Glu  Leu Cys Ile His Tyr  Leu Asn Lys
    3695                3700                3705

His Ile  Glu Gln Phe Pro His  Pro Lys Ser Phe Leu  Met Pro Phe
    3710                3715                3720

Phe Phe  Leu Arg Arg Cys Leu  Thr Leu Ser Pro Arg  Leu Tyr Ser
    3725                3730                3735

Gly Ala  Ile Ser Ala His Cys  Asn Leu Arg Leu Leu  Gly Ser Arg
    3740                3745                3750

Asp Ser  Pro Ala Ser Ala Ser  Val Ser Gly Thr Thr  Asp Met Cys
    3755                3760                3765

Tyr His  Thr Trp Leu Ile Phe  Val Phe Leu Gln Asn  Thr Lys Ile
    3770                3775                3780

Val Leu  Phe Cys Ile Thr Ile  Ile Gly Ala Gly Leu  Lys Leu Leu
    3785                3790                3795

Thr Ser  Gly Asp Gln Pro Ala  Leu Ala Ser Gln Ser  Ala Gly Ile
    3800                3805                3810

Thr Gly  Met Ser His Pro Ala  Phe Ser Cys Leu Phe  Ala Val Thr
    3815                3820                3825

Tyr Val  Ile Phe Lys Asn Gly  Thr Ile Ile Tyr Thr  Tyr Thr His
    3830                3835                3840

Thr Tyr  Ile Tyr Ile Tyr Thr  His Ile Tyr Thr His  Ile Tyr Thr
    3845                3850                3855

His Ile  Tyr Thr Tyr Ile His  Ile Tyr Thr His Ile  Tyr Thr Tyr
    3860                3865                3870

Ile His  Thr Tyr Ile His Thr  Tyr Ile His Ile Tyr  Ile His Ile
    3875                3880                3885

Tyr Thr  Tyr Ile His Ile Tyr  Thr His Ile Tyr Thr  Tyr Ile His
    3890                3895                3900

Ile Tyr  Thr Tyr Ile His Thr  Tyr Ile His Ile Tyr  Thr His Ile
    3905                3910                3915

Tyr Ile  Tyr Thr His Ile Tyr  Thr Tyr Ile Tyr Thr  His Ile Tyr
    3920                3925                3930

Ile Leu  Phe Phe Ile Leu Arg  Trp Ser Leu Ala Leu  Ser Leu Gly
    3935                3940                3945

Leu Glu  Cys Ser Gly Thr Ile  Ser Ala His Cys Asn  Ile Cys Leu
    3950                3955                3960

Pro Gly  Ser Ser Asp Ser Pro  Ala Ser Ala Ser Gln  Val Ala Gly
    3965                3970                3975

Ile Thr  Gly Thr Cys Leu His  Ala Gly Leu Ile Leu  Tyr Phe Trp
    3980                3985                3990
```

```
Arg Gln  Gly Phe Thr Thr Leu  Ala Arg Val Val Ser  Asn Ser Pro
    3995                 4000                 4005

Arg Asp  Pro Pro Ala Ser Ala  Ser Gln Ser Ala Arg  Ile Thr Asp
    4010                 4015                 4020

Val Ser  His Arg Ala Gln His  Ile Tyr Tyr Phe Leu  Thr Val Phe
    4025                 4030                 4035

Leu Arg  Cys Thr Gly Gly Lys  Lys Met His Thr Ser  Leu Tyr Gly
    4040                 4045                 4050

Asn Tyr  Ile Val Leu Gln His  Asn Phe Asn Gly Cys  Ile Leu Ser
    4055                 4060                 4065

Asn Glu  Cys Phe Ile Ile Tyr  Leu Thr Asn Val Leu  Leu Phe Cys
    4070                 4075                 4080

Thr Tyr  Ile Asn Asn Val Leu  Leu Pro Leu Pro Gly  Ile Ile Phe
    4085                 4090                 4095

Leu Phe  Leu Leu Gln Tyr Arg  Ser Leu Leu Phe Phe  Asn Phe Ser
    4100                 4105                 4110

Tyr Leu  Ser Asp Thr Ser Leu  Ser Val Leu Leu Ala  Leu Cys Pro
    4115                 4120                 4125

Leu Phe  Phe Phe Phe Phe Phe  Asp Arg Val Ser Leu  Cys Cys Pro
    4130                 4135                 4140

Gly Trp  Ser Val Val Ala Gln  Ser Gln Leu Thr Ala  Thr Ser Ala
    4145                 4150                 4155

Ser Tyr  Val Gln Ala Ile Leu  Leu Pro Gln Pro Leu  Glu Lys Leu
    4160                 4165                 4170

Glu Leu  Thr Gly Ala Arg His  His Ala Trp Ile Ile  Phe Asn Arg
    4175                 4180                 4185

Asn Arg  Val Ser Pro Cys Trp  Leu Gly Trp Ser Thr  Pro Asp Leu
    4190                 4195                 4200

Arg Ser  Thr His Leu Ser Val  Gln Ser Ala Gly Ile  Thr Gly Met
    4205                 4210                 4215

Ser His  His Thr Trp Pro Leu  Cys Pro Leu Ser Thr  Phe Pro Arg
    4220                 4225                 4230

Phe Cys  Thr Ile Phe Phe Phe  Phe Phe Tyr Phe Asp  Arg Val Leu
    4235                 4240                 4245

Leu Leu  Leu Cys Cys Pro Gly  Trp Ser Ala Val Ala  Leu Ser Gln
    4250                 4255                 4260

Leu Thr  Ala Ala Thr Ser Pro  Gly Ser Gly Asp Pro  Pro Thr Ser
    4265                 4270                 4275

Ala Ser  Gln Val Ala Gly Ile  Thr Gly Met Cys His  His Thr Arg
    4280                 4285                 4290

Leu Ile  Phe Ala Val Phe Val  Glu Ser Gly Ser His  His Val Ala
    4295                 4300                 4305

Gln Ala  Gly Leu Lys Leu Leu  Gly Ser Ser Asn Pro  Pro Thr Leu
    4310                 4315                 4320

Val Ser  Gln Asn Ala Gly Ile  Thr Gly Met Ser His  Arg Ala Leu
    4325                 4330                 4335

Pro Lys  Ser Ser Tyr Ser Ile  Ile Ser Leu Val Ile  Asn Phe Ser
    4340                 4345                 4350

Pro Asp  Pro Leu Thr Leu Trp  Ile Ser Ser Leu Leu  Phe Phe Ser
    4355                 4360                 4365

Thr Pro  Asp Pro Asn Ser Gln  Leu Ser Thr Gly Tyr  Tyr Ile His
    4370                 4375                 4380
```

-continued

```
Arg Asp Val Leu Leu Ala Ile Gln Met Pro His Val Lys Asn Thr
    4385                4390                4395

Pro Ile Pro Phe Ala Lys Ser Leu Cys Phe Ser Leu Ser Leu Ser
    4400                4405                4410

Phe Leu Leu Pro Ile Ser Gly Arg Gly Ser Gly Val Leu Pro Ala
    4415                4420                4425

Thr Gln Ala Arg Asn Leu Lys Val Leu Phe Leu Leu Ser Ser Leu
    4430                4435                4440

Ile Ser His Ile Gln Ser Ile Lys Cys Tyr Phe Ser Ser Gln Met
    4445                4450                4455

Pro Leu Ser Leu Cys Pro Ser Phe Pro Phe Pro Pro Leu Ser Gln
    4460                4465                4470

Leu Leu Arg Ser His Asp Ser Ser Pro Glu Trp Gln Leu Pro Asn
    4475                4480                4485

Ile Ser Gln Pro Pro Ser Pro Arg Tyr Ser Ala Leu Leu Pro Glu
    4490                4495                4500

Leu Thr Leu Arg Asn Arg Glu Ile Ile Phe Leu Ser Cys Leu Lys
    4505                4510                4515

Ile Ser Asp Asp Phe Leu Ser Leu Thr Glu Ala Ser Leu Asn Phe
    4520                4525                4530

Pro Leu Ser Pro Pro Thr Leu Pro Pro His Thr Thr Phe Leu Arg
    4535                4540                4545

Arg Leu Arg Gln Pro Arg Thr Phe Leu Asn Ala Leu Leu Phe Leu
    4550                4555                4560

Cys Phe Tyr Ser Arg Ser Pro Gln Leu Pro Asn Leu Cys Val Leu
    4565                4570                4575

Leu Thr Pro Gly Ala Leu Ala Phe Pro Glu Ala Phe Leu His Asp
    4580                4585                4590

Cys Arg Gln Glu Lys Ala Leu Pro Thr Gly Pro Ser Trp Leu Ala
    4595                4600                4605

Arg Ser Thr Pro Pro Gln Arg Gln Leu Trp Thr Lys Ser Pro Gln
    4610                4615                4620

Arg Ile Ser Gly Tyr Glu Gly Gly Ala Gly Arg Gly Asp Gly Ser
    4625                4630                4635

Ala Ser Phe Val Phe Pro Ala Gly Lys Arg Trp Asp Leu Gly Gly
    4640                4645                4650

Gln Gly Thr Arg Ser Pro Pro Val Trp Lys Thr Leu Val Leu Glu
    4655                4660                4665

His Cys Ser Arg Pro Asp Val Ala Cys Pro His Phe Pro His Ser
    4670                4675                4680

Arg Val Gly Gln Thr Glu Val Gly Glu Gln Ser Pro Glu Ala Asp
    4685                4690                4695

Ser Pro Gly Lys Lys Lys Lys Gly Lys Lys Ala Pro Ala Asp Leu
    4700                4705                4710

Phe Thr Gly Ala Arg Gly Trp Lys Asp Arg Ala Ser Leu Glu Gln
    4715                4720                4725

Thr Glu Ser Asp Lys Leu Gly Gly Arg Leu Ala Pro Ala Trp Ser
    4730                4735                4740

Gly Ala Gly Gly Leu Leu Val Ile Ala Leu Glu Gly Pro Gly Leu
    4745                4750                4755

Pro Ala Val Thr Pro Ala Arg Val Gly Gly Glu Gly Gly Ala Ser
    4760                4765                4770

Ser Pro Phe Met Ser Ala Ala Ser Gln Ala Arg Ala Gly Arg Pro
```

-continued

```
    4775                4780                4785

Phe Ser  Gly Gly Asp Trp Ala  Gly Arg Gly Asp Gly  Cys Leu Arg
    4790                4795                4800

Arg Ser  Ala Gly Leu Lys Val  Lys His Ser Pro Ala  Gly Leu Ser
    4805                4810                4815

Gln Ser  Trp His Leu Pro His  Arg Ala Pro Ser Tyr  Leu Leu Leu
    4820                4825                4830

Lys Ser  Leu Met Cys Ser Gly  Gly Pro Arg Arg Trp  Arg Ser Leu
    4835                4840                4845

Gly Gly  Phe Tyr Gly Val Ala  Leu Met Ala Val Val  Gly Val Pro
    4850                4855                4860

Pro Gln  Gly Gly Gly Ser Leu  Ser Ser Pro Pro Pro  Gly His Arg
    4865                4870                4875

Ile Leu  Phe Ala Glu Lys Val  Arg Met Glu Ala Trp  Ile Val Phe
    4880                4885                4890

Leu Leu  Glu Met Gln Leu Leu  Pro Pro Ser Thr Pro  Gly Glu Arg
    4895                4900                4905

Glu Val  Cys Gly Glu Leu Ala  Leu Lys Val Gly Lys  Arg Lys Gly
    4910                4915                4920

Thr Asn  Gly Tyr Thr Leu Arg  Arg Gly Leu Ser Tyr  Ile Ala Gly
    4925                4930                4935

Glu Asn  Leu Lys Trp Cys Ser  His Trp Gly Asn Ser  Leu Met Val
    4940                4945                4950

Pro Gln  Lys Val Lys Tyr Gln  Ile Ser Ile Trp Pro  Ser Asn Ser
    4955                4960                4965

Thr Pro  Arg Tyr Lys Pro Ile  Ile Asn Gly Tyr Ser  Tyr Leu His
    4970                4975                4980

Ser Asn  Val His Gly Ser Ala  Ile His Asn Asn Gln  Lys Val Glu
    4985                4990                4995

Ala Thr  Pro Val Phe Ile Asn  Ile Ser Lys Pro Thr  Val Val Tyr
    5000                5005                5010

Ser Tyr  Asn Gly Ile Ile Gly  Asn Lys Gln Glu Ser  Thr Asp Ile
    5015                5020                5025

Cys Ser  Asn Gly Asp Glu His  Lys Ile Met Pro Arg  Glu Gly Ser
    5030                5035                5040

Gln Thr  Gln Lys Val Ile Tyr  Cys Thr Ile Pro Cys  Ile Gly Asn
    5045                5050                5055

Ile Leu  Lys Trp Ile His Arg  Asp Arg Lys Gln Thr  Asp Gly His
    5060                5065                5070

Gln Gly  Pro Ser Val Gly Gly  Lys Met Gly Asn His  Cys Met Gly
    5075                5080                5085

Ser Ser  Phe Leu Leu Gly Lys  Cys Phe Arg Thr Lys  Gly Ser Val
    5090                5095                5100

Cys Thr  Met Leu Met His Val  Pro Gln Asn Trp Ser  Ile Asn Gly
    5105                5110                5115

Phe Gly  Leu Ala Arg Trp Leu  Thr Pro Val Ile Pro  Ala Leu Glu
    5120                5125                5130

Gly Gly  Ala Gly Gly Ser Pro  Glu Val Arg Ser Leu  Arg Leu Ala
    5135                5140                5145

Trp Pro  Thr Trp Asn Pro Ile  Ser Pro Lys Lys Lys  Lys Lys Lys
    5150                5155                5160

Lys Glu  Arg Lys Lys Lys Lys  Asp Gly His Gly Gly  Arg Cys Leu
    5165                5170                5175
```

-continued

```
Ser Gln Leu Leu Arg Arg Leu Lys Gln Glu Asn Arg Leu Asn Pro
    5180                5185                5190

Gly Gly Glu Gly Cys Ser Asp Pro Arg Ser Ser His Cys Thr Pro
    5195                5200                5205

Ala Trp Ala Thr Arg Ala Lys Leu Cys Leu Lys Ile Asn Lys Asn
    5210                5215                5220

Lys Met Val Ser Leu Ala Gly His Gly Gly Ser His Leu Ser Ser
    5225                5230                5235

Gln His Phe Gly Arg Pro Arg Glu Glu Asp His Leu Ser Pro Gly
    5240                5245                5250

Val Asp Gln Pro Gly Gln Tyr Ser Glu Thr Pro Ile Ser Ile Asn
    5255                5260                5265

Lys Val Val Ser Phe Ile Leu Cys Glu Leu Ser Leu Asn Asn Val
    5270                5275                5280

Ser Leu Ser Leu Ser Leu Ser Leu Ser Leu Ser Gln Thr Asn Gln
    5285                5290                5295

Thr Lys Arg Val Leu Pro Ala Val His Asn Ser Leu Arg Lys Lys
    5300                5305                5310

Glu Thr Ala Ile Leu Ser Pro Leu Leu Pro Phe Thr Ser Thr Phe
    5315                5320                5325

Leu Ser Val Phe Ser Leu Ala Trp Ser Trp Leu Leu Thr Ala Pro
    5330                5335                5340

His Gly Lys Trp Pro Gly Gly Arg Gly Pro Leu Pro Pro Leu Glu
    5345                5350                5355

Gly Pro Arg Leu Gly Pro Glu Pro Leu Val Ser Pro Ala Tyr Thr
    5360                5365                5370

His Ala Phe Val Ser Ala Leu Trp Pro Gly Cys Ser Trp Leu Gly
    5375                5380                5385

Gly Thr Ala Trp Gly Lys Gly Arg Ser Gly Ser Lys Trp Glu Gly
    5390                5395                5400

Phe Cys Leu Gln Gln Pro Gln Tyr Gly Ile Ser Thr Pro Trp Ser
    5405                5410                5415

Leu Gln Leu Gly Pro Val Ala Phe Val Pro Lys Ser Val Tyr Lys
    5420                5425                5430

Asn Gln Arg Phe Ala Cys Ser Thr Glu Ser Leu Gln Val Thr Lys
    5435                5440                5445

Tyr Asp Ser Tyr Ser Leu His Phe Thr Gln Phe Val Ala Val Thr
    5450                5455                5460

Glu Phe Arg Ala Arg His Glu Leu Ile Leu Ser Phe Pro Val Leu
    5465                5470                5475

Thr Val Gly Gln Gly Asp Ile Ser Glu Arg Gly Arg Cys Phe Gly
    5480                5485                5490

Ala His Asn Leu Ile Gly Gly Ser Val Val Glu Lys Thr Gly Asn
    5495                5500                5505

Val Gly Tyr Val Ser Met Val Glu Glu Ser Leu Lys Pro Arg Cys
    5510                5515                5520

Asp Met Leu Arg Arg Val Arg Arg Trp Ser Glu Leu Gly Ser Ser
    5525                5530                5535

Gly Thr Val Asp Ala Ser Ala Val Cys Ala Lys Leu Lys Leu Pro
    5540                5545                5550

Ala Thr Ala Thr Gln Gly Gly Gly Ser His His Gln Ala Leu Pro
    5555                5560                5565
```

-continued

```
Leu Ser Ile Thr Glu Tyr Cys Gln Ala Tyr Ser Trp Thr Tyr Asp
    5570                5575                5580

Arg Leu Arg His Ile Phe Val Ile Cys Ser Thr Pro Ser Arg Ala
    5585                5590                5595

Ser Ser Asp His Arg Ser Gly Thr Arg Ser Gln His Tyr Thr Phe
    5600                5605                5610

Ser His Ser Phe Phe Ser Lys Thr Gln Leu Pro His Gln Asn Pro
    5615                5620                5625

Gly Asn Asn Asn Thr Cys Phe Gly Cys Gly Ala Ile Thr His Cys
    5630                5635                5640

Gln Ala Phe Ser Thr Val Pro Ser Ser Ser Lys Tyr Cys Tyr Cys
    5645                5650                5655

Tyr Tyr Asp Cys Ile His Lys Ser Asp Gly Leu Arg Thr Leu Ile
    5660                5665                5670

Ser His Ser Lys Gly Ser Val Cys Val Tyr Ala Val Ala Thr Pro
    5675                5680                5685

Leu Thr Lys Cys Arg Thr Trp Tyr Leu Asp Phe Ser Lys Leu Gly
    5690                5695                5700

Thr Ala Lys Leu Ser Tyr Tyr Thr Pro Val Tyr Ser Ser Leu Pro
    5705                5710                5715

Phe Leu Met Trp Leu Val Phe Val Pro Leu Lys Phe Glu Thr Arg
    5720                5725                5730

Asp Tyr Ile Thr Ala Leu Arg Glu His Gly Leu Gly Val Val Ser
    5735                5740                5745

His Ala Cys Asn Pro Ser Thr Leu Gly Gly Arg Ser Gly Gln Ile
    5750                5755                5760

Thr Arg Glu Leu Glu Thr Thr Leu Ala Asn Met Val Lys Pro His
    5765                5770                5775

Leu Tyr Lys Tyr Lys Asn Pro Gly Ile Val Ala Asp Ala Tyr Asn
    5780                5785                5790

Leu Ser Tyr Leu Gly Gly Gly Arg Arg Leu Ala Thr Arg Glu Ala
    5795                5800                5805

Glu Val Ala Val Ser Arg Glu Arg Ala Thr Ala Leu Gln Pro Gly
    5810                5815                5820

Gln Gln Ser Glu Thr Leu Ser Gln Lys Lys Lys Lys Arg Glu Arg
    5825                5830                5835

Glu Arg Ile Trp Ser Thr Ser Phe Asn Gln Lys Ile Tyr Phe His
    5840                5845                5850

Gln Tyr Leu Ile Tyr Leu Gly Leu Cys Leu Ser Tyr Asn Trp Asn
    5855                5860                5865

Ile Lys Arg Val Phe Asn Ile Ile Phe Tyr Gln Asp Ile Ile Tyr
    5870                5875                5880

Ile Pro Asn Tyr Ser Phe Ser Val Cys Arg His Phe Tyr Ile His
    5885                5890                5895

Arg Asp Met Gln Pro Leu Pro Lys Ser Thr Arg Thr Phe Ser Ser
    5900                5905                5910

Leu Pro Thr Glu Pro Met His Ile Gly Asn Pro Ser Pro Ser Leu
    5915                5920                5925

Gln Pro Gln Ile Asn Phe Leu Ser Leu Asp Val Pro Phe Trp Thr
    5930                5935                5940

Phe His Asn Lys Asn His Thr Ile Tyr Ser Phe Leu Cys Leu Thr
    5945                5950                5955

Ser Leu Pro Ser
```

5960

<210> SEQ ID NO 49
<211> LENGTH: 5965
<212> TYPE: PRT
<213> ORGANISM: Homo sapiens

<400> SEQUENCE: 49

Ser Asn Arg Ala Val Tyr Phe Thr Trp Val Gln Ala Gly Val Gln Lys
1 5 10 15

Glu Ser Gln Gln Arg Val Val Gly Leu Ser Leu Val Leu Ile Gly Leu
20 25 30

Gly Val Tyr Lys Val His Ser Gln Gly Arg Gly Lys Asn Ile Trp Tyr
35 40 45

Gln Leu Ala Trp Gly Arg Asn Lys Ser Gln Trp Trp Asn Val Ile Ser
50 55 60

Gly Tyr Phe His Phe Phe Cys Gly Ser Ser Val Ala Ser Gly His Leu
65 70 75 80

Asp Val His Val Gln Val Thr Gly Asp Leu Met Ala Leu Gly Leu Arg
85 90 95

Gly Leu Thr Leu Leu Ser Ser Tyr Ile Ser Met Lys Asn Lys Thr Lys
100 105 110

Trp Ser Val Glu Ala Ala Lys Ile Phe Gly Gly Gly Met Glu Arg Trp
115 120 125

Ala Met Phe Leu Gly Ala Ala Leu Ser Gly Ile Gly Val Ala Trp Glu
130 135 140

Pro Arg Val Gly Glu Ile Lys Leu Lys Lys Asp Leu Gly Ile Arg Gly
145 150 155 160

Asp Ile Val Gly Leu Leu Glu Gly Val Phe Val Val Asn Asp Cys Trp
165 170 175

Pro Gly Cys Ser Phe Val Ile Glu Lys Leu Asn Arg Arg Lys Thr Gln
180 185 190

Gly Pro Asn Lys Arg Lys Arg Lys Ile Gly Ile Lys Gly Leu Arg Ile
195 200 205

Gly Arg Thr Gln Asp Ile Gln Leu Gly Ser Ala Gln Gly Gly Ser Ala
210 215 220

Leu Phe Ala Trp Leu Ala Asn Phe Trp Gly Leu Ser Leu Ser Phe Phe
225 230 235 240

Met Leu Ser Tyr Thr Arg Pro Asp Phe Arg Lys Gln His Ser Ser Phe
245 250 255

Lys Asn Ile Gln Gly Pro Leu Phe Leu Ala Val Ser Lys Ser Arg Pro
260 265 270

Trp Arg Phe Trp Arg Lys Glu Lys Cys Lys Ala Ser Ser Cys Leu Leu
275 280 285

Lys Lys Asp Arg Ala Gly His Ser Gly Ser Arg Leu Ser Gln His Phe
290 295 300

Gly Arg Leu Arg Trp Ala Asp Arg Glu Val Arg Arg Trp Arg Pro Ser
305 310 315 320

Trp Leu Thr Trp Asn Pro Ile Ser Thr Lys Asn Thr Lys Asn Pro Gly
325 330 335

Met Val Ala Gly Thr Ser Ser Pro Ser Tyr Leu Gly Gly Gly Arg Arg
340 345 350

Met Val Thr Gln Glu Ala Glu Leu Ala Val Ser Gln Asp His Thr Thr
355 360 365

```
Ala Leu Gln Pro Gly Gly Gln Ser Lys Thr Pro Ser Gln Lys Lys Lys
    370                 375                 380

Lys Asp Tyr Lys Arg Gly Glu Arg Val Arg Leu Ile Val Trp Trp Arg
385                 390                 395                 400

Leu Gly Arg Gly Arg Gly Trp His Lys Ile Gly Asn Gln Asn Lys Asn
                405                 410                 415

Glu Tyr Lys Ser Lys Glu Asp Phe Ile Arg Val Lys Val Ser Glu Gly
            420                 425                 430

Thr Leu Pro Leu Lys Ile Tyr Pro Leu Gln Glu Ser Leu Lys Gly Gly
        435                 440                 445

Val Leu Arg Asn Gln Glu Pro Leu Asn Thr Lys Arg Leu Arg Ser Cys
    450                 455                 460

Leu Gly Asp Leu Thr Asn Lys Gly Arg Ser Val Phe Thr Leu Tyr Arg
465                 470                 475                 480

Gly Gly Lys Ala Lys Trp Arg Asn Tyr Val Gln Lys Gly Arg Asn Asp
                485                 490                 495

Arg Gly Gly Leu Leu Thr Pro Cys Gly Lys Gly Leu Tyr Pro Ser Ser
            500                 505                 510

Glu Ser Val Tyr Pro Tyr Gln Glu Val Phe Phe Pro Asp Ser Ala His
        515                 520                 525

Val Ser Lys Val Asn Leu Pro Val Leu Gly Arg Gly Lys Phe Pro Ser
    530                 535                 540

Leu Met Cys Arg Glu Gly Lys Gly Pro Glu Gln Ser Leu Arg Asp Ser
545                 550                 555                 560

Arg Ile Val Asp Glu His Glu Val Ile Phe Phe Arg Thr Asp Phe His
                565                 570                 575

Asp Gly Asn Glu Met Arg Gly Tyr Lys Arg Trp Ala Ser Gly Leu Pro
            580                 585                 590

Thr Arg Lys Arg Leu Asn Asp Asp Arg Ile Glu Trp Ala Cys Glu Ala
        595                 600                 605

Gly Arg Arg Tyr Phe Pro Ser Lys Asn His Leu Pro Cys Val Gly Lys
    610                 615                 620

Asp Tyr Val Glu Val Ser Met Arg Glu Val Gly Val Thr Asp Lys Lys
625                 630                 635                 640

Glu Lys Asn Trp Pro Gly Thr Glu Val Gly Met Leu Ala Ala Ser Leu
                645                 650                 655

Ala Thr Leu Ser Ala Ala Leu Pro Val Met Gly Ser Asp Ala Phe Trp
            660                 665                 670

Pro Leu Gln Met Thr Pro Ala Ser Phe Gly Ser Lys Ala Ala Leu Arg
        675                 680                 685

Arg Val Phe Ile Lys Glu Ala Leu Met Met Lys Asp Pro Cys Ile Val
    690                 695                 700

Arg Lys Pro Leu Ser Thr His Ile Thr Ala Trp Trp Trp Arg Ile Lys
705                 710                 715                 720

Ala Tyr Leu Glu Ser Val Ile Leu Thr Arg Ser Pro Phe Ala Arg Val
                725                 730                 735

Arg Ala Arg Val Lys Ala Met Ser Leu Ala Cys Glu Val Val Glu Arg
            740                 745                 750

Gly Arg Ala Val Ala Ser Arg Ile Asp Val Glu Asp Ser Ile Ala Pro
        755                 760                 765

Ala Phe Ala Gly Glu Trp Arg Leu Gly Leu Val Glu Leu Pro Ser Ile
    770                 775                 780

Asn Gln Val Ser Gly Gly Thr Gly Lys Lys Glu Ile Trp Gly Asn Gly
```

-continued

```
785                 790                 795                 800

Val Asn Ala Arg Trp Ile Arg Glu Ile Val Met Glu Val Arg Cys Gly
                805                 810                 815

Ile Arg Asn Asn Val Gly Gly Arg Ile Glu Val Gln Ala Arg Asn Asn
            820                 825                 830

Gly Asn Cys Gly Arg Leu Ser Lys Glu Val Ala Gly Cys Gly Gly Ser
        835                 840                 845

Cys Leu Ser Gln His Phe Gly Arg Pro Arg Trp Ala Asp His Phe Arg
    850                 855                 860

Ser Gly Val Gln Asp Gln Leu Gly His Gly Glu Thr Pro Ser Leu Leu
865                 870                 875                 880

Lys Ile Gln Lys Ile Ser Arg Val Trp Gly Thr His Leu Ser Gln Leu
                885                 890                 895

Leu Gln Arg Leu Arg Gln Glu Asn Arg Trp Asn Leu Gly Ser Gly Gly
            900                 905                 910

Cys Ser Glu Pro Arg Leu Cys His Cys Met Pro Ala Trp Glu Thr Glu
        915                 920                 925

Asp Ser Val Ser Lys Lys Ser Val Leu Lys Glu Pro Gly Ser Gly Lys
    930                 935                 940

Tyr Met Arg Gln Val Gly Arg Lys Ile Leu Glu Val Met Arg Thr Val
945                 950                 955                 960

Glu Ser Glu Leu Ser Ile Met Phe Gly Pro Leu Lys Val Ser Lys Gln
                965                 970                 975

Gln Gln Pro Pro His Thr Asp Met Arg Ala Arg Leu Lys Gln Gly Gln
            980                 985                 990

Val Val Trp Thr Glu Arg Leu Gln  Gly Met Leu Leu Ala  Leu Val Glu
        995                 1000                1005

Phe Arg  Pro His Ser Pro Ala  Leu Trp Leu Cys Val  Met Lys Lys
    1010                1015                1020

Leu Gly  Val Arg Glu Ser Cys  Gly Ser Ser Phe Gly  Cys Phe Leu
    1025                1030                1035

Arg Asn  Gly Lys Gly Ser Gly  Glu Arg Ile Asp Leu  Trp Gly Gln
    1040                1045                1050

Leu Gly  Leu Phe Arg Thr Glu  Trp Val Val Gly Gly  Arg Tyr Gly
    1055                1060                1065

Glu Gly  Ile Trp Val Trp His  Tyr Gly Val His Arg  Gln Asp Asn
    1070                1075                1080

Phe Val  Asp Lys Ala Gln Ile  Leu Asn Pro Val Arg  Leu Val Trp
    1085                1090                1095

Phe Leu  Asp Arg Asn Gly Gly  Ile Val Arg Arg Val  Tyr Arg Leu
    1100                1105                1110

Lys Ala  Met Leu Gln Ala Ser  Asp Asn Arg Leu Ser  Phe Ser Val
    1115                1120                1125

Leu Trp  Asp Pro Phe Lys Val  Cys Cys Gly Met Gly  Tyr Trp His
    1130                1135                1140

Val Gly  Gly Leu Gly Phe Asn  Gly Met Val Arg Gly  Ala Ser Val
    1145                1150                1155

Ala Lys  Glu Gly Ile Glu Val  Ser His Thr Cys Gly  Leu Arg Trp
    1160                1165                1170

Gly Asp  Thr Arg Gly Gly Cys  Glu Gly Gly Phe Glu  Leu Gly Lys
    1175                1180                1185

Arg Ala  Ala Met Arg Cys Gly  Cys Ser Pro Gly Thr  Val Arg Glu
    1190                1195                1200
```

```
Ala Asp Asn Leu Val Lys Met Ser Pro Asn Lys Gly Ala Gly Gln
    1205                1210                1215

Val Gly Ile Thr Lys Lys Glu Cys Ile Lys Glu Cys Cys Pro Ser
    1220                1225                1230

Trp His Gln Ser Trp Gly Val Leu Thr Gly Leu Ala Ala Trp Pro
    1235                1240                1245

Ser Ile Pro Thr Thr Val Met Glu Ala Arg Glu Thr Gly Pro Lys
    1250                1255                1260

Glu Gly Ile Val Glu Trp Val Ala Ser Val Leu Arg Arg Gly Gln
    1265                1270                1275

Thr Ser Pro Ser Leu Glu Leu Pro Lys Ala Ser Val Met Val Gln
    1280                1285                1290

Glu Ala Ser Glu Ala Ile Gly Gln His Gln Phe Ser Ala Ala Lys
    1295                1300                1305

Pro Arg Thr Ser Gly Lys Glu Ser Glu Ser Leu Gly Pro Glu Phe
    1310                1315                1320

Gln Gln Leu Trp Glu Trp Leu Leu Gly Lys Leu Asp Ser Leu Ile
    1325                1330                1335

Ser Ser Arg Val Trp His Arg Trp Asp Met Ala Gln Glu Glu Ser
    1340                1345                1350

Gln Ala Ala Gly Ile Pro Trp Pro Ser Asp Gln Ile Ser Ser Thr
    1355                1360                1365

Arg Lys Ile Leu Gly Glu Ala Val Leu Glu Glu His Leu Ala Ala
    1370                1375                1380

Ala Ile Gln Val Phe Ser Ser Cys Val Leu Glu Met Trp Leu Gly
    1385                1390                1395

Phe Leu Ser Gln Trp Arg Gln Val Ile Ala Thr Gln Lys Tyr Val
    1400                1405                1410

Ala Ser Thr Leu Leu Leu Tyr Thr Leu Lys Val Arg Leu Ile Lys
    1415                1420                1425

Ser Cys Cys Gly Val Gly Leu Glu Ser Asn Phe Trp Ser Phe Phe
    1430                1435                1440

Cys Pro Glu Arg Val Gly Asn Ala Tyr Glu Asp Gly Leu Leu Ala
    1445                1450                1455

Pro Leu Gly Leu Gly Arg Ser Ile Gly Leu Leu Pro Asn Gly Pro
    1460                1465                1470

Thr Gly Leu Gly Phe Tyr Ile Lys Thr Ala Thr Leu Thr Asp Trp
    1475                1480                1485

Glu Arg Ser Asp Glu Glu Lys Gly Ala Leu Thr Leu Thr Thr Pro
    1490                1495                1500

Ser Ala Pro Ala Thr Ser Phe Phe Phe Phe Phe Ala Leu Lys Cys
    1505                1510                1515

Phe Asn Trp Ser Ser Ser His Ser Gly Phe Gln Gly Pro Cys Leu
    1520                1525                1530

Asp Thr Ala Asn Pro Gln Leu Glu Gly His Leu Arg His Ile Ile
    1535                1540                1545

Leu Leu Glu Leu His Lys Val Leu Ile Leu Gln Leu Gln Asn His
    1550                1555                1560

Thr Gln Phe Ser Leu Ile Ile Asn Thr Leu Phe Asn Ala Leu Leu
    1565                1570                1575

Ser Gln Lys Ile Ser Ser Thr Gln Tyr Ile Glu Leu Cys Asn Lys
    1580                1585                1590
```

```
Ile Ile  Phe Glu Ile Gln Lys  Glu Ile Val Ile Ser  Ser Ile Cys
    1595                 1600                 1605

Leu Ser  Tyr His Lys Val Gly  Gln Ser Ser Val Leu  Asn Lys Ile
    1610                 1615                 1620

Ser Lys  Phe Val Gln Val Phe  Leu Arg Asn Tyr Ile  Arg Lys Thr
    1625                 1630                 1635

Val Tyr  Leu Leu Phe Asp Ser  Ser Asp Arg Asn Val  Gly Ile Pro
    1640                 1645                 1650

Thr His  Asp Glu Ser Leu Ala  Leu Gly Ser His Pro  Gln Pro Arg
    1655                 1660                 1665

Arg Thr  Ala Ser Pro Gly Gly  Val Gln Pro Gly Leu  Leu Arg Val
    1670                 1675                 1680

Arg Phe  Pro His Leu Glu Leu  Trp Phe His Val Cys  Ala Pro Val
    1685                 1690                 1695

Arg Phe  Trp Thr Gln Lys Thr  Cys Leu Ser Thr Pro  Ser Ala Glu
    1700                 1705                 1710

Asp Leu  Val Lys Glu Val Leu  Val Arg Val Leu Cys  Ser Pro Cys
    1715                 1720                 1725

Gly Asp  Gln Ala Val Ile Thr  Ala Ser Ser Leu Leu  Thr Leu Val
    1730                 1735                 1740

Thr Gly  Cys Pro Glu Arg Ser  Asp Arg Glu Trp Pro  Ser Gly Cys
    1745                 1750                 1755

Leu Asp  Ser Ala Ser Asp Ser  Ala Ala Gly Ser Gln  Met Gln Ala
    1760                 1765                 1770

Gln Gly  Ser Arg Gly Val Val  Gln Arg Leu Glu Ser  Pro Cys Thr
    1775                 1780                 1785

Ala Leu  Trp Ala Ala Arg His  Ser Cys Cys Val Leu  Pro Gly Thr
    1790                 1795                 1800

Asn Arg  His Leu Glu Gly Asn  Phe Ala Pro Leu Ala  Thr Arg Arg
    1805                 1810                 1815

Pro Leu  Gly Gly Ala Asp Gly  Thr Asn Trp Gly Pro  Val Arg Thr
    1820                 1825                 1830

Pro Thr  His Ser Arg Lys Ala  Arg His Gln Pro Ala  Leu Met Lys
    1835                 1840                 1845

Ser Gly  Ser Ala Ile Ser Leu  Thr Gly Asn Cys Trp  Ala Asp Arg
    1850                 1855                 1860

Gly Glu  Leu Val Glu Glu Arg  Asn Cys Lys Leu Asp  Gln Val Gly
    1865                 1870                 1875

Gly Glu  Val Ile Lys Gly Leu  Gly Gly Gly Ala Glu  Ala Lys Glu
    1880                 1885                 1890

Leu Gly  Pro Gly Ser Ala Trp  Arg Gly Ala Ala Trp  Gly Glu Gly
    1895                 1900                 1905

Gly Arg  Ser Asp Glu Ser Ile  Glu Lys Lys Asp Ser  Glu Asp Ser
    1910                 1915                 1920

Glu Leu  Gly Val Glu Thr Glu  Gly Thr Glu Arg Arg  Glu Arg Arg
    1925                 1930                 1935

Lys Ile  Trp Asp Glu Ser His  Trp Glu Gln Arg Leu  Gly Arg Asp
    1940                 1945                 1950

Gln Cys  Val Lys Glu Cys Leu  Asp Val Arg His Leu  Arg Pro Phe
    1955                 1960                 1965

Ala His  Phe Met Thr Arg Ile  Ile Asn Leu Asp Gly  Glu Leu Glu
    1970                 1975                 1980

Ser Ala  Val Phe Trp Leu Phe  Gly Ile Ile Val Glu  Phe Val Leu
```

```
    1985                1990                1995

Gly Pro  Ser Gly Val Ala Glu  Glu Asn Lys Thr Leu  Arg Phe Val
    2000                2005                2010

Arg Cys  Glu Leu Lys Arg Phe  Val Phe Glu Asn Thr  Gly Gly Arg
    2015                2020                2025

Arg Arg  Arg Asn Gly Gly Trp  Lys Val Ala His Ser  Glu Gly Gly
    2030                2035                2040

Lys Pro  Glu Lys Arg Glu Gly  Arg Gly Thr Glu Lys  Ala Gly Gly
    2045                2050                2055

Ala Ala  Gly Gly Ile Glu Gln  Pro Trp Ala Ala Met  Trp Val Ser
    2060                2065                2070

Ser Gln  Ser Arg Cys Pro Arg  Asn Leu Val Thr Lys  Gly Met Trp
    2075                2080                2085

Val Asn  Asp Gln Gly Arg His  Pro Arg Gly Asp Gln  Thr Pro Met
    2090                2095                2100

Glu Cys  Gly Ile Ile Arg Gln  Ala Ser Pro Gln Leu  Asn Thr Lys
    2105                2110                2115

Gly Arg  Leu Ser Ser Arg Val  Arg Asp Arg Trp Ser  Phe Gly Ser
    2120                2125                2130

Thr Asp  Lys Met Cys Leu Leu  Ile Ser Thr Arg Glu  Glu Lys Glu
    2135                2140                2145

Arg Glu  Leu Glu Gly Gln Gly  Asp Arg Val Val Arg  Glu Glu Asp
    2150                2155                2160

Arg Val  Ala Arg Lys Ala Gly  Glu Glu Lys Asp His  Leu Pro Asp
    2165                2170                2175

Leu Lys  Leu Ala Arg Cys Ser  Leu Gly Trp Leu Val  Gly Pro Glu
    2180                2185                2190

Ile Ile  Gly Gly Ser Pro His  Gly Val Arg Ala Thr  Thr Gly His
    2195                2200                2205

Trp Ser  Pro Lys Gly Val Leu  Leu Ser Trp Val Phe  Ser Thr Lys
    2210                2215                2220

Cys His  Met His Pro Cys Glu  Glu Thr Thr Lys Gln  Ala Leu Cys
    2225                2230                2235

Glu Gln  Gln Gly Cys Ile Phe  His Leu Gly Ala Gly  Gly Leu Ser
    2240                2245                2250

Leu Lys  Arg Ser Gln Gln Arg  Val Val Gly Leu Ser  Leu Val Leu
    2255                2260                2265

Ile Gly  Leu Gly Ala Tyr Lys  Val His Ser Gln Gly  Gln Gly Glu
    2270                2275                2280

Tyr His  Lys Val Pro Ser Gly  Arg Gly Arg Ile Tyr  Arg Ile Ser
    2285                2290                2295

Gly Gly  Ala Gly Thr Asn Leu  Asn Gly Gly Met Ser  Ser Val Lys
    2300                2305                2310

Ala Ile  Phe Thr Ser Phe Val  Asp Leu Gln Leu Leu  Gln Ala Ile
    2315                2320                2325

Cys Met  Tyr Thr Cys Arg Ser  Gln Gly Ile Trp Leu  Ser Leu Gly
    2330                2335                2340

Ser Glu  Ala His Val Val Ser  Arg Leu Ile Ala Leu  Gly Ile Asn
    2345                2350                2355

His Ser  Asn Glu Phe Phe Val  Phe His Tyr Ile Ile  Leu His Trp
    2360                2365                2370

Ser Asn  Leu His Phe Phe Phe  Phe Cys Phe Val Phe  Glu Thr Trp
    2375                2380                2385
```

Ser Tyr Ser Ile Thr Gln Ala Gly Gly Gln Trp His Asn His Ser
2390 2395 2400

Phe Leu Pro Gln Thr Pro Lys Leu Lys Pro Ser Ser His Arg Ser
2405 2410 2415

Leu Pro Ser Ser Asp Phe Thr Arg Met Pro Pro Cys Leu Ala Asn
2420 2425 2430

Ser Leu Thr Leu Ile Ile Phe Arg Asp Arg Ile Leu Leu Cys Trp
2435 2440 2445

Pro Gly Trp Ser Gln Met Pro Gly Leu Lys Ser Ser Ser Leu Cys
2450 2455 2460

Leu Pro Lys Cys Trp Asp Arg His Glu Pro Pro His Leu Ala Ser
2465 2470 2475

Phe Ala Phe Ser Met His Leu Leu Ser Met His Asp Phe Val Thr
2480 2485 2490

Leu Cys Phe Gly His Leu Lys Ser Ile Gly Ser Leu Ser Tyr Ala
2495 2500 2505

Asn Leu Leu Lys Cys Trp His Ile Leu Phe Tyr Asn Ile Lys Leu
2510 2515 2520

Thr Phe Leu Asn Ile Thr Thr Asp Ser Ile Arg Arg Val Phe Asn
2525 2530 2535

Tyr Glu Ala Val Lys Leu Ser Thr Thr Cys Lys Ile Thr Thr Ile
2540 2545 2550

Leu Ser Phe Ala Lys Leu Phe Phe Leu Phe Phe Phe Leu Phe Phe
2555 2560 2565

Phe Phe Leu Thr Arg Ser Cys Ser Val Ala Trp Ala Gly Val Gln
2570 2575 2580

Trp Tyr Asn His Gly Ser Leu Gln Pro Trp Pro Pro Arg Leu Lys
2585 2590 2595

Cys Ser Phe His Leu Ser Trp Cys Met Pro Pro Cys Leu Ala Asn
2600 2605 2610

Phe Phe Phe Leu Phe Gly Glu Thr Ala Gln Ala Gly Leu Lys Leu
2615 2620 2625

Leu Ser Ser Ser Ala Pro Pro Ala Ser Ala Ser Leu Ser Ala Gly
2630 2635 2640

Ile Ile Gly Met Ser His Cys Gln Lys Leu Lys Phe Tyr His Trp
2645 2650 2655

Asn Lys Tyr Cys Lys Leu Leu Leu Ser Asn Asn Phe Thr Leu Leu
2660 2665 2670

Met Phe Leu Lys Leu Gln Asn Thr Lys Val Thr Thr Ser Leu Ser
2675 2680 2685

Val Ile Leu Ser Asn Lys Lys Asp Ile Thr Ile Lys Gly Leu Ile
2690 2695 2700

Gln Leu Thr Thr Ile Met Ile Thr Leu Met Phe Ser Leu Lys Thr
2705 2710 2715

Thr Thr Val Leu His Ile Ala Glu Val Leu Tyr Lys Tyr Phe Leu
2720 2725 2730

Leu Pro Ile Ser Cys His Arg Ile Phe Lys Arg Cys Ser Gly Ser
2735 2740 2745

Lys Phe Asn Lys Leu Ile Ile Phe Ile Leu Ser Arg Thr Ser Trp
2750 2755 2760

Leu Gly Met Val Ala His Thr Cys Asn Pro Ser Thr Leu Glu Gly
2765 2770 2775

Gln Gly Arg Trp Ile Thr Gly Gln Glu Phe Glu Thr Ser Leu Ala
2780 2785 2790

Asn Met Val Lys Leu Leu Lys Ile Gln Lys Leu Ala Arg Arg Gly
2795 2800 2805

Gly Arg His Leu Ser Leu Leu Gly Lys Leu Arg Gln Glu Asn Arg
2810 2815 2820

Leu Asn Pro Gly Gly Arg Gly Cys Ser Glu Pro Arg Ser Leu His
2825 2830 2835

Ser Ser Leu Gly Asp Ile Pro Leu Gln Val Gln Gly Ser Glu Glu
2840 2845 2850

Cys Asn Ala His Trp Tyr Ser Leu Val Leu Leu Pro Phe Leu Ser
2855 2860 2865

Arg Cys Lys Glu Phe Pro Thr Ile Arg Arg Asn Val Asn Val Met
2870 2875 2880

Val Lys Lys Gly Lys Gly Leu Ile Ser Pro Thr Ser Phe Trp Ser
2885 2890 2895

Tyr Gly Tyr Pro Glu Asn Tyr Leu Gly Tyr Ala Gln Gly Ser Met
2900 2905 2910

Asp Tyr Thr Ser Lys Thr Ser Ala Met Pro Phe Pro Lys Ala Ile
2915 2920 2925

His Leu Leu Ser Ser Arg Thr Ser Thr Asn Trp Val Thr Leu Thr
2930 2935 2940

Pro Ser Leu Met Val Ser Leu Leu Tyr His Ser Met Gln Asn Glu
2945 2950 2955

Tyr Arg Tyr Glu Val Glu Leu Thr Leu Arg Ala Gly His Gly Gly
2960 2965 2970

Leu Pro Leu Ser Gln His Phe Arg Arg Pro Arg Trp Ala Asp His
2975 2980 2985

Glu Val Arg Arg Ser Arg Pro Ser Trp Pro Ile Trp Asn Pro Ile
2990 2995 3000

Ser Thr Lys Asn Lys Lys Leu Ala Arg Cys Gly Gly His Thr Cys
3005 3010 3015

Ser Pro Ser Tyr Ser Glu Gly Gly Arg Arg Ile Ala Thr Arg Glu
3020 3025 3030

Ala Glu Val Ala Val Ser Gln Asp His Ala Thr Ala Leu Gln Pro
3035 3040 3045

Gly Asp Arg Ala Arg Leu Cys Leu Lys Lys Gln Asn Lys Thr Lys
3050 3055 3060

Gln Asn Ser Ser His Asn Gln Ile Ile Lys Phe Leu Pro Ala Ala
3065 3070 3075

Tyr Leu Glu Met Gln Leu Val Phe Ile Ser Gln Val Ser Leu Ala
3080 3085 3090

His Leu Val Gln Ile Ile Lys Thr Ala Thr Asp Leu Ile Lys Thr
3095 3100 3105

Met Lys Lys Trp Glu Leu Ala Gln Ser Lys Glu Met Arg Leu Thr
3110 3115 3120

Ser Ile Pro Thr Glu Asn Asn Ile Thr Pro Ile Thr Leu Cys Leu
3125 3130 3135

Val Glu Glu Leu Cys Ala Leu Tyr His Ser Leu Lys Thr Arg Trp
3140 3145 3150

Asn Leu Arg Gly Ile Ser Ile Ile Ser Ser His Ser Gly Thr Cys
3155 3160 3165

Leu Gln Asn Leu Gly Arg Val Glu Gln Ile Trp Glu Lys Gln Leu

```
    3170                3175                3180

Ile Pro  Pro Lys Thr Leu Asn  Ser Ser Ser Tyr Leu  Ser Cys Leu
    3185                3190                3195

Pro Val  His Ser His Ala Cys  Ser His Ser His Ile  Val Leu Phe
    3200                3205                3210

Leu Tyr  Ser Thr Leu Trp Thr  Ile Arg Asn Arg Phe  Ile Ser Ser
    3215                3220                3225

Phe Val  Ser Tyr Ser Lys Ser  Ala Thr Lys Val Pro  His Lys Pro
    3230                3235                3240

Ser Pro  Pro Phe Phe Phe Phe  Asp Ser Leu Ala Leu  Leu Pro Arg
    3245                3250                3255

Arg Asp  Tyr Ser Gly Val Ile  Val Ala His Gln Ser  Arg Asn Leu
    3260                3265                3270

Ser Gly  Ser Ser Asn Pro Pro  Thr Ser Ala Ser Gln  Val Ala Gly
    3275                3280                3285

Thr Thr  Asp Val Tyr His His  Ile Pro Leu Ile Ile  Phe Tyr Phe
    3290                3295                3300

Leu Arg  Gln Gly Leu Arg Met  Leu Ser Arg Leu Val  Leu Asn Ser
    3305                3310                3315

Trp Ala  Gln Ala Ile Leu Leu  Cys Trp Pro Leu Lys  Val Leu Gly
    3320                3325                3330

Leu Ala  Val Thr Met Pro Arg  Ala Leu Phe Gln Ser  Ser Phe Gln
    3335                3340                3345

Phe Leu  Asn Phe Pro Phe Cys  Leu Asp Pro Phe Gly  Leu Leu Phe
    3350                3355                3360

Val Gly  Gly Phe Val Leu Glu  Ala Gln Val Trp Pro  Leu Pro Ile
    3365                3370                3375

Leu Arg  Ala Leu Leu Pro Val  Ser Pro Pro Pro Cys  Cys Gly Pro
    3380                3385                3390

Gly Ser  Ser Phe Pro Ser Leu  Leu Ile Glu Pro Phe  Leu Tyr Ser
    3395                3400                3405

Arg Gln  Tyr Ala Leu Val Cys  His Leu Ile Pro Arg  Thr Thr Leu
    3410                3415                3420

Ser Gly  Tyr His Gln Gln Ser  Pro Ser Cys Asn Gly  Ile Gln Leu
    3425                3430                3435

Gly Met  Val Pro His Ala Cys  Asn Pro Ser Thr Leu  Gly Gly Arg
    3440                3445                3450

Gly Gly  Gln Ile Thr Gly Gln  Glu Phe Glu Thr Ser  Leu Ala Asn
    3455                3460                3465

Met Val  Lys Pro Arg Leu Tyr  Lys Tyr Lys Asn Leu  Gly Val Val
    3470                3475                3480

Leu His  Thr Cys Asn Pro Ser  Tyr Ser Arg Gly Gly  Arg Arg Ile
    3485                3490                3495

Thr Thr  Trp Glu Val Glu Val  Ala Val Ser Arg Glu  His Ala Ile
    3500                3505                3510

Ala Leu  Gln Pro Gly Gln Ser  Glu Thr Gln Ser Leu  Lys Lys Asn
    3515                3520                3525

Lys Asn  Lys Lys Lys Phe Lys  Glu Phe Phe Glu Cys  Ser Arg Thr
    3530                3535                3540

Ser Arg  Arg Gln Asn Pro Leu  Asp Thr Glu Leu Lys  Lys Glu Gly
    3545                3550                3555

Leu Tyr  Leu Ala Gly Ser Ile  Gly Lys Thr His Val  Ser Lys Thr
    3560                3565                3570
```

-continued

```
Glu Leu Pro Glu Ala Ile Pro Val Pro Leu Lys Gly Gln Leu Gly
    3575                3580                3585

Gly Pro Arg Glu Arg Val Leu Ile Asp Ala Ser Lys Gly Tyr Val
    3590                3595                3600

Thr Gly Gly Cys Met His Trp Leu Glu Gln Asn Arg Thr Gly Gln
    3605                3610                3615

Gly Phe Ser Gln Cys Phe Ser Thr Gln Leu Phe Arg Asp Asn Ile
    3620                3625                3630

Thr Asp Val Arg Gly Arg Ser Leu Thr Thr Arg Pro Arg Val Trp
    3635                3640                3645

Arg Arg Ala Val Cys Leu Trp Ile Ser Phe Leu Ser Leu Ser Phe
    3650                3655                3660

Tyr Phe Phe Phe Leu Trp Arg Gln Lys Leu Gly Ile Arg Gln Tyr
    3665                3670                3675

Glu Gly Trp Ser Pro Pro Leu Gly Phe Trp Ile Ile Val Gln Ser
    3680                3685                3690

Cys Val Tyr Ile Thr Ser Thr Asn Ile Asn Ser Ser Leu Ile Leu
    3695                3700                3705

Lys Val Ser Ser Cys Leu Phe Phe Phe Asp Gly Val Ser Leu Cys
    3710                3715                3720

His Pro Gly Cys Ser Thr Val Val Gln Ser Gln Leu Thr Ala Thr
    3725                3730                3735

Ser Ala Ser Trp Val Gln Gly Ile Leu Leu Pro Gln Pro Pro Glu
    3740                3745                3750

Val Gly Leu Gln Thr Cys Ala Thr Thr Pro Gly Phe Leu Tyr Phe
    3755                3760                3765

Tyr Lys Ile Gln Lys Leu Phe Tyr Phe Val Gln Leu Leu Ala Arg
    3770                3775                3780

Leu Val Ser Asn Ser Pro Gln Val Ile Ser Leu Pro Trp Pro Pro
    3785                3790                3795

Lys Val Leu Gly Leu Gln Ala Ala Thr Gln Pro Ser His Ala Phe
    3800                3805                3810

Leu Gln Ser His Met Phe Leu Lys Met Val Gln Leu Tyr Ile His
    3815                3820                3825

Ile His Thr His Ile Tyr Thr Tyr Ile His Thr Tyr Ile Arg Ile
    3830                3835                3840

Tyr Thr His Ile Tyr Thr His Ile Tyr Ile Tyr Thr His Ile Tyr
    3845                3850                3855

Thr His Ile Tyr Thr His Ile Tyr Thr His Ile Tyr Thr Tyr Ile
    3860                3865                3870

Tyr Ile Tyr Thr His Ile Tyr Thr Tyr Ile His Ile Tyr Ile His
    3875                3880                3885

Ile Tyr Thr Tyr Ile His Ile Tyr Thr His Ile Tyr Ile Tyr Thr
    3890                3895                3900

His Ile Tyr Thr Tyr Ile His Ile Tyr Ile His Ile Tyr Thr His
    3905                3910                3915

Ile Tyr Ile Tyr Phe Phe Leu Phe Asp Gly Val Ser His Cys His
    3920                3925                3930

Leu Gly Trp Ser Ala Val Ala Gln Ser Leu Leu Thr Ala Thr Ser
    3935                3940                3945

Ala Ser Gln Val Gln Val Ile Leu Leu Pro Gln Pro Pro Lys Leu
    3950                3955                3960
```

-continued

```
Gly Leu  Gln Ala Pro Ala Ser  Met Pro Gly Phe Cys  Ile Phe Gly
    3965                 3970                 3975

Arg Asp  Arg Val Ser Leu His  Trp Pro Gly Trp Ser  Gln Thr Pro
    3980                 3985                 3990

Asp Leu  Val Ile His Leu Pro  Gln Pro Pro Lys Val  Leu Gly Leu
    3995                 4000                 4005

Gln Thr  Ala Thr Val Pro Ser  Ile Tyr Thr Ile Phe  Pro Glu Cys
    4010                 4015                 4020

Phe Asp  Ala Leu Gly Glu Lys  Arg Cys Ile Glu His  Leu Phe Met
    4025                 4030                 4035

Ala Ile  Ile Phe Cys Asn Ile  Ile Leu Met Ala Val  Phe Tyr Gln
    4040                 4045                 4050

Met Asn  Ala Leu Phe Ile Pro  Met Ser Tyr Cys Phe  Val His Thr
    4055                 4060                 4065

Thr Met  Ser Cys Phe Leu Phe  Leu Glu Leu Phe Ser  Tyr Phe Tyr
    4070                 4075                 4080

Tyr Ser  Ile Val Val Cys Phe  Phe Leu Ile Phe His  Ile Phe Leu
    4085                 4090                 4095

Ile Leu  Leu Cys Leu Phe Cys  Leu Cys Val Leu Phe  Phe Phe Phe
    4100                 4105                 4110

Phe Phe  Phe Glu Thr Glu Ser  His Ser Val Ala Gln  Ala Gly Val
    4115                 4120                 4125

Trp His  Asn Leu Ser Ser Leu  Gln Pro Leu Pro Pro  Met Phe Lys
    4130                 4135                 4140

Pro Phe  Ser Tyr Leu Ser Leu  Ser Arg Ser Trp Asn  Gln Ala Pro
    4145                 4150                 4155

Ala Thr  Met Pro Gly Phe Leu  Ile Glu Thr Gly Phe  His His Val
    4160                 4165                 4170

Gly Ala  Gly Leu Glu Leu Leu  Thr Ser Asp Asp Pro  Pro Thr Ser
    4175                 4180                 4185

Ala Ser  Lys Val Leu Gly Ser  Gln Ala Ala Thr Thr  Pro Gly Leu
    4190                 4195                 4200

Cys Val  Leu Phe Leu Pro Ser  Gln Asp Ser Val Leu  Glu Ser Ser
    4205                 4210                 4215

Phe Phe  Phe Phe Thr Phe Glu  Thr Gly Ser Cys Ser  Cys Tyr Val
    4220                 4225                 4230

Ala Gln  Val Gly Val Gln Trp  His Tyr Leu Ser Ser  Leu Gln Pro
    4235                 4240                 4245

Arg Pro  Pro Gln Ala Gln Val  Ile Pro Pro Pro Gln  Pro Pro Lys
    4250                 4255                 4260

Leu Glu  Leu Gln Val Cys Val  Thr Thr Pro Gly Phe  Leu Gln Phe
    4265                 4270                 4275

Leu Ser  Arg Gly Leu Thr Met  Leu Pro Arg Leu Val  Ser Asn Ser
    4280                 4285                 4290

Trp Ala  Gln Ala Ile Leu Leu  Pro Trp Ser Pro Lys  Met Leu Gly
    4295                 4300                 4305

Leu Gln  Ala Ala Thr Val Pro  Cys Pro Asn Leu Leu  Ile Leu Phe
    4310                 4315                 4320

Leu Phe  Arg Ser Ser Ile Ser  Leu Pro Ile His Tyr  Lys Pro Phe
    4325                 4330                 4335

Gly Ser  His Leu Tyr Phe Ser  Ser Arg His Gln Ile  Leu Ile Pro
    4340                 4345                 4350

Asn Cys  Leu Leu Gly Ile Thr  Ser Thr Gly Met Tyr  Phe Leu Gln
```

-continued

```
    4355                4360                4365

Phe Lys  Cys His Met Ser Lys  Thr Glu Leu Leu Phe  Pro Leu Gln
    4370                4375                4380

Asn Pro  Ser Ala Ser Leu Phe  Leu Ser Pro Phe Cys  Tyr Leu Phe
    4385                4390                4395

Gln Val  Gly Glu Val Val Ser  Phe Gln Pro Leu Arg  Leu Glu Thr
    4400                4405                4410

Ser Lys  Ser Ser Ser Asp Cys  Cys Pro His Ser Ser  His Thr Ser
    4415                4420                4425

Ser Gln  Ser Ala Ile Asp Ser  Pro Pro Lys Cys Leu  Ser Ala Cys
    4430                4435                4440

Ala Leu  Pro Phe His Ser His  Arg Asp Tyr Pro Ser  Phe Gly Pro
    4445                4450                4455

Met Thr  Leu His Gln Ser Gly  Asn Asn Ser Phe Pro  Thr Ser Pro
    4460                4465                4470

Ser Pro  His Pro Pro Ala Thr  Leu Leu Cys Cys His  Glu Ser Leu
    4475                4480                4485

Cys Glu  Thr Glu Arg Leu Phe  Ser Ser Pro Ala Lys  Tyr Leu Met
    4490                4495                4500

Thr Ser  Tyr His Leu Gln Lys  Gln Val Thr Phe His  Cys Leu Leu
    4505                4510                4515

Pro Leu  Ser His His Thr Pro  Pro Ser Cys Ala Gly  Cys Val Ser
    4520                4525                4530

Leu Glu  Arg Ser Thr Leu Cys  Cys Ser Cys Ala Phe  Thr His Val
    4535                4540                4545

Leu Pro  Ser Asp Cys Pro Ile  Phe Ser Val Phe Cys  Leu Leu Ala
    4550                4555                4560

Leu Trp  Leu Phe His Lys Arg  Arg Phe Cys Thr Ile  Ala Asp Arg
    4565                4570                4575

Asn Lys  Asn Glu Leu Cys Leu  Leu Gly Arg Pro Gly  Gln Gly Leu
    4580                4585                4590

His His  Leu Lys Gly Ser Tyr  Gly Leu Arg Ala His  Lys Glu Ser
    4595                4600                4605

Arg Val  Met Arg Glu Gly Leu  Ala Val Glu Thr Ala  Lys Ala Pro
    4610                4615                4620

His Leu  Ser Ser Gln Gln Gly  Ser Asp Gly Thr Ser  Ala Gly Arg
    4625                4630                4635

Glu Arg  Asp Leu His Pro Ser  Gly Lys Leu Ser Glu  Phe Trp Ser
    4640                4645                4650

Thr Val  Arg Gly Arg Thr Glu  Trp His Val Arg Ile  Phe Pro Ile
    4655                4660                4665

Pro Gly  Gly Arg Leu Arg Glu  Ser Arg Ala Pro Arg  Pro Thr Pro
    4670                4675                4680

Arg Glu  Lys Lys Lys Lys Glu  Lys Arg Leu Pro Pro  Thr Cys Asp
    4685                4690                4695

Ser Gln  Glu Gln Glu Ala Gly  Arg Thr Ala Pro Pro  Asp Trp Ser
    4700                4705                4710

Arg Gln  Asn Gln Thr Ser Leu  Gly Ala Ala Asp Trp  Leu Arg Arg
    4715                4720                4725

Gly Gln  Ala Leu Val Gly Cys  Cys Arg Cys Lys Leu  Leu Lys Ala
    4730                4735                4740

Arg Val  Cys Asp Arg Gln Pro  Arg Arg Glu Trp Val  Glu Arg Glu
    4745                4750                4755
```

-continued

```
Ala Leu Pro Leu His Ser Cys Gln Leu Pro Ala Arg Pro Gly Gln
    4760                4765                4770

Ala Gly Pro Leu Ala Glu Gly Thr Gly Gln Asp Glu Ala Met Gly
    4775                4780                4785

Val Phe Gly Asp Leu Lys Leu Gly Lys Leu Asn Thr His Pro Gln
    4790                4795                4800

Gly Ala Arg Ala Gly Thr Phe His Thr Glu Pro Leu Pro Ile Cys
    4805                4810                4815

Asp Cys Lys Val Cys Asp Val Leu Gly Glu Asp Arg Gly Val Gly
    4820                4825                4830

Gly Arg Glu Gly Ser Phe Thr Glu Ser Arg Trp Leu Trp Val Tyr
    4835                4840                4845

Leu Ser Asp His Arg Glu Val Ala Ala Cys Pro Leu Leu Leu Leu
    4850                4855                4860

Val Thr Val Phe Tyr Leu Arg Lys Arg Glu Trp Arg Leu Gly Ser
    4865                4870                4875

Phe Tyr Arg Cys Asn Phe Ser His Pro Leu Leu Gln Gly Lys Glu
    4880                4885                4890

Lys Ser Val Gly Asn Trp Leu Cys Lys Lys Glu Arg Gly Lys Gly
    4895                4900                4905

Gln Met Gly Thr Arg Glu Glu Gly Asp Ser His Thr Leu Leu Glu
    4910                4915                4920

Lys Ile Ser Gly Ala Ala Thr Gly Glu Thr Val Trp Cys His Lys
    4925                4930                4935

Arg Leu Asn Ile Lys Leu Ala Ser Gly Pro Ala Thr Pro Leu Leu
    4940                4945                4950

Asp Ile Asn Pro Asn Lys Leu Thr Gly Thr His Ile Cys Thr Gln
    4955                4960                4965

Met Phe Met Ala Val Leu Phe Thr Ile Thr Lys Arg Trp Lys Gln
    4970                4975                4980

Leu Gln Cys Ser Ser Ile Asp Lys Ser Val Asn Gln Leu Trp Cys
    4985                4990                4995

Ile His Thr Met Glu Tyr Glu Val Ile Asn Arg Asn Glu Val Leu
    5000                5005                5010

Ile Tyr Ala Pro Met Gly Met Asn Ile Glu Arg Leu Cys Gln Glu
    5015                5020                5025

Lys Glu Ala Arg His Arg Arg Ser Tyr Ile Val Arg Phe His Val
    5030                5035                5040

Glu Ile Ser Ser Gly Lys Ser Thr Glu Thr Glu Ser Arg Leu Met
    5045                5050                5055

Val Thr Arg Gly Arg Val Trp Val Gly Arg Trp Gly Ile Thr Val
    5060                5065                5070

Glu Trp Val Gln Val Phe Phe Trp Gly Glu Asn Val Leu Glu Gln
    5075                5080                5085

Lys Val Val Phe Ala Gln Cys Tyr Glu Cys Thr Lys Cys His Arg
    5090                5095                5100

Thr Gly Gln Phe Lys Met Val Ser Ser Ala Trp His Gly Gly Ser
    5105                5110                5115

His Leu Ser Gln His Phe Glu Arg Val Gly Arg Ala Asp His Leu
    5120                5125                5130

Arg Ser Gly Val Asp Pro Gly Gln Arg Gly Glu Thr Pro Ser Leu
    5135                5140                5145
```

```
Leu Lys Lys Lys Lys Lys Arg Lys Lys Glu Arg Lys Lys Lys Met
    5150                5155                5160

Gly Met Val Ala Gly Ala Cys Asn Pro Ser Tyr Ser Gly Gly Ser
    5165                5170                5175

Arg Arg Ile Val Thr Arg Glu Ala Lys Val Ala Val Ile Arg Asp
    5180                5185                5190

His Pro Ile Ala Leu Gln Pro Gly Arg Gln Glu Gln Asn Ser Val
    5195                5200                5205

Ser Lys Ile Asn Lys Ile Lys Trp Leu Val Pro Gly Thr Val Ala
    5210                5215                5220

His Thr Cys His Pro Ser Thr Leu Gly Gly Gln Gly Arg Arg Ile
    5225                5230                5235

Thr Ala Gln Glu Phe Glu Thr Ser Leu Gly Asn Ile Val Arg Pro
    5240                5245                5250

Leu Ser Gln Ile Lys Trp Leu Val Leu Tyr Cys Val Asn Cys Leu
    5255                5260                5265

Ser Ile Lys Met Tyr Leu Ser Leu Ser Leu Ser Leu Ser Leu Ser
    5270                5275                5280

Arg Lys Gln Thr Asp Arg Leu Lys Gly Glu Ser Phe Leu Leu Ser
    5285                5290                5295

Ile Ile Leu Glu Arg Asn Lys Lys Gln Gln Phe Val Leu Cys Cys
    5300                5305                5310

Leu Ser Leu Pro Leu Ser Ser Leu Phe Phe Glu Val Trp His Gly
    5315                5320                5325

Pro Gly Tyr Leu Leu Pro Met Glu Asn Gly Gln Glu Gly Glu Gly
    5330                5335                5340

Pro Phe Arg Pro Ser Glu Lys Val Leu Ala Trp Ala Gln Asn His
    5345                5350                5355

Cys Glu Ser Ala Arg His Thr His Thr Glu Pro Leu Ala Leu Cys
    5360                5365                5370

Gly Gln Gly Val Ala Gly Trp Ala Gly Pro Arg Gly Gly Arg Ala
    5375                5380                5385

Gly Pro Gly Pro Glu Ser Gly Lys Ala Ser Ala Ser Ser Asn Pro
    5390                5395                5400

Ser Met Glu Ser Gln Leu Leu Gly Ala Cys Asn Gly Leu Trp His
    5405                5410                5415

Leu Phe Gln Ser Gln Cys Thr Arg Ile Ser Ala Leu Pro Ala Ala
    5420                5425                5430

Arg Lys Val Asn Tyr Arg Ser Gln Asn Met Thr Pro Thr Pro Cys
    5435                5440                5445

Asp Ile Ser His Ser Leu Gln Gln Asn Leu Glu Gln Asp Met Ser
    5450                5455                5460

Ser Phe Cys His Phe Gln Cys Leu Phe Arg Gly Arg Glu Thr Phe
    5465                5470                5475

Leu Lys Glu Glu Asp Ala Phe Glu Glu Leu Thr Ile Leu Glu Gly
    5480                5485                5490

Glu Val Phe Arg Lys Ser Arg Gln Glu Met Leu Gly Thr Tyr Leu
    5495                5500                5505

Trp Phe Glu Arg Lys Ala Asn Pro Gly Val Thr Glu Cys Asp Gly
    5510                5515                5520

Ser Gly Gly Gly Val Ser Trp Val Leu Pro Glu Gln Trp Met His
    5525                5530                5535

Leu Leu Phe Val Gln Asn Leu Ser Ser Leu Pro Leu Pro Pro Arg
```

```
    5540                5545                5550

Glu Glu  Gly His Ile Thr Arg  Leu Cys Leu Val Leu  Asn Ile Ala
    5555                5560                5565

Arg His  Thr Val Gly His Met  Thr Asp Tyr Asp Ile  Ser Ser Leu
    5570                5575                5580

Ser Ser  Ala Pro His Pro Val  Glu Pro Val Val Lys  Thr Ile Gly
    5585                5590                5595

Leu Glu  Pro Asp His Ser Asn  Ile Thr His Phe Leu  Thr Ala Phe
    5600                5605                5610

Ser Pro  Ser Glu Leu Ser Tyr  Leu Ile Ser Lys Ile  Gln Val Thr
    5615                5620                5625

Ile Thr  Pro Ala Ser Asp Val  Val Arg His Thr Ala  Lys His Ser
    5630                5635                5640

Val Gln  Cys Pro Ala Leu Val  Asn Ile Val Ile Val  Ile Met Ile
    5645                5650                5655

Val Ser  Thr Ser Leu Met Asp  Ser Glu Leu Phe Pro  Thr Gln Lys
    5660                5665                5670

Glu Val  Arg Ser Val Phe Met  Gln Leu Pro Lys Pro  Leu Leu Asn
    5675                5680                5685

Val Glu  His Gly Ile Ser Ile  Phe Pro Ser Asn Leu  Val Gln Pro
    5690                5695                5700

Asn Cys  His Ile Ile Leu Gln  Phe Ile Ala Ala Cys  Leu Phe Ser
    5705                5710                5715

Cys Gly  Ser Leu Ser Leu Ser  Leu Arg Leu Glu Thr  Thr Ser Leu
    5720                5725                5730

His Asn  Glu Asn Met Asp Trp  Val Trp Cys Leu Met  Pro Val Ile
    5735                5740                5745

Pro Ala  Leu Trp Glu Ala Glu  Val Gly Arg Ser Leu  Asp Val Arg
    5750                5755                5760

Ser Ser  Arg Pro Pro Trp Pro  Thr Trp Asn Pro Ile  Ser Thr Lys
    5765                5770                5775

Asn Thr  Lys Ile Ser Gln Ala  Trp Gln Met Pro Ile  Ile Ser Ala
    5780                5785                5790

Thr Trp  Glu Ala Glu Ala Gly  Asp Ser Leu Glu Pro  Gly Arg Gln
    5795                5800                5805

Arg Leu  Gln Ala Glu Asn Val  Pro Leu His Ser Ser  Leu Asp Asn
    5810                5815                5820

Arg Val  Arg Leu Tyr Leu Lys  Lys Lys Lys Lys Glu  Arg Glu Arg
    5825                5830                5835

Glu Tyr  Gly Ala Leu Pro Leu  Ile Lys Lys Phe Ile  Phe Ile Ser
    5840                5845                5850

Thr Tyr  Ile Trp Val Cys Val  Ser Ala Thr Thr Ser  Gly Lys Thr
    5855                5860                5865

Leu Arg  Gly Phe Phe Lys Ile  Phe Phe Ile Lys Ile  Phe Ile Tyr
    5870                5875                5880

His Lys  Ile Thr Leu Leu Val  Tyr Asp Ala Asp Ile  Phe Ser Ile
    5885                5890                5895

Phe Thr  Glu Thr Cys Asn Pro  Tyr Gln Asn Leu Pro  Lys Glu His
    5900                5905                5910

Phe His  His Ser Pro Gln Asn  Pro Cys Thr Leu Ala  Thr Leu Pro
    5915                5920                5925

Pro Val  Ser Ser Asn His Arg  Ser Thr Phe Cys Leu  Met Ser His
    5930                5935                5940
```

-continued

```
Ser Gly  His Phe Ile Ile Asn  Glu Ile Ile Arg Tyr  Ile Val Phe
    5945                 5950                 5955

Cys Val  Leu Leu Cys Leu Leu
    5960                 5965
```

*OLMALINC* AS A DIAGNOSTIC AND THERAPEUTIC TARGET FOR NAFLD, NASH, METABOLIC SYNDROME, AND HEPATIC FIBROSIS

This application claims benefit of U.S. provisional patent application No. 62/569,397, filed Oct. 6, 2017, the entire contents of which are incorporated by reference into this application.

ACKNOWLEDGEMENT OF GOVERNMENT SUPPORT

This invention was made with Government support under DK007180, HL028481, and HL127921, awarded by the National Institutes of Health. The Government has certain rights in the invention.

This work was supported by the U.S. Department of Veterans Affairs, and the Federal Government has certain rights in the invention.

REFERENCE TO A SEQUENCE LISTING SUBMITTED VIA EFS-WEB

The content of the ASCII text file of the sequence listing named "UCLA258WOU1_seq" which is 344 kb in size was created on Oct. 5, 2018, and electronically submitted via EFS-Web herewith the application is incorporated herein by reference in its entirety.

BACKGROUND OF THE INVENTION

The metabolic syndrome (MetS) as defined by the clustering of phenotypic, biochemical and clinical factors including dyslipidemia, hyperglycemia, hypertension and central obesity, has reached epidemic proportions in the United States and is one of the major disease states with increasing prevalence. Non-alcoholic fatty liver disease (NAFLD), the liver manifestation of MetS has also increased in parallel to other determinants of the MetS. NAFLD ranges from simple steatosis to inflammatory non-alcoholic steatohepatitis (NASH), which can lead to fibrosis, cirrhosis, and hepatocellular carcinoma.

The pathophysiology of the MetS is complex, multi-factorial, and includes genetic and environmental contributions. Over the years, the use of systems biology to understand the genetic perturbations of NAFLD/NASH has opened new avenues for understanding their pathophysiology. This has included the study of non-coding long intergenic RNAs (lincRNAs), which have emerged as important regulators of biological and disease processes.

There remains a need for methods and materials for diagnosing and treating MetS and related disorders.

SUMMARY OF THE INVENTION

The molecules, compositions, and methods described herein address these needs and others. The invention provides molecules that can be used in the detection of a metabolic disorder, and in the treatment of related disorders.

In one embodiment, the invention provides an oligonucleotide that inhibits expression of an OLMALINC nucleic acid molecule. In a typical embodiment, the OLMALINC nucleic acid molecule is SEQ ID NO: 1. In one embodiment, the oligonucleotide is a small inhibitory RNA (siRNA) molecule, antisense oligonucleotide (ASO), or equivalent thereof, that specifically binds to and inactivates the nucleic acid molecule of SEQ ID NO: 1. In some embodiments, the siRNA is ACATGCATCC (SEQ ID NO: 2); ACTTACCCGA (SEQ ID NO: 3); or CTCCGTGAGGAGATCCACCTA (SEQ ID NO: 4). In one embodiment, the siRNA is CTCCGTGAGGAGATCCACCTA (SEQ ID NO: 4).

Also provided is a method of inhibiting the expression of OLMALINC in a subject. In one embodiment, the method comprises administering to the subject an effective amount of an oligonucleotide as described herein, or an antibody or equivalent thereof, that specifically binds to and inactivates an OLMALINC nucleic acid molecule or an expression product thereof. Inhibiting the expression of OLMALINC can be achieved by inactivating OLMALINC, such as by effecting the degradation of OLMALINC mRNA as described herein.

The invention also provides a method of assaying for OLMALINC in a tissue sample. In one embodiment, the method comprises contacting the tissue sample with reagents that bind the nucleic acid molecule of SEQ ID NO: 1, or with reagents that bind an expression product of the nucleic acid molecule of SEQ ID NO: 1, and detecting the amount of binding of the reagents. In one embodiment, the invention provides a method of detecting a disorder associated with obesity and/or type 2 diabetes in a tissue sample obtained from a subject. In one embodiment, the method comprises contacting the tissue sample with reagents that bind an OLMALINC nucleic acid molecule or expression product thereof, and detecting the amount of binding of the reagents. Representative examples of detection methods include, but are not limited to, polymerase chain reaction (PCR)-based methods and immunoassays. In some embodiments of these assaying and detection methods, the reagents, such as primers, probes, and antibodies or fragments thereof, are labeled with a detectable marker. In some embodiments, the tissue sample is a liver biopsy. In other embodiments, the tissue sample is peripheral blood, adipose tissue, blood, plasma, serum, saliva, urine, stool, bile, tissue, cell culture, other bodily fluids, or other tissue specimen.

The invention additionally provides a method of ameliorating symptoms associated with obesity and/or type 2 diabetes. In one embodiment, the method comprises administering to a subject in need thereof an effective amount of an oligonucleotide of the invention or an antibody or equivalent thereof that specifically binds to and inactivates an OLMALINC nucleic acid molecule or an expression product thereof. Representative examples of a disorder associated with obesity and/or type 2 diabetes include, but are not limited to, a disorder of appetite, glycemia, body weight, liver steatosis, NASH, NAFLD, or a lipid disorder.

The invention further provides a pharmaceutical composition comprising an OLMALINC nucleic acid molecule as described herein, or an antibody or fragment thereof that is directed against OLMALINC, formulated for delivery to a patient. The patient is typically a patient in need of ameliorating appetite, glycemia, body weight, obesity, liver steatosis, NASH, NAFLD, lipid disorder, and/or other symptoms associated with obesity disorders and type 2 diabetes. The pharmaceutical composition optionally further comprises a pharmaceutically acceptable carrier. In some embodiments of the methods described herein, such as the method of detecting a disorder associated with obesity and/or type 2 diabetes, the method further comprises administering to the subject an inhibitor or pharmaceutical composition of the invention.

BRIEF DESCRIPTION OF THE DRAWINGS

In FIG. 3C, LXRE/DR4 sequences of human FAS (SEQ ID NO: 7) and mouse SBREBP1c (SEQ ID NO: 8) are shown for comparison with that of OLMALINC (SEQ ID NO: 9).

FIGS. 10A-10Q: Predicted peptide sequence created using ExPAsy. Encoded peptides are indicated by shading.

DETAILED DESCRIPTION OF THE INVENTION

Figure 1A:
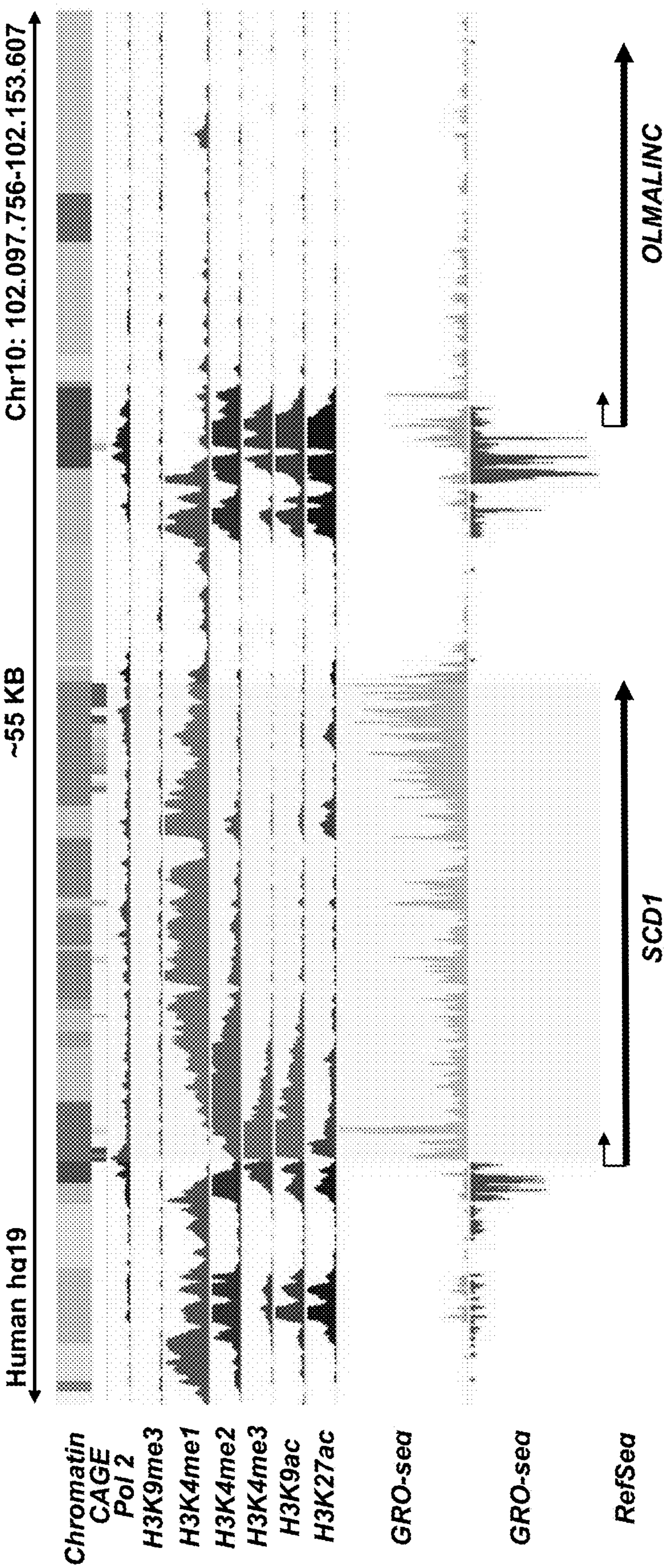
FIG. 1A: Methylation markers and transcription factors in OLMALINC exon 1 demonstrating the transcription start site. Using data from the ENCODE project and chromatin immunoprecipitation sequencing (ChIP-seq) from human HepG2 and hepatocytes, the RNA polymerase II binding, 5' CAGE, and active histone modification markers were identified, which demonstrate two active transcription start sites (TSS) in OLMALINC.

During the course of our research to discover novel RNA in patients with appetite/satiety regulation disorders, metabolic syndrome, glucose metabolism, insulin resistance, pre-diabetic syndrome, diabetes type 2 (T2D), chronic inflammation, obesity and liver steatosis, we discovered that the novel long non-coding RNA, OLMALINC, can be used to detect and treat disorders of body fat mass, fatty liver, type 2 diabetes, chronic inflammation, non-alcoholic steatohepatitis (NASH), and hepatic fibrosis. In certain embodiments, these lincRNAs can be used as a biomarker to detect NAFLD and NASH and related disorders. Using weighted gene co-expression analysis on the RNA-seq data of the subgroup of patients on statin therapy, we identified 75 genes that correlate unique molecular signals in this group of patients. Among those, the majority included well characterized genes in the cholesterol biosynthesis pathway and one new gene, OLMALINC, a novel lincRNA that has been described to play a role in glucose sensing in pancreatic islet cells.

We have demonstrated that OLMALINC is one of the 75 genes in a liver co-expression network module that is correlated significantly with total peripheral triglyceride levels. Further, silencing RNAs directed against OLMALINC can be used therapeutically to treat NAFLD and NASH and related disorders given the decrease in SREBP2 and its target gene by using anti-sense oligonucleotides. For pharmaceutical or radiopharmaceutical compositions of the invention, OLMALINC antagonists that target OLMALINC can be used therapeutically. The antagonists can be formulated together with ingredients that are selected from a group of agents consisting of excipients, binders, lubricants, sweeting agent, syrup and absorption delaying agent or carrier. This can include stabilized liposomes, micelles that are sterically stabilized or mixed forms of micelles.

Definitions

All scientific and technical terms used in this application have meanings commonly used in the art unless otherwise specified. As used in this application, the following words or phrases have the meanings specified.

The term "nucleic acid" or "polynucleotide" or "oligonucleotide" refers to a sequence of nucleotides, a deoxyribonucleotide or ribonucleotide polymer in either single- or double-stranded form, and unless otherwise limited, encompasses known analogs of natural nucleotides that hybridize to nucleic acids in a manner similar to naturally occurring nucleotides.

The term "primer," as used herein, means an oligonucleotide designed to flank a region of DNA to be amplified. In a primer pair, one primer is complementary to nucleotides present on the sense strand at one end of a polynucleotide fragment to be amplified and another primer is complementary to nucleotides present on the antisense strand at the other end of the polynucleotide fragment to be amplified. A primer can have at least about 11 nucleotides, and preferably, at least about 16 nucleotides and no more than about 35 nucleotides. Typically, a primer has at least about 80% sequence identity, preferably at least about 90% sequence identity with a target polynucleotide to which the primer hybridizes.

As used herein, the term "probe" refers to an oligonucleotide, naturally or synthetically produced, via recombinant methods or by PCR amplification, that hybridizes to at least part of another oligonucleotide of interest. A probe can be single-stranded or double-stranded.

As used herein, the term "active fragment" refers to a substantial portion of an oligonucleotide that is capable of performing the same function of specifically hybridizing to a target polynucleotide.

As used herein, "hybridizes," "hybridizing," and "hybridization" means that the oligonucleotide forms a noncovalent interaction with the target DNA molecule under standard conditions. Standard hybridizing conditions are those conditions that allow an oligonucleotide probe or primer to hybridize to a target DNA molecule. Such conditions are readily determined for an oligonucleotide probe or primer and the target DNA molecule using techniques well known to those skilled in the art. The nucleotide sequence of a target polynucleotide is generally a sequence complementary to the oligonucleotide primer or probe. The hybridizing oligonucleotide may contain nonhybridizing nucleotides that do not interfere with forming the noncovalent interaction. The nonhybridizing nucleotides of an oligonucleotide primer or probe may be located at an end of the hybridizing oligonucleotide or within the hybridizing oligonucleotide. Thus, an oligonucleotide probe or primer does not have to be complementary to all the nucleotides of the target sequence as long as there is hybridization under standard hybridization conditions.

The term "complement" and "complementary" as used herein, refers to the ability of two DNA molecules to base pair with each other, where an adenine on one DNA molecule will base pair to a guanine on a second DNA molecule and a cytosine on one DNA molecule will base pair to a thymine on a second DNA molecule. Two DNA molecules are complementary to each other when a nucleotide sequence in one DNA molecule can base pair with a nucleotide sequence in a second DNA molecule. For instance, the two DNA molecules 5'-ATGC and 5-GOAT are complementary, and the complement of the DNA molecule 5'-ATGC is 5'-GOAT. The term complement and complementary also encompasses two DNA molecules where one DNA molecule contains at least one nucleotide that will not base pair to at least one nucleotide present on a second DNA molecule. For instance, the third nucleotide of each of the two DNA molecules 5'-ATTGC and 5'-GCTAT will not base pair, but these two DNA molecules are complementary as defined herein. Typically, two DNA molecules are complementary if they hybridize under the standard conditions referred to above. Typically, two DNA molecules are complementary if they have at least about 80% sequence identity, preferably at least about 90% sequence identity.

The term "effective amount" or "therapeutically effective amount" or "prophylactically effective amount", or "diagnostically effective amount", refer to an amount of an active agent (e.g., OLMALINC antagonists) described herein that is effective to provide the desired/intended result and/or biological activity. Thus, for example, in various embodiments, an effective amount of a OLMALINC antagonist or silencing RNA molecule described herein ("inhibitors of OLMALINC") is an amount that is effective to downregulate appetite and/or to reduce obesity and/or to reduce body weight, and/or to inhibit adipogenesis and/or body fat accumulation, and/or reduce and/or regulate glucose homeostasis, and/or to improve or cure diabetes mellitus symptoms, and/or to reduce or cure inflammatory bowel diseases, and/or to reduce or cure chronic inflammatory diseases; and/or to ameliorate symptoms of and/or to treat systemic and organ-specific autoimmune diseases, and/or to reduce or cure dry eye syndrome, and/or to prevent or reduce organs, tissues and stem cells transplant rejection, and/or to improve embryo implant in uterus for in vitro fertilization, and/or to ameliorate one or more symptoms of osteoarthritis and/or rheumatoid arthritis, and/or psoriatic arthritis, and/or to prevent, or to reverse systemic hypertension, and/or to ameliorate one or more symptoms of atherosclerosis, and/or to slow the progression of, or to prevent, or to reverse non-alcoholic fatty liver disease (NAFLD), and/or NASH, and/or to ameliorate one or more symptoms of, and/or to slow, and/or to prevent, and/or to reverse hepatosteatosis (fatty liver including in pre-liver transplantation or donor liver organs, e.g., to remove fat content prior to transplant), and/or to ameliorate one or more symptoms of, and/or to slow the progression of, and/or to prevent; and/or to reverse metabolic syndrome, and/or to ameliorate one or more symptoms of, and/or to slow the progression of, and/or to prevent, and/or to reverse insulin resistance, and/or to ameliorate one or more symptoms of, and/or to slow the progression of, and/or to prevent, and/or to reverse prediabetic syndrome, and/or to slow the progression of, and/or to prevent, and/or to reverse renal hypertension and/or chronic kidney diseases, and/or to slow the progression of, and/or to inhibit, and/or to reverse growth of tumors expressing OLMALINC, and/or to slow the progression of, and/or to prevent; and/or to reverse mast cell and/or basophil degranulation and release of allergic mediators, and/or to ameliorate the symptoms of, and/or to treat cystic fibrosis, and/or to ameliorate the symptoms of, and/or to treat celiac disease, and/or to slow the progression of, and/or to prevent, and/or to reverse schizophrenic and paranoid disorders, and/or to slow the progression of, and/or to prevent; and/or to reverse Alzheimer's disease; and/or to slow the progression of, and/or to ameliorate the symptoms, and/or to reverse neuromuscular dystrophy, and/or to slow the progression of, and/or to prevent, and/or to reverse neurological paralysis, and/or to slow the progression of, and/or to ameliorate the symptoms of, and/or to nerve injury paralysis, and/or to slow the progression of, and/or to ameliorate the symptoms of, and/or to reverse traumatic brain injury, and/or to ameliorate the symptoms of, and/or to reverse post-traumatic stress disorder, and/or to ameliorate the symptoms of, and/or to reverse neuropathic disorders, and/or to ameliorate the symptoms of, and/or to reverse asthmatic syndrome; and/or ameliorating spermatogenesis and/or male infertility; and/or ameliorating female ovulation and/or female fertility; and/or to ameliorate the symptoms of, and/or to reverse chronic obstructive pulmonary disease, and/or to ameliorate the symptoms of, and/or to reverse lymphoproliferative disorders and/or myeloproliferative disorders, and/or to ameliorate the symptoms of, and/or to reverse thrombocytopenia, and/or to ameliorate the symptoms of, and/or to treat multiple myeloma, and/or to ameliorate the symptoms of, and/or to reverse acute or chronic nephropathies, and/or transient arterial stenosis and/or hemorrhagic shock, and/or antibiotic induced nephrotoxicity, and/or to ameliorate the symptoms of, and/or to treat polycystic kidney disease, and/or to ameliorate the symptoms of, and/or to reverse ocular hypertension, and/or glaucoma, and/or retinitis pigmentosa, and/or to ameliorate the symptoms of, and/or to prevent ischemic/reperfusion of tissue and/or organs (such as during liver transplantation), and/or to ameliorate the symptoms of, and/or to prevent chronic pulmonary fibrotic processes, and/or to ameliorate the symptoms of, and/or to reverse, and/or coupled to radionuclide or fluorescent tracers to localize, and/or to diagnose, and/or to treat cancer and metastases.

A "diagnostically effective amount" refers to an amount effective to localize and/or diagnose a disease state when the agent(s) described herein are could to a detectable label (e.g., a radiopaque label, an MRI label, an NMR label, a radionuclide, and a fluorescent tracer.

As used herein, the term "isolated" means that a naturally occurring DNA fragment, DNA molecule, coding sequence, or oligonucleotide is removed from its natural environment, or is a synthetic molecule or cloned product. Preferably, the DNA fragment, DNA molecule, coding sequence, or oligonucleotide is purified, i.e., essentially free from any other DNA fragment, DNA molecule, coding sequence, or oligonucleotide and associated cellular products or other impurities.

As used herein, "a" or "an" means at least one, unless clearly indicated otherwise.

As used herein, to "prevent" or "protect against" a condition or disease means to hinder, reduce or delay the onset or progression of the condition or disease.

OLMALINC Molecules

OLMALINC is a long non-coding RNA (lncRNA or lincRNA). Long non-coding RNAs can function as regulators of gene expression, for example, and carry out gene inhibition and gene activation through a variety of mechanisms. The development of silencing RNA molecules or inactivating CRISPR-Cas9 knockdown of this gene lead to amelioration of NAFLD. These molecules thus regulate the digestive process physiology. Preliminary evidence has shown that OLMALINC has a role in regulation of intracellular lipogenesis. However, the mechanism by which this molecule is involved in the regulation of appetite and body metabolism have not been investigated previously, nor has its potential use in therapeutic compounds in clinical practice been fully explored.

In various embodiments, novel OLMALINC silencing RNAs and ASOs are provided herein that are able to specifically bind to and inactivate OLMALINC. The target can be the entire sequence shown in SEQ ID NO: 1. In some embodiments, the target is one or more of exons 1-3 shown in SEQ ID NO: 1. In some embodiments, the target is intronic sequences of SEQ ID NO: 1. In some embodiments, the target is sequences involved in gene-gene interactions with SCD1 and/or Wnt7. OLMALINC is typically inactivated by degradation of the mRNA subsequent to binding of inhibitory molecules. As shown below, OLMALINC has three exons, and undergoes splicing. Examples of ways in which OLMALINC can be inactivated include, but are not limited to, inhibition via antisense oligonucleotides (ASOs), small inhibitory RNAs (siRNAs), and knockdown via genome editing tools.

The role of these OLMALINC molecules in the regulation of appetite, food intake, feeding behavior, body fat and lean mass composition, glycemia, and liver steatosis leads to new methods as described herein. It has been demonstrated that siRNAs reduce lipogenesis. In vivo these molecules may play a role in appetite suppression, lower glycemia, body weight and fat mass loss, improvement of obesity, liver steatosis, lipid disorder (e.g., elevated triglycerides), NASH and NAFLD, all of which are conditions that can occur commonly in patients with obesity disorders and in type 2 diabetes.

Accordingly, in various embodiments, the OLMALINC siRNAs or ASOs (antagonists) described herein (and/or pharmaceutical formulations thereof) are contemplated for use in one or more of the following:

i) downregulating appetite and/or reducing obesity; and/or ii) inhibiting adipogenesis and/or fat accumulation; and/or iii) ameliorating one or more symptoms of, or slowing the progression of, or preventing, or reversing type 2 diabetes; and/or iv) ameliorating one or more symptoms of atherosclerosis; and/or hypertension v) slowing the progression of, or preventing, or reversing non-alcoholic fatty liver disease (NAFLD); and/or vi) ameliorating one or more symptoms of, and/or slowing, and/or preventing, and/or reversing hepatosteatosis (fatty liver); and/or vii) ameliorating one or more symptoms of, and/or slowing the progression of, and/or preventing, and/or reversing metabolic syndrome; and/or viii) ameliorating one or more symptoms of, and/or slowing the progression of, and/or preventing, and/or reversing insulin resistance; and/or ix) ameliorating one or more symptoms of, and/or slowing the progression of, and/or preventing, and/or reversing prediabetic syndrome; and/or x) ameliorating hepatosteatosis; and/or xi) ameliorating, and/or preventing, and/or reversing NASH and/or NAFLD.

These molecules and compositions can also be used for:

i) downregulating appetite and/or reducing obesity; and/or ii) inhibiting adipogenesis and/or fat accumulation; and/or iii) ameliorating one or more symptoms of, or slowing the progression of, or preventing, or reversing type 2 diabetes; and/or iv) ameliorating one or more symptoms of atherosclerosis; and/or hypertension v) slowing the progression of, or preventing, or reversing non-alcoholic fatty liver disease (NAFLD); and/or vi) ameliorating one or more symptoms of, and/or slowing, and/or preventing, and/or reversing hepatosteatosis (fatty liver); and/or vii) ameliorating one or more symptoms of, and/or slowing the progression of, and/or preventing, and/or reversing metabolic syndrome; and/or viii) ameliorating one or more symptoms of, and/or slowing the progression of, and/or preventing, and/or reversing insulin resistance; and/or ix) ameliorating one or more symptoms of, and/or slowing the progression of, and/or preventing, and/or reversing prediabetic syndrome; and/or x) ameliorating hepatosteatosis; and/or xi) ameliorating, and/or preventing, and/or reversing NASH and/or NAFLD.

In certain embodiments, targeting sequences that bind the structure of OLMALINC and/or sequences that activate the transcription of the OLMALINC gene and/or fusion proteins comprising both sequences compromising at least 80%, or at least 85% or 90%, or at least 95% or 98% sequence identity with any of the sequences described herein are also contemplated. The terms "identical" or percent "identity," refer to two or more sequences that are the same or have a specified percentage of amino acid residues that are the same, when compared and aligned for maximum correspondence, as measured using one of the following sequence comparison algorithms or by visual inspection. With respect to the peptides of this invention sequence identity is determined over the full length of the peptide. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman (1981) *Adv. Appl. Math.* 2: 482, by the homology alignment algorithm of Needleman & Wunsch (1970) *J. Mol. Biol.* 48: 443, by the search for similarity method of Pearson & Lipman (1988) *Proc. Natl. Acad. Sci., USA,* 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

Sequences:

RefSeq OLMALINC (Exons are depicted in upper case while introns in lower case).

```
>hg19_refGene_NR_026762 range = chr10: 102131333-102148111 5'pad = 0 3'pad = 0
strand = + repeatMasking = none (SEQ ID NO: 1):
cttcaaaaaacagagaggaaagtggaagtgaaaggcagcagaggactcagaattgctgtttcttatttctttcttagagaattatg

gacagcaggaaggactcaccttttagtctgtcagtttgtttgcgagagagagagagagagagagagagagagatacatttta

attgagagacaattcacacaatataaaactaaccactttatttattgagataggggtctcactatattgcccaggctggtctcaaact

cctgggctcaagtgatcctcctcccttggcctcccaaagtgctgggatgacaggtgtgagccaccgtgcccggctaaactaacca

ttttattttatttatttattttgagacagagttttgctcttgtcgcccaggctggagtgcaatgggatgatctcggatcactgcaaccttcgc

ctcccgggttcaaacgattctcctgcttcagcctcctgagtagctgggattacaggcacctgccaccatgcccatcttttttttctttcttt

ctttcttttttttttttttttaggagagatggggtttcaccacgttggccaggctagtctcaaactcctgacctcaggtgatccgcccgccc

caccctctcaaagtgctgggattacaggtgtgagccaccgtgccaggccgaactaaccattttaaattgaccagttctgtggcactt

agtgcattcataacattgtgcaaacactaccttttgttctaaaacattttcaccccaaaagaaaacttgaacccattcaacagtgattc

cccatcttcccacccacactcggcccctggtgaccatcagtctgctttctgtctctgtggatttaccacttcaggatatttcctatacatg

gaatcgtacaatatatgaccttctgtgtctggcttccttctcttggcataatctttcaatgttcatccccattggagcatatatcagtacttc

attcctgtttattacctattcatattccattgtatgaatacaccacagttggtttactgatttatcaattgatgaacactggagttgcttccac

cttttggttattgtgaatagcactgccatgaacatttgagtgcaaatatgagtacccgtttataatttattagggtttatatctaggagtgg

agttgctgggccagatgctaatttgatatttaaccttttgtggcaccatcaaactgtttccccagtggctgcaccactttaaattttctcca

gcaatgtatgagagtcaccctcttcttaacgtgtacccatttgtccctttcctctttcctacttttacaaagccagttccccacagacttct

ctttcccctggagtagagggtgggagaagttgcatactagtagaaagactatccaagcctccattcttaccttttccgcaaataga

atacggtgaccaggaggaggagaggacaggctgccacctccctgtggtcactaaggtacacccactacagccattaacgcga

ctccgtaaaactaccctcctagcgacctccaacgcctcggtcctcacccagaacatcacattaaacttttcaacagtcacagatag

gaaggggctoggtgtggaaggtgccagctctggctcagccctgcgggtgagtgtttaactttcagcccagcttaagatctccgaa

gacacccatcgcctcgtcctgcccagtcccctccgctaaagggccggcctgcccgggcctggctggcagctgacatgaatgga

gaggaagcgcctccctctccacccactctcgccggggttactgccggtcacagacccgggccttcaagagctatttacacctaca

acagcccaccagcgcctgaccacgccggagccaatcagcggcccccaagcttgtctgattctgtctgctccaatcaggaggcg

cggtccttccagcctcttgctcctgtgaatcacaggtcggcgggagcctttttccTTTTTTTTTTTTTCCCGGGGAGT

CGGCCTCGGGGCTCTGCTCTCCTACCICAGTCTGCCCTACCCTGGAATGGGGAAAATG

CGGACATGCCACTCAGTCCGGCCGCGAACAGTGCTCCAGAACTCAGAGAGTTTTCCAG

ACGGGTGGAGATCGCGTTCCCTGCCCGCCGAGGTCCCATCGCTTCCCTGCTGGGAAG
```

-continued

ACAAATGAGGCGCTTTAGCCGTCTCCACGGCCAGCCCCTCCCTCATAACCCGAGATTC

TTTGTGGGCTCTTAGTCCATAGCTGCCTTTGAGGTGGTGTAGACCTTGCTAACCAGGAC

GGCCCAGTAGGCAGAGCTCATTTTTATTCCTGTCTGCAATCGTGCAAAAACGCCTCTTA

TGGAAAAGCCAGAGCGCCAGGAGTCAGCAAAACACACTAAAGATTGGGCAGTCACTGG

GGAGAACgtgagtaaaagcacaggaacagcaaagcgttcaggaacgttcgaggctgacgcaaccggcgcaggaaggt ggtgtgtggtgggagagtgggaggagacagtggaaagtttagacttgcttctgtaagtgataagaagtcatcagatattttcaagc aggagaggaaaataatctctctgtttcgcaaagttaactctcatggcaacagagcagagtagcggggggatgggggctgggag atgttgggaagctattgttaccactctggtgaagagtcatgggacctcaaaagctgggatagtcacggtgggaatggaaaggaa gggcacaagctgagaggcatttgggaggagaatcaatagcactttattgactggatgtgtgagatgagtgaggacagcaatca gaagaggactttgaggtttctagcctgagtggctggaaggacaccacttcccctacctgaaataggtagcaaaaaggagagag aaagagagaagcagagggattttgcaaagggaataggagttcagtttttgacatgtggcatttgaattgcaagaagtacatccct gtggatgtaatacccagtagacagttgggaattaggatctggtgtcgagaagaaaagtagagatgagatccaaagggtttatagt ggatcgggagagaaattgatgacctaaagagaaattatagaataagaagatttgggcagggcacggtggctcatgcctgtaat cccagcattttgggagaccaaggtaggaggattgcttgagcccaggagtttgagaccagcctgggcaacatggtgagaccccg actctacaaaaactgcaaaaattaccgggtgtggtgacacatacctgtaattccagctacttgggaggctgaggtgggggatca cctgagcctggggaggtctaggctgcagtgagctgagatagtgccactgcactccaacctgggcaacatagcaagagcaaga ccctgtctcaaaagtaaaaaaaaaaaaagaagattcaagtacagaatcttgggaaggtagaaagaggacacagaggccag gtgtggtggctcatgcctgtgatcccagcactttggacgctgaggtgggtggatcatctgaggtcaggagttcaagaccagcctag ccaacatggtgaaaccctgtttctattaaaaattatccaggcatggtggcgggcgcctgttaattccagcttctcgagaggctgagg taggagaatggcttgaacataggaggcagaggttgcagtgagctgagattgtgccactacactccagcctgggcaacagagtg agactctgtctcaaaaaaaaaaaaaaaaaaaaagaggacacagagctagcaaaacagacaaagaagtatcagaaagat atgaaaaattaaaaaaaagcaaactacgatactgtaatagaaataagaaaataattccaggaagaggaagcaggacattgttt atgtatgtacaaaacagtaagacattggttaaataaattataaagcattcatttgatagaatacagccattaaaattatgttgcaaaa ctatataattgccataaagagatgttcaatgcatctttttttcccccagtgcatcttagaaacactcaggttaaaaaatagtatatatgct gggcacggtggctcacgtctgtaatcctagcactttgggaggctgaggcaggtggatcacgaggtcaggagtttgagaccaccc tggccaatgtagtgaaaccctgtctctaccaaaaatacaaaattagcccggcatggaggcaggtgcctgtaatcccagctacttg ggaggctgaggcaggagaatcacttgaacctgggaggcagatgttgcagtgagcagagattgtgccactgcactccagccca agtgacaatgcgagactccatctcaaaataaaaaaaagtatatatatatgtgtgtatatatatgtatatatatgtgtatatatgtatata tgtgtgtatatatgtatatatgtgtgtatatatgtatatatgtgtatatatgtatatatatgtgtatatatgtgtatatatgtgtatatatgtatata tatgtgtatatatgtgtgtatatatgtgtgtatatatgtgtatatatgtgtgtatatatgtatatatgtgtatatatgtgtgtatatatgcgtatat atgtgtgtatatatgtatatatatgtgtgtgtatatgtatatataattgtaccatttttaaaaattacatatgtgactgcaaaaaggcatga gaaggctgggtggctcatgcctgtaatcccagcactttgggaggccaaggcaggctgatcacctgaggtcaggagtttgagacc agcctagccaataattgttatacaaaatagaacaatttttgtattttgtaaaaatacaaaaattagccaggtgtggtagcacatgtctg tagtcccacttactcaggaggctgaggcaggagaatcccttgaacccaagaggcggaggttgcagtgagctgagattgcacca ctgtactacagcctgggtgacagagtgagacaccgtctcaaaaaaaaaaaaaggcatgaggaaacttttaggatgagggaact gttctatatgtttgttgaggtaatgtatacacagctctgtacaattatccaaaatcctcataagggaggagaccacccctcatattgtct tatgcccaatttctgcctccaaagaaagaagaagtaaaaacttaaagacagaaatgaaatccacaggcagacagcccggcg ccacaccctgggcctggtagttaaagatcgacccctgacctaatcagttatgttatctctaaattacagtcattgtgtggaaaagcac tgtgaaaatccctgtcctgttctgttctgttctaattaccagtgcatgcagcccccagtcacataccccttgcttgctcaatcgatcaag accctttcacgcggacccccttagagttgtcagcccttaagagggacaggaattgcttactcagggagctcggtttttgagacgtga gtcttgccgatgctcccggccaaataaagcccttccttctttaactcggtgtctaagggggttttgtctgcggctcgtcctgctacactca -continued aactagaattccttaaattttatttttatttatttatttttttttagagactgagtctcactctgtcatccaggctggagtgcaatggcatgct ctcggctcactgcaacctccacctcccaggttcaagtgattctcctgcctcagcccctggagtagctgggattacaggtgtgcagc accacgcccagctaattttgtatttttagtagagacggggtttcaccatgttggccaggctggtctcgaactcctgacctcaggtgat ctgcccacctcggcctcccaaagtgctgggattacaggcatgaggcaccatgcccagctgaatgccttaattttaacaagaggg ggactgttgatggtacccacttcacagcgttgtcctggggattaaatggcagaccagagcatactgcctggaatataagaagggc tcaatcagtagagaagggaaggatgacccaggaccacagcacggaggaggcgagactgggagcaaggcccggagtatg ggtaaaggccacacctgggcctctaaaacaaaaccaccaacaaataaaagaccctagaatgggtccagacaaaaaggaa agttgagaaactgaaaactttaagactgaaaaagggctctgggcatggtgactcatgcctataatcccaacactttgagaggcca acataggagaattgcttgagcccaggagttcaagaccagcctggacaacatacggagaccctgtctctacaaaaaataaaaa ataattagtgggatgtggtggtacacgtctgtggtcccagctacttgggaggctgaggtgggaggattgcttgagcctgagaggttg cggctttggtgagccacaatcacaccactgtagtcccgcctgggtaacagagcgagactgtctcaaaaaaaaaaaaaaggggg gggaaggtttatgagggaccttggtagctgacttagaatatgacacaaatgaggaaataaacctattccttattgtccagagggttg aataaaggaataaaactatgtgggaatgagagcaagcatggctatggacaggaaggcagctcaaataacttgagctgttctac agtgtcttgggaggaataagctgcttctctcaccatatttgttcaactcgtccaagattctgtaaacatgttcctgaatgggatgagata atggattagatacctcttaggttccacctagttttaagactatgatataaagcacatcaaagctcttcaaccaaacataaggtaatag gagttatgttattttcagtctatggaatggatgtcaatctcatctcttttgattgtcaagctagttcccatttcttcatggttttgatcaaatctg tttaagctgtctttatgatctggactaggtgagcttaaagtgatcatacctggctgataaatactaattgcatttctaagtaggccgctg gtagaaatttaattatttggttttaatgtgagctgttttgttttgttttgttttgtttttgagacagagtctcgctctgtcgccaggctggagtgc agtggcgtgatcttggctaactgcaacctccgcctcccgggttcaagcaattctcctgcctcagccttccgagtagctgggactaca tgtgtgcccaccacacctggctaatttttatttttagtagagatagggtttcaccatattggccaggatggtcttgatctcctgacctcgt gatctgcccaccttggcctcctgaagtgctgggattataggggtaagccaccatgcccggcccttaatgttagttcttattatacttcat atctatatcattcattttgcatactatggtacaatagagaaaccattaggctaggagtcagtgtgacccagtttcaagtactggttctac tacttaatagatgtatggctttggggaaaggcatttatgcagaggttttcgatgtgtagtccatggacccctgagcgtaccccaaata attttcagggtatccataagaccaaaatgatgttcatggtgatattaagccttatttgcctttttcaccatcacattgacatttcttctgatg gtgggaaattctttgcaccttgataggaatcacggtagtagcaccaaactgtaccagtgggcattacattcctcactgccctgcactt ggaggggaattcagtcccccaggctggaatgcaatgatctcggctcactgcaacctctgcctcctgggttcaagcgattctcctgc ctcaacttcccaagtaactaggattacaggtgcctgccaccacgcctggctaattttgtatttttagtagtttcaccatgttggccagg ctggtctcgaactcctggcctcaggtgatccacctaccttggccttccaaagtgctgggattacaggtgtgagccaccatgcccag ccaagatgttcttgataaaataaaaattattaatttattaaatttgatccttaagagcaccttttaaaaattctgtggcatgaaatggga agtaggaagtacttataaagtacttctgctatatgtcaaagaacagtggttgtcttgagggaaaacattagtgtgatcattatagttgt gagctgaattaacccctttattcatgtaatatcctttttgtttgaaagaatgactgacaaactggttgttcagactttggtattttgcagctt caagaacattaataaagtaaaattgttacttcaaagtaacaacttgcaatatttgttccaatgataaaatttgagcttttggcagtggct catgcctataatcccagcacttagggaggctgaggcgggaggagcacttgagctcaggagtttgagaccagcctgggcagtct ctccaaaaagaaaaaaaaaattagccaggcatggtggcatgcaccagctgaggtggaaggagcacttgagcctgggaggc caaggctgcagtgagccatgattgtaccactgcactccagcccaggcaacagagcaagatcttgtcaaaaaaaaaaaaaaa agaaaaaagaaaagaaaaaatagctttcaagcaaaactcagaattgtagtgatcttgcatgtggtactaagcttgacagcttcct aataattaaaaactcttctgatgctatcagtggtgatgttcaaaaatgtcaatttttaaatattatagaataaaatgtgccaacattttag aagatttgcataactcagtgaaccaatacttttcaaatgaccaaaacataatgttacaaaatcatgcatggataaaaggtgcattg aaaatgcaaatgaggccaggtgtggtggctcatgcctctaatcccagcattttgggaggcagaggctggaggatcacttgaggc caggcatttgagaccagcctggccaacatagcaagatcctatctctaaaaataataagagtaagagaattagccaggcatggtg -continued gcatgcgcgtgaagtcttagctacttgggaggctacggtgggaggatggcttgagcttaggagtttgaggttacaggaagctatg attgtgccactgccctccagcctgggtgatggagtaagaccatgatcaaaaacaaaacaaaaaaaaaagaaatgcaagttag accaatgaagtataatgtaatgaaatacaaaaaattcattgctatggtttcaaattcccagtgcaattaacctttaagatactacgtgt caggcctctgagcccaaactaagccatcatatcccctgtgacctgcatgtatacatacagatggcctgaagcaactgaagatcc acaaaagaagtgaaaatagccttaactgatgacattccaccattgagatttgttcctgccccaccctaactgatacgatatattctcc cccgcccttaagaaggtactttgtgatattctccctgcccttgagaatgtactttgtacgcctatcccaaacctataagaactaatgat aatcccaccaccctttgttgactccttttttagACTCAGCCCGCCTGCACCCAGGTGAAATATACAGCCTT

GTTGCTCACACAAAGCCTGTTTGGTGGTTTCTTCACACGGATGCATGTGACATTTGGTG

CTGAAGACCCAGGACAGGAGGACTCCTTTGGGAGACCAGTGCCCTGTTGTCGCCCTCA

CTCCGTGAGGAGATCCACCTATGATCTCAGGTCCTCAGACCAACCAGCCCAAGGAACA

TCTTGCCAATTTCAAATCGGgtaagtggtcttttcactcttctccagcctttcttgctacccttcaatcttcctctctcactac ccttcaatctccctgtccttccaattcccgttctttttcctctctagtagagataaggagacacattttatctgtggacccaaaactccag cgtcagtcacggactcgggaagacagtcttcccttggtgtttaatcactgtggggacgcctgcctgattattcacccacactccattg gtgtctgatcaccacggggatgcctgccttggtcattcacccacattcccttggtgacaagtcaattgcggggacacctgctttggct gctcacccacattgcagcccagggctgctcaatgccccccgctgccccacccgccttctccgtgcctctaccctctcttttctcgggtt tacctccttcactatgggcaaccttccaccctccattcctccttcttctcccttagcctgtgttctcaaaaacttaaaacctcttcaactca cacctgacctaaaacctaagtgtcttatttcttctgcaacaccgcttggccccaatacaaactcgacaatgattccaaatagccag aaaacggcactttcgagttctccatcctacaagttctagataattcttgtcataaaatgggcaaatggtctgaggtgcctgacgtcca ggcattcttttacacattggtccctccctagtctctgctcccaatgtgactcatcccaaatctttcttctttctctcctttctgttccttcggtctc caccccaagttccgagtcctctgaatccttcttttctatggactcatctgacctccccccttctccccaggctgctcctcgccaggctga gccaggtcccaattctcacttagcctctgctcccccaccctataatccttttatcacctcccctcctcacacctggtccagcttacagttt cgttcctcgactagctctccccgatctgcccaacaatttcctgttaaagagatggctgactatcctgacttcatcagagcaggctggt gcctggccttcctggaatgagtgggtgttctgacaggcccccagtttgtcccatctgcaccgccaagaggtctccgggtggccaga ggagcaaagttgccttccaagtgcctgttggtgcctgggagaacacagcaggagtgtcgtgcggcccacagcgcagtgcatgg tgattccaggcgctgaacaactccccttgacccttgggcctgcatctgactcccggctgcagaatcagaagctgagtccaggcaa ccgctcggccactcccggtcactcctctctggacacccagttactaaagtcagcaaagaagatgcggtaatcaccgcctgatctc cacatggtgaacacaacactctcactaacacctccttgaccagtcagtcttcagcactgggggtggacaggcaggttttctgtgttt accagaatcgcacaggctaagcacaaacatggaaccagagttccaggtgaggaaacctcactcgcagaagcccaggctgc accccaccaggtgatgcagtgcgcctaggctgtgggtgctaggagccaagtgctagggactcgtcatgagtgggaatccccac gttcctgtcactgctgtcaaacagaaggtaaacagtcttacgaatgtaattccttaggaagacttgtacaaacttttattaggatatct atttatttaatactgaactttggcctactttgtgataagactataaacaaattgaggaaatcactatttctcacttctgtatttctcaaaaa ataattttgttacagagttcaatatactgtgtactactgatcttctattgtgaaagcaaagcatttcatcaaaacaaagtattttaaattat gagtgaaaattgtgtatgttaattttgcagctgtaatattaatcaaactttgtgtaattctaatcacaaaatgatgtgccttaaatgcccct ccagctgtgggttggcagtgtccagacagggaccctgaaatcctgaatgactgctagaccaattctattaaaaacatttcaaggc aaaaaaaaaaaaaaaagaggtggctggagctgaaggcgtagtcaaggttaatgctcctttttcttcatctgacctctcccaatcag ttagcgtttaggctgtttttcatcaaatataaaaacccagcccagttcatggcccatttggcaacaacccttagatgctttaccgccct agacccagaggggccagaaggccgtcttattctcaatatgcattttattacccaacccgctccggacattagaaaaagctccaaa aattagattccagccctcaaaccccacaacaggacttaattaacctcaccttcaaggtgtacagtaatagagtagaggcaacata tttctgagttgcaattacttgcctccactgtgagagaaaccccagccacatctccagcacacaagaacttcaaaacacctgaatcg cagcggccaggtgttcctccaggaccgcctcccccaggatctttcttcaagtgctggaaatctggtcactgggccaaggaatgcct gcagcctgggattcctcctgagccatgtcccatctgtgccagaccctactggaaatcagactgtccaacttacccaggagccact -continued cccagagctgctggaactctggcccaagactctctgactccttcccagatgttctcggcttagcggctgaaaactgatgctgccca atcgcctcagaagcctcttggaccatcacagatgctttgggtaactcttacagtgaaggggaagtctgtccccttcttaatacagag gctacccactccacaataccttcttttcaagggcctgtttcccttgcctccataactgttgtgggtattgatggccaggctgctaaacct gtcaaaactccccaactctggtgccaacttggacaacattcttttatacactctttttttagttatccctacctgcccagctcccttattagg tcaagacattttaaccaaattatctgcttccctgactgttcctggactacagccacacctcattgccgcccttttccccagttcaaagcc tccttcgcatcctccccttgtatctccccaccttaatccacaagtatgggacacctctattccctccttggcaaccgatcatgcacccct taccatcccattaaaacctaatcacccttaccccactcaatgccaatatcccatcccacagcacactttaaaaggatcccacagc acactttaaaaggattaaagcctgttatcactcgcctgctatagcatggccttctaaagcctataaactctccttacaattcccccattt tacctgtccaaaaaccagacaagtcttacaggttagttcaggatctgtgccttatcaacaaaattgtcttgcctatgcaccccatagt gccaaacccatataccctcctatcctcaatacctccctcccacaacccattattctgttctaaataaacctagctgaccccataaatc ctaaatcctttccccactcccctttccattccttaaaaaacagccctaaaagctgctcccacactagctctccctaactcatcccaact ttttcattacacacagccaaagtgcagggctgtgtggtcggaattcttacacaagagccagaagcatgccctgtagcctttctgtcc aaacaacttgaccttactgttttagcctagccctcatgtctgtgtgtggtggctgctgctgctttgatacttttagaggccctcaaaatca cattatgctcaactcactctctacagttctataacttccaaaatctattttcttcctcatacctgacgcatatactttccactccctggctcct tcagctatactcaactctttttttgagacagagtctcactccgtctcccaggctggcatgcagtggcacaatcttggctcactgcaacct ccgcttcccaggttccagcgattctcctgcctcagcctctggagtagctgggattacaggtgtgtgccccacacccggctaatttttttg tatttttagtagagatggggtttcaccatgttaaccaagctggtcttgaactcctgacctaaagtgatctgcccatctcggcctcccaa agtgctgggattacaggcatgagccaccacacccagcctatactcactctttgctgagtctcccacaattaccattgttcctggcctg gacttcaatccggcctcccacattattcctgataccacacctgacctccatgactatctctctgatccacctggcattcactccatttcc ccatatttccttctttcctgttcctcaccctgatcacacttggtttattgatggcagttccaccaggcctaatcgccattcaccggcaaag gcaggctatgctatactatcttccacatctatccttgaggctaccgctctgccccgctccactacctctcagcaagccaaactcattg ccttaactcgggccctcactcttgcaaagggactacgtgtcaatatttatactgactctaaatatgcctttcatatcctccaccaccatg ctgttatatgggttgaaagaggtttcctcactatgcaagggtccttcatcattagtgcctctttaataaaaactcttctcaaggctgcttta cttccaaaggaagctggagtcattcactgcaagggccatcaaaaggcatcagatcccatcactcagggcaacgcttatgctgat aaggtagctaaagaagcagctagcattccaacttctgtccctcagggccagtttttctccttcttatcggtcactcccacctactccct cattgaaacttccacgtatcaatcttttcccacacaaggcaaatggttcttggatcaaggaaaatatctccttccagcctcacaggc ccattctattctgtcgtcatttcataacctcttccgtgtaggttacaagccgctagcccatctcttataacctctcatttcatttccatcgtga aaatctgtcctgaagaaaatcacttctcagtgttcatctactattctactatccctcagggattgttcaggccccttcccttccctacaca tcaagctggggaatttgcccctgcccaggactggcaaattgactttactgacatgtgccgagtcaggaaactaaaatacctcttgg tatgggtagacactttcactggatgggtacaggcctttcccacagggtgtgagaaggccaccacggtcatttcttcccttctgtcaga cataattcctccatttagccttgccacctctatacagtgtgaaaacagaccggcctttattagtcaaatcacccaagcagcttctcag cctcttggtatttagtggctcctggttttacctcaaaacaccacccttaaggctctcttgaagtggatagatcttcagtggcaaggtacc ctccgatactttcaccctgatgaagtcctattctttacttttatactcattcttattctggttcccgatcttatgccaccctctacctctcccca gctatctccaccacactatcaatctcactctctcctagccccgtttataatccttcttttttttttgagatggagtcttgctctgtcccccagg ctggagtgcagtggtgtgatcttggctcactgcaagctccgcctcctgggttcacaccattctcctgcctcagcctcccaagtagctg ggactagaggtgcctgccaccatgcctggctaatttttttgtatttttagtagagatggggtttcaccatgttagccaggatggtctccat ctcctgacctcacgatccgcccacctcagcctcccaaagtgctgggattacaggcgtgagccactatgcccggccctctaatcctt ctttaacaaacaactgctggctttgcatttctctttcctccaaaatcgccaaggcctcgacttactcactgctaaaaaaagaggaccc tgtatatttttaaacgaagagtgttgtttttacctaaatcaatctggcctggtgtatgacaacataaaaaaactcaaggatagacccc aaaaattcgccaaccaagcaaataattatgctgaacccccttgggcactccctaattggatgtcctgggtccttccaattcttagtcc -continued

```
tttaatacctatttttctctttctcttattcggaccttgtgtcttccttctgtttagtttctcaattcatacaaaactgcatccaggccatcaaca

atcattctatacgacaaatactccttctaacaagcccacaatatcaccccttatacccaaatctttcttcagtttaatctctcctactcta

ggttcccatgccaccccaatcccactcaaagcagccccgagaaacatcgcccattatctctccataccacccccaaaaattttcg

ctgcctcaacacttcaccactattttgttttgtttttcatactaatataagaagATAGGAGTGTCAGGCCTCTGAGTCC

AAGCTAAGCCATCAAATCCCCTGTGACCTGCACGTGTACATCCAGATGACCTGAAGCAA

CTGAAGATCCACAAAAGAAGTGAAAGTAGCCTTAACTGATGACATTCCACCATTGTGAT

TTGTTCCTGCCCCACGCTAACTGATACCATATATTCTTCCCCCGCCCTTGAGAATGTACT

TTGTACACCTATCCCAAACCTATAAGAACTAATGATAATCCTACCACCCTTTGCTGACTC

TCTTTTTGGACTCAGCCCGCCTGCACCCAGGTGAAATAAACAGCCCTGTTGCTCA.
```

OLMALINC is also known as LINC00263 and HI-LNC80. This sequence has not previously been described in liver cell lines or in the context of NAFLD/NASH In one embodiment, the siRNA that inhibits OLMALINC is ACATGCATCC (SEQ ID NO: 2); or, in another embodiment: ACTTACCCGA (SEQ ID NO: 3). In one embodiment, the siRNA is 5'-CTCCGTGAGGAGATCCACCTA-3' (SEQ ID NO: 4). In other embodiments, the siRNA is 5'-CTCCGTGAGGAGATCCACCTACTG-3' (SEQ ID NO: 5). Additional siRNAs include the following:

```
QIAGEN KIT:
                                    (SEQ ID NO: 10)
5'-TACACCTATCCCAAACCTATA

                                    (SEQ ID NO: 11)
5'-GAGATTCTTTGTGGGCTCTTA

                                    (SEQ ID NO: 12)
5'-CCCACGCTAACTGATACCATA

IDT:
                                    (SEQ ID NO: 13)
5'-AAGGAACAUCUUGCCAAUUUCAAAT

                                    (SEQ ID NO: 14)
5'-UGCCCCACGCUAACUGAUACCAUAT
```

Select inhibitors include anti-sense oligos (ASOs) that were designed specifically for OLMALINC as follows:

```
                                          (SEQ ID NO: 2)
a) ASO1: /52MOErA/*/i2MOErT/*/i2MOErG/*/i2MOErT/*/

i2MOErC/*A*C*A*T*G*C*A*T*C*C*/i2MOErG/*/i2MOErT/*/

i2MOErG/*/i2MOErT/*/32MOErG/

                                          (SEQ ID NO: 3)
b) ASO2: /52MOErA/*/i2MOErG/*/i2MOErA/*/i2MOErC/*/

i2MOErC/*A*C*T*T*A*C*C*C*G*A*/i2MOErT/*/i2MOErT/*/

i2MOErT/*/i2MOErG/*/32MOErA/

                                         (SEQ ID NO: 15)
c) Control ASO: /52MOErG/*/i2MOErC/*/i2MOErG/*/

i2MOErA/*/i2MOErC/*T*A*T*A*C*G*C*G*C*A*/i2MOErA/*/

i2MOErT/*/i2MOErA/*/i2MOErT/*/32MOErG/
```

The control ASO above is not directed against any gene, but was designed specifically to control for the other 2 ASOs (a) and (b) above.

The OLMALINC nucleic acid sequence contains several open reading frames. ExPAsy was used to create a predicted peptide sequence, which is shown in FIG. 10. Encoded peptides are indicated by shading. These peptides can be the targets of inhibition or inactivation of OLMALINC and can be used to generate antibodies.

Primers and Probes

Primers are useful in the synthesis of copies of a target sequence of OLMALINC, and, along with probes, can be useful in methods of detecting and assaying levels of OLMALINC, Assay Standards The invention provides standards, which can be used in assays as described herein. Standards can provide a reference or control against which detected amounts of OLMALINC can be compared so that increases or decreases relative to the standard can be analyzed and/or detected.

Kits

The invention provides kits comprising a set of oligonucleotides as described herein, and optionally, one or more suitable containers containing oligonucleotides of the invention. Oligonucleotides of the invention can be modified or unmodified, such as by linkages and other modifications known to improve stability and efficacy.

Kits of the invention optionally further comprise an enzyme having polymerase activity, deoxynucleotide triphosphates (dNTP), and an enzyme having reverse transcriptase activity. Kits can include one or more primer pairs, and in some embodiments, at least one corresponding probe of the invention, as well as internal control primer and probe sequences. In some embodiments, the kit comprises antibodies, antisense inhibitors, and other molecules capable of specifically binding to OLMALINC molecules of the invention.

The kit can further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

In one embodiment, the kit further comprises a solid support onto which the antibodies, probes, or other reagents are immobilized. Examples of a solid support include, but are not limited to, a microtiter plate, beads, a membrane or other support known to those skilled in the art. In one embodiment, the antibodies are immobilized via binding to antigen that is immobilized to the solid support. In one embodiment, the antibodies are immobilized via binding to a bead or particle such as luminex. In one embodiment, the kit further comprises a chromogenic substrate.

Methods of the Invention

The invention provides methods for detecting and treating appetite, glycemia, body weight, obesity, liver steatosis, NASH, NAFLD, hypercholesterolemia, and other symptoms associated with obesity disorders and type 2 diabetes. In a representative embodiment, the method of treating one or more of these diseases or disorders comprises administering to a subject in need thereof an effective amount of an oligonucleotide of the invention. An effective amount is an amount sufficient to ameliorate symptoms of the disease or disorder.

Administration can be via methods known in the art, and selected in accordance with the judgment of the treating physician. Representative methods of administration include, but are not limited to, the use of nanoparticles, viral vectors, formulation with peptides, and non-peptides, which can effect the delivery of the siRNA to the liver and adipose tissue. Delivery methods would include, but not be limited to, intravenous infusions, oral administration, through the bile duct using endoscopic retrograde cholangiopancreatography (ERCP), direct administration to the liver by injection.

In a representative embodiment, the method of detecting one or more of these diseases or disorders comprises assaying for OLMALINC in a tissue sample, such as by contacting the tissue sample with reagents that bind the nucleic acid molecule of the invention, and detecting the amount of binding of the reagents. The amount of binding can be compared to a reference amount, a control, or other sample that is representative of a normal, healthy subject. Alternatively, in some embodiments, the amount of binding is compared to that measured in the same subject at an earlier point in time.

In some embodiments, the assaying comprises an immunoassay. In other embodiments, the measuring comprises detection of nucleic acid hybridization. Representative examples of reagents include, but are not limited to, an antibody, a nucleic acid probe, or a synthetic probe. The probe or antibody may optionally be labeled with a detectable marker.

For use in the methods described herein, representative examples of the sample include, but are not limited to, a liver sample, peripheral blood, and adipose tissue. In other embodiments, the sample is selected from blood, plasma or serum, saliva, urine, stool, bile, tissue, cell cultures, and other bodily fluids or tissue specimens.

EXAMPLES

The following examples are presented to illustrate the present invention and to assist one of ordinary skill in making and using the same. The examples are not intended in any way to otherwise limit the scope of the invention.

Example 1: The Long Intervening Noncoding RNA, OLMALINC, is a Novel Regulator of Lipid Biosynthesis Genes This Example demonstrates that OLMALINC expression is highly correlated with Sterol Responsive Binding Protein 2 (SREBP2) and stearoyl-CoA desaturase (SCD)), two important proteins implicated in NAFLD and NASH. Furthermore, the data show that OLMALINC is statin, sterol, and LXR responsive, as demonstrated by ChiP-Seq analysis and in vitro cellular models. The genomic structure of OLMALINC suggests that it regulates SCD expression in cis, which was confirmed using CRISPR-dCas9. Additionally, deletion or silencing of OLMALINC demonstrates dysregulation of sterol metabolism. OLMALINC is a novel regulator of hepatic sterol metabolism and implicates it in the pathogenesis of NAFLD/NASH.

Methods

Genome and phenotypic correlation in KOBS. A detailed description of the quality control, alignment and WGCNA analysis is provided in Ko et al. (Ko et al., 2018, submitted). Briefly, the normalized adjusted OLMALINC gene expression was used as the dependent variable and a linear regression model was used again each phenotype and all genome-wide expression. To determine the protein-protein interactions between the OLMALINC correlated genes, we used the publicly available STRING Database. Gene Ontology was also conducted using the STRING analysis (Szklarczyk, Morris et al. 2017, "The STRING database in 2017: quality-controlled protein-protein association networks, made broadly accessible." *Nucleic Acids Res* 45(D1): D362-D368).

Cell culture. We maintained HepG2 (ATCC) cells in a monolayer culture at 37° C. and 5% CO2. The base medium was EMEM (Corning) containing 100 U/ml penicillin and 100 μg/ml streptomycin sulfate (HyClone). We tested the cells for mycoplasma contamination using SoutherBiotech Mycoplasma Detection Kit (13100-01).

Activating CRISPR dCas9 stable cell lines. For the generation of the activating CRISPR dead Cas9-VP64 (aCRISPR dCas9) cell lines, we used the pHAGE EF10apha dCas9-VP64 (Addgene #50918) plasmid which were packaged in to a third-generation lentivirus system (Konermann, Brigham et al. 2015, "Genome-scale transcriptional activation by an engineered CRISPR-Cas9 complex," *Nature* 517(7536): 583-588). Viral titration was conducted prior to the final cell line expansion. Cells were then transduced with polybrene (1 μg/ml) for 2-3 days followed by selection with 4 ug/ml of puromycin for 7 days. Single clone isolation was obtained following serial dilutions. Clones expressing the dCas9 were confirmed by RT-qPCR of the dCas9 gene. We used two OLMALINC guide RNAs (gRNAs) targeting the promoter region of OLMALINC that were previously validated in Liu et al. guide RNA design to prevent off-target effects and ChiP-Seq pull down of histone methylation markers (Liu, Horlbeck et al. 2017, "CRISPRi-based genome-scale identification of functional long noncoding RNA loci in human cells." *Science* 355(6320)). OLMALINC and scramble gRNAs were obtained from VectorBuilder which were confirmed by Sanger sequencing and restriction enzyme digestion.

Reagents and Transfections. We performed transient transfections using Lipofectamine RNAiMax (Invitrogen 13778100) with small interfering RNAs (siRNA) using 0.5 million cells that were plated in a 6-well plate in triplicates and were grown to ~70% confluency in 10% FBS containing 1 g/L of glucose with penicillin/ampicillin. The following day, we treated the cells with Optimem (Gibco 31985062) and Lipofectamine RNAiMax (Invitrogen 13778100) and the appropriate siRNA at 30 pmoles. We used scramble siRNAs as negative control (IDT #51-01-19-08). The sequence of other siRNas is provided in the list below. After 24-48 hours, we removed the medium and washed cells with PBS once prior to treating with Trizol (Invitrogen 15596026). For the anti-sense oligonucleotides transfections, HepG2 cells were transfected with RNAiMax with a final concentration of 50 nM fo2 24 hours. For DNA plasmid transfections, we used Lipofectamine 3000 (Invitrogen L3000008) with 1-2 ug of DNA. For the time points experiments, we plated cells followed by overnight starvation the following day in 0.25% BSA (Sigma A8806). Lipoprotein deficient medium (LPDS) was obtained from Kalen Biomedical LLC (880100). Simvastatin sodium salt was from Calbiochem (567021). We obtained Mavelonic acid from Sigma Aldrich. For cellular localization experiments, we used the PARIS Kit (Invitrogen AM1921) to isolate cytoplasmic and nuclear extracts prior to RT-qPCR. GFP control and OLMALINC cDNA plasmids were obtained from GeneCopoeia.

SiRNA Sequences

| | | |
|---|---|---|
| OLMALINC siRNA | CTCCGTGAGGAGATCCACCTA | SEQ ID NO: 4 |
| SCD sRNA | AGGGGAGTACGCTAGACTTGTCTGA | SEQ ID NO: 16 |
| SCD sRNA | GGCTTGAGCTAGAGATAAAACAGAA | SEQ ID NO: 17 |
| SCAR siRNA | GCTATTACAACATCACACTGGCCAA | SEQ ID NO: 18 |
| SCAR sRNA | CCAGAGGAGGUACUACAAATT | SEQ ID NO: 19 |
| SREBP1 sRNA | CAGCUUAUCAACAACCAAGACAGTG | SEQ ID NO: 20 |
| SREBP2 sRNA | GCCUUUGAUAUACCAGAAUTT | SEQ ID NO: 21 |

RNA Purification, cDNA Synthesis and Quantitative PCR. We harvested and re-suspended cells in TRIzol (Invitrogen 15596018) and extracted their RNA using Direct-Zol (Zymo Research R2061) according to the manufacturer's protocol. We synthesized cDNA using Maxima First Strand cDNA Synthesis Kit (Thermo Scientific K1642). Quantitative PCR was done using SYBRGreen reaction mix (Applied Biosystems) and Studio 5 detection system (Applied Biosystems). 36B4 was measured for all quantitative PCR reactions as an internal control and used to normalize the data. The list of other primers used is provided in the following list.

Primer Sequences Used for RT-qPCR

| Primer or siRNA | Forward sequence (5'→3') | SEQ ID NO: | Reverse sequence (5'→3') | SEQ ID NO: |
|---|---|---|---|---|
| 3684 (RPLPO) | CCACGCTGCTGAACATGCT | 22 | TCGAACACCTGCTGGATGAC | 23 |
| GAPDH | GGGTGTGAACCATGAGAAGT | 24 | CCTTCCACGATACCAAAGTT | 25 |
| OLMALINC | CCAGGAGTCAGCAAAACACA | 26 | CTGGGTCTTCAGCACCAAAT | 27 |
| SCD | TGCCCACCTCTTCGGATATC | 28 | GATGTGCCAGCGGTACTCACT | 29 |
| SREBP2 | GACGCCAAGATGCACAAGTC | 30 | ACCAGACTGCCTAGGTCGAT | 31 |
| SRE8P1a | TCAGCGAGGCGGCTTTGGAGCAG | 32 | CATGTCTTCGATGTCGGTCAG | 3 |
| SRE8P1c | CGCTCCTCCATCAATGACA | 34 | TGCGCAAGACAGCAGATTTA | 35 |
| SCAP | CCTGACTGAAAGGCTGCGTGAGAAGATATC | 36 | GGGTAGCAGCAGGCTAAGATGCA | 37 |
| HMGCS1 | GATGTGGGAATTGTTGCCCTT | 38 | ATTGTCTCTGTTCCAACTTCCAG | 39 |
| LDLR | AGGCTGTGGGCTCCATCGCCTA | 40 | AGTCAGTCCAGTACATGAAGCCA | 41 |
| MALAT1 | GGTAACGATGGTGTCGAGGTC | 42 | CCAGCATTACAGTTCTTGAACATG | 43 |

RNA-seq. We prepared the libraries using the Illumina TruSeq Stranded mRNA library kit. Libraries were sequenced at a depth of 25-30 M paired-end reads on an Illumina HiSeq4000 platform (N=3). We mapped the reads using the STAR 2-pass protocol, and counted against the Gencode version 26 annotation using HTSeq. Differentially expressed (DE) genes were identified using the edgeR pipeline, using FDR <0.05. To determine the expression of OLMALINC in other human tissues, we utilized the Genotype-Tissue Expression Consortium data GTEx (Consortium 2013, "The Genotype-Tissue Expression (GTEx) project." *Nat Genet* 45(6): 580-585).

Conservation and synteny of OLMALINC. To study the conservation of the OLMALINC locus, we used the NCBI HomoloGene as (http://www.ncbi.nlm.nih.gov/homologene) as well as the mouse and human ENSEMBL data (http://www.ensembl.org). We also blasted the different regions of OLMALINC separately to identify shorter segments of homology. We also used the mouse ENCODE data (Mouse mm10) to identify RNA polymerase II and histone methylation markers.

Promoter Capture Hi-C. A detailed description of the experimental method appears in Pan and Garske et al., 2018 ("Integration of human adipocyte chromosomal interactions with adipose gene expression prioritizes obesity-related genes from GWAS." *Nat Commun* 9(1): 1512.).

Statistical Methods. For the in vitro over expression and knock down HepG2 experiments, numeric outcomes are summarized as means+/−standard error of the mean (SEM). All relative expression values were measured using the ΔΔCt. HepG2 experimental groups were compared using unpaired Student's t test (for two groups). Analyses were performed using Excel and GraphPad Prism. Statistical significance was defined as P<0.05. All experiments were conducted 2-3 times.

Results

To gain insight into the function of OLMALINC, we first correlated its expression in the liver with all human genes expressed in the liver using the KOBS liver RNA-sequence data (n=259). We found 6183 genes passing a false discovery rate (FDR) of <0.05 of the genes tested genome-wide. Among the significantly correlated genes, Acetyl-CoA Carboxylate Alpha (ACACA) was the gene most highly correlated with OLMALINC expression in the liver (ß=0.71, FDR=9.06E-37), followed by Sterol Regulatory Binding Protein 2 (SREBP2) (ß=0.67, FDR=3.96E-34), of which the latter is the main transcription factor of cholesterol biosynthesis in the liver. Consistent with these findings, SREBP2-dependent downstream target genes also showed similar highly significant correlations, suggesting that SREBP2 is regulating or is being regulated by OLMALINC, therefore affecting downstream SREBP2-dependent genes. Gene Ontology enrichment analysis of all OLMALINC correlated genes expression passing FDR <0.1% significance (n=3292) also confirms that cholesterol biosynthesis pathways were highly enriched (p=1.12e-05 by Bonferroni). To examine protein-protein interactions of the correlated genes expressed, we conducted a STRING analysis of the top 10% genes passing significance by FDR <0.5% (n=681). STRING analysis confirmed high correlation between proteins involved in the cholesterol and lipid biosynthesis pathways including cytochrome P450 family 51 subfamily A polypeptide 1 (CYP51A1), which appeared to be the main node protein.

However, when correlating OLMALINC expression with the metabolic phenotypes in KOBS, we only observe a significant association with fasting serum triglyceride (TG) levels (ß=0.27, p=0.0012) (Table 1). Additionally, there was no differential gene expression between OLMALINC in NASH or control patients with healthy livers (Ko et al. manuscript submitted, 2018). These data suggest that OLMALINC affects the expression of key lipid and cholesterol pathway genes that are dysregulated in NASH without directly being causative in NAFLD and/or NASH pathogenesis.

Conversely, when using an ASO which targets OLMALINC expression at the nuclear level more readily, we observe that SREBP2 mRNA expression decreases as do its target genes without affecting SCD expression.

OLMALINC expression is known to be highest in the brain, specifically in white cortical matter, where it was originally described to play a role in oligodendrocyte maturation. To identify the abundance of OLMALINC gene expression in other human tissues, we used the RNA-seq data from the Genotype-Tissue Expression (GTEx) Project and found that, as expected from a lincRNA, overall OLMALINC is relatively lowly expressed. After the brain, the most abundant OLMALINC expression can be seen in the liver and other endocrine/hormone-regulated organs, such as the adrenal and pituitary glands, consistent with our liver RNA-seq data in the KOBS cohort.

OLMALINC is Statin, Sterol, and LXR Responsive.

Figure 1B:
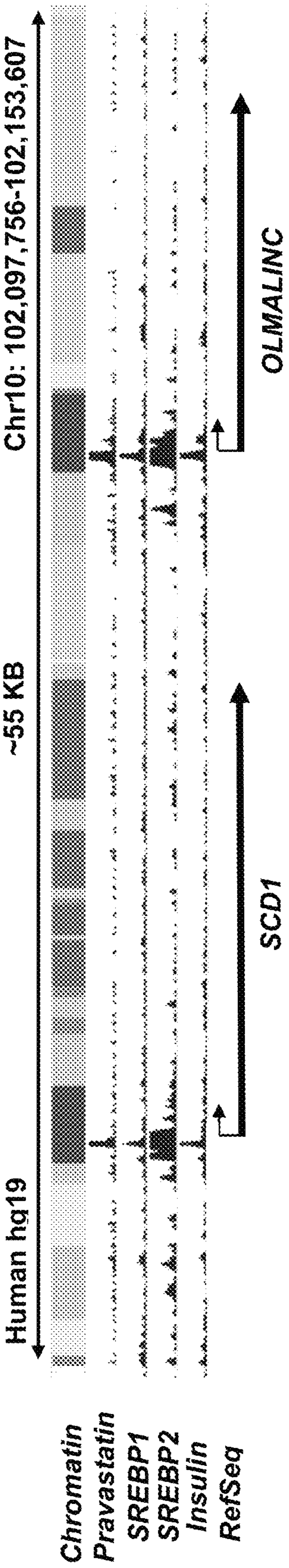
FIG. 1B: OLMALINC locus. Promoter capture Hi-C demonstrates DNA-DNA interactions on chromosome 10 between the OLMALINC enhancer/promoter and its upstream gene SCD1 promoter in the WashU Epigenome Browser in HepG2, CD34 and GM12878 cell lines. Using the ENCODE project data, SREBP1, SREBP2, insulin and pravastatin ChIP-Seq sites were identified at the OLMALINC TSS.
Figure 2:
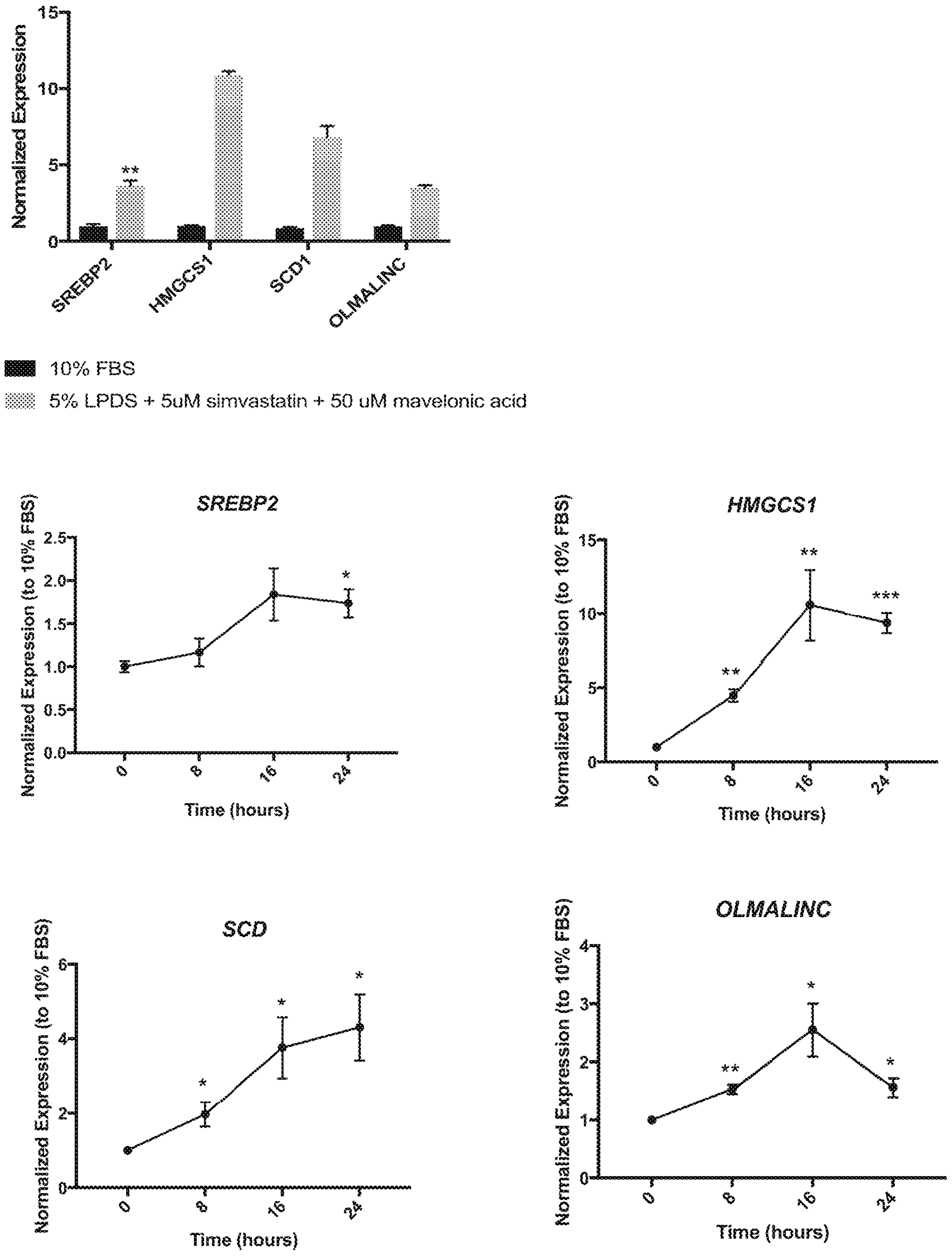
FIG. 2: RT-qPCR was used to demonstrate that OLMALINC expression is responsive in a time-dependent manner to sterols and statin treatment * $p<0.05$;  $p<0.01$; * $p<0.001$.
Figure 3A:
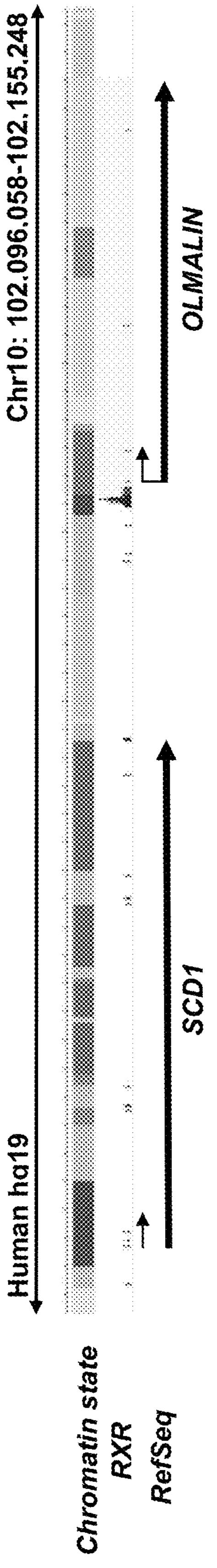
FIGS. 3A-3C: OLMALINC is LXR responsive, as shown after treating the cells with the synthetic liver LXRα and LXRβ agonist, GW3965 (FIG. 3B). * $p<0.05$;  $p<0.01$; * $p<0.001$ This is in line with OLMALINC having a retinoid X receptor (RXR) ChIP-Seq binding site which forms a heterodimer with LXRα and LXRβ for its function (FIG. 3A). This led us to look for the regulatory sequence LXR responsive element (LXRE-DR4) using previously identified consensus sequence T(G/A)A(C/A)C(T/C) XXXXT(G/A)A(C/A)C(T/C) (SEQ ID NO: 6), which we identified in the promoter region of OLMALINC.
Figure 3B:
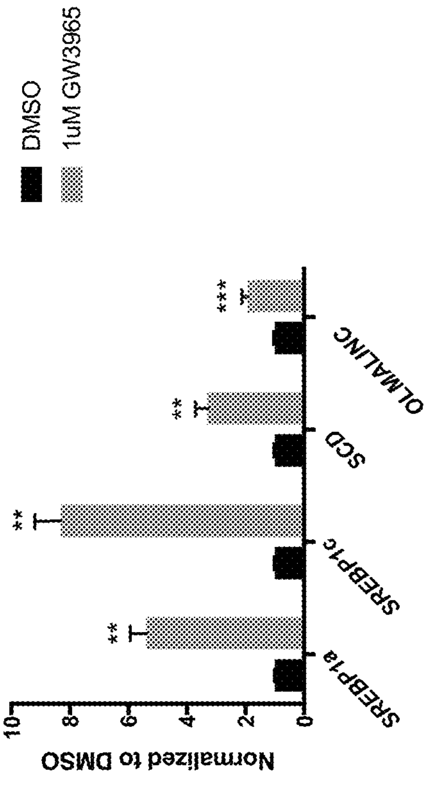

Using data from the ENCODE project and chromatin immunoprecipitation sequencing (ChIP-seq) from human HepG2 and hepatocytes, we identified the RNA polymerase II binding, 5' CAGE, and active histone modification markers, which demonstrate two active transcription start sites (TSS) in OLMALINC (FIG. 1A). GRO-seq data, used to assess the nascent RNA, not only confirms two active TSSs of OLMALINC, one in the annotated enhancer and one in the promoter, but also demonstrates bi-directional transcription, which points to potential enhancer role of OLMALINC, likely regulating its adjacent upstream gene, SCD. Given the correlation data, we hypothesized that OLMALINC would be regulated by SREBP1 and SREBP2 transcription factors. Similarly, we predicted that OLMALINC expression would be statin, sterol as well as LXR responsive. Using the ENCODE project data, we identified SREBP1, SREBP2, insulin and pravastatin ChIP-Seq sites at the OLMALINC TSS (FIG. 1B). Using RT-qPCR, we demonstrate that OLMALINC expression is responsive in a time-dependent manner to sterols and statin treatment (FIG. 2). We also show that OLMALINC expression is LXR responsive after treating the cells with the synthetic liver LXRα and LXRβ agonist, GW3965. This is in line with OLMALINC having a retinoid X receptor (RXR) ChIP-Seq binding site which forms a heterodimer with LXRα and LXRβ for its function. This led us to look for the regulatory sequence LXR responsive element (LXRE-DR4) using previously identified consensus sequence T(G/A)A(C/A)C(T/C)XXXXT(G/A)A(C/A)C(T/C) (SEQ ID NO: 6), which we identified in the promoter region of OLMALINC (FIG. 3).

The Cis Effects of OLMALINC on SCD Expression.

Figure 4:
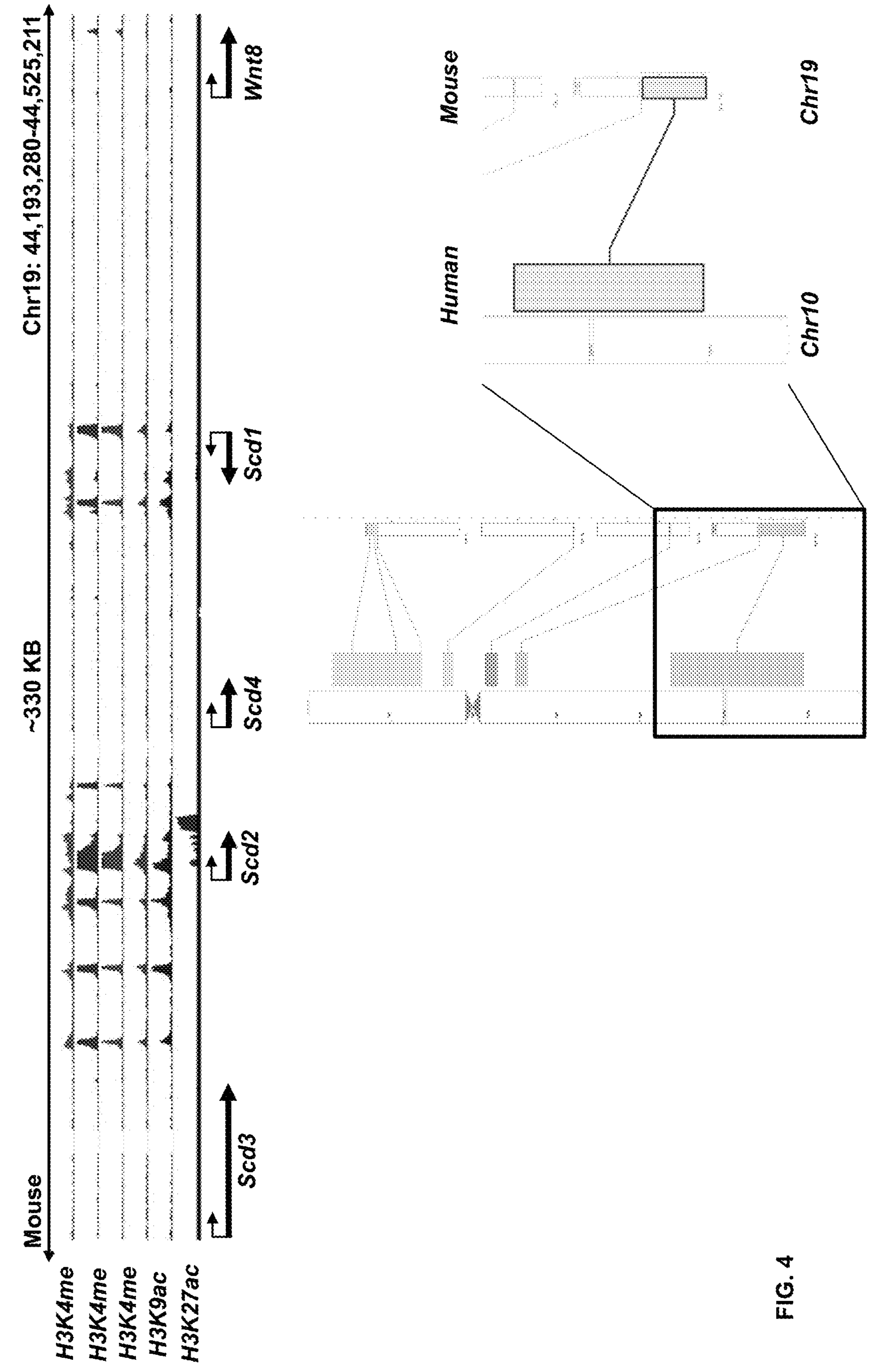
FIG. 4: The chromosome 10 region of OLMALINC and SCD in humans has synteny with chromosome 19 of the mouse genome where WNT8B, SCD1, SCD2, SCD3 and SCD4 are localized in a ~330 kb region. No histone methylation markers or RNA polymerase II ChIP-Seq sites were found in the mouse genome between WNT8B and SCD1 to suggest a TSS.

As shown in FIG. 6, OLMALINC resides directly downstream of SCD, the microsomal enzyme that converts polysaturated fatty acids into monosaturated fatty acids (MUFAs). Although SCD gene expression was not amongst the top genes correlated with OLMALINC expression, the correlation of OLMALINC expression with SCD still passes the genome-wide corrected p-value cut-point (ß=0.44; FDR=4.57E-11). Additionally, OLMALINC expression is significantly associated with the TGs phenotype, suggesting an important role of OLMALINC in TG biology. The chromosome 10 region of OLMALINC and SCD in humans has synteny with chromosome 19 of the mouse genome where WNT8B, SCD1, SCD2, SCD3 and SCD4 are localized in a ~330 kb region. However, no orthologues of OLMALINC were identified in the mouse. Consistent with these findings, no histone methylation markers or RNA polymerase II ChIP-Seq sites were found in the mouse genome between WNT8B and SCD1 to suggest a TSS (FIG. 4). Similarly to other lincRNAs, OLMALINC shows high homology with higher primates. These data suggest that OLMALINC is a primate-specific lincRNA.

Figure 3C:
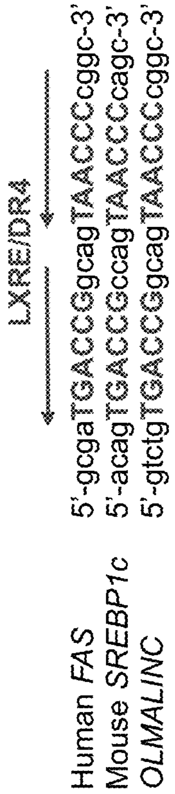
Figure 6A:
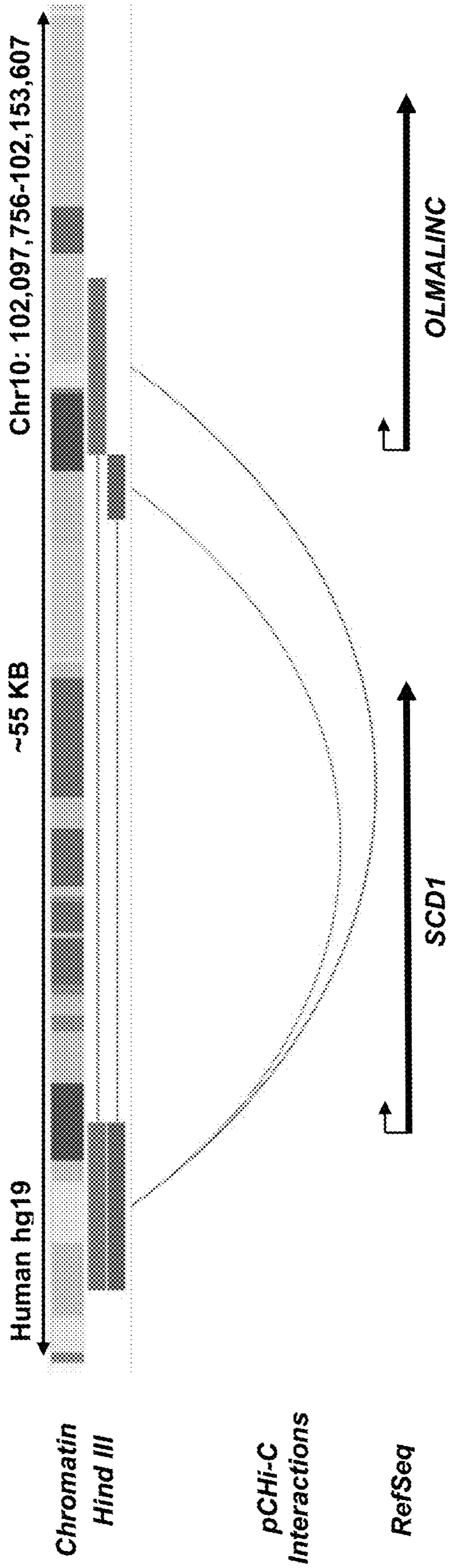
FIGS. 6A-6C: OLMALINC locus. (6A) OLMALINC resides directly downstream of SCD, the microsomal enzyme that converts polysaturated fatty acids into monosaturated fatty acids (MUFAs). OLMALINC acts in cis to affect SCD expression at the transcriptional level. (6B) SREBP2 (and its downstream targets) and SCD also increase in expression. Although SCD gene expression was not amongst the top genes correlated with OLMALINC expression, the correlation of OLMALINC expression with SCD still passes the genome-wide corrected p-value cutpoint (ß=0.44; FDR=4.57E-11). Endogenous OLMALINC over-expression affects cholesterol genes. OLMALINC endogenous over-expression using stable aCRISPR dCas9 HepG2 cell lines and its downstream genes in 2 different clones (72H transfection). All values are means+/−s.e.m. * $p<0.05$;  $p<0.01$; * $p<0.001$. (6C) When OLMALINC was overexpressed at the transcript level using a cDNA construct expressing exons 1-3, no downstream effects on SCD and SREBP2 gene expression were observed.

Since many lincRNAs exert their function by affecting near-by genes, we hypothesized that OLMALINC may regulate or affect SCD expression in cis. To further investigate this, we performed promoter capture Hi-C in liver HepG2 cells under standard conditions (10% FBS). We additionally utilized publicly available data that used the same HindIII fragments (for promoter capture Hi-C) to confirm our findings in HepG2 and found that human erythroblasts, foetal thymus, macrophages, total CD8, and activated CD4 cells all have the same looping interactions. These DNA-DNA looping interactions were identified between the promoter of SCD and the annotated promoter/enhancer region of OLMALINC, which encompass the LXRE-DR4 region of the gene (FIG. 3C). These data suggest that OLMALINC acts in cis to affect SCD expression at the transcriptional level (FIG. 6A).

Figure 6B:
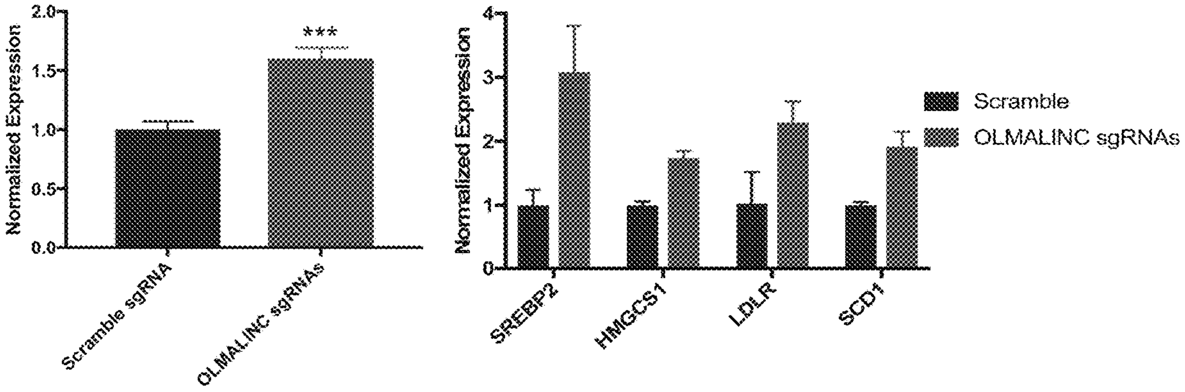

We used an activating CRISPR dead Cas9-VP64 (aCRISPR dCas9) to over-express OLMALINC at the transcriptional level (Konermann, Brigham et al. 2015). We found that with ~1.8-fold increase in OLMALINC expression, SREBP2 (and its downstream targets) and SCD also increase in expression (FIG. 6B). Given that SREBP2 is a transcription factor of SCD, it remained unknown if the effects seen were direct or secondary to SREBP2 over-expression. We therefore chose to knock out the promoter and enhancer region of OLMALINC based on the looping interactions observed.

Figure 5:
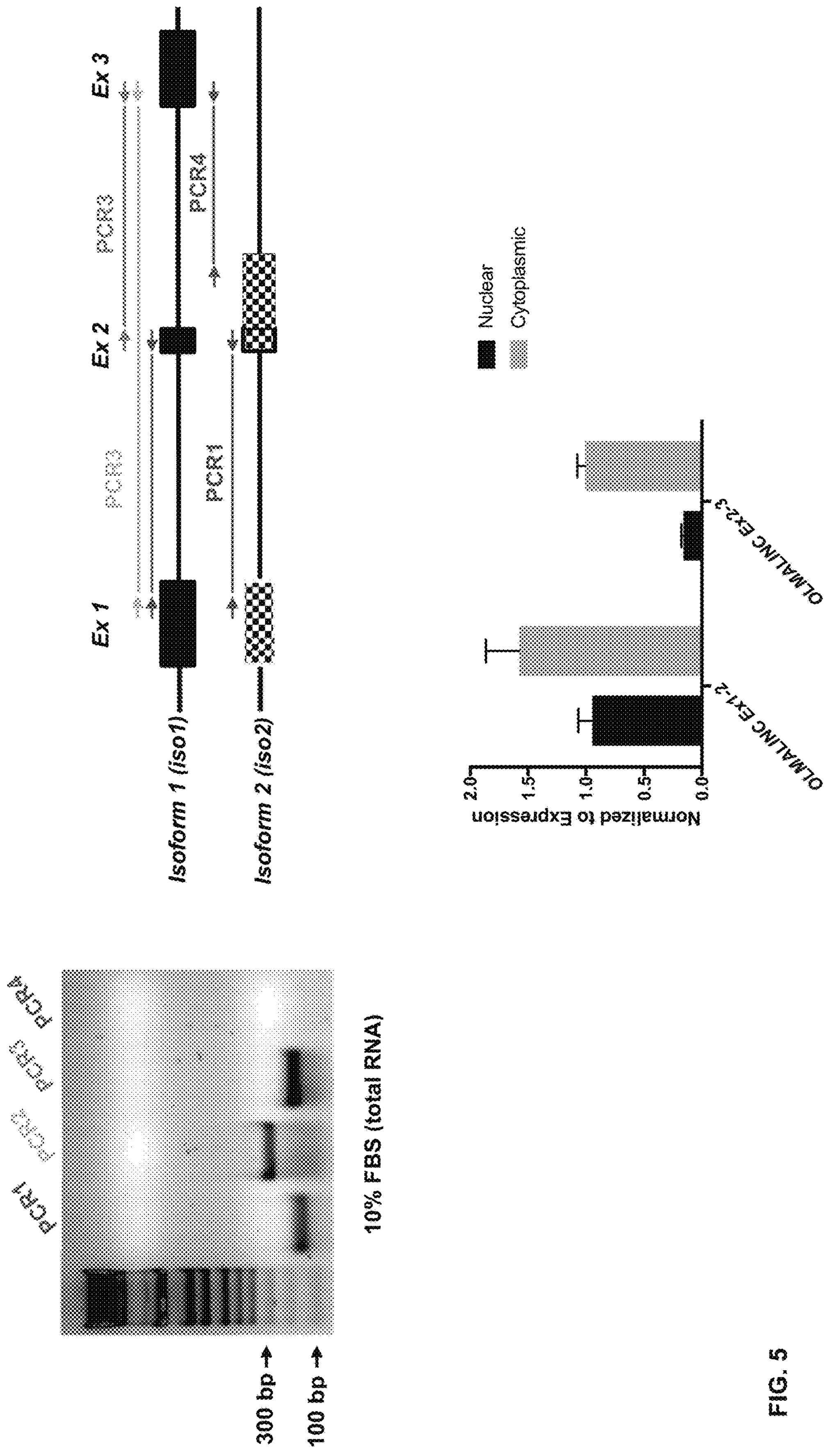
FIG. 5: Measurement of the expression of exons 1-3 by RT-qPCR and Sanger sequencing of the PCR products.
Figure 6C:
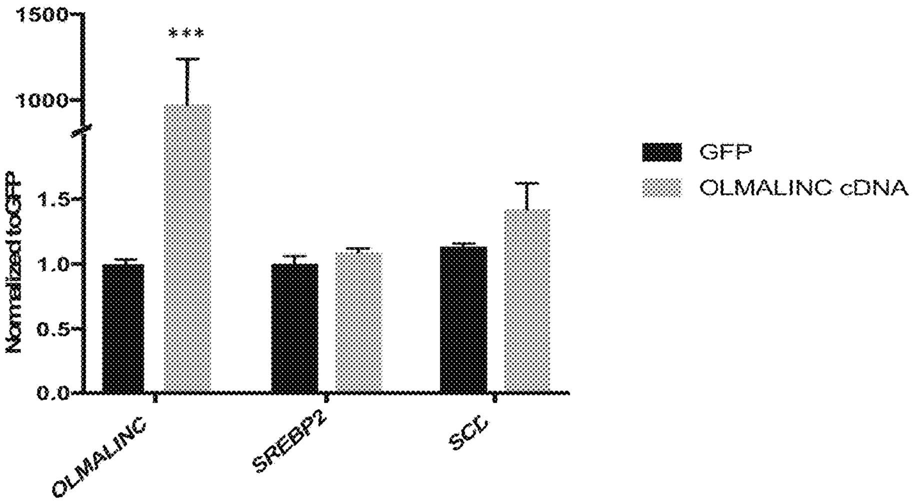

To further tease out the transcriptional versus post-transcriptional effects of OLMALINC, we sought to determine the effects of the mature transcript. OLMALINC is annotated to have several transcripts. We were able to measure the expression of exons 1-3 by RT-qPCR and Sanger sequencing of the PCR products (FIG. 5). When we over-expressed OLMALINC the transcript level using a cDNA construct expressing exons 1-3, we observed no downstream effects on SCD and SREBP2 gene expression (FIG. 6C). Taken together, these data demonstrate that OLMALINC affects the gene expression of SREBP2 and SCD at the transcriptional level (while being transcribed or immediately thereafter for SREBP2 and likely through DNA-DNA looping for SCD by recruitment of enhancers and transcription factors).

Figure 7A:
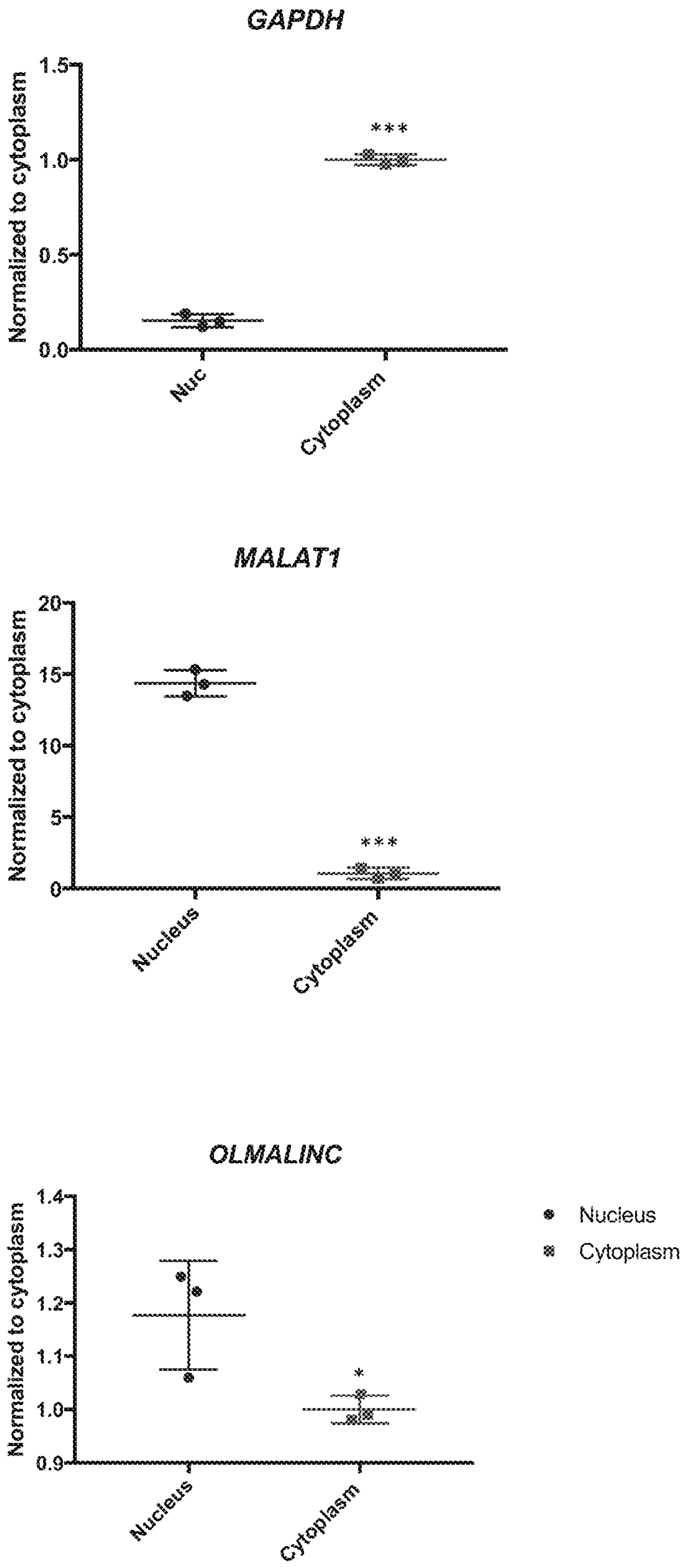
FIGS. 7A-7C: OLMALINC Localization and transcripts. (7A) OLMALINC localization does not demonstrate a significant difference between the cytoplasmic and nuclear extracts. (7B) Transient OLMALINC knock down in HepG2 cells. Right Panel—RNA-seq (n=3) in HepG2 of OLMALINC knock down with genes in SREBP2 pathway. FC=fold change. FDR=false discovery rate. (7C) SCD knock down increases OLMALINC expression (48H transfection). All values are means+/−s.e.m. * $p<0.05$;  $p<0.01$; * $p<0.001$.
Figure 7B:
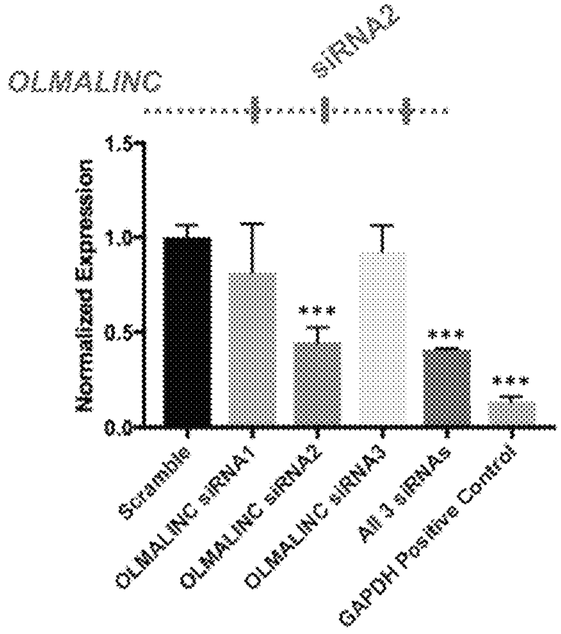
Figure 7C:
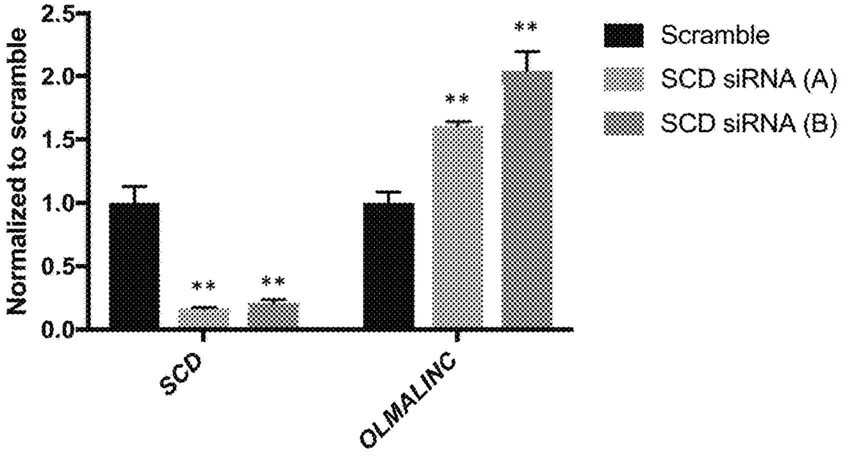
Figure 8:
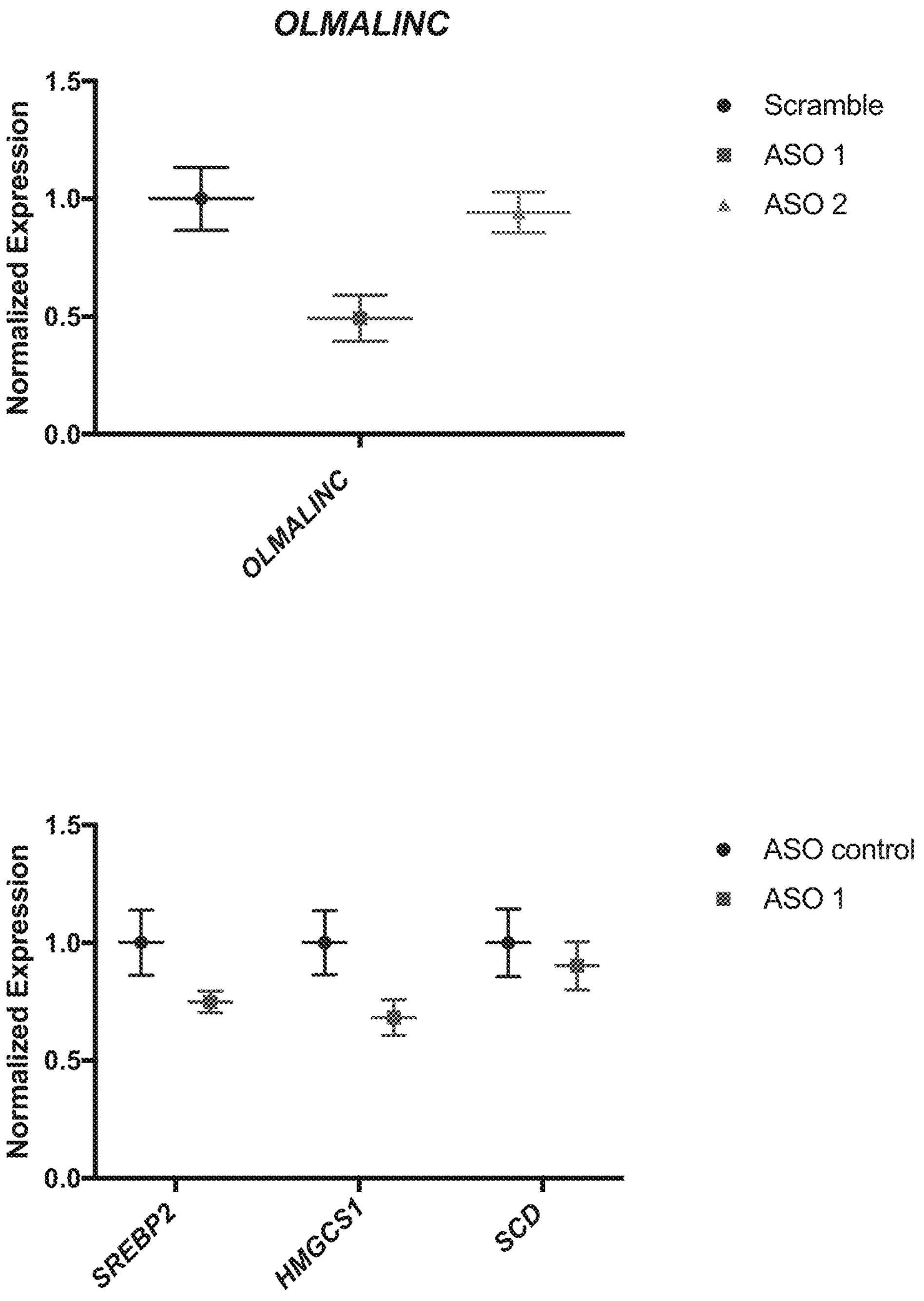
FIG. 8: OLMALINC knock down, using an antisense oligonucleotide that localizes more to the cytoplasm, causes a decrease in the SREBP2 gene and its target HMGCS1 without affecting SCD gene expression.
Figure 9A:
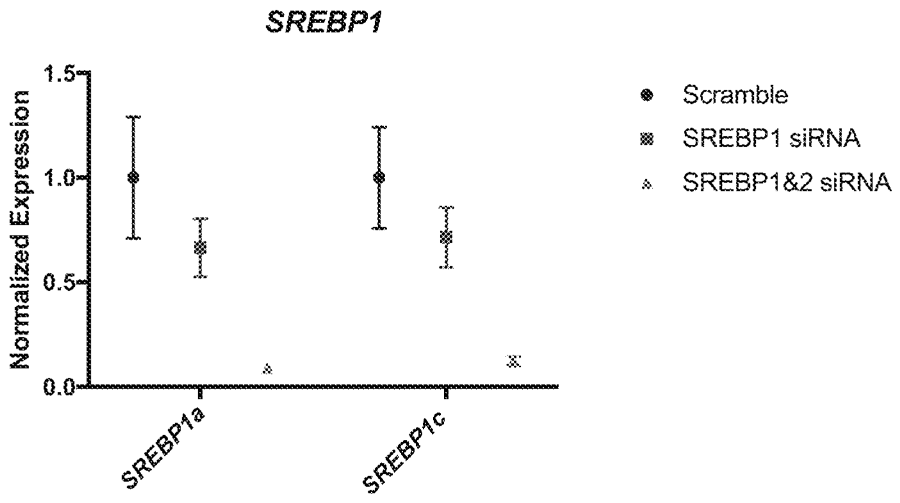
FIGS. 9A-9C: OLMALINC regulation. SREBP1, SREBP2, and SCAR were knocked down using siRNAs to study those effects on its gene expression. Knock down of SREBP2 decreases OLMALINC expression similarly to other SREBP2-dependent genes, and knock down of SREBP1 does not affect OLMALINC expression, potentially from compensatory effects of SREBPs. When SREBP1 and SREBP2 are knocked down together, there is a significant and synergistic decrease in OLMALINC, similarly to SCD expression.
Figure 9B:
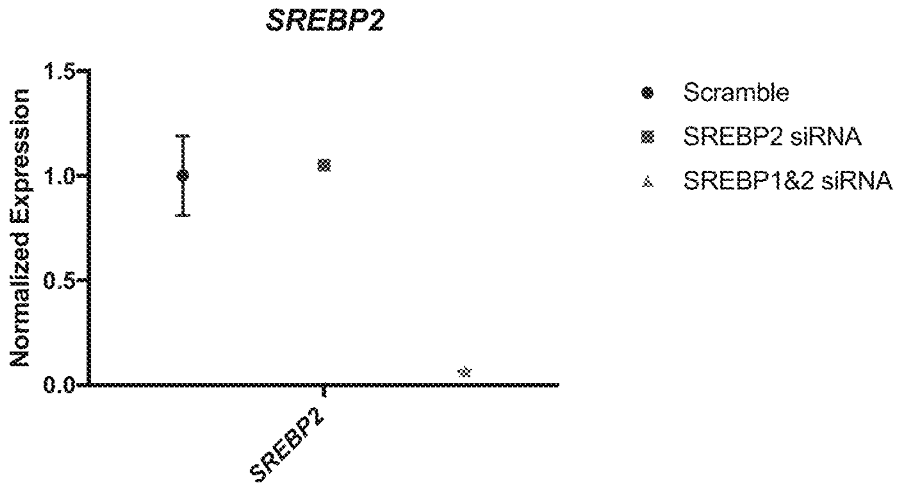
Figure 9C:
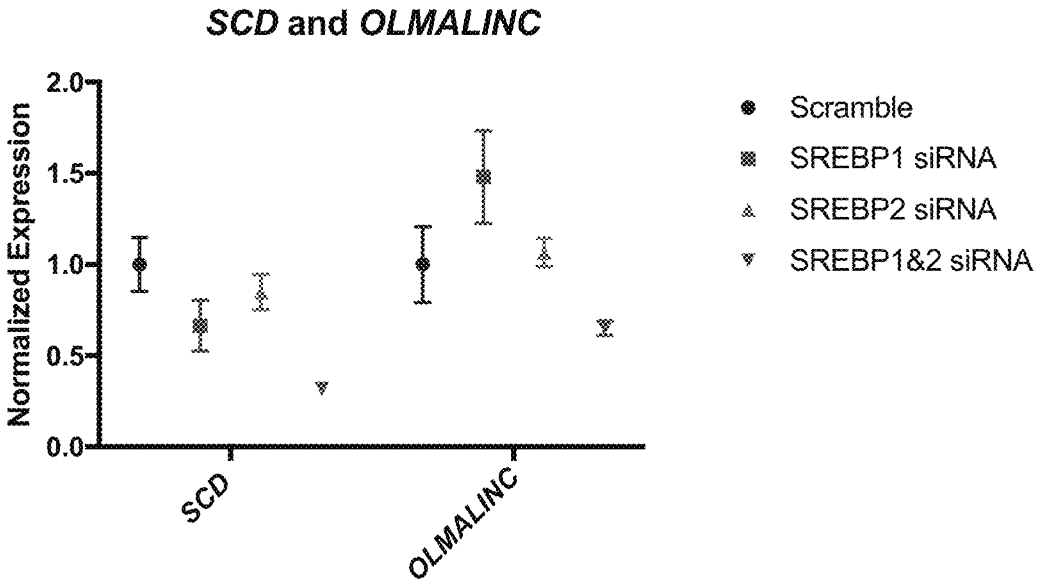
Figure 9D:
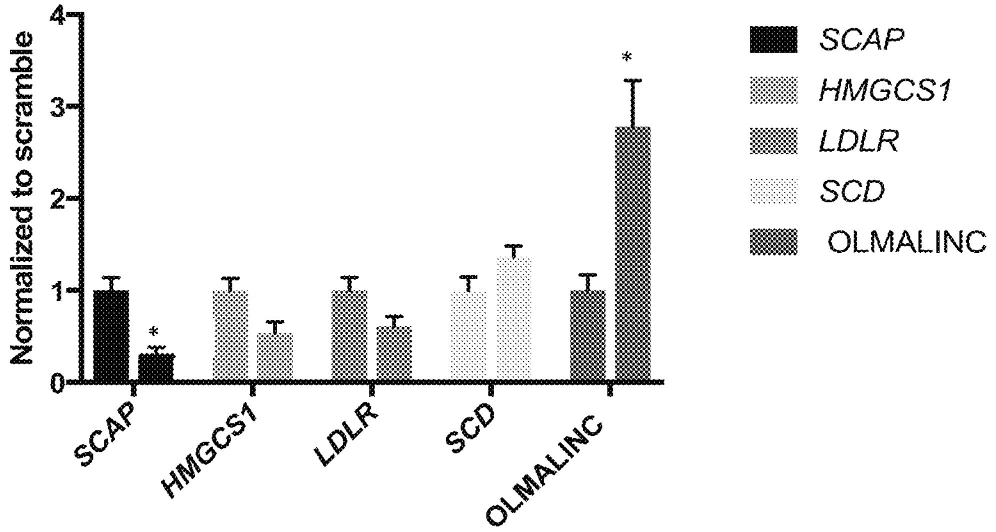
FIG. 9D: SCAP knock down increases OLMALINC gene expression.

OLMALINC Function. OLMALINC localization does not demonstrate a significant difference between the cytoplasmic and nuclear extracts (FIG. 7A). To further investigate its function and differentiate its cis versus post-transcriptional effect, we applied siRNA to HepG2 cells targeting exon 2 for 48 hours and obtained a ~50% knock down. Our cellular RNA-sequencing of the treated cells demonstrates an increase in SREBP2-dependent genes, including HMGCR, HMGCS1, and LDLR using FDR <0.05, which were confirmed by RT-q-PCR (FIG. 7B). However, SCD and other genes in lipid synthesis were not changed. In conjunction with our cis data, these results indicate that that the cis and post-transcriptional effects of OLMALINC affect different genes. Conversely, when SCD is knocked down, we see an increase in OLMALINC expression (FIG. 7C). These data suggest that OLMALINC expression is responsive to SCD levels or its byproduct of MUFAs. OLMALINC may therefore be a "check point" for SCD expression, providing yet another layer for its regulation that is only available in higher primates.

OLMALINC regulation. In conjunction with the ENCODE data, we demonstrated that OLMALINC is sterol, statin and LXR responsive and that its knock down affects SREBP2 pathways genes. Given the cis effect of OLMALINC on SCD and the known differential regulation of the SREBP1 pathway when compared with SREBP2, we sought to further understand OLMALINC regulation by these pathways. To accomplish this, we knocked down SREBP1, SREBP2, and SCAP using siRNAs to study those effects on its gene expression. We observed that knock down of SREBP2 does not affect OLMALINC expression similarly to other SREBP2-dependent genes and that knock down SREBP1 does not affect OLMALINC expression, potentially from compensatory effects of SREBPs. To circumvent these effects, we knocked down SCAP, the sterol sensor and escort of SREBPs which downregulates SREBP1, SREBP2 and their downstream genes. With the SCAP knock down, we observed an increased OLMALINC expression (FIG. 9) thereby confirming an indirect regulatory role.

TABLE 1

Correlation of OLMALINC liver expression with cardiometabolic and liver histology phenotypes in the KOBS cohort. Gene Ontology (GO) using Protein String analysis of the top 10% genes correlated with OLMALINC expression passing a false discovery rate of <0.1% (n = 681). STRING analysis confirmed high correlation between proteins involved in the cholesterol and lipid biosynthesis pathways.

| Clinical phenotype | ß estimate | Standard error | p-value |
|---|---|---|---|
| NAFLD | 0.210 | 0.126 | 0.097 |
| NASH | 0.069 | 0.167 | 0.677 |
| Liver fibrosis | 0.131 | 0.124 | 0.292 |
| Type 2 Diabetes | 0.237 | 0.127 | 0.064 |
| Total cholesterol (mmol/L) | −0.06 | 0.069 | 0.366 |
| Triglycerides (mmol/L) | 0.275 | 0.084 | 0.001 |

TABLE 2

Correlation of OLMALINC gene expression with human traits in the KOBS liver cohort demonstrating a significant correlation with total peripheral triglycerides with a ß = 0.275 (p = 0.001).

| Pathway description | Gene Counts | FDR |
|---|---|---|
| Cholesterol biosynthesis process | 19 | 3.42e−16 |
| Sterol biosynthesis process | 20 | 3.42e−16 |
| Small molecule biosynthesis process | 45 | 1.15e−12 |
| Cholesterol metabolic process | 24 | 1.19e−11 |
| Sterol metabolic process | 25 | 1.19e−11 |

Example 2: Role of a Novel Long Intergenic Non-Coding RNA, OLMALINC, in the Regulation of Lipid Metabolism Liver RNA-sequence (RNA-seq) samples from 259 Finnish obese patients undergoing bariatric surgery, with two thirds of the patients having a diagnosis of NAFLD and/or NASH by liver histology. Weighted gene co-expression network analysis (WGCNA) on the RNA-seq data for statin usage identified a network module of 75 co-expressed genes. Among those, there were both well characterized genes in the cholesterol biosynthesis pathway and several new candidates for cholesterol metabolism. The latter included OLMALINC, a novel lincRNA which has been described to play a role in glucose sensing in pancreatic islet cells. OLMALINC was also associated with type 2 diabetes, fatty liver and liver fibrosis modules.

Publicly available data including GTEx and ENCODE were used to understand the regulation of OLMALINC. In vitro model in HepG2 hepatic cell lines were used to characterize OLMALINC. Cells are grown in 1×DMEM with 1% penicillin/streptomycin in 10% FBS or 5% lipoprotein-deficient media (LPDS) with 5 uM simvastatin and 50 uM mavelonic acid. We extracted RNA using Direct-Zol RNA Isolation kit and cDNA was synthesized using Maxima Reverse Transcriptase. We conducted transient transfections using Lipofectamine RNAiMax and Lipofectamine 3000.

For RNA-seq, we prepared the libraries using the Illumina TruSeq Stranded mRNA library kit. Libraries were sequenced at a depth of 25-30 M paired-end reads on an Illumina HiSeq4000 platform (n=3). We mapped the reads using the STAR 2-pass protocol, and counted against the Gencode version 26 annotation using HTSeq. Differentially expressed (DE) genes were identified using the edgeR pipeline, using FDR <0.05.

For endogenous over-expression experiments, activating CRISPR dead Cas9 stable (aCRISPR dCs9) cell lines were generated in HepG2 using a third generation lentivirus system.

OLMALINC is a lincRNA expressed in livers that we identified in a module associated with statin use in the WGCNA analysis of liver RNA-seq data from liver biopsy samples in morbidly obese patients. OLMALINC expression correlates highly with key cholesterol and lipid biosynthesis genes. The OLMALINC knock down demonstrates an increase in the cholesterol and lipid, SREPB2 and SREBP1 respectively, dependent pathways. This Example shows that OLMALINC endogenous expression also causes an increase in SREBP2 and its downstream genes, and that OLMALINC promoter/enhancer interacts with SCD promoter, likely affecting its regulation in cis.

Throughout this application various publications are referenced. The disclosures of these publications in their entireties are hereby incorporated by reference into this application in order to describe more fully the state of the art to which this invention pertains.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An oligonucleotide that inhibits expression of an OLMALINC nucleic acid molecule, wherein the oligonucleotide is selected from SEQ ID NO: 2, SEQ ID NO: 3, or SEQ ID NO: 4.

2. The oligonucleotide of claim 1, wherein the OLMALINC nucleic acid molecule is SEQ ID NO: 1.

3. The oligonucleotide of claim 1, which is CTCCGTGAGGAGATCCACCTA (SEQ ID NO: 4).

4. A method of inhibiting the expression of OLMALINC in a subject, the method comprising administering to the subject an effective amount of an oligonucleotide of claim 1 or equivalent thereof that specifically binds to and inactivates an OLMALINC nucleic acid molecule.

5. A method of ameliorating symptoms associated with obesity and/or type 2 diabetes, the method comprising administering to a subject in need thereof an effective amount of an oligonucleotide of claim 1 or equivalent thereof that specifically binds to and inactivates an OLMALINC nucleic acid molecule, wherein the equivalent thereof is selected from TACACCTATCCCAAACCTATA (SEQ ID NO: 10); GAGATTCTTTGTGGGCTCTTA (SEQ ID NO: 11); CCCACGCTAACTGATACCATA (SEQ ID NO: 12); AAGGAACAUCUUGCCAAUUUCAAAT (SEQ ID NO: 13); and UGCCCCACGCUAACUGAUACCAUAT (SEQ ID NO: 14).

6. A pharmaceutical composition comprising an oligonucleotide of claim 1, formulated for delivery to a patient in need of ameliorating appetite, glycemia, body weight, obesity, liver steatosis, NASH, NAFLD, lipid disorder, and/or other symptoms associated with obesity disorders and type 2 diabetes.

7. The pharmaceutical composition of claim 6, further comprising a pharmaceutically acceptable carrier.

8. The method of claim 5, wherein the disorder associated with obesity and/or type 2 diabetes is a disorder of appetite, glycemia, body weight, liver steatosis, NASH, NAFLD, or a lipid disorder.

9. The method of claim 5, wherein the method comprises administering an oligonucleotide selected from SEQ ID NO: 2, SEQ ID NO: 3, or SEQ ID NO: 4, to the subject.

10. The method of claim 9, wherein the oligonucleotide is SEQ ID NO: 4.

* * * * *